United States Patent
Önder et al.

(10) Patent No.: US 10,322,110 B2
(45) Date of Patent: *Jun. 18, 2019

(54) IMIDAZOLE-BASED ANTIMICROBIAL AGENTS

(71) Applicant: Procomcure Biotech GmbH, Krems (AT)

(72) Inventors: Kamil Önder, Salzburg (AT); Roelf Datema, The Hague (NL); Dale Mitchell, Essex (GB); Ivan Kondratov, Kyiv (UA)

(73) Assignee: Procomcure Biotech GmbH, Thalgau (AT)

( * ) Notice: Subject to any disclaimer, the term of this patent is extended or adjusted under 35 U.S.C. 154(b) by 0 days.

This patent is subject to a terminal disclaimer.

(21) Appl. No.: 15/532,668

(22) PCT Filed: Dec. 3, 2015

(86) PCT No.: PCT/EP2015/078587
§ 371 (c)(1),
(2) Date: Jun. 2, 2017

(87) PCT Pub. No.: WO2016/087618
PCT Pub. Date: Jun. 9, 2016

(65) Prior Publication Data
US 2017/0368032 A1  Dec. 28, 2017

(30) Foreign Application Priority Data
Dec. 4, 2014 (EP) .................................. 14196335

(51) Int. Cl.
*A61K 31/4178* (2006.01)
*A61K 45/06* (2006.01)
(Continued)

(52) U.S. Cl.
CPC ........ *A61K 31/4178* (2013.01); *A61K 31/352* (2013.01); *A61K 31/4164* (2013.01); *A61K 31/4184* (2013.01); *A61K 31/4188* (2013.01); *A61K 31/4192* (2013.01); *A61K 31/4196* (2013.01); *A61K 31/422* (2013.01); *A61K 31/427* (2013.01); *A61K 45/06* (2013.01);
(Continued)

(58) Field of Classification Search
CPC .................................................. A61K 31/4178
USPC ...................................................... 514/365
See application file for complete search history.

(56) References Cited

U.S. PATENT DOCUMENTS 4,012,414 A   3/1977 Pelosi, Jr.
4,895,867 A   1/1990 Huang et al.
(Continued)

FOREIGN PATENT DOCUMENTS

EP    0 251 380 A3    1/1988
EP    1067165    * 10/2001    ............. C09K 11/06
(Continued)

OTHER PUBLICATIONS

Garton, et. al., Bioorganic & Medicinal Chemistry Letters (2010), 20(3), 1049-1054.*

(Continued)

*Primary Examiner* — Jeffrey H Murray
(74) *Attorney, Agent, or Firm* — Dority & Manning, P.A.

(57) ABSTRACT

The present invention relates to therapeutic agents suitable for use in the treatment of microbial infection in mammals. The present invention further relates to the use of pharmaceutical compositions comprising said agents in the treatment of medical conditions in mammals, in particular in the treatment of microbial infection. The agents and pharmaceutical compositions of the invention are of particular relevance in the treatment of diseases associated with antibiotic-resistant microbes. In one particular embodiment, the pharmaceutical composition can have the structural moiety of formula (I) or a pharmaceutically-acceptable salt of said compound:

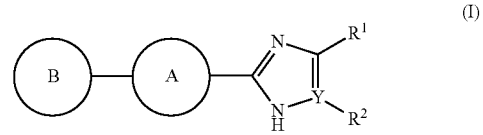

wherein group A is selected from the formulae

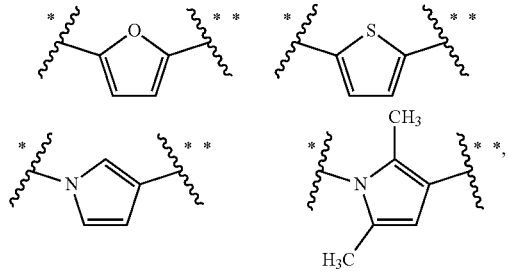

Group B is aryl, $R^1$ is an optionally substituted aryl ring, an optionally substituted benzyl ring, $CH_3$, or $C_{2\ to\ 6}$ alkyl, and $R^2$ is hydrogen, an alkyl group, a halogen, or $-(CH_2)_nN(CH_3)_2$ where n is an integer from 1 to 3.

11 Claims, No Drawings

(51) Int. Cl.

| | |
|---|---|
| *A61K 31/352* | (2006.01) |
| *A61K 31/4164* | (2006.01) |
| *A61K 31/4184* | (2006.01) |
| *A61K 31/4188* | (2006.01) |
| *A61K 31/4196* | (2006.01) |
| *A61K 31/422* | (2006.01) |
| *A61K 31/427* | (2006.01) |
| *A61K 31/4192* | (2006.01) |
| *C07D 403/04* | (2006.01) |
| *C07D 405/04* | (2006.01) |
| *C07D 409/04* | (2006.01) |
| *C07D 417/04* | (2006.01) |

(52) U.S. Cl.
CPC ......... *C07D 403/04* (2013.01); *C07D 405/04* (2013.01); *C07D 409/04* (2013.01); *C07D 417/04* (2013.01); *A61K 2300/00* (2013.01)

(56) References Cited

U.S. PATENT DOCUMENTS

| | | |
|---|---|---|
| 6,372,752 B1 | 4/2002 | Staveski et al. |
| 2004/0077650 A1 | 4/2004 | Dow |
| 2004/0192743 A1 | 9/2004 | Mjalli et al. |
| 2010/0152162 A1 | 6/2010 | Uesaka et al. |
| 2010/0280023 A1 | 11/2010 | Sugawara et al. |
| 2011/0130397 A1 | 6/2011 | Choi et al. |
| 2017/0334887 A1 | 11/2017 | Önder et al. |

FOREIGN PATENT DOCUMENTS

| | | | | |
|---|---|---|---|---|
| EP | 2 465 859 A1 | | 6/2012 | |
| WO | WO 99/35142 A1 | | 7/1999 | |
| WO | WO 2004/056817 A1 | | 7/2004 | |
| WO | WO 2004/071447 A2 | | 8/2004 | |
| WO | WO 2007/061153 A1 | | 5/2007 | |
| WO | WO 2008/006793 A1 | | 1/2008 | |
| WO | WO 2008/59258 A2 | | 5/2008 | |
| WO | WO2009051705 | * | 4/2009 | ............ A01N 43/82 |
| WO | WO 2009/143039 A2 | | 11/2009 | |
| WO | WO 2012/076974 A1 | | 6/2012 | |
| WO | WO 2013/029548 A1 | | 3/2013 | |
| WO | WO 2013/052588 A1 | | 4/2013 | |
| WO | WO 2013/070659 A1 | | 5/2013 | |
| WO | WO 2013070659 | * | 5/2013 | ........... C07D 471/04 |

OTHER PUBLICATIONS https://pubchem.ncbi.nlm.nih.gov/compound/46231802#section=Top; last accessed Mar. 5, 2018.*
Cheng, et al., Insights into binding modes of adenosine A2B antagonists with ligand-based and receptor-based methods, European Journal of Medicinal Chemistry, 2010, 13 pages.
Dalvie, et al., Biotransformation Reactions of Five-Membered Aromatic Heterocyclic Rings, Chemical Research in Toxicology, Vol. 15, No. 3, Mar. 2002, 31 pages.
Dow, et al., Bioisosteric replacement of the hydrazide pharmacophore of the cannabinoid-1 receptor, antagonist SR141716A. Part I: Potent, orally-active 1,4-disubstituted imidazoles, Bioorganic & Medicinal Chemistry Letters. 2009, 4 pages.
Heerding, et al., 1,4-Disubstituted Imidazoles are Potential Antibacterial Agents Functioning as Inhibitors of Enoyl Acyl Carrier Protein Reductase (Fab1), Bioorganic & Medicinal Chemistry Letters, 2001, 5 pages.
Kalla, et al., Novel 1,3-Disubstituted 8-(1-benzyl-1H-pyrazol-4-yl) Xanthines: High Affinity and Selective A2B Adenosine Receptor Antagonists, J. Med. Chem., 2006, 11 pages.
Rida, et al., Synthesis of Some Novel Substituted Purine Derivatives as a Potential Anticancer, Anti-HIV-1 and Antimicrobial Agents, Arch. Pharm. Chem. Life Sci., 2007, 10 pages.
International Search Report for PCT/EP2015/078587, dated Jan. 28, 2016, 3 pages.
STN Registry database entry: CAS RN 1445740-92-0 (Entered STN: Jul. 19, 2013). (Year: 2013), 1 page.
STN Registry database entry: CAS RN 1445737-78-9 (Entered STN: Jul. 19, 2013). (Year: 2013), 1 page.
STN Registry database entry: CAS RN 1445733-05-0 (Entered STN: Jul. 19, 2013). (Year: 2013), 1 page.
STN Registry database entry: CAS RN 1445749-52-9 (Entered STN: Jul. 19, 2013). (Year: 2013), 1 page.
Bassyouni et al., "Synthesis, Pharmacological Activity Evaluation and Molecular Modeling of New Polynuclear Heterocyclic Compounds Containing Benzimidazole Derivatives", Archives of Pharmacal Research, vol. 35, No. 12, pp. 20-63-2075.
Clayden et al., "Organic Chemistry", Oxford University Press, 2001, 4 pages.
Desai et al., "Synthesis, characterization and antimicrobial screening of hybrid molecules containing benzimidazole-pyrazole and pyridine nucleus", Medical Chemistry Research, 2012, pp.4463-4472.
Fridman et al., "Crystal structures and solution spectroscopy of Iophine dieriviatives", Journal of Molecular Structure, 2009, pp. 101-109.
Fridman et al., "Structures and photophysics of Iophine and double Iphine derivatives", Sensors and Actuators B, 2007, pp. 107-115.
Friedrichsen et al., "Tautomerism of Heterocycles: Five-Membered Rings with One Heteroatom", Advances in Heterocyclic Chemistry, vol. 76, 2000, 4 pages.
Jourshari et al., "An expedient one-pot synthesis of highly substituted imidazoles using supported ionic liquid-like phase (SILLP) as a green and efficient catalyst and evaluation of their anti-microbial activity", Chinese Chemical Letters 24, 2013, pp. 993-996.
Kalirajan et al., "Microwave assisted synthesis of some novel pyrazole substituted benzimidazoles and evaluation of their biological activities", Indian Journal of Chemistry, vol. 50B, Dec. 2011, pp. 1794-1799.
Patel et al., "Novel Charge-Transfer Chromophores Featuring Imidazole as Ti-Linkage", Heterocycles, vol. 78, No. 4, 2009, 16 pages.
Vijesh et al., "Synthesis characterization and antimicrobial studies of some new pyrazole incorporated imidazole derivatives", European Journal of Medicinal Chemistry 46, 2011, pp. 3531-3536.
"*Caffeine*" from Wikipedia, last accessed Mar. 10, 2016, 15 pages.
William et al., "Synthetic Small Molecules that Induce Neurogenesis in Skeletal Msucle", Department of Chemistry, Yonsei University, Seoul, Korea, Apr. 23, 2007, 2 pages.
International Search Report and Written Opinion for PCT/EP2015/078584, dated Jan. 28, 2016, 17 pages.
Partial European Search Report, dated May 27, 2015, 11 pages.
STN Registry database entry: CAS RN 299426-26-9 (Entered STN: Oct. 26, 2000). (Year: 2000), 1 page.
STN Registry database entry: CAS RN 328243-45-4 (Entered STN: Mar. 21, 2001). (Year: 2001), 1 page.
STN Registry database entry: CAS RN 328243-55-6 (Entered STN: Mar. 21, 2001). (Year: 2001), 1 page.
STN Registry database entry: CAS RN 330841-80-0 (Entered STN: Apr. 11, 2001). (Year: 2001), 1 page.
STN Registry database entry: CAS RN 401612-16-6 (Entered STN: Mar. 18, 2002). (Year: 2002), 1 page.
STN Registry database entry: CAS RN 747398-80-7 (Entered STN: Sep. 19, 2004). (Year: 2004), 1 page.
STN Registry database entry: CAS RN 851288-42-1 (Entered STN: May 27, 2005). (Year: 2005), 1 page.
STN Registry database entry: CAS RN 930696-37-0 (Entered STN: Apr. 18, 2007). (Year: 2007), 1 page.
STN Registry database entry: CAS RN 1026970-39-7 (Entered STN: Jun. 10, 2008). (Year: 2008), 1 page.

* cited by examiner

IMIDAZOLE-BASED ANTIMICROBIAL AGENTS

CROSS REFERENCE TO RELATED APPLICATIONS

This application is the national stage entry of International Patent Application No. PCT/EP2015/078587 having a filing date of Dec. 3, 2015, which claims priority to and the benefit of European Patent Application No, 14196335.5 filed in the European Patent Office on Dec. 4, 2014, the entire contents of which are incorporated herein by reference.

The present application claims priority from European Patent Application EP 14196335, the content of which is hereby incorporated by reference in its entirety.

FIELD OF INVENTION

The present invention relates to novel therapeutic agents suitable for use in the treatment of mammalian disease and in particular to novel therapeutic agents suitable for use in the treatment of microbial infection in mammals. The present invention further relates to the use of pharmaceutical compositions comprising said agents in the treatment of medical conditions in mammals, in particular in the treatment of microbial infection. The agents and pharmaceutical compositions of the invention are of particular relevance in the treatment of diseases associated with antibiotic-resistant microbes.

BACKGROUND OF THE INVENTION

Antibiotic resistance is a serious and growing phenomenon in contemporary medicine and has emerged as one of the pre-eminent public health concerns of the 21st century, especially in the case of hospital-acquired infections. According to data from the Centers for Disease Control and Prevention (CDC) available in 2008, the six so-called ESKAPE bacteria (*Enterococcus faecium* (gram positive), *Staphylococcus aureus* (gram positive), *Klebsiella pneumoniae* (gram negative), *Acinetobacter baumanii* (gram negative), *Pseudomonas aeruginosa* (gram negative), and *Enterobacter* (gram negative)) are responsible for two thirds of all health care-associated infections. The increasing prevalence of antibiotic-resistant bacterial infections seen in clinical practice stems from antibiotic use both within human medicine and veterinary medicine in which the use of antibiotics can increase selective pressure in a population of bacteria to allow the resistant bacteria to thrive and the susceptible bacteria to die off.

Infection by several drug-resistant Gram-negative bacteria—such as multidrug-resistant (MDR) *Pseudomonas aeruginosa* and carbapenem-resistant *Klebsiella* species is of great concern. The therapeutic options for these pathogens are so limited that clinicians are often forced to use older, previously discarded drugs, which are associated with significant toxicity.

With respect to gram-positive bacteria, the percentage of bloodstream infections caused by antibiotic-resistant gram-positive bacteria is increasing. As of 2006, approximately 60% of staphylococcal infections in intensive care units in the United States were caused by methicillin-resistant *Staphylococcus aureus* (MRSA), with percentages continuing to rise. Hospital-acquired MRSA strains are generally multidrug-resistant. As a means of highlighting the scale of the problem at hand, more people now die of MRSA infection in US hospitals than of HIV/AIDS and tuberculosis combined. Vancomycin is the standard treatment for serious MRSA infections, but cases of vancomycin-resistant *Staphylococcus aureus* (VRSA) also emerge. The increase in resistant Gram-positive strains may be explained, in part, by scientists concentrating in the 1970s and 1980s on the development of drugs active against Gram-negative pathogens, thereby permitting the slow evolution and selection of resistant Gram-positive bacteria.

Furthermore, multi-drug resistant (MDR) infections are also increasing and infections now occur that are resistant to all current antibacterial options (so-called pan-antibiotic-resistance). As resistance towards antibiotics becomes more common, a greater need for alternative treatments arises. However, despite a push for new antibiotic therapies, there has been a continued decline in the number of newly approved drugs. Antibiotic resistance and, in particular, the antibiotic resistance of gram-positive bacteria therefore poses a significant global health problem.

U.S. Pat. No. 4,012,414 discloses 2-furylimidazoles in which, with the exception of the bond to the furan ring, the imidazoles are unsubstituted. These compounds are disclosed to be suitable for use as antidepressants.

EP 0251380 discloses 2-furanylimidizoles for use as cardiotonic agents whereby the two carbon atoms of the imidazole ring which are not bonded to the furan ring may be substituted with H, methyl or ethyl.

It is therefore an object of the present invention to provide chemical species which can overcome the above-highlighted deficiencies in the treatment of mammalian microbial infections, in particular those resulting from gram-positive bacteria, and especially gram-positive bacteria strains known to show resistance to existing antibiotics/therapies.

SUMMARY OF THE INVENTION

The present invention relates to novel therapeutic agents suitable for use in the treatment of mammalian disease and in particular to novel therapeutic agents suitable for use in the treatment of microbial infection.

In particular, the present invention relates to a compound comprising or consisting of the structural moiety of formula (I) or a pharmaceutically-acceptable salt of said compound, for use as a medicament

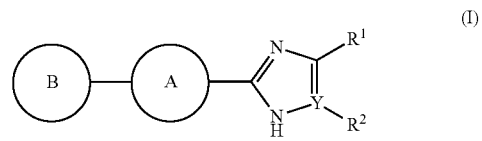

wherein
(i) Y is C or N;
(ii) $R^1$ and $R^2$ are independently selected from the group consisting of:
H, —$CH_3$, $C_{2 to 6}$alkyl, $C_{3 to 6}$cycloalkyl, halogen, —$(CH_2)_n N(CH_3)_2$ where n is an integer from 1 to 3, benzyl optionally substituted on the phenyl ring, heteroaryl, and aryl,
with the proviso that at least one of $R^1$ or $R^2$ possesses 3 or more carbon atoms; or
$R^1$ and $R^2$ are connected to form a four-, five- or six-membered non-aromatic carbocyclic ring thus providing a fused bicyclic moiety in which one or more of the carbon atoms of the ring comprising groups $R^1$ and $R^2$ is optionally replaced by a heteroatom selected from O, N, or S, and where one or more of the atoms of the ring comprising groups $R^1$ and $R^2$ is optionally substituted with one or more substituents independently selected from the group consisting of —$CH_3$, $C_{2to4}$alkyl, halogen, hydroxyl, —$OCH_3$, —$OC_{2to4}$alkyl, ethynyl, —$OCF_3$, and —$CF_3$;

with the proviso for all of the above-mentioned alternatives that when:

Y is N, $R^2$ represents a lone pair of electrons belonging to the N atom; and (iii) A is aryl or heteroaryl; and (iv) B is aryl, heteroaryl, a bicyclic system comprising at least one aromatic ring, or styryl.

Preferred embodiments of the invention are evident from the dependent claims.

The invention also relates to the use of compounds comprising the moiety of formula (I) or a pharmaceutically-acceptable salt of said compound, for use in the treatment of mammalian microbial infection.

In the present invention, in the structural moiety of formula (I) A is preferably 5-membered heteroaryl, and when A is 5-membered heteroaryl, A is preferably selected from the group consisting of

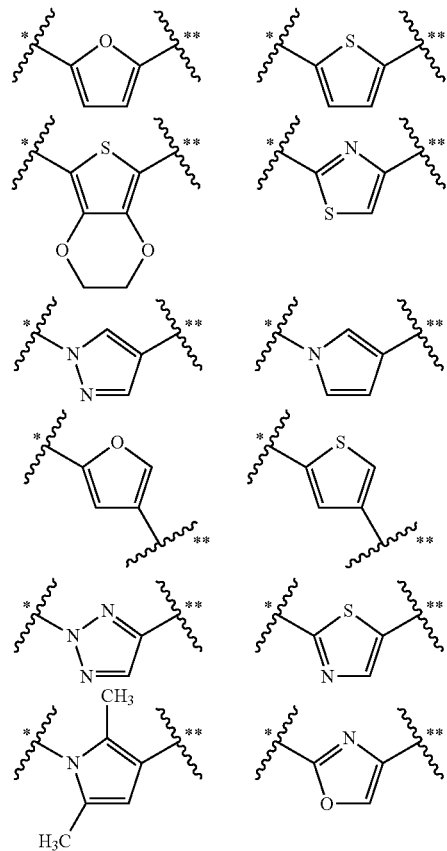

where * is the point of connection to the correspondingly-labeled atom of B and ** is the point of connection to the correspondingly-labeled atom of,

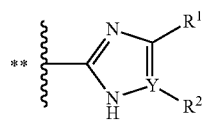

wherein the aromatic ring of A is optionally substituted, preferably by one or more substituents independently selected from —$CH_3$, $C_{2to4}$alkyl, halogen, —$OCH_3$, and —$OC_{2to4}$alkyl. When aromatic ring of A is substituted by one or more substituents, aromatic ring of A is more preferably substituted by one or more substituents independently selected from —$CH_3$, $C_{2to4}$alkyl, and halogen, most preferably by one or more —$CH_3$ substituents.

In the present invention, in the structural moiety of formula (I) B is preferably selected from the group consisting of

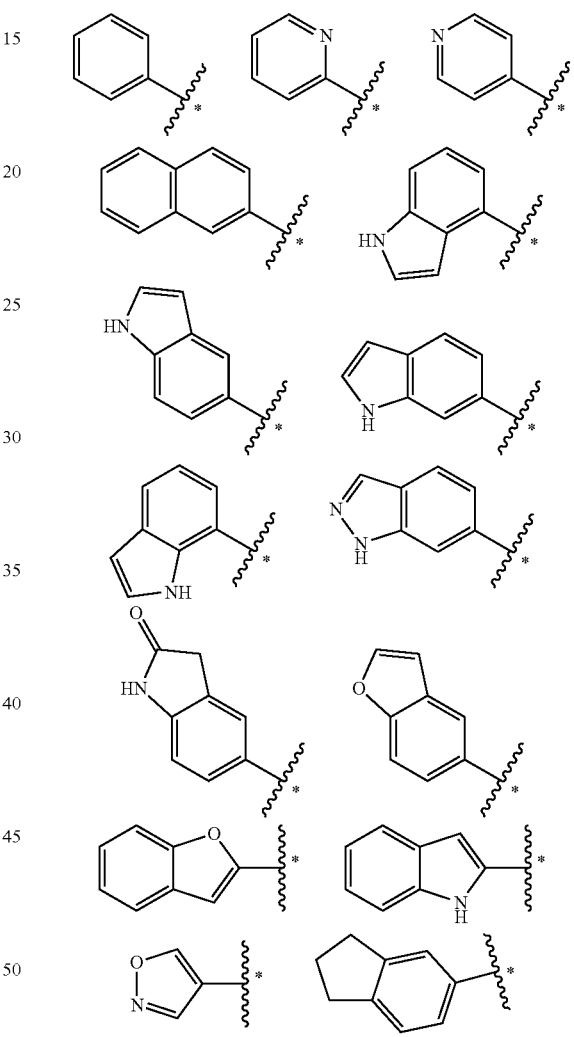

where * is the point of connection to the correspondingly-labeled atom of A. When B is a phenyl ring, the phenyl ring may optionally be substituted. When B is a substituted phenyl ring, the phenyl ring is preferably substituted with one or more substituents independently selected from the group consisting of —$CH_3$, $C_{2to4}$alkyl, halogen, hydroxyl, —$OCH_3$, —$OC_{2to4}$alkyl, —$CF_3$, —$OCF_3$, —$NH_2$, —$CH_2NH_2$, —$N(CH_3)_2$, —$NO_2$, —$CH_2OH$, —$CO_2CH_3$, —$CO_2C_{2to4}$alkyl, —$CO_2H$, —N(alkyl)$_2$ where the two alkyl groups are independently selected from —$CH_3$ or $C_{2to4}$alkyl, —NH(alkyl) where the alkyl group is selected from —$CH_3$ or $C_{2to4}$alkyl, 4-morpholinyl, 1-piperidinyl, 4H-piperazinyl, 4-$C_{1to4}$alkyl-piperazinyl, and 4-$C_{3 to 6}$cycloalkyl-piperazinyl, preferably independently selected from the group consisting of —$CH_3$, $C_{2 to 4}$alkyl, iso-propyl, tert-butyl, halogen wherein halogen is preferably F or Cl or Br, hydroxyl, —$OCH_3$, —$CF_3$, —$OCF_3$, —$N(CH_3)_2$, —$NO_2$, and 4-methylpiperazinyl, more preferably independently selected from the group consisting of —$CH_3$, —$CH_2CH_3$, iso-propyl, —$N(CH_3)_2$, halogen wherein halogen is preferably F or Cl or Br, —$OCH_3$, —$CF_3$, and —$OCF_3$.

In the structural moiety of formula (I), when B is other than a unsubstituted or substituted phenyl ring, B may be optionally substituted, and when B is substituted it is preferably substituted with one or more substituents independently selected from the group consisting of —$CH_3$, $C_{2 to 4}$alkyl, halogen wherein halogen is preferably F or Cl or Br, hydroxyl, —$OCH_3$, —$OC_{2 to 4}$alkyl, —$CF_3$, —$OCF_3$, —$CO_2CH_3$, —$CO_2C_{2 to 4}$alkyl, and —$CO_2H$, more preferably selected from the group consisting of —$CH_3$, —$CF_3$, —$OCF_3$ and halogen, wherein halogen is preferably F or Cl or Br.

The term "styryl" as used in the present application is to be understood to mean the following structural moiety

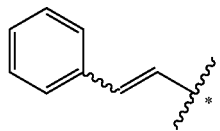

where * is the point of connection to the correspondingly-labeled atom of A, and preferably to mean

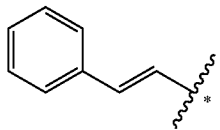 [SMILES: */C=C/c1ccccc1]

In the present invention, when $R^1$ and $R^2$ are connected to form a four-, five- or six-membered non-aromatic carbocyclic ring thus providing a fused bicyclic moiety in the structural moiety of formula (I), the bicyclic moiety is preferably selected from the group consisting of

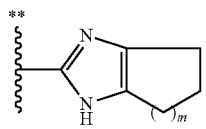

where m is 0, 1 or 2, and is most preferably 2, and ** is the point of connection to the correspondingly-labeled atom of A.

In the structural moiety of formula (I) of the present invention, when $R^1$ or $R^2$ is benzyl optionally substituted on the phenyl ring, they are preferably substituted with one or more substituents independently selected from the group consisting of —$CH_3$, $C_{2 to 4}$alkyl, halogen, hydroxyl, —$OCH_3$, —$OC_{2 to 4}$alkyl, ethynyl, —$OCF_3$, and —$CF_3$, more preferably with one or more substituents independently selected from the group consisting of halogen and hydroxyl, and are most preferably 4-halobenzyl, for example 4-bromobenzyl.

In the structural moiety of formula (I) of present invention, when $R^1$ or $R^2$ is aryl they are preferably substituted or unsubstituted phenyl, and when they are substituted phenyl they are preferably phenyl substituted with one or more substituents independently selected from the group consisting of —$CH_3$, $C_{2 to 4}$alkyl, halogen, hydroxyl, —$OCH_3$, —$OC_{2 to 4}$alkyl, ethynyl, —$OCF_3$, and —$CF_3$, more preferably with one or more substituents independently selected from the group consisting of —$CH_3$, —$CH_2CH_3$, —$OH$, —$CF_3$, —$OCF_3$, ethynyl, and halogen, wherein halogen is preferably F or Cl or Br, most preferably with one or more substituents independently selected from the group consisting of —$CH_3$, —$CH_2CH_3$, —$CF_3$, —$OCF_3$, ethynyl, and halogen, wherein halogen is preferably F or Cl or Br.

In the structural moiety of formula (I) of the present invention, when $R^1$ is aryl, heteroaryl, or benzyl or benzyl substituted on the phenyl ring, and Y is C, $R^2$ is preferably —$CH_3$, —$CH_2N(CH_3)_2$, Cl, or H. In some embodiments $R^2$ is —$CH_3$. In some embodiments $R^2$ is —$CH_2N(CH_3)_2$. In some embodiments $R^2$ is Cl. In some embodiments $R^2$ is H.

In the structural moiety of formula (I) of the present invention, when $R^2$ is aryl, heteroaryl, or benzyl or benzyl substituted on the phenyl ring, $R^1$ is preferably —$CH_3$, —$CH_2N(CH_3)_2$, Cl, or H. In some embodiments $R^1$ is —$CH_3$. In some embodiments $R^1$ is —$CH_2N(CH_3)_2$. In some embodiments $R^1$ is Cl. In some embodiments $R^1$ is H.

In some embodiments of the present invention, in the structural moiety of formula (I) $R^1$ and $R^2$ are preferably independently selected from the group consisting of H, —$CH_3$, n-propyl, n-butyl, iso-butyl, 4-bromobenzyl, 4-hydroxybenzyl, —$CH_2N(CH_3)_2$, halogen where halogen is preferably Cl, and phenyl, where phenyl is optionally substituted with one or more substituents independently selected from —$CH_3$, —$CH_2CH_3$, —$OH$, —$CF_3$, —$OCF_3$, ethynyl, and halogen, wherein halogen is preferably F or Cl or Br, and are more preferably independently selected from the group consisting of H, —$CH_3$, 4-bromobenzyl, —$CH_2N(CH_3)_2$, halogen where halogen is preferably Cl, and phenyl, where phenyl is optionally substituted with one or more substituents independently selected from —$CH_3$, —$CH_2CH_3$, —$CF_3$, —$OCF_3$, ethynyl, and halogen, wherein halogen is preferably F or Cl or Br.

In some preferred embodiments of the invention, when $R^1$ is H, $R^2$ is not H and when $R^2$ is H, $R^1$ is not H.

In some preferred embodiments of the invention, when $R^1$ is —$CH_3$, $R^2$ is not H and when $R^2$ is —$CH_3$, $R^1$ is not H.

In some preferred embodiments of the invention when $R^1$ is aryl, heteroaryl, or benzyl or benzyl substituted on the phenyl ring, then when Y is C, $R^2$ is H, —$CH_3$, —$CH_2N(CH_3)_2$, or halogen where halogen is preferably Cl.

In some preferred embodiments of the invention when $R^2$ is aryl, heteroaryl, or benzyl or benzyl substituted on the phenyl ring, $R^1$ is H, —$CH_3$, —$CH_2N(CH_3)_2$, or halogen where halogen is preferably Cl.

In the remainder of the application, unless specified otherwise all generic groups $R^1$, $R^2$, A, B, Y, m are as defined for the moiety of formula (I) and regardless of whether these groups have been further defined and/or restricted relative to their most generic nature in the structural moiety of formula (I), the provisos stipulated for the structural moiety of formula (I) apply for all structures, formulae and embodiments herein.

Hereinafter, when reference is made to a group/substituent being "as defined for formula (I)", "as defined for the moieties of formula (I)" etc, e.g. "In the moiety of List 1, $R^1$, $R^2$, group A and group B are as defined for formula (I)", this is to be understood to mean all possible definitions of the respective groups/substituents as described hereinabove for formula (I), including any of the "preferred", "more preferred" variants of a particular group/substituent. Moreover, any specific examples or lists of groups or substituents which are stated hereinabove to be "preferred", "more preferred" etc for the moieties of formula (I) are also to be understood to be "preferred", "more preferred" etc for any of the formulae listed hereinafter which fall under the wider scope of formula (I).

Hereinafter, when a formula or specific compound is depicted in such a way that the full valency of an atom, for example a heteroatom, would appear not to be satisfied, it is to be understood that the valency of said atom is satisfied through the presence of non-depicted hydrogen atoms, i.e. the depicted species is not a radical, cation, anion, carbine etc., but instead a neutral species. By way of example, the following structures/situations are presented:

Structural moieties depicted as

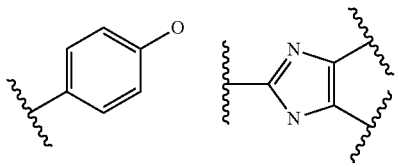 [SMILES: *c1ccc(O)cc1 ; *c1nc(*)c(*)[nH]1]

are to be understood to respectively represent

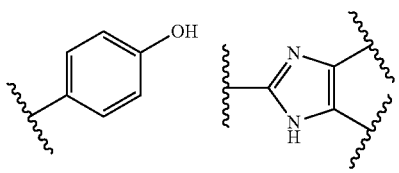 [SMILES: *c1ccc(O)cc1 ; *c1nc(*)c(*)[nH]1]

Moreover, in certain cases herein graphical depictions for a given specific structural moiety which are equally understood by the skilled person but which are different from one another are used. These are to be understood to represent the structural moiety that the skilled person would understand upon analyzing said moiety in isolation and not through comparison to other depictions of the same moiety presented elsewhere herein. For example, a methyl group may be depicted by explicitly writing the formula "CH$_3$" or may be equally depicted using the standard "linear" formula which is equally well understood by the skilled person. The following two structures thus both comprise a methyl group:

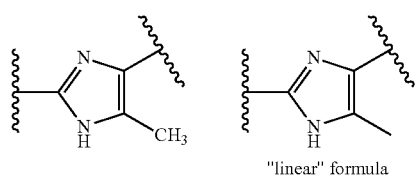

"linear" formula

DETAILED DESCRIPTION OF THE INVENTION

When a compound of the invention can exist in different tautomeric forms, the present invention includes any possible tautomers and pharmaceutically acceptable salts thereof, and mixtures thereof, except where specifically drawn or stated otherwise. For example, imidazoles which have no N-substitution are known to exist in two tautomeric forms in which the —NH hydrogen atom may reside on either of the nitrogen atoms of the imidazole ring. In such an instance where only one tautomeric form is graphically depicted in the present invention, its corresponding tautomer may be implicitly included. For example, when the following structure is depicted,

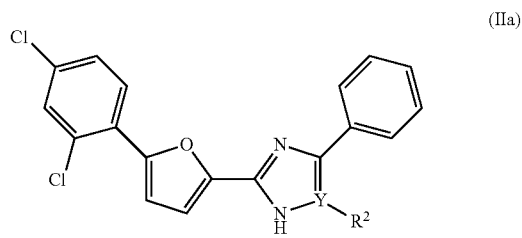

(IIa)

its corresponding tautomer

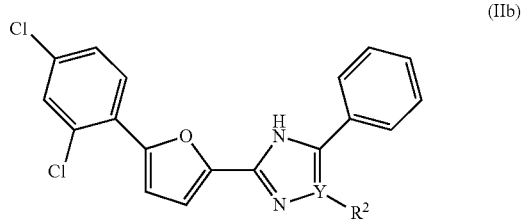

(IIb)

may be implicitly also included. This applies for all structures and moieties of the invention which may exist in different tautomeric forms.

In a preferred embodiment of the invention, the moiety of formula (I) is represented by the formula (III) shown in List 1.

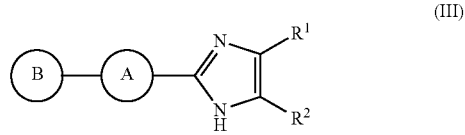

(III)

In the moiety of List 1, $R^1$, $R^2$, group A and group B are as defined for formula (I).

In some embodiments of the invention, the moiety of formula (I) is selected from the formulae comprised in List 1a.

List 1a

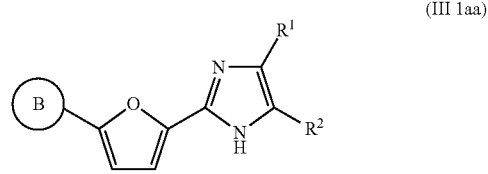

(III 1aa)

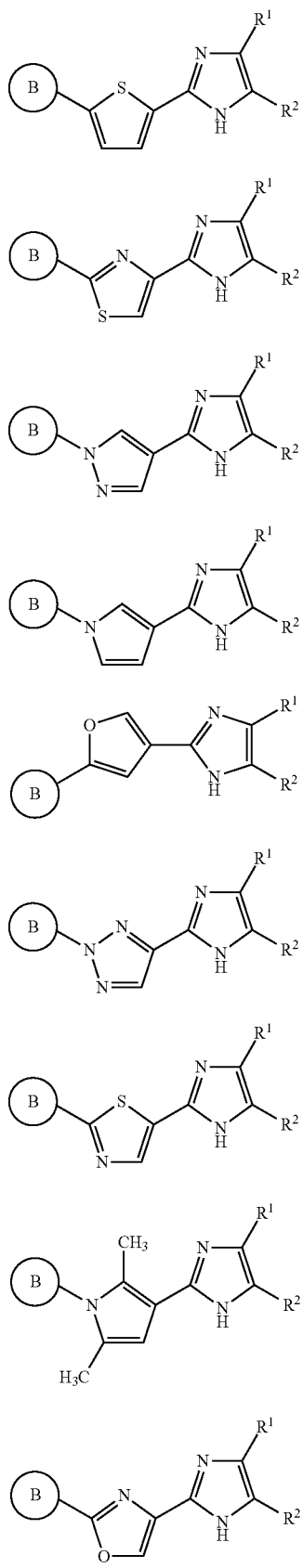

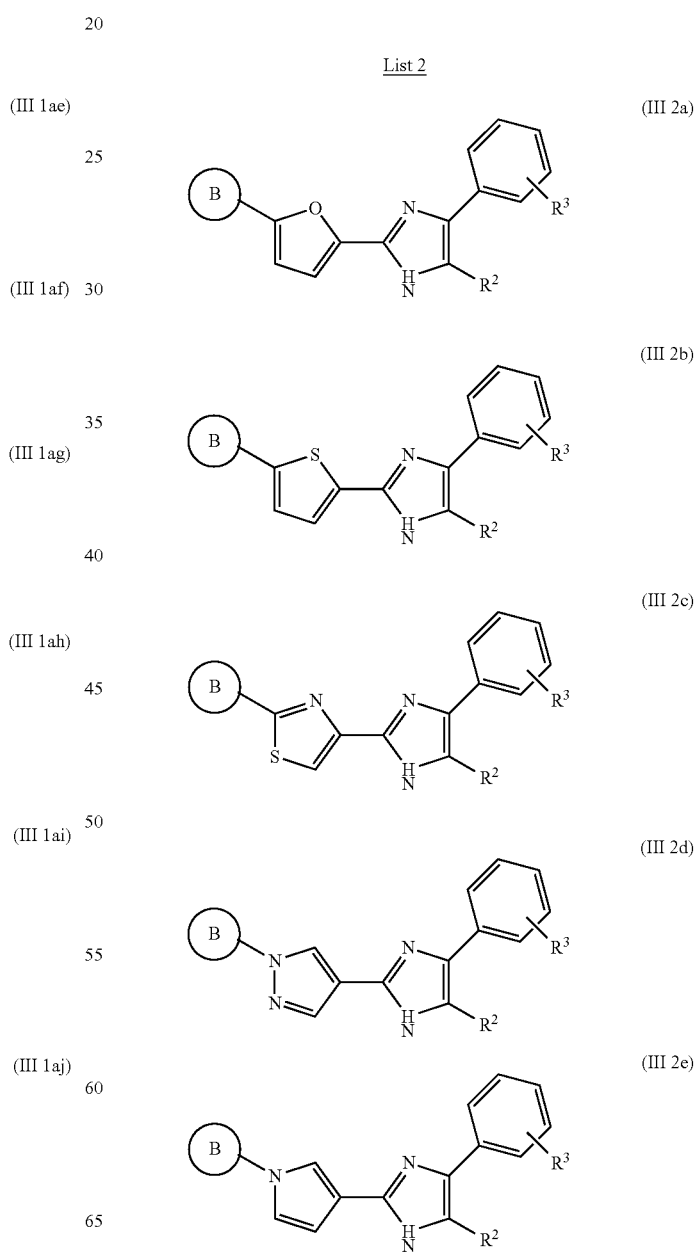

In the formulae of List 1a, $R^1$, $R^2$ and B are as defined for moieties of formula (I) and the rings which correspond to group A of formula (I) (i.e. the furan, thiophene, pyrrole, etc rings) may be optionally substituted, preferably by one or more substituents independently selected from —$CH_3$, $C_{2to4}$alkyl, halogen, —$OCH_3$, and —$OC_{2to4}$alkyl, more preferably by one or more substituents independently selected from —$CH_3$, $C_{2to4}$alkyl, and halogen, most preferably by one or more —$CH_3$ substituents.

In the moieties of Lists 1 and 1a, one of $R^1$ and $R^2$ is preferably benzyl optionally substituted on the phenyl ring, or heteroaryl, or aryl, each of said benzyl optionally substituted on the phenyl ring, or heteroaryl, or aryl being as defined for formula (I) above.

In some embodiments of the invention, the moiety of formula (I) is selected from the formulae comprised in List 2.

-continued

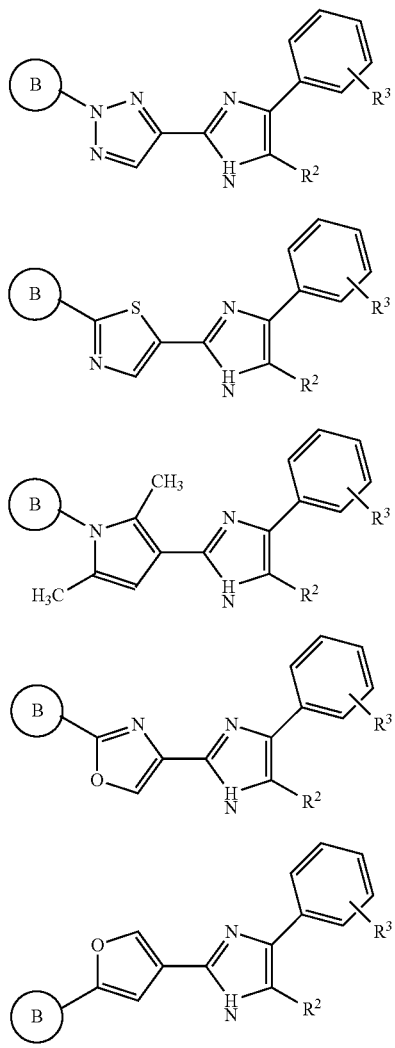

(III 2f)
(III 2g)
(III 2h)
(III 2i)
(III 2j)

In the formulae of List 2, B is as defined for moieties of formula (I) and R² is selected from the group consisting of H, —CH₃, C$_{2 to 6}$alkyl, C$_{3 to 6}$cycloalkyl, halogen, and —(CH₂)$_n$N(CH₃)₂ where n is an integer from 1 to 3, preferably selected from the group consisting of H, —CH₃, n-propyl, n-butyl, iso-butyl, —CH₂N(CH₃)₂, and halogen where halogen is preferably Cl, and more preferably selected from the group consisting of H, —CH₃, —CH₂N(CH₃)₂, and halogen where halogen is preferably Cl, R³ represents optional substituents on an otherwise unsubstituted phenyl ring and is preferably one or more substituents independently selected from the group consisting of —CH₃, C$_{2 to 4}$alkyl, halogen, hydroxyl, —OCH₃, —OC$_{2 to 4}$alkyl, ethynyl, —OCF₃, and —CF₃, more preferably one or more substituents independently selected from the group consisting of —CH₃, —CH₂CH₃, —OH, —CF₃, —OCF₃, ethynyl, and halogen, wherein halogen is preferably F or Cl or Br, most preferably independently selected from one or more substituents selected the group consisting of —CH₃, —CH₂CH₃, —CF₃, —OCF₃, ethynyl, and halogen, wherein halogen is preferably F or Cl or Br, and the rings which correspond to group A of formula (I) (e.g. the furan, thiophene, pyrrole rings) may be optionally substituted, preferably by one or more substituents independently selected from —CH₃, C$_{2 to 4}$alkyl, halogen, —OCH₃, and —OC$_{2 to 4}$alkyl, more preferably by one or more substituents independently selected from —CH₃, C$_{2 to 4}$alkyl, and halogen, most preferably by one or more —CH₃ substituents.

In some embodiments of the invention, the moiety of formula (I) is selected from the formulae comprised in List 3.

List 3

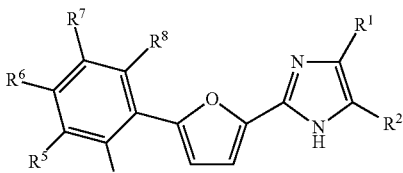

(III 3a)

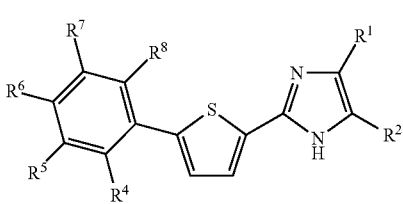

(III 3b)

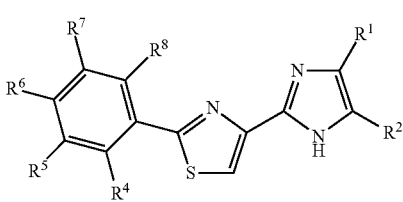

(III 3c)

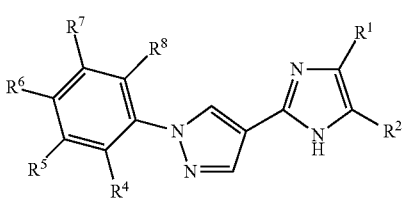

(III 3d)

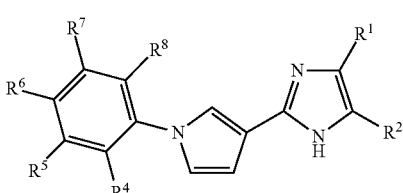

(III 3e)

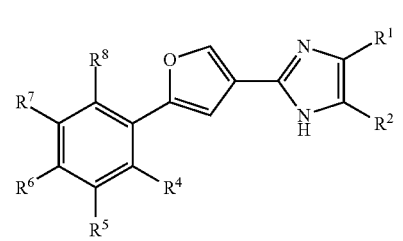

(III 3f)

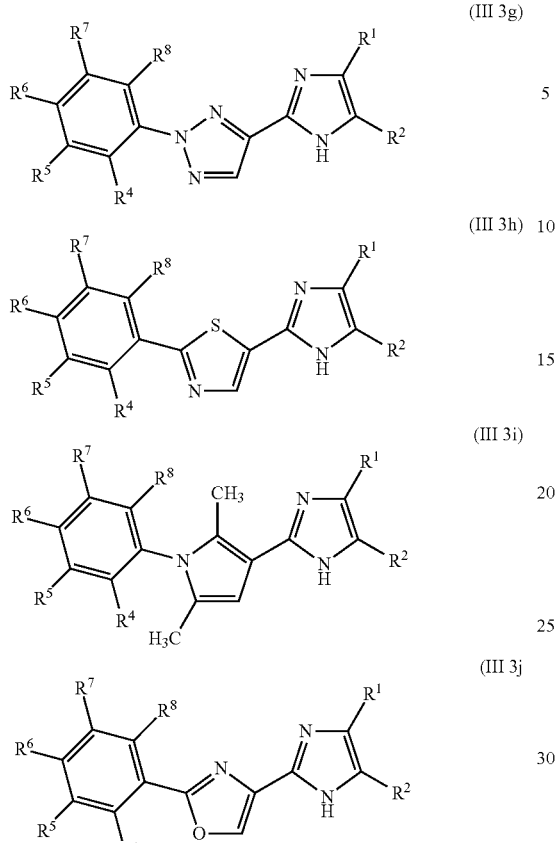

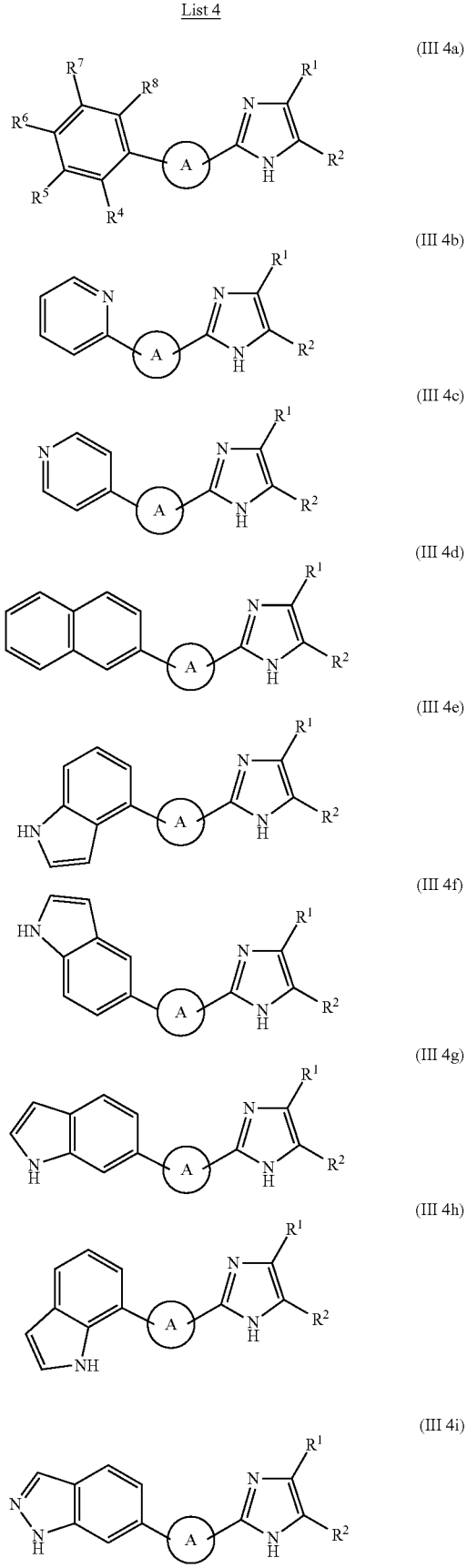

List 4

In the formulae of List 3, $R^1$ and $R^2$ are as defined for formula (I) and $R^4$ to $R^8$ are independently selected from the group consisting of H, —$CH_3$, $C_{2to4}$alkyl, halogen, hydroxyl, —$OCH_3$, —$OC_{2to4}$alkyl, —$CF_3$, —$OCF_3$, —$NH_2$, —$CH_2NH_2$, —$N(CH_3)_2$, —$NO_2$, —$CH_2OH$, —$CO_2CH_3$, —$CO_2C_{2to4}$alkyl, —$CO_2H$, —N(alkyl)$_2$ where the two alkyl groups are independently selected from —$CH_3$ or $C_{2to4}$alkyl, —NH(alkyl) where the alkyl group is selected from —$CH_3$ or $C_{2to4}$alkyl, 4-morpholinyl, 1-piperidinyl, 4H-piperazinyl, 4-$C_{1to4}$alkyl-piperazinyl, and 4-$C_{3to6}$cycloalkyl-piperazinyl, preferably independently selected from the group consisting of H, —$CH_3$, $C_{2to4}$alkyl, iso-propyl, tert-butyl, halogen wherein halogen is preferably F or Cl or Br, hydroxyl, —$OCH_3$, —$CF_3$, —$OCF_3$, —$N(CH_3)_2$, —$NO_2$, and 4-methylpiperazinyl, more preferably independently selected from the group consisting of H, —$CH_3$, —$CH_2CH_3$, iso-propyl, —$N(CH_3)_2$, halogen wherein halogen is preferably F or Cl or Br, —$OCH_3$, —$CF_3$, and —$OCF_3$, and the rings which correspond to group A of formula (I) (e.g. the furan, thiophene, pyrrole etc rings) may be optionally substituted, preferably by one or more substituents independently selected from —$CH_3$, $C_{2to4}$alkyl, halogen, —$OCH_3$, and —$OC_{2to4}$alkyl, more preferably by one or more substituents independently selected from —$CH_3$, $C_{2to4}$alkyl or halogen, most preferably by one or more —$CH_3$ substituents. In a preferred embodiment of the invention, in the formulae of List 3 at least two, preferably three or four, of $R^4$, $R^5$, $R^6$, $R^7$ and $R^8$ are H.

In some embodiments of the invention, the moiety of formula (I) is selected from the formulae comprised in List 4.

In the formulae of List 4, $R^1$, $R^2$ and A are as defined for formula (I), $R^4$ to $R^8$ are independently selected from the group consisting of H, —$CH_3$, $C_{2to4}$alkyl, halogen, hydroxyl, —$OCH_3$, —$OC_{2to4}$alkyl, —$CF_3$, —$OCF_3$, —$NH_2$, —$CH_2NH_2$, —$N(CH_3)_2$, —$NO_2$, —$CH_2OH$, —$CO_2CH_3$, —$CO_2C_{2to4}$alkyl, —$CO_2H$, —N(alkyl)$_2$ where the two alkyl groups are independently selected from —$CH_3$ or $C_{2to4}$alkyl, —NH(alkyl) where the alkyl group is selected from —$CH_3$ or $C_{2to4}$alkyl, 4-morpholinyl, 1-piperidinyl, 4H-piperazinyl, 4-$C_{1to4}$alkyl-piperazinyl, and 4-$C_{3to6}$cycloalkyl-piperazinyl, preferably independently selected from the group consisting of H, —$CH_3$, $C_{2to4}$alkyl, iso-propyl, tert-butyl, halogen wherein halogen is preferably F or Cl or Br, hydroxyl, —$OCH_3$, —$CF_3$, —$OCF_3$, —$N(CH_3)_2$, —$NO_2$, and 4-methylpiperazinyl, more preferably independently selected from the group consisting of H, —$CH_3$, —$CH_2CH_3$, iso-propyl, —$N(CH_3)_2$, halogen wherein halogen is preferably F or Cl or Br, —$OCH_3$, —$CF_3$ and —$OCF_3$, and all moieties corresponding to group B of formula (I) which are not unsubstituted- or substituted-phenyl may be optionally substituted, and when substituted then preferably with one or more substituents, preferably with one or two substituents, independently selected from the group consisting of —$CH_3$, $C_{2to4}$alkyl, halogen, hydroxyl, —$OCH_3$, —$OC_{2to4}$alkyl, —$CF_3$, —$OCF_3$, —$CO_2CH_3$, —$CO_2C_{2to4}$alkyl, and —$CO_2H$, more preferably independently selected from the group consisting of halogen, —$CH_3$, —$CF_3$, and —$OCF_3$. In a preferred embodiment of the invention in which B corresponds to a phenyl ring in the formulae of List 4, at least two, preferably three or four, of $R^4$, $R^5$, $R^6$, $R^7$ and $R^8$ are H.

In some embodiments of the invention, the moiety of formula (I) is selected from the formulae comprised in List 5.

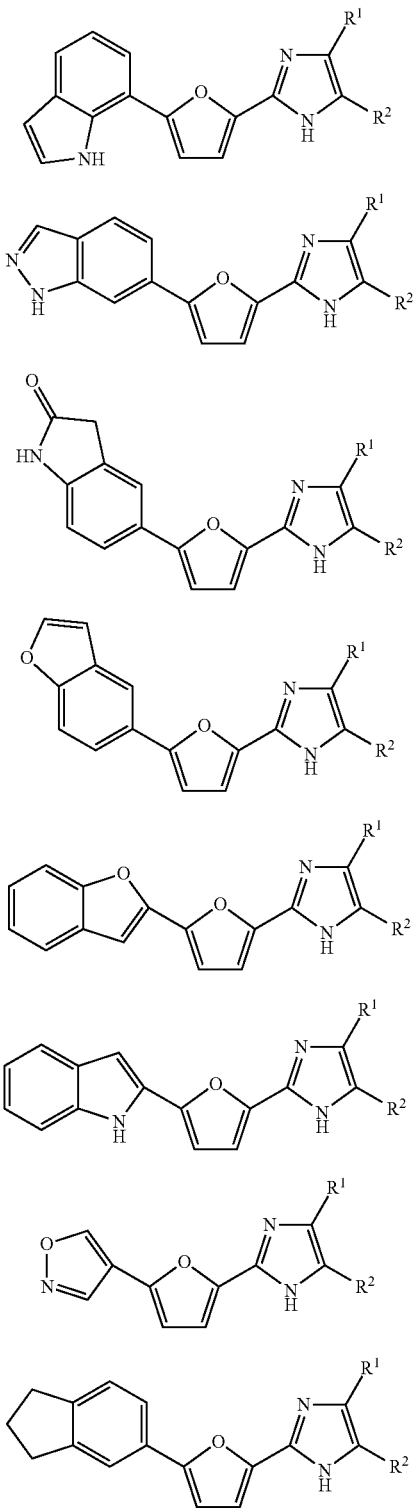

(III 5h)
(III 5i)
(III 5j)
(III 5k)
(III 5l)
(III 5m)
(III 5n)
(III 5o)

In the formulae of List 5, $R^1$ and $R^2$ are as defined for formula (I), $R^4$ to $R^8$ are independently selected from the group consisting of H, —$CH_3$, $C_{2to4}$alkyl, halogen, hydroxyl, —$OCH_3$, —$OC_{2to4}$alkyl, —$CF_3$, —$OCF_3$, —$NH_2$, —$CH_2NH_2$, —$N(CH_3)_2$, —$NO_2$, —$CH_2OH$, —$CO_2CH_3$, —$CO_2C_{2to4}$alkyl, —$CO_2H$, —$N(alkyl)_2$ where the two alkyl groups are independently selected from —$CH_3$ or $C_{2to4}$alkyl, —NH(alkyl) where the alkyl group is selected from —$CH_3$ or $C_{2to4}$alkyl, 4-morpholinyl, 1-piperidinyl, 4H-piperazinyl, 4-$C_{1to4}$alkyl-piperazinyl, and 4-$C_{3to6}$cycloalkyl-piperazinyl, preferably independently selected from the group consisting of H, —$CH_3$, $C_{2to4}$alkyl, iso-propyl, tert-butyl, halogen wherein halogen is preferably F or Cl or Br, hydroxyl, —$OCH_3$, —$CF_3$, —$OCF_3$, —$N(CH_3)_2$, —$NO_2$, and 4-methylpiperazinyl, more preferably independently selected from the group consisting of H, —$CH_3$, —$CH_2CH_3$, iso-propyl, —$N(CH_3)_2$, halogen wherein halogen is preferably F or Cl or Br, —$OCH_3$, —$CF_3$, and —$OCF_3$, and all moieties corresponding to group B of formula (I) which are not unsubstituted- or substituted-phenyl may be optionally substituted, and when substituted then preferably with one or more substituents, preferably with one or two substituents, independently selected from the group consisting of —$CH_3$, $C_{2to4}$alkyl, halogen, hydroxyl, —$OCH_3$, —$OC_{2to4}$alkyl, —$CF_3$, —$OCF_3$, —$CO_2CH_3$, —$CO_2C_{2to4}$alkyl, and —$CO_2H$, more preferably independently selected from the group consisting of halogen, —$CH_3$, —$CF_3$, and —$OCF_3$, and all moieties corresponding to group A of formula (I) (e.g. the furan, thiophene, pyrrole rings) may be optionally substituted, preferably by one or more substituents independently selected from —$CH_3$, $C_{2to4}$alkyl, halogen, —$OCH_3$, and —$OC_{2to4}$alkyl, more preferably by one or more substituents independently selected from —$CH_3$, $C_{2to4}$alkyl, and halogen, most preferably by one or more —$CH_3$ substituents. In a preferred embodiment of the invention in which B corresponds to a phenyl ring in the formulae of List 5, at least two, preferably three or four, of $R^4$, $R^5$, $R^6$, $R^7$ and $R^8$ are H.

In some embodiments of the invention, the moiety of formula (I) is selected from the formulae comprised in List 6.

List 6

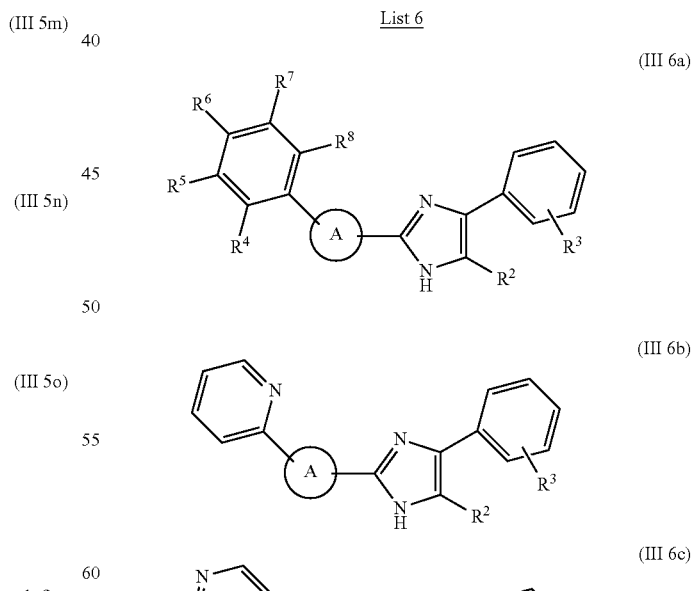

(III 6a)
(III 6b)
(III 6c)

-continued

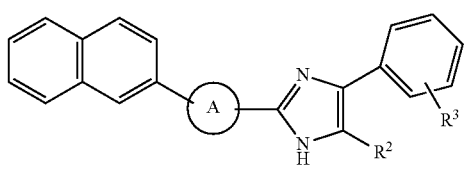
(III 6d)

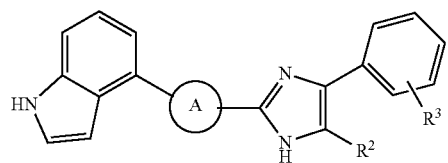
(III 6e)

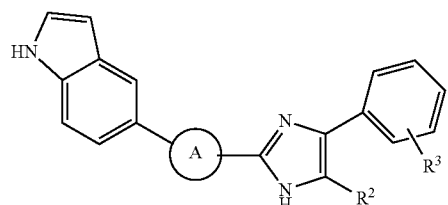
(III 6f)

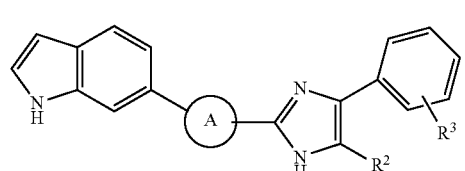
(III 6g)

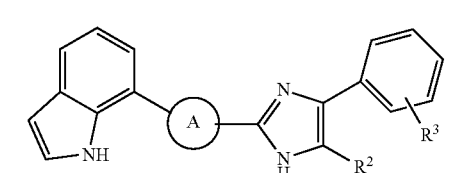
(III 6h)

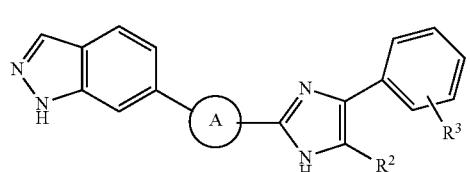
(III 6i)

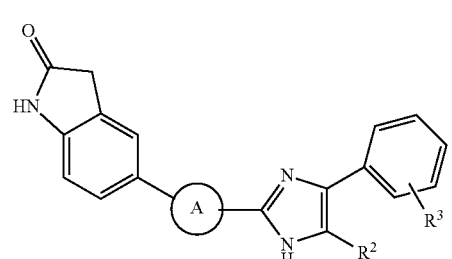
(III 6j)

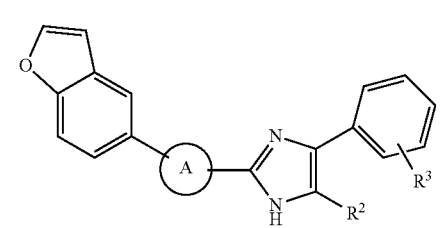
(III 6k)

-continued

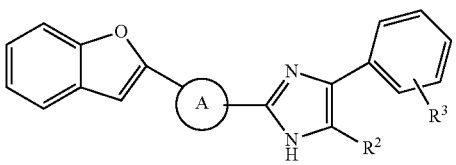
(III 6l)

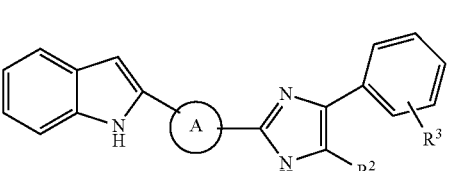
(III 6m)

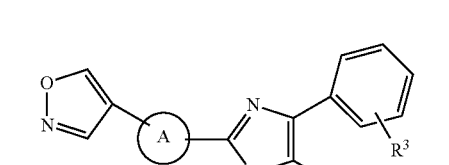
(III 6n)

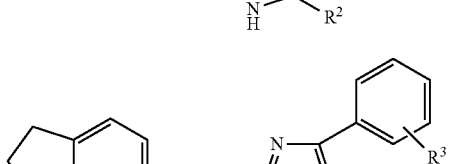
(III 6o)

In the formulae of List 6, A is as defined for moieties of formula (I), $R^2$ is selected from the group consisting of H, —$CH_3$, $C_{2 to 6}$alkyl, $C_{3 to 6}$cycloalkyl, halogen, —$(CH_2)_nN(CH_3)_2$ where n is an integer from 1 to 3, preferably selected from the group consisting of H, —$CH_3$, n-propyl, n-butyl, iso-butyl, —$CH_2N(CH_3)_2$, and halogen where halogen is preferably Cl, more preferably selected from the group consisting of H, —$CH_3$, —$CH_2N(CH_3)_2$, and halogen where halogen is preferably Cl, $R^4$ to $R^8$ are independently selected from the group consisting of H, —$CH_3$, $C_{2 to 4}$alkyl, halogen, hydroxyl, —$OCH_3$, —$OC_{2 to 4}$alkyl, —$CF_3$, —$OCF_3$, —$NH_2$, —$CH_2NH_2$, —$N(CH_3)_2$, —$NO_2$, —$CH_2OH$, —$CO_2CH_3$, —$CO_2C_{2 to 4}$alkyl, —$CO_2H$, —N(alkyl)$_2$ where the two alkyl groups are independently selected from —$CH_3$ or $C_{2 to 4}$alkyl, —NH(alkyl) where the alkyl group is selected from —$CH_3$ or $C_{2 to 4}$alkyl, 4-morpholinyl, 1-piperidinyl, 4H-piperazinyl, 4-$C_{1 to 4}$alkyl-piperazinyl, and 4-$C_{3 to 6}$cycloalkyl-piperazinyl, preferably independently selected from the group consisting of H, —$CH_3$, $C_{2 to 4}$alkyl, iso-propyl, tert-butyl, halogen wherein halogen is preferably F or Cl or Br, hydroxyl, —$OCH_3$, —$CF_3$, —$OCF_3$, —$N(CH_3)_2$, —$NO_2$, and 4-methylpiperazinyl, more preferably independently selected from the group consisting of H, —$CH_3$, —$CH_2CH_3$, iso-propyl, —$N(CH_3)_2$, halogen wherein halogen is preferably F or Cl or Br, —$OCH_3$, —$CF_3$, and —$OCF_3$, and all moieties corresponding to group B of formula (I) which are not unsubstituted- or substituted-phenyl may be optionally substituted, and when substituted then preferably with one or more, preferably with one or two, substituents independently selected from the group consisting of —$CH_3$, $C_{2 to 4}$alkyl, halogen, hydroxyl, —$OCH_3$, —$OC_{2 to 4}$alkyl, —$CF_3$, —$OCF_3$, —$CO_2CH_3$, —$CO_2C_{2 to 4}$alkyl, and —$CO_2H$, more preferably independently selected from the group consisting of halogen, —CH₃, —CF₃, and —OCF₃, and R³ represents optional substituents on an otherwise unsubstituted phenyl ring and is preferably one or more substituents independently selected from the group consisting of —CH₃, $C_{2to4}$alkyl, halogen, hydroxyl, —OCH₃, —OC$_{2to4}$alkyl, ethynyl, —OCF₃, and —CF₃, more preferably one or more substituents independently selected from the group consisting of —CH₃, —CH₂CH₃, —OH, —CF₃, —OCF₃, ethynyl, and halogen, wherein halogen is preferably F or Cl or Br, most preferably independently selected from one or more substituents selected the group consisting of —CH₃, —CH₂CH₃, —CF₃, —OCF₃, ethynyl, and halogen, wherein halogen is preferably F or Cl or Br. In a preferred embodiment of the invention in which B corresponds to a phenyl ring in the formulae of List 6, at least two, preferably three or four, of R⁴, R⁵, R⁶, R⁷ and R⁸ are H.

In some embodiments, the moiety of formula (I) is represented by the formula (IV)

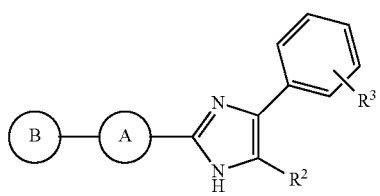

(IV)

wherein A and B are as defined for formula (I), R² is selected from the group consisting of H, —CH₃, $C_{2to6}$alkyl, $C_{3to6}$cycloalkyl, halogen, and —(CH₂)$_n$N(CH₃)₂ where n is an integer from 1 to 3, preferably selected from the group consisting of H, —CH₃, n-propyl, n-butyl, iso-butyl, —CH₂N(CH₃)₂, and halogen where halogen is preferably Cl, more preferably selected from the group consisting of H, —CH₃, —CH₂N(CH₃)₂, and halogen where halogen is preferably Cl, and R³ represents optional substituents on an otherwise unsubstituted phenyl ring and is preferably one or more substituents independently selected from the group consisting of —CH₃, $C_{2to4}$alkyl, halogen, hydroxyl, —OCH₃, —OC$_{2to4}$alkyl, ethynyl, —OCF₃, and —CF₃, more preferably one or more substituents independently selected from the group consisting of —CH₃, —CH₂CH₃, —OH, —CF₃, —OCF₃, ethynyl, and halogen, wherein halogen is preferably F or Cl or Br, most preferably independently selected from one or more substituents selected the group consisting of —CH₃, —CH₂CH₃, —CF₃, —OCF₃, ethynyl, and halogen, wherein halogen is preferably F or Cl or Br.

In some embodiments, in the moiety represented by the formula (IV) R² is —CH₃. In some embodiments, in the moiety represented by the formula (IV) R² is H. In some embodiments, in the moiety represented by the formula (IV) R² is —CH₂N(CH₃)₂. In some embodiments, in the moiety represented by the formula (IV) R² is Cl.

In some embodiments of the invention, the compounds comprising the moiety of formula (I) are represented by the formula (V)

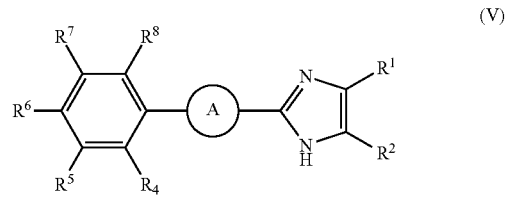

(V)

wherein R¹, R² and A are as defined for formula (I), and R⁴ to R⁸ are independently selected from the group consisting of H, —CH₃, $C_{2to4}$alkyl, halogen, hydroxyl, —OCH₃, —OC$_{2to4}$alkyl, —CF₃, —OCF₃, —NH₂, —CH₂NH₂, —N(CH₃)₂, —NO₂, —CH₂OH, —CO₂CH₃, —CO₂C$_{2to4}$alkyl, —CO₂H, —N(alkyl)₂ where the two alkyl groups are independently selected from —CH₃ or $C_{2to4}$alkyl, —NH(alkyl) where the alkyl group is selected from —CH₃ or $C_{2to4}$alkyl, 4-morpholinyl, 1-piperidinyl, 4H-piperazinyl, 4-$C_{1to4}$alkyl-piperazinyl, and 4-$C_{3to6}$cycloalkyl-piperazinyl, preferably independently selected from the group consisting of H, —CH₃, $C_{2to4}$alkyl, iso-propyl, tert-butyl, halogen wherein halogen is preferably F or Cl or Br, hydroxyl, —OCH₃, —CF₃, —OCF₃, —N(CH₃)₂, —NO₂, and 4-methylpiperazinyl, more preferably independently selected from the group consisting of H, —CH₃, —CH₂CH₃, iso-propyl, —N(CH₃)₂, halogen wherein halogen is preferably F or Cl or Br, —OCH₃, —CF₃ and —OCF₃. In a preferred embodiment of the invention at least two, preferably three or four, of R⁴, R⁵, R⁶, R⁷ and R⁸ are H.

In the compounds comprising the moiety of formulae (I), (IV) and (V) of the invention, group A is preferably a moiety selected from the group containing

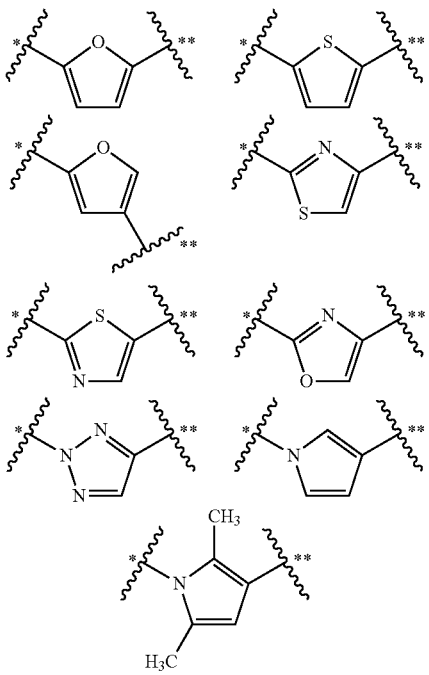

wherein * and ** are as defined above.

In some embodiments, in the compounds comprising the moiety of formulae (I), (IV) and (V) of the invention, group A is a moiety selected from the group containing

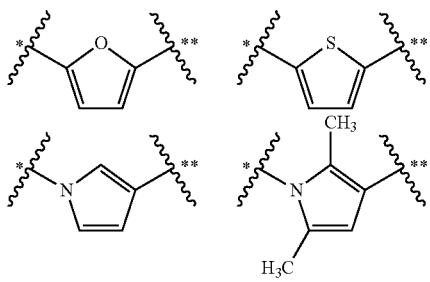

wherein * and ** are as defined above.

In some embodiments, in the compounds comprising the moiety of formulae (I), (IV) and (V) of the invention, group A is preferably

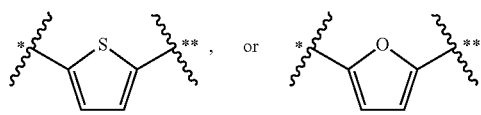 [SMILES: *c1ccc(*)s1 ; *c1ccc(*)o1]

wherein * and ** are as defined above.

In the compounds comprising the moiety of formulae (I) and (V) of the invention, $R^1$ and $R^2$ are preferably independently selected from the group consisting of H, —$CH_3$, n-propyl, —$CH_2N(CH_3)_2$, halogen where halogen is preferably Cl, and phenyl optionally substituted with one or more substituents independently selected from the group consisting of —$CH_3$, —$CH_2CH_3$, —$CF_3$, —$OCF_3$, ethynyl, halogen where halogen is preferably F or Cl or Br, and 4-halobenzyl where 4-halobenzyl is preferably 4-bromobenzyl, with the provisos that:

when Y is N, $R^2$ represents a lone pair of electrons belonging to the N atom; and at least one of $R^1$ or $R^2$ possesses 3 or more carbon atoms; and it is preferred that when $R^1$ is unsubstituted- or substituted-phenyl, or 4-halobenzyl, then when Y is C, $R^2$ is H, —$CH_3$, —$CH_2N(CH_3)_2$, or halogen where halogen is preferably Cl; and it is preferred that when $R^2$ is unsubstituted or substituted-phenyl, or 4-halobenzyl, $R^1$ is H, —$CH_3$, —$CH_2N(CH_3)_2$, or halogen where halogen is preferably Cl; and it is preferred that when $R^1$ is H, $R^2$ is not H and that when $R^2$ is H, $R^1$ is not H; and it is further preferred that when $R^1$ is —$CH_3$, $R^2$ is not H and when $R^2$ is —$CH_3$, $R^1$ is not H.

In the compounds of the present invention, when one of $R^1$ or $R^2$ is halogen they are preferably Cl.

In a further embodiment of the invention, the compounds comprising the moiety of formulae (I) and (V) are represented by the formula (VI)

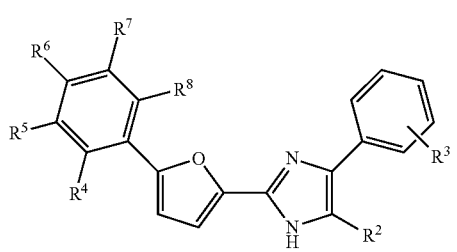

In another embodiment of the invention, the compounds comprising the moiety of formulae (I) and (V) are represented by the formula (VII)

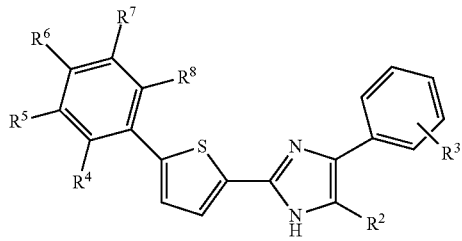

In still another embodiment of the invention, the compounds comprising the moiety of formulae (I) and (V) are represented by the formula (VIII)

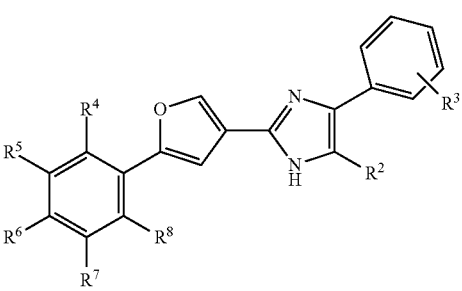

In another embodiment of the invention, the compounds comprising the moiety of formulae (I) and (V) are represented by the formula (IX)

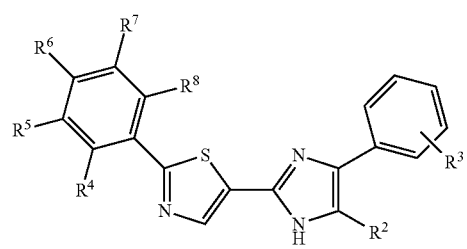

In another embodiment of the invention, the compounds comprising the moiety of formulae (I) and (V) are represented by the formula (X)

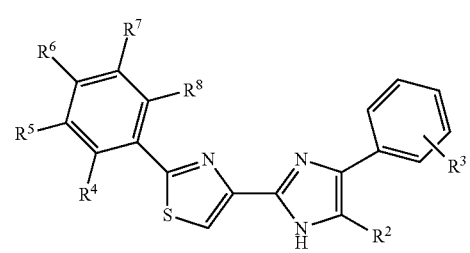

In another embodiment of the invention, the compounds comprising the moiety of formulae (I) and (V) are represented by the formula (XI)

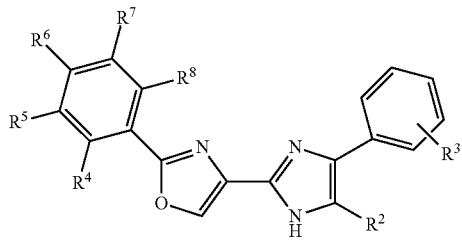

(XI)

In another embodiment of the invention, the compounds comprising the moiety of formulae (I) and (V) are represented by the formula (XII)

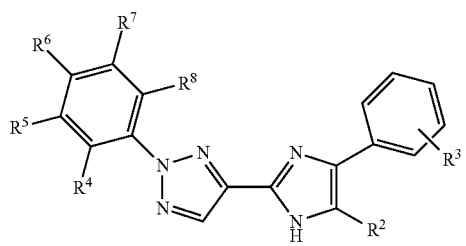

(XII)

In another embodiment of the invention, the compounds comprising the moiety of formulae (I) and (V) are represented by the formula (XIII)

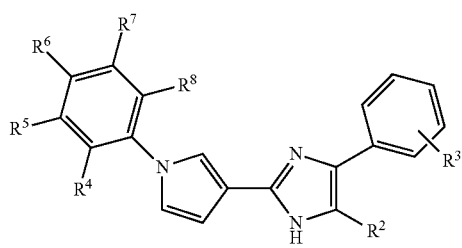

(XIII)

In another embodiment of the invention, the compounds comprising the moiety of formulae (I) and (V) are represented by the formula (XIV)

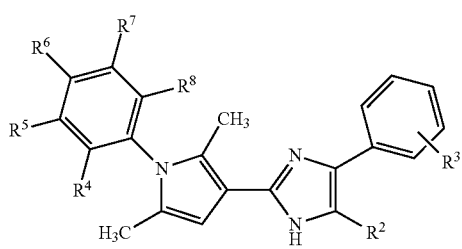

(XIV)

In the moieties represented by the formulae (VI) to (XIV), $R^2$ is selected from the group consisting of H, —CH$_3$, $C_{2to6}$alkyl, $C_{3to6}$cycloalkyl, halogen, and —(CH$_2$)$_n$N(CH$_3$)$_2$ where n is an integer from 1 to 3, preferably selected from the group consisting of H, —CH$_3$, n-propyl, n-butyl, iso-butyl, —CH$_2$N(CH$_3$)$_2$, and halogen where halogen is preferably Cl, more preferably selected from the group consisting of H, —CH$_3$, —CH$_2$N(CH$_3$)$_2$, and halogen where halogen is preferably Cl, $R^3$ represents optional substituents on an otherwise unsubstituted phenyl ring and is preferably one or more substituents independently selected from the group consisting of —CH$_3$, $C_{2to4}$alkyl, halogen, hydroxyl, —OCH$_3$, —OC$_{2to4}$alkyl, ethynyl, —OCF$_3$, and —CF$_3$, more preferably one or more substituents independently selected from the group consisting of —CH$_3$, —CH$_2$CH$_3$, —OH, —CF$_3$, —OCF$_3$, ethynyl, and halogen, wherein halogen is preferably F or Cl or Br, most preferably independently selected from one or more substituents selected the group consisting of —CH$_3$, —CH$_2$CH$_3$, —CF$_3$, —OCF$_3$, ethynyl, and halogen, wherein halogen is preferably F or Cl or Br, and $R^4$ to $R^8$ are independently selected from the group consisting of H, —CH$_3$, $C_{2to4}$alkyl, halogen, hydroxyl, —OCH$_3$, —OC$_{2to4}$alkyl, —CF$_3$, —OCF$_3$, —NH$_2$, —CH$_2$NH$_2$, —N(CH$_3$)$_2$, —NO$_2$, —CH$_2$OH, —CO$_2$CH$_3$, —CO$_2$C$_{2to4}$alkyl, —CO$_2$H, —N(alkyl)$_2$ where the two alkyl groups are independently selected from —CH$_3$ or $C_{2to4}$alkyl, —NH(alkyl) where the alkyl group is selected from —CH$_3$ or $C_{2to4}$alkyl, 4-morpholinyl, 1-piperidinyl, 4H-piperazinyl, 4-$C_{1to4}$alkyl-piperazinyl, and 4-$C_{3to6}$cycloalkyl-piperazinyl, preferably independently selected from the group consisting of H, —CH$_3$, $C_{2to4}$alkyl, iso-propyl, tert-butyl, halogen wherein halogen is preferably F or Cl or Br, hydroxyl, —OCH$_3$, —CF$_3$, —OCF$_3$, —N(CH$_3$)$_2$, —NO$_2$, 4-methylpiperazinyl, more preferably independently selected from the group consisting of H, —CH$_3$, —CH$_2$CH$_3$, iso-propyl, —N(CH$_3$)$_2$, halogen wherein halogen is preferably F or Cl or Br, —OCH$_3$, —CF$_3$, and —OCF$_3$, In a preferred embodiment of the invention at least two, preferably three or, of $R^4$, $R^5$, $R^6$, $R^7$ and $R^8$ are H.

In some embodiments of the invention, $R^1$ and $R^2$ are independently selected from the group consisting of H, —CH$_3$, —CH$_2$N(CH$_3$)$_2$, 4-bromobenzyl, halogen where halogen is preferably Cl, and phenyl, where phenyl is optionally substituted with one or more substituents independently selected from —CH$_3$, —CH$_2$CH$_3$, —CF$_3$, —OCF$_3$, ethynyl, and halogen, wherein halogen is preferably F or Cl or Br.

In some embodiments of the invention, $R^4$ to $R^8$ are independently selected from the group consisting of H, —CH$_3$, —CH$_2$CH$_3$, iso-propyl, —N(CH$_3$)$_2$, halogen wherein halogen is preferably F or Cl or Br, —OCH$_3$, —CF$_3$, and —OCF$_3$.

In a preferred embodiment of the invention in which B corresponds to a phenyl ring, at least two, preferably three or four, of $R^4$, $R^5$, $R^6$, $R^7$ and $R^8$ are H.

In some embodiments of the invention, $R^3$ represents optional substituents on an otherwise unsubstituted phenyl ring and is one or more substituents independently selected from the group consisting of —CH$_3$, —CH$_2$CH$_3$, —CF$_3$, —OCF$_3$, ethynyl, and halogen, wherein halogen is preferably F or Cl or Br.

In some embodiments of the invention, $R^1$ and $R^2$ are independently selected from the group consisting of H, —CH$_3$, —CH$_2$N(CH$_3$)$_2$, 4-bromobenzyl, halogen where halogen is preferably Cl, and phenyl, where phenyl is optionally substituted with one or more substituents independently selected from —CH$_3$, —CH$_2$CH$_3$, —CF$_3$, —OCF$_3$, ethynyl, and halogen, wherein halogen is preferably F or Cl or Br, and $R^4$ to $R^8$ are independently selected from the group consisting of H, —$CH_3$, —$CH_2CH_3$, iso-propyl, —$N(CH_3)_2$, halogen wherein halogen is preferably F or Cl or Br, —$OCH_3$, —$CF_3$, and —$OCF_3$.

In some embodiments of the present invention, $R^4$ to $R^8$ are independently selected from the group consisting of H, —$CH_3$, —$CH_2CH_3$, iso-propyl, —$N(CH_3)_2$, halogen wherein halogen is preferably F or Cl or Br, —$OCH_3$, —$CF_3$ and —$OCF_3$, and $R^3$ represents optional substituents on an otherwise unsubstituted phenyl ring and is one or more substituents independently selected from the group consisting of —$CH_3$, —$CH_2CH_3$, —$CF_3$, —$OCF_3$, ethynyl, and halogen wherein halogen is preferably F or Cl or Br.

In any one of the moieties represented by the formulae (IV) or (VI) to (XIV), $R^2$ may be a hydrogen atom. In any one of the moieties represented by the formulae (IV) or (VI) to (XIV), $R^2$ may be a halogen atom, preferably a chlorine atom. In the moieties represented by the formulae (IV) and (VI) to (VII), $R^2$ may be —$CH_2N(CH_3)_2$. In the moieties represented by the formulae (IV) and (VI) to (XIV), $R^2$ is preferably —$CH_3$.

In any one of the moieties represented by the formulae (VI) to (XIV), $R^4$ may be as defined for formulae (V). $R^4$ may also be selected from the group consisting of —$CF_3$, —$OCF_3$, —$CH_3$, —$N(CH_3)_2$, and halogen. In some embodiments, $R^4$ is —$CF_3$. In other embodiments, $R^4$ is —$OCF_3$. In other embodiments, $R^4$ is —$CH_3$. In other embodiments, $R^4$ is —$N(CH_3)_2$. In other embodiments, $R^4$ is halogen.

In some embodiments, in the moieties represented by the formulae (V) or (VI) to (XIV) $R^4$ is —$CF_3$ and each of $R^5$ to $R^8$ is H. In some embodiments, in the moieties represented by the formulae (V) or (VI) to (XIV) $R^4$ is —$CF_3$ and two of $R^5$ to $R^8$ are H. In some embodiments, in the moieties represented by the formulae (V) or (VI) to (XIV) $R^4$ is —$CF_3$ and three of $R^5$ to $R^8$ are H. In some embodiments represented by the formulae (VI) to (XIV), $R^4$ is —$CF_3$, and $R^2$ is —$CH_3$. In other embodiments represented by the formulae (VI) to (XIV), $R^4$ is —$CF_3$, and $R^2$ is a hydrogen atom. In other embodiments represented by the formulae (VI) to (XIV), $R^4$ is —$CF_3$, and $R^2$ is halogen. In some embodiments represented by the formulae (VI) to (XIV), $R^4$ is —$CF_3$, each of $R^5$ to $R^8$ is H and $R^2$ is —$CH_3$. In some embodiments represented by the formulae (VI) to (XIV), $R^4$ is —$CF_3$, two of $R^5$ to $R^8$ are H and $R^2$ is —$CH_3$. In some embodiments represented by the formulae (VI) to (XIV), $R^4$ is —$CF_3$, three of $R^5$ to $R^8$ are H and $R^2$ is —$CH_3$. In other embodiments represented by the formulae (VI) to (XIV), $R^4$ is —$CF_3$, each of $R^5$ to $R^8$ is H and $R^2$ is a hydrogen atom. In some embodiments represented by the formulae (VI) to (XIV), $R^4$ is —$CF_3$, two of $R^5$ to $R^8$ are H and $R^2$ is a hydrogen atom. In some embodiments represented by the formulae (VI) to (XIV), $R^4$ is —$CF_3$, three of $R^5$ to $R^8$ are H and $R^2$ is a hydrogen atom. In other embodiments represented by the formulae (VI) to (XIV), $R^4$ is —$CF_3$, each of $R^5$ to $R^8$ is H and $R^2$ is halogen. In some embodiments represented by the formulae (VI) to (XIV), $R^4$ is —$CF_3$, two of $R^5$ to $R^8$ are H and $R^2$ is halogen. In some embodiments represented by the formulae (VI) to (XIV), $R^4$ is —$CF_3$, three of $R^5$ to $R^8$ are H and $R^2$ is halogen. In the formulae (VI) to (XIV), when $R^4$ is —$CF_3$, and $R^2$ is halogen, $R^2$ is preferably Cl.

In some embodiments, in the moieties represented by the formulae (V) or (VI) to (XIV) $R^4$ is —$OCF_3$ and each of $R^5$ to $R^8$ is H. In some embodiments, in the moieties represented by the formulae (V) or (VI) to (XIV) $R^4$ is —$OCF_3$ and two of $R^5$ to $R^8$ are H. In some embodiments, in the moieties represented by the formulae (V) or (VI) to (XIV) $R^4$ is —$OCF_3$ and three of $R^5$ to $R^8$ are H. In some embodiments represented by the formulae (VI) to (XIV), $R^4$ is —$OCF_3$, and $R^2$ is —$CH_3$. In other embodiments represented by the formulae (VI) to (XIV), $R^4$ is —$OCF_3$, and $R^2$ is a hydrogen atom. In other embodiments represented by the formulae (VI) to (XIV), $R^4$ is —$OCF_3$, and $R^2$ is halogen. In some embodiments represented by the formulae (VI) to (XIV), $R^4$ is —$OCF_3$, each of $R^5$ to $R^8$ is H and $R^2$ is —$CH_3$. In some embodiments represented by the formulae (VI) to (XIV), $R^4$ is —$OCF_3$, two of $R^5$ to $R^8$ are H and $R^2$ is —$CH_3$. In some embodiments represented by the formulae (VI) to (XIV), $R^4$ is —$OCF_3$, three of $R^5$ to $R^8$ are H and $R^2$ is —$CH_3$. In other embodiments represented by the formulae (VI) to (XIV), $R^4$ is —$OCF_3$, each of $R^5$ to $R^8$ is H and $R^2$ is a hydrogen atom. In some embodiments represented by the formulae (VI) to (XIV), $R^4$ is —$OCF_3$, two of $R^5$ to $R^8$ are H and $R^2$ is a hydrogen atom. In some embodiments represented by the formulae (VI) to (XIV), $R^4$ is —$OCF_3$, three of $R^5$ to $R^8$ are H and $R^2$ is a hydrogen atom. In other embodiments represented by the formulae (VI) to (XIV), $R^4$ is —$OCF_3$, each of $R^5$ to $R^8$ is H and $R^2$ is halogen. In some embodiments represented by the formulae (VI) to (XIV), $R^4$ is —$OCF_3$, two of $R^5$ to $R^8$ are H and $R^2$ is halogen. In some embodiments represented by the formulae (VI) to (XIV), $R^4$ is —$OCF_3$, three of $R^5$ to $R^8$ are H and $R^2$ is halogen. In the formulae (VI) to (XIV), when $R^4$ is —$OCF_3$, and $R^2$ is halogen, $R^2$ is preferably Cl.

In some embodiments, in the moieties represented by the formulae (V) or (VI) to (XIV) $R^4$ is —$CH_3$ and each of $R^5$ to $R^8$ is H. In some embodiments, in the moieties represented by the formulae (V) or (VI) to (XIV) $R^4$ is —$CH_3$ and two of $R^5$ to $R^8$ are H. In some embodiments, in the moieties represented by the formulae (V) or (VI) to (XIV) $R^4$ is —$CH_3$ and three of $R^5$ to $R^8$ are H. In some embodiments represented by the formulae (VI) to (XIV), $R^4$ is —$CH_3$, and $R^2$ is —$CH_3$. In other embodiments represented by the formulae (VI) to (XIV), $R^4$ is —$CH_3$, and $R^2$ is a hydrogen atom. In other embodiments represented by the formulae (VI) to (XIV), $R^4$ is —$CH_3$, and $R^2$ is halogen. In some embodiments represented by the formulae (VI) to (XIV), $R^4$ is —$CH_3$, each of $R^5$ to $R^8$ is H and $R^2$ is —$CH_3$. In some embodiments represented by the formulae (VI) to (XIV), $R^4$ is —$CH_3$, two of $R^5$ to $R^8$ are H and $R^2$ is —$CH_3$. In some embodiments represented by the formulae (VI) to (XIV), $R^4$ is —$CH_3$, three of $R^5$ to $R^8$ are H and $R^2$ is —$CH_3$. In other embodiments represented by the formulae (VI) to (XIV), $R^4$ is —$CH_3$, each of $R^5$ to $R^8$ is H and $R^2$ is a hydrogen atom. In some embodiments represented by the formulae (VI) to (XIV), $R^4$ is —$CH_3$, two of $R^5$ to $R^8$ are H and $R^2$ is a hydrogen atom. In some embodiments represented by the formulae (VI) to (XIV), $R^4$ is —$CH_3$, three of $R^5$ to $R^8$ are H and $R^2$ is a hydrogen atom. In other embodiments represented by the formulae (VI) to (XIV), $R^4$ is —$CH_3$, each of $R^5$ to $R^8$ is H and $R^2$ is halogen. In some embodiments represented by the formulae (VI) to (XIV), $R^4$ is —$CH_3$, two of $R^5$ to $R^8$ are H and $R^2$ is halogen. In some embodiments represented by the formulae (VI) to (XIV), $R^4$ is —$CH_3$, three of $R^5$ to $R^8$ are H and $R^2$ is halogen. In the formulae (VI) to (XIV), when $R^4$ is —$CH_3$, and $R^2$ is halogen, $R^2$ is preferably Cl.

In some embodiments, in the moieties represented by the formulae (V) or (VI) to (XIV) $R^4$ is —$N(CH_3)_2$ and each of $R^5$ to $R^8$ is H. In some embodiments, in the moieties represented by the formulae (V) or (VI) to (XIV) $R^4$ is —$N(CH_3)_2$ and two of $R^5$ to $R^8$ are H. In some embodiments, in the moieties represented by the formulae (V) or (VI) to (XIV) $R^4$ is —$N(CH_3)_2$ and three of $R^5$ to $R^8$ are H.

In some embodiments represented by the formulae (VI) to (XIV), $R^4$ is —N(CH$_3$)$_2$, and $R^2$ is —CH$_3$. In other embodiments represented by the formulae (VI) to (XIV), $R^4$ is —N(CH$_3$)$_2$, and $R^2$ is a hydrogen atom. In other embodiments represented by the formulae (VI) to (XIV), $R^4$ is —N(CH$_3$)$_2$, and $R^2$ is halogen. In some embodiments represented by the formulae (VI) to (XIV), $R^4$ is —N(CH$_3$)$_2$, each of $R^5$ to $R^8$ is H and $R^2$ is —CH$_3$. In some embodiments represented by the formulae (VI) to (XIV), $R^4$ is —N(CH$_3$)$_2$, two of $R^5$ to $R^8$ are H and $R^2$ is —CH$_3$. In some embodiments represented by the formulae (VI) to (XIV), $R^4$ is —N(CH$_3$)$_2$, three of $R^5$ to $R^8$ are H and $R^2$ is —CH$_3$. In other embodiments represented by the formulae (VI) to (XIV), $R^4$ is —N(CH$_3$)$_2$, each of $R^5$ to $R^8$ is H and $R^2$ is a hydrogen atom. In some embodiments represented by the formulae (VI) to (XIV), $R^4$ is —N(CH$_3$)$_2$, two of $R^5$ to $R^8$ are H and $R^2$ is a hydrogen atom. In some embodiments represented by the formulae (VI) to (XIV), $R^4$ is —N(CH$_3$)$_2$, three of $R^5$ to $R^8$ are H and $R^2$ is a hydrogen atom. In other embodiments represented by the formulae (VI) to (XIV), $R^4$ is —N(CH$_3$)$_2$, each of $R^5$ to $R^8$ is H and $R^2$ is halogen. In some embodiments represented by the formulae (VI) to (XIV), $R^4$ is —N(CH$_3$)$_2$, two of $R^5$ to $R^8$ are H and $R^2$ is halogen. In some embodiments represented by the formulae (VI) to (XIV), $R^4$ is —N(CH$_3$)$_2$, three of $R^5$ to $R^8$ are H and $R^2$ is halogen. In the formulae (VI) to (XIV), when $R^4$ is —N(CH$_3$)$_2$, and $R^2$ is halogen, $R^2$ is preferably Cl.

In some embodiments, in the moieties represented by the formulae (V) or (VI) to (XIV) $R^4$ is halogen and each of $R^5$ to $R^8$ is H. In some embodiments, in the moieties represented by the formulae (V) or (VI) to (XIV) $R^4$ is halogen and two of $R^5$ to $R^8$ are H. In some embodiments, in the moieties represented by the formulae (V) or (VI) to (XIV) $R^4$ is halogen and three of $R^5$ to $R^8$ are H. In some embodiments represented by the formulae (VI) to (XIV), $R^4$ is halogen, and $R^2$ is —CH$_3$. In other embodiments represented by the formulae (VI) to (XIV), $R^4$ is halogen, and $R^2$ is a hydrogen atom. In other embodiments represented by the formulae (VI) to (XIV), $R^4$ is halogen, and $R^2$ is halogen. In some embodiments represented by the formulae (VI) to (XIV), $R^4$ is halogen, each of $R^5$ to $R^8$ is H and $R^2$ is —CH$_3$. In some embodiments represented by the formulae (VI) to (XIV), $R^4$ is halogen, two of $R^5$ to $R^8$ are H and $R^2$ is —CH$_3$. In some embodiments represented by the formulae (VI) to (XIV), $R^4$ is halogen, three of $R^5$ to $R^8$ are H and $R^2$ is —CH$_3$. In other embodiments represented by the formulae (VI) to (XIV), $R^4$ is halogen, each of $R^5$ to $R^8$ is H and $R^2$ is a hydrogen atom. In some embodiments represented by the formulae (VI) to (XIV), $R^4$ is halogen, two of $R^5$ to $R^8$ are H and $R^2$ is a hydrogen atom. In some embodiments represented by the formulae (VI) to (XIV), $R^4$ is halogen, three of $R^5$ to $R^8$ are H and $R^2$ is a hydrogen atom. In other embodiments represented by the formulae (VI) to (XIV), $R^4$ is halogen, each of $R^5$ to $R^8$ is H and $R^2$ is halogen. In some embodiments represented by the formulae (VI) to (XIV), $R^4$ is halogen, two of $R^5$ to $R^8$ are H and $R^2$ is halogen. In some embodiments represented by the formulae (VI) to (XIV), $R^4$ is halogen, three of $R^5$ to $R^8$ are H and $R^2$ is halogen. In some embodiments where $R^4$ is halogen, $R^4$ is chlorine. In some embodiments where $R^4$ is halogen, $R^4$ is fluorine. In some embodiments where $R^4$ is halogen, $R^4$ is bromine. When $R^4$ is halogen, $R^4$ is preferably F, more preferably Cl. In the formulae (VI) to (XIV), when $R^4$ is halogen, and $R^2$ is halogen, $R^2$ is preferably Cl.

In any one of the moieties represented by the formulae (VI) to (XIV), $R^5$ may be as defined for formulae (V). $R^5$ may also be selected from the group consisting of —CF$_3$, —OCF$_3$, and halogen. In some embodiments, $R^5$ is —CF$_3$. In some embodiments, $R^5$ is —OCF$_3$. In some embodiments, $R^5$ is halogen.

In some embodiments, in the moieties represented by the formulae (V) or (VI) to (XIV) $R^5$ is —CF$_3$ and each of $R^4$ and $R^6$ to $R^8$ is H. In some embodiments, in the moieties represented by the formulae (V) or (VI) to (XIV) $R^5$ is —CF$_3$ and two of $R^4$ and $R^6$ to $R^8$ are H. In some embodiments, in the moieties represented by the formulae (V) or (VI) to (XIV) $R^5$ is —CF$_3$ and three of $R^4$ and $R^6$ to $R^8$ are H. In some embodiments represented by the formulae (VI) to (XIV), $R^5$ is —CF$_3$, and $R^2$ is —CH$_3$. In other embodiments represented by the formulae (VI) to (XIV), $R^5$ is —CF$_3$, and $R^2$ is a hydrogen atom. In other embodiments represented by the formulae (VI) to (XIV), $R^5$ is —CF$_3$, and $R^2$ is halogen. In some embodiments represented by the formulae (VI) to (XIV), $R^5$ is —CF$_3$, each of $R^4$ and $R^6$ to $R^8$ is H, and $R^2$ is —CH$_3$. In some embodiments represented by the formulae (VI) to (XIV), $R^5$ is —CF$_3$, two of $R^4$ and $R^6$ to $R^8$ are H, and $R^2$ is —CH$_3$. In some embodiments represented by the formulae (VI) to (XIV), $R^5$ is —CF$_3$, three of $R^4$ and $R^6$ to $R^8$ are H, and $R^2$ is —CH$_3$. In other embodiments represented by the formulae (VI) to (XIV), $R^5$ is —CF$_3$, each of $R^4$ and $R^6$ to $R^8$ is H, and $R^2$ is a hydrogen atom. In other embodiments represented by the formulae (VI) to (XIV), $R^5$ is —CF$_3$, two of $R^4$ and $R^6$ to $R^8$ are H, and $R^2$ is a hydrogen atom. In other embodiments represented by the formulae (VI) to (XIV), $R^5$ is —CF$_3$, three of $R^4$ and $R^6$ to $R^8$ are H, and $R^2$ is a hydrogen atom. In other embodiments represented by the formulae (VI) to (XIV), $R^5$ is —CF$_3$, each of $R^4$ and $R^6$ to $R^8$ is H, and $R^2$ is halogen. In other embodiments represented by the formulae (VI) to (XIV), $R^5$ is —CF$_3$, two of $R^4$ and $R^6$ to $R^8$ are H, and $R^2$ is halogen. In other embodiments represented by the formulae (VI) to (XIV), $R^5$ is —CF$_3$, three of $R^4$ and $R^6$ to $R^8$ are H, and $R^2$ is halogen. In the formulae (VI) to (XIV), when $R^5$ is —CF$_3$, and $R^2$ is halogen, $R^2$ is preferably Cl.

In some embodiments, in the moieties represented by the formulae (V) or (VI) to (XIV) $R^5$ is —OCF$_3$ and each of $R^4$ and $R^6$ to $R^8$ is H. In some embodiments, in the moieties represented by the formulae (V) or (VI) to (XIV) $R^5$ is —OCF$_3$ and two of $R^4$ and $R^6$ to $R^8$ are H. In some embodiments, in the moieties represented by the formulae (V) or (VI) to (XIV) $R^5$ is —OCF$_3$ and three of $R^4$ and $R^6$ to $R^8$ are H. In some embodiments represented by the formulae (VI) to (XIV), $R^5$ is —OCF$_3$, and $R^2$ is —CH$_3$. In other embodiments represented by the formulae (VI) to (XIV), $R^5$ is —OCF$_3$, and $R^2$ is a hydrogen atom. In other embodiments represented by the formulae (VI) to (XIV), $R^5$ is —OCF$_3$, and $R^2$ is halogen. In some embodiments represented by the formulae (VI) to (XIV), $R^5$ is —OCF$_3$, each of $R^4$ and $R^6$ to $R^8$ is H, and $R^2$ is —CH$_3$. In some embodiments represented by the formulae (VI) to (XIV), $R^5$ is —OCF$_3$, two of $R^4$ and $R^6$ to $R^8$ are H, and $R^2$ is —CH$_3$. In some embodiments represented by the formulae (VI) to (XIV), $R^5$ is —OCF$_3$, three of $R^4$ and $R^6$ to $R^8$ are H, and $R^2$ is —CH$_3$. In other embodiments represented by the formulae (VI) to (XIV), $R^5$ is —OCF$_3$, each of $R^4$ and $R^6$ to $R^8$ is H, and $R^2$ is a hydrogen atom. In other embodiments represented by the formulae (VI) to (XIV), $R^5$ is —OCF$_3$, two of $R^4$ and $R^6$ to $R^8$ are H, and $R^2$ is a hydrogen atom. In other embodiments represented by the formulae (VI) to (XIV), $R^5$ is —OCF$_3$, three of $R^4$ and $R^6$ to $R^8$ are H, and $R^2$ is a hydrogen atom. In other embodiments represented by the formulae (VI) to (XIV), $R^5$ is —OCF$_3$, each of $R^4$ and $R^6$ to $R^8$ is H, and $R^2$ is halogen. In other embodiments represented by the formulae (VI) to (XIV), $R^5$ is —OCF$_3$, two of $R^4$ and $R^6$ to $R^8$ are H, and $R^2$ is halogen. In other embodiments represented by the formulae (VI) to (XIV), $R^5$ is —OCF$_3$, three of $R^4$ and $R^6$ to $R^8$ are H, and $R^2$ is halogen. In the formulae (VI) to (XIV), when $R^5$ is —OCF$_3$, and $R^2$ is halogen, $R^2$ is preferably Cl.

In some embodiments, in the moieties represented by the formulae (V) or (VI) to (XIV) $R^5$ is halogen and each of $R^4$ and $R^6$ to $R^8$ is H. In some embodiments, in the moieties represented by the formulae (V) or (VI) to (XIV) $R^5$ is halogen and two of $R^4$ and $R^6$ to $R^8$ are H. In some embodiments, in the moieties represented by the formulae (V) or (VI) to (XIV) $R^5$ is halogen and three of $R^4$ and $R^6$ to $R^8$ are H. In some embodiments represented by the formulae (VI) to (XIV), $R^5$ is halogen, and $R^2$ is —CH$_3$. In other embodiments represented by the formulae (VI) to (XIV), $R^5$ is halogen, and $R^2$ is a hydrogen atom. In other embodiments represented by the formulae (VI) to (XIV), $R^5$ is halogen, and $R^2$ is halogen. In some embodiments represented by the formulae (VI) to (XIV), $R^5$ is halogen, each of $R^4$ and $R^6$ to $R^8$ is H, and $R^2$ is —CH$_3$. In some embodiments represented by the formulae (VI) to (XIV), $R^5$ is halogen, two of $R^4$ and $R^6$ to $R^8$ are H, and $R^2$ is —CH$_3$. In some embodiments represented by the formulae (VI) to (XIV), $R^5$ is halogen, three of $R^4$ and $R^6$ to $R^8$ are H, and $R^2$ is —CH$_3$. In other embodiments represented by the formulae (VI) to (XIV), $R^5$ is halogen, each of $R^4$ and $R^6$ to $R^8$ is H, and $R^2$ is a hydrogen atom. In other embodiments represented by the formulae (VI) to (XIV), $R^5$ is halogen, two of $R^4$ and $R^6$ to $R^8$ are H, and $R^2$ is a hydrogen atom. In other embodiments represented by the formulae (VI) to (XIV), $R^5$ is halogen, three of $R^4$ and $R^6$ to $R^8$ are H, and $R^2$ is a hydrogen atom. In other embodiments represented by the formulae (VI) to (XIV), $R^5$ is halogen, each of $R^4$ and $R^6$ to $R^8$ is H, and $R^2$ is halogen. In other embodiments represented by the formulae (VI) to (XIV), $R^5$ is halogen, two of $R^4$ and $R^6$ to $R^8$ are H, and $R^2$ is halogen. In other embodiments represented by the formulae (VI) to (XIV), $R^5$ is halogen, three of $R^4$ and $R^6$ to $R^8$ are H, and $R^2$ is halogen. In some embodiments where $R^5$ is halogen, $R^5$ is chlorine. In some embodiments where $R^5$ is halogen, $R^5$ is fluorine. In some embodiments where $R^5$ is halogen, $R^5$ is bromine. When $R^5$ is halogen, $R^5$ is preferably F, more preferably Cl. In the formulae (VI) to (XIV), when $R^5$ is halogen, and $R^2$ is halogen, $R^2$ is preferably Cl.

In some embodiments, in the moieties represented by the formulae (V) or (VI) to (XIV) $R^6$ is halogen. In some embodiments represented by the formulae (V) or (VI) to (XIV), $R^6$ is halogen and each of $R^4$, $R^5$, $R^7$ and $R^8$ is H. In some embodiments represented by the formulae (V) or (VI) to (XIV), $R^6$ is halogen and two of $R^4$, $R^5$, $R^7$ and $R^8$ are H. In some embodiments represented by the formulae (V) or (VI) to (XIV), $R^6$ is halogen and three of $R^4$, $R^5$, $R^7$ and $R^8$ are H. In some embodiments represented by the formulae (VI) to (XIV), $R^6$ is halogen, and $R^2$ is —CH$_3$. In other embodiments represented by the formulae (VI) to (XIV), $R^6$ is halogen, and $R^2$ is a hydrogen atom. In other embodiments represented by the formulae (VI) to (XIV), $R^6$ is halogen, and $R^2$ is halogen. In some embodiments represented by the formulae (VI) to (XIV), $R^6$ is halogen, each of $R^4$, $R^5$, $R^7$ and $R^8$ is H, and $R^2$ is —CH$_3$. In some embodiments represented by the formulae (VI) to (XIV), $R^6$ is halogen, two of $R^4$, $R^5$, $R^7$ and $R^8$ are H, and $R^2$ is —CH$_3$. In some embodiments represented by the formulae (VI) to (XIV), $R^6$ is halogen, three of $R^4$, $R^5$, $R^7$ and $R^8$ are H, and $R^2$ is —CH$_3$. In other embodiments represented by the formulae (VI) to (XIV), $R^6$ is halogen, each of $R^4$, $R^5$, $R^7$ and $R^8$ is H, and $R^2$ is a hydrogen atom. In other embodiments represented by the formulae (VI) to (XIV), $R^6$ is halogen, two of $R^4$, $R^5$, $R^7$ and $R^8$ are H, and $R^2$ is a hydrogen atom. In other embodiments represented by the formulae (VI) to (XIV), $R^6$ is halogen, three of $R^4$, $R^5$, $R^7$ and $R^8$ are H, and $R^2$ is a hydrogen atom. In other embodiments represented by the formulae (VI) to (XIV), $R^6$ is halogen, each of $R^4$, $R^5$, $R^7$ and $R^8$ is H, and $R^2$ is halogen. In other embodiments represented by the formulae (VI) to (XIV), $R^6$ is halogen, two of $R^4$, $R^5$, $R^7$ and $R^8$ are H, and $R^2$ is halogen. In other embodiments represented by the formulae (VI) to (XIV), $R^6$ is halogen, three of $R^4$, $R^5$, $R^7$ and $R^8$ are H, and $R^2$ is halogen. In some embodiments where $R^6$ is halogen, $R^6$ is chlorine. In some embodiments where $R^6$ is halogen, $R^6$ is fluorine. In some embodiments where $R^6$ is halogen, $R^6$ is bromine. When $R^6$ is halogen, $R^6$ is preferably F, more preferably Cl. In the formulae (VI) to (XIV), when $R^6$ is halogen, and $R^2$ is halogen, $R^2$ is preferably Cl.

In some embodiments, in the moieties represented by the formula (V) or (VI) to (XIV) $R^6$ is —OCH$_3$ or —OC$_{2to4}$alkyl. In some embodiments moieties represented by the formula (V) or (VI) to (XIV), $R^6$ is —OCH$_3$ or —OC$_{2to4}$alkyl and each of $R^4$ and $R^6$ to $R^8$ is H. In some embodiments represented by the formulae (V) or (VI) to (XIV), $R^6$ is —OCH$_3$ or —OC$_{2to4}$alkyl and two of $R^4$, $R^5$, $R^7$ and $R^8$ are H. In some embodiments represented by the formulae (V) or (VI) to (XIV), $R^6$ is —OCH$_3$ or —OC$_{2to4}$alkyl and three of $R^4$, $R^5$, $R^7$ and $R^8$ are H. In some embodiments represented by the formulae (VI) to (XIV), $R^6$ is —OCH$_3$ or —OC$_{2to4}$alkyl, and $R^2$ is —CH$_3$. In other embodiments represented by the formulae (VI) to (XIV) $R^6$ is —OCH$_3$ or —OC$_{2to4}$alkyl, and $R^2$ is a hydrogen atom. In other embodiments represented by the formulae (VI) to (XIV), $R^6$ is —OCH$_3$ or —OC$_{2to4}$alkyl, and $R^2$ is halogen. In some embodiments represented by the formulae (VI) to (XIV), $R^6$ is —OCH$_3$ or —OC$_{2to4}$alkyl, each of $R^4$ and $R^6$ to $R^8$ is H, and $R^2$ is —CH$_3$. In some embodiments represented by the formulae (VI) to (XIV), $R^6$ is —OCH$_3$ or —OC$_{2to4}$alkyl, two of $R^4$, $R^5$, $R^7$ and $R^8$ are H, and $R^2$ is —CH$_3$. In some embodiments represented by the formulae (VI) to (XIV), $R^6$ is —OCH$_3$ or —OC$_{2to4}$alkyl, three of $R^4$, $R^5$, $R^7$ and $R^8$ are H, and $R^2$ is —CH$_3$. In other embodiments represented by the formulae (VI) to (XIV), $R^6$ is —OCH$_3$ or —OC$_{2to4}$alkyl, each of $R^4$ and $R^6$ to $R^8$ is H, and $R^2$ is a hydrogen atom. In other embodiments represented by the formulae (VI) to (XIV), $R^6$ is —OCH$_3$ or —OC$_{2to4}$alkyl, two of $R^4$, $R^5$, $R^7$ and $R^8$ are H, and $R^2$ is a hydrogen atom. In other embodiments represented by the formulae (VI) to (XIV), $R^6$ is —OCH$_3$ or —OC$_{2to4}$alkyl, three of $R^4$, $R^5$, $R^7$ and $R^8$ are H, and $R^2$ is a hydrogen atom. In other embodiments represented by the formulae (VI) to (XIV), $R^6$ is —OCH$_3$ or —OC$_{2to4}$alkyl, each of $R^4$ and $R^6$ to $R^8$ is H, and $R^2$ is halogen. In other embodiments represented by the formulae (VI) to (XIV), $R^6$ is —OCH$_3$ or —OC$_{2to4}$alkyl, two of $R^4$, $R^5$, $R^7$ and $R^8$ are H, and $R^2$ is halogen. In other embodiments represented by the formulae (VI) to (XIV), $R^6$ is —OCH$_3$ or —OC$_{2to4}$alkyl, three of $R^4$, $R^5$, $R^7$ and $R^8$ are H, and $R^2$ is halogen. When $R^6$ is —OCH$_3$ or —OC$_{2to4}$alkyl, $R^6$ is preferably —OCH$_3$. In the formulae (VI) to (XIV), when $R^6$ is —OCH$_3$ or —OC$_{2to4}$alkyl, and $R^2$ is halogen, $R^2$ is preferably Cl.

In some embodiments, in the moieties represented by the formulae (V) or (VI) to (XIV) $R^6$ is —CF$_3$. In some embodiments represented by the formulae (V) or (VI) to (XIV), $R^6$ is —CF$_3$ and each of $R^4$, $R^5$, $R^7$ and $R^8$ is H. In some embodiments represented by the formulae (V) or (VI) to (XIV), $R^6$ is —CF$_3$ and two of $R^4$, $R^5$, $R^7$ and $R^8$ are H. In some embodiments represented by the formulae (V) or (VI) to (XIV), $R^6$ is —$CF_3$ and three of $R^4$, $R^5$, $R^7$ and $R^8$ are H. In some embodiments represented by the formulae (VI) to (XIV), $R^6$ is —$CF_3$, and $R^2$ is —$CH_3$. In other embodiments represented by the formulae (VI) to (XIV), $R^6$ is —$CF_3$, and $R^2$ is a hydrogen atom. In other embodiments represented by the formulae (VI) to (XIV), $R^6$ is —$CF_3$, and $R^2$ is halogen. In some embodiments represented by the formulae (VI) to (XIV), $R^6$ is —$CF_3$, each of $R^4$, $R^5$, $R^7$ and $R^8$ is H, and $R^2$ is —$CH_3$. In some embodiments represented by the formulae (VI) to (XIV), $R^6$ is —$CF_3$, two of $R^4$, $R^5$, $R^7$ and $R^8$ are H, and $R^2$ is —$CH_3$. In some embodiments represented by the formulae (VI) to (XIV), $R^6$ is —$CF_3$, three of $R^4$, $R^5$, $R^7$ and $R^8$ are H, and $R^2$ is —$CH_3$. In other embodiments represented by the formulae (VI) to (XIV), $R^6$ is —$CF_3$, each of $R^4$, $R^5$, $R^7$ and $R^8$ is H, and $R^2$ is a hydrogen atom. In other embodiments represented by the formulae (VI) to (XIV), $R^6$ is —$CF_3$, two of $R^4$, $R^5$, $R^7$ and $R^8$ are H, and $R^2$ is a hydrogen atom. In other embodiments represented by the formulae (VI) to (XIV), $R^6$ is —$CF_3$, three of $R^4$, $R^5$, $R^7$ and $R^8$ are H, and $R^2$ is a hydrogen atom. In other embodiments represented by the formulae (VI) to (XIV), $R^6$ is —$CF_3$, each of $R^4$, $R^5$, $R^7$ and $R^8$ is H, and $R^2$ is halogen. In other embodiments represented by the formulae (VI) to (XIV), $R^6$ is —$CF_3$, two of $R^4$, $R^5$, $R^7$ and $R^8$ are H, and $R^2$ is halogen. In other embodiments represented by the formulae (VI) to (XIV), $R^6$ is —$CF_3$, three of $R^4$, $R^5$, $R^7$ and $R^8$ are H, and $R^2$ is halogen. In the formulae (VI) to (XIV), when $R^6$ is —$CF_3$, and $R^2$ is halogen, $R^2$ is preferably Cl.

In some embodiments, in the moieties represented by the formulae (V) or (VI) to (XIV) $R^6$ is —$CH_3$. In some embodiments represented by the formulae (V) or (VI) to (XIV), $R^6$ is —$CH_3$ and each of $R^4$, $R^5$, $R^7$ and $R^8$ is H. In some embodiments represented by the formulae (V) or (VI) to (XIV), $R^6$ is —$CH_3$ and two of $R^4$, $R^5$, $R^7$ and $R^8$ are H. In some embodiments represented by the formulae (V) or (VI) to (XIV), $R^6$ is —$CH_3$ and three of $R^4$, $R^5$, $R^7$ and $R^8$ are H. In some embodiments represented by the formulae (VI) to (XIV), $R^6$ is —$CH_3$, and $R^2$ is —$CH_3$. In other embodiments represented by the formulae (VI) to (XIV), $R^6$ is —$CH_3$, and $R^2$ is a hydrogen atom. In other embodiments represented by the formulae (VI) to (XIV), $R^6$ is —$CH_3$, and $R^2$ is halogen. In some embodiments represented by the formulae (VI) to (XIV), $R^6$ is —$CH_3$, each of $R^4$, $R^5$, $R^7$ and $R^8$ is H, and $R^2$ is —$CH_3$. In some embodiments represented by the formulae (VI) to (XIV), $R^6$ is —$CH_3$, two of $R^4$, $R^5$, $R^7$ and $R^8$ are H, and $R^2$ is —$CH_3$. In some embodiments represented by the formulae (VI) to (XIV), $R^6$ is —$CH_3$, three of $R^4$, $R^5$, $R^7$ and $R^8$ are H, and $R^2$ is —$CH_3$. In other embodiments represented by the formulae (VI) to (XIV), $R^6$ is —$CH_3$, each of $R^4$, $R^5$, $R^7$ and $R^8$ is H, and $R^2$ is a hydrogen atom. In other embodiments represented by the formulae (VI) to (XIV), $R^6$ is —$CH_3$, two of $R^4$, $R^5$, $R^7$ and $R^8$ are H, and $R^2$ is a hydrogen atom. In other embodiments represented by the formulae (VI) to (XIV), $R^6$ is —$CH_3$, three of $R^4$, $R^5$, $R^7$ and $R^8$ are H, and $R^2$ is a hydrogen atom. In other embodiments represented by the formulae (VI) to (XIV), $R^6$ is —$CH_3$, each of $R^4$, $R^5$, $R^7$ and $R^8$ is H, and $R^2$ is halogen. In other embodiments represented by the formulae (VI) to (XIV), $R^6$ is —$CH_3$, two of $R^4$, $R^5$, $R^7$ and $R^8$ are H, and $R^2$ is halogen. In other embodiments represented by the formulae (VI) to (XIV), $R^6$ is —$CH_3$, three of $R^4$, $R^5$, $R^7$ and $R^8$ are H, and $R^2$ is halogen. In the formulae (VI) to (XIV), when $R^6$ is —$CH_3$, and $R^2$ is halogen, $R^2$ is preferably Cl.

In some embodiments, in the moieties represented by the formulae (V) or (VI) to (XIV) $R^6$ is —$OCF_3$. In some embodiments represented by the formulae (V) or (VI) to (XIV), $R^6$ is —$OCF_3$ and each of $R^4$, $R^5$, $R^7$ and $R^8$ is H. In some embodiments represented by the formulae (V) or (VI) to (XIV), $R^6$ is —$OCF_3$ and two of $R^4$, $R^5$, $R^7$ and $R^8$ are H. In some embodiments represented by the formulae (V) or (VI) to (XIV), $R^6$ is —$OCF_3$ and three of $R^4$, $R^5$, $R^7$ and $R^8$ are H. In some embodiments represented by the formulae (VI) to (XIV), $R^6$ is —$OCF_3$, and $R^2$ is —$CH_3$. In other embodiments represented by the formulae (VI) to (XIV), $R^6$ is —$OCF_3$, and $R^2$ is a hydrogen atom. In other embodiments represented by the formulae (VI) to (XIV), $R^6$ is —$OCF_3$, and $R^2$ is halogen. In some embodiments represented by the formulae (VI) to (XIV), $R^6$ is —$OCF_3$, each of $R^4$, $R^5$, $R^7$ and $R^8$ is H, and $R^2$ is —$CH_3$. In some embodiments represented by the formulae (VI) to (XIV), $R^6$ is —$OCF_3$, two of $R^4$, $R^5$, $R^7$ and $R^8$ are H, and $R^2$ is —$CH_3$. In some embodiments represented by the formulae (VI) to (XIV), $R^6$ is —$OCF_3$, three of $R^4$, $R^5$, $R^7$ and $R^8$ are H, and $R^2$ is —$CH_3$. In other embodiments represented by the formulae (VI) to (XIV), $R^6$ is —$OCF_3$, each of $R^4$, $R^5$, $R^7$ and $R^8$ is H, and $R^2$ is a hydrogen atom. In other embodiments represented by the formulae (VI) to (XIV), $R^6$ is —$OCF_3$, two of $R^4$, $R^5$, $R^7$ and $R^8$ are H, and $R^2$ is a hydrogen atom. In other embodiments represented by the formulae (VI) to (XIV), $R^6$ is —$OCF_3$, three of $R^4$, $R^5$, $R^7$ and $R^8$ are H, and $R^2$ is a hydrogen atom. In other embodiments represented by the formulae (VI) to (XIV), $R^6$ is —$OCF_3$, each of $R^4$, $R^5$, $R^7$ and $R^8$ is H, and $R^2$ is halogen. In other embodiments represented by the formulae (VI) to (XIV), $R^6$ is —$OCF_3$, two of $R^4$, $R^5$, $R^7$ and $R^8$ are H, and $R^2$ is halogen. In other embodiments represented by the formulae (VI) to (XIV), $R^6$ is —$OCF_3$, three of $R^4$, $R^5$, $R^7$ and $R^8$ are H, and $R^2$ is halogen. In the formulae (VI) to (XIV), when $R^6$ is —$OCF_3$, and $R^2$ is halogen, $R^2$ is preferably Cl.

In some embodiments, in the moieties represented by the formulae (V) or (VI) to (XIV) $R^6$ is ethyl. In some embodiments represented by the formulae (V) or (VI) to (XIV), $R^6$ is ethyl and each of $R^4$, $R^5$, $R^7$ and $R^8$ is H. In some embodiments represented by the formulae (V) or (VI) to (XIV), $R^6$ is ethyl and two of $R^4$, $R^5$, $R^7$ and $R^8$ are H. In some embodiments represented by the formulae (V) or (VI) to (XIV), $R^6$ is ethyl and three of $R^4$, $R^5$, $R^7$ and $R^8$ are H. In some embodiments represented by the formulae (VI) to (XIV), $R^6$ is ethyl, and $R^2$ is —$CH_3$. In other embodiments represented by the formulae (VI) to (XIV), $R^6$ is ethyl, and $R^2$ is a hydrogen atom. In other embodiments represented by the formulae (VI) to (XIV), $R^6$ is ethyl, and $R^2$ is halogen. In some embodiments represented by the formulae (VI) to (XIV), $R^6$ is ethyl, each of $R^4$, $R^5$, $R^7$ and $R^8$ is H, and $R^2$ is —$CH_3$. In some embodiments represented by the formulae (VI) to (XIV), $R^6$ is ethyl, two of $R^4$, $R^5$, $R^7$ and $R^8$ are H, and $R^2$ is —$CH_3$. In some embodiments represented by the formulae (VI) to (XIV), $R^6$ is ethyl, three of $R^4$, $R^5$, $R^7$ and $R^8$ are H, and $R^2$ is —$CH_3$. In other embodiments represented by the formulae (VI) to (XIV), $R^6$ is ethyl, each of $R^4$, $R^5$, $R^7$ and $R^8$ is H, and $R^2$ is a hydrogen atom. In other embodiments represented by the formulae (VI) to (XIV), $R^6$ is ethyl, two of $R^4$, $R^5$, $R^7$ and $R^8$ are H, and $R^2$ is a hydrogen atom. In other embodiments represented by the formulae (VI) to (XIV), $R^6$ is ethyl, three of $R^4$, $R^5$, $R^7$ and $R^8$ are H, and $R^2$ is a hydrogen atom. In other embodiments represented by the formulae (VI) to (XIV), $R^6$ is ethyl, each of $R^4$, $R^5$, $R^7$ and $R^8$ is H, and $R^2$ is halogen. In other embodiments represented by the formulae (VI) to (XIV), $R^6$ is ethyl, two of $R^4$, $R^5$, $R^7$ and $R^8$ are H, and $R^2$ is halogen. In other embodiments represented by the formulae (VI) to (XIV), $R^6$ is ethyl, three of $R^4$, $R^5$, $R^7$ and $R^8$ are H, and $R^2$ is halogen. In the formulae (VI) to (XIV), when $R^6$ is ethyl, and $R^2$ is halogen, $R^2$ is preferably Cl.

In some embodiments, in the moieties represented by the formulae (V) or (VI) to (XIV) $R^6$ is iso-propyl. In some embodiments represented by the formulae (V) or (VI) to (XIV), $R^6$ is iso-propyl and each of $R^4$, $R^5$, $R^7$ and $R^8$ is H. In some embodiments represented by the formulae (V) or (VI) to (XIV), $R^6$ is iso-propyl and two of $R^4$, $R^5$, $R^7$ and $R^8$ are H. In some embodiments represented by the formulae (V) or (VI) to (XIV), $R^6$ is iso-propyl and three of $R^4$, $R^5$, $R^7$ and $R^8$ are H. In some embodiments represented by the formulae (VI) to (XIV), $R^6$ is iso-propyl, and $R^2$ is —$CH_3$. In other embodiments represented by the formulae (VI) to (XIV), $R^6$ is iso-propyl, and $R^2$ is a hydrogen atom. In other embodiments represented by the formulae (VI) to (XIV), $R^6$ is iso-propyl, and $R^2$ is halogen. In some embodiments represented by the formulae (VI) to (XIV), $R^6$ is iso-propyl, each of $R^4$, $R^5$, $R^7$ and $R^8$ is H, and $R^2$ is —$CH_3$. In some embodiments represented by the formulae (VI) to (XIV), $R^6$ is iso-propyl, two of $R^4$, $R^5$, $R^7$ and $R^8$ are H, and $R^2$ is —$CH_3$. In some embodiments represented by the formulae (VI) to (XIV), $R^6$ is iso-propyl, three of $R^4$, $R^5$, $R^7$ and $R^8$ are H, and $R^2$ is —$CH_3$. In other embodiments represented by the formulae (VI) to (XIV), $R^6$ is iso-propyl, each of $R^4$, $R^5$, $R^7$ and $R^8$ is H, and $R^2$ is a hydrogen atom. In other embodiments represented by the formulae (VI) to (XIV), $R^6$ is iso-propyl, two of $R^4$, $R^5$, $R^7$ and $R^8$ are H, and $R^2$ is a hydrogen atom. In other embodiments represented by the formulae (VI) to (XIV), $R^6$ is iso-propyl, three of $R^4$, $R^5$, $R^7$ and $R^8$ are H, and $R^2$ is a hydrogen atom. In other embodiments represented by the formulae (VI) to (XIV), $R^6$ is iso-propyl, each of $R^4$, $R^5$, $R^7$ and $R^8$ is H, and $R^2$ is halogen. In other embodiments represented by the formulae (VI) to (XIV), $R^6$ is iso-propyl, two of $R^4$, $R^5$, $R^7$ and $R^8$ are H, and $R^2$ is halogen. In other embodiments represented by the formulae (VI) to (XIV), $R^6$ is iso-propyl, three of $R^4$, $R^5$, $R^7$ and $R^8$ are H, and $R^2$ is halogen. In the formulae (VI) to (XIV), when $R^6$ is iso-propyl, and $R^2$ is halogen, $R^2$ is preferably Cl.

In some embodiments of the present invention, all of $R^4$ to $R^8$ are hydrogen. In some embodiments of the present invention, only $R^4$ is not hydrogen. In some embodiments of the present invention, only $R^5$ is not hydrogen. In some embodiments of the present invention, only $R^6$ is not hydrogen. In the moieties of the compounds of the present invention, more than one of $R^4$ to $R^8$ may be a group other than hydrogen. In some embodiments, when more than one of $R^4$ to $R^8$ is a group other than hydrogen in the moieties of the compounds of the present invention, it is preferred that two of $R^4$ to $R^8$ are a group other than hydrogen. In some embodiments, $R^4$ and $R^5$ are groups other than hydrogen. In some embodiments, $R^4$ and $R^5$ are groups other than hydrogen and $R^6$ to $R^8$ are hydrogen. In some embodiments, $R^4$ and $R^6$ are groups other than hydrogen. In some embodiments, $R^4$ and $R^6$ are groups other than hydrogen and $R^5$, $R^7$ and $R^8$ are hydrogen. In some embodiments, $R^4$ and $R^7$ are groups other than hydrogen. In some embodiments, $R^4$ and $R^7$ are groups other than hydrogen and $R^5$, $R^6$ and $R^8$ are hydrogen. In some embodiments, $R^4$ and $R^8$ are groups other than hydrogen. In some embodiments, $R^4$ and $R^8$ are groups other than hydrogen and $R^5$, $R^6$ and $R^7$ are hydrogen. In some embodiments, $R^5$ and $R^6$ are groups other than hydrogen. In some embodiments, $R^5$ and $R^6$ are groups other than hydrogen and $R^4$, $R^7$ and $R^8$ are hydrogen. Particularly preferred is when $R^4$ and $R^6$ are groups other than hydrogen and $R^5$, $R^7$ and $R^8$ are hydrogen, still more preferred $R^5$ and $R^6$ are groups other than hydrogen and $R^4$, $R^7$ and $R^8$ are hydrogen. In a preferred embodiment of the invention at least two, preferably three or four, of $R^4$, $R^5$, $R^6$, $R^7$ and $R^8$ are H.

In some embodiments, when two of $R^4$ to $R^8$ are a group other than hydrogen in the moieties of the compounds of the present invention, $R^5$ is $CF_3$ and $R^6$ is Cl. In some embodiments, when two of $R^4$ to $R^8$ are a group other than hydrogen in the moieties of the compounds of the present invention, $R^5$ is $OCF_3$ and $R^6$ is Cl. In some embodiments, when two of $R^4$ to $R^8$ are a group other than hydrogen in the moieties of the compounds of the present invention, $R^6$ is $CF_3$ and $R^5$ is Cl. In some embodiments, when two of $R^4$ to $R^8$ are a group other than hydrogen in the moieties of the compounds of the present invention, $R^6$ is $OCF_3$ and $R^5$ is Cl. These specific substitution combinations in respect of $R^5$ and $R^6$ may also be present in the moieties of the compounds of the present invention in which only two of $R^4$, $R^5$, $R^6$, $R^7$ and $R^8$ are H.

When two of $R^4$ to $R^8$ are a group other than hydrogen in the moieties of the compounds of the present invention, group B as defined in formula (I) is preferably selected from the group consisting of

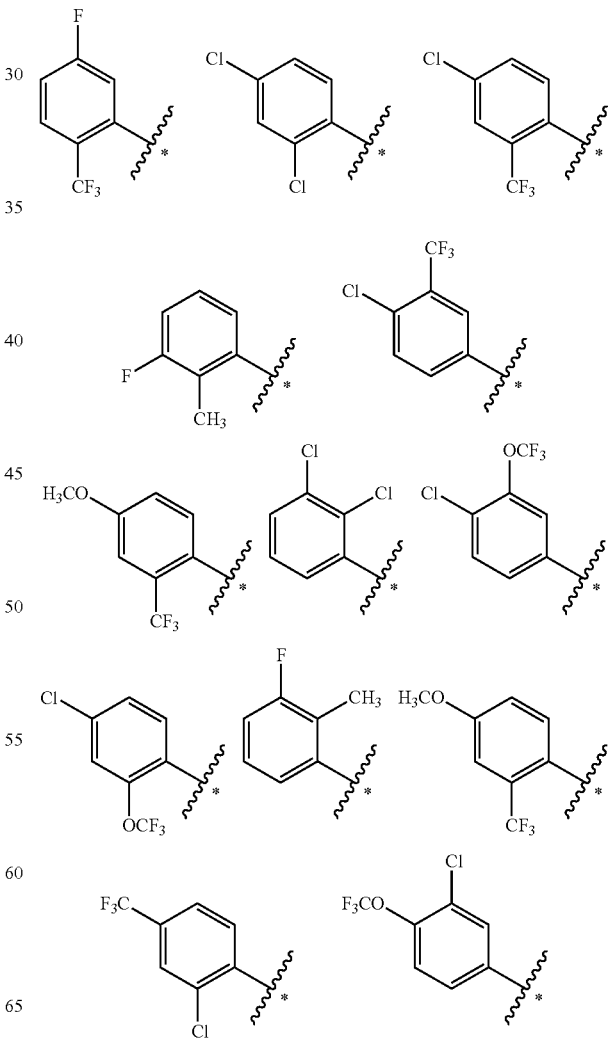

-continued

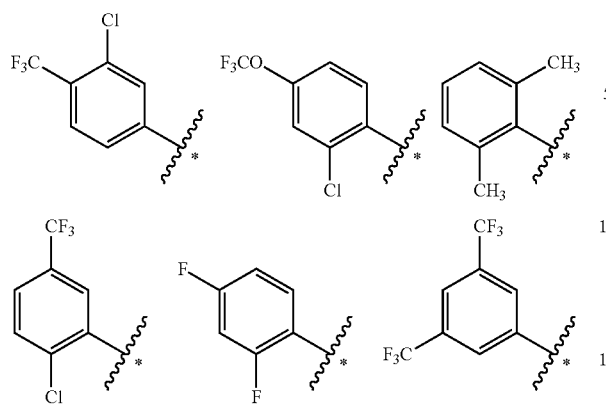

where * is as previously defined. When group B as defined in formula (I) is selected from this group and one of $R^1$ or $R^2$ is a phenyl group substituted with at least one substituent represented by the group $R^3$, in some embodiments $R^3$ may be selected from the group consisting of H, Cl, F, Br, —$CF_3$, —$OCF_3$, and ethynyl. In these embodiments, the other of $R^1$ or $R^2$ (i.e. that which is not a phenyl group substituted with at least one substituent represented by the group $R^3$) is —$CH_2N(CH_3)_2$ or chlorine, preferably hydrogen, more preferably —$CH_3$. In some such embodiments, at least one of the substituents represented by $R^3$ is selected from the group consisting of para-Br, para-$CF_3$, para-$OCF_3$ and para-ethynyl, and in some of these embodiments $R^3$ represents a single substituent selected from the group consisting of para-Br, para-$CF_3$, para-$OCF_3$ and para-ethynyl.

In the moieties of the compounds of the present invention, more than one of $R^4$ to $R^8$ may be a group other than hydrogen. In some embodiments of the present invention only one of $R^4$ to $R^8$ is a group other than hydrogen. In some embodiments only $R^4$ is a group other than hydrogen. In some embodiments only $R^5$ is a group other than hydrogen. In some embodiments only $R^6$ is a group other than hydrogen. In some embodiments only $R^7$ is a group other than hydrogen. In some embodiments only $R^8$ is a group other than hydrogen.

When only one of $R^4$ to $R^8$ is a group other than hydrogen in the moieties of the compounds of the present invention, group B as defined in formula (I) is preferably selected from the group consisting of

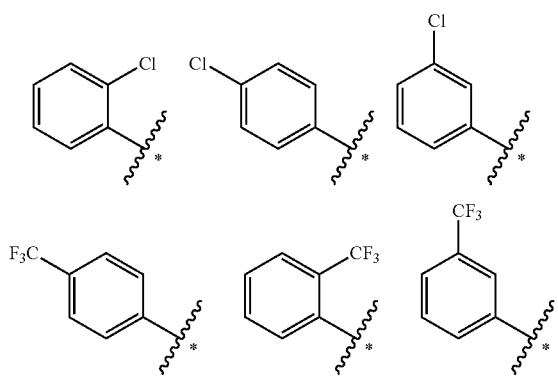

-continued

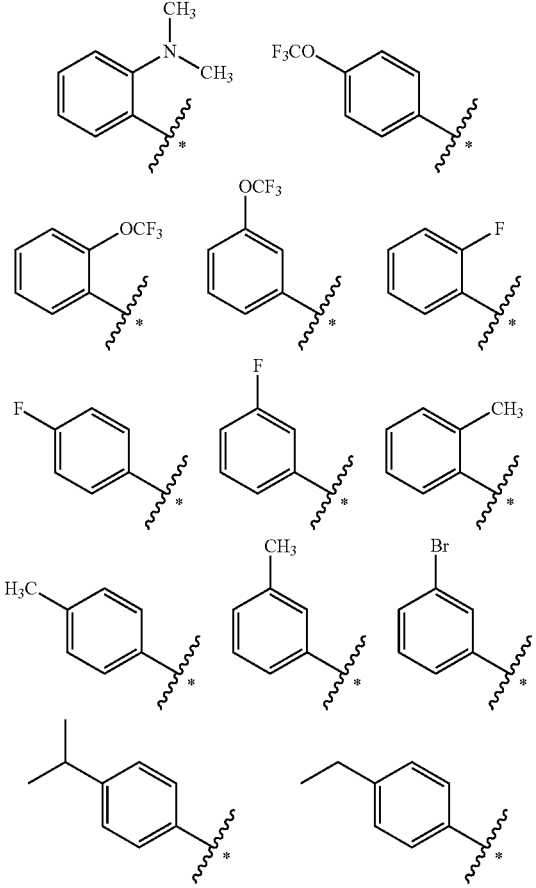

In some embodiments of the present invention, three of $R^4$ to $R^8$ may be a group other than hydrogen. When three of $R^4$ to $R^8$ is a group other than hydrogen in the moieties of the compounds of the present invention, group B as defined in formula (I) is preferably

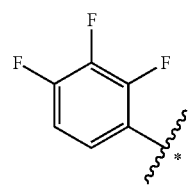 [SMILES: *c1ccc(F)c(F)c1F]

where * is as defined above.

In the moieties of the compounds of the present invention, $R^3$ represents optional substituents on an otherwise unsubstituted phenyl ring and is preferably independently selected from the group consisting of one or more substituents selected from the group consisting of —$CH_3$, $C_{2to4}$alkyl, halogen, hydroxyl, —$OCH_3$, —$OC_{2to4}$alkyl, ethynyl, —$OCF_3$, and —$CF_3$, more preferably one or more substituents independently selected from the group consisting of —$CH_3$, —$CH_2CH_3$, —OH, —$CF_3$, —$OCF_3$, ethynyl, and halogen, wherein halogen is preferably F or Cl or Br, most preferably independently selected from one or more substituents selected the group consisting of —$CH_3$, —$CH_2CH_3$, —$CF_3$, —$OCF_3$, ethynyl, and halogen, wherein halogen is preferably F or Cl or Br. In some embodiments, R³ can be one substituent, two substituents or three substituents independently selected from either of these lists. R³ is preferably two substituents independently selected from either these lists, more preferably one substituent selected from either of these lists.

R³ may represent an ortho-, meta- or para-substituent. In some embodiments of the invention, one of the at least one substituents represented by R³ is selected from the group consisting of para-Br, para-F, para-Cl, para-ethyl, para-CF₃, para-OCF₃ and para-ethynyl. In some embodiments of the invention, R³ represents a single substituent on the phenyl ring and is selected from the group consisting of para-Br, para-F, para-Cl, para-ethyl, para-CF₃, para-OCF₃ and para-ethynyl. In some embodiments of the invention, one of the at least one substituents represented by R³ is meta-Cl. In some embodiments of the invention, one of the at least one substituents represented by R³ is ortho-Cl. In some embodiments of the invention, one of the at least one substituents represented by R³ is ortho-methyl. In some embodiments of the invention, R³ represents at least two substituents. In some embodiments of the invention in which R³ represents at least two substituents, two of the substituents represented by R³ are ortho-Cl and para-Cl.

When R³ represents two substituents, they may be ortho, meta or para to one another. In such embodiments, the phenyl ring which is substituted with the two R³ substituents may be a 2,3-disubstituted phenyl ring, a 2,4-disubstituted phenyl ring, a 2,5-disubstituted phenyl ring, a 2,6-disubstituted phenyl ring, a 3,4-disubstituted phenyl ring or a 3,5-disubstituted phenyl ring.

When R¹ or R² is an optionally substituted phenyl ring in the present invention, they are preferably selected from

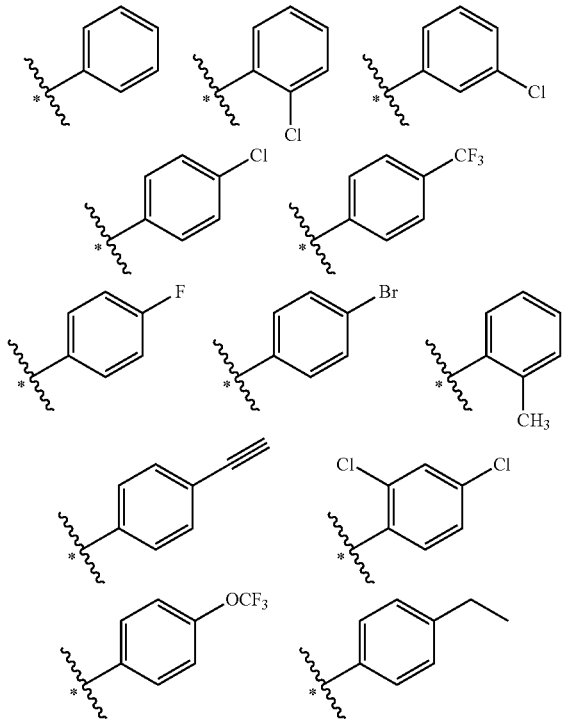

In a further embodiment of the present invention, the moieties of formula (I) are represented by the formulae of List 7, where R³ represents optional substituents on an otherwise unsubstituted phenyl ring and is preferably selected from the group consisting of one or more substituents selected from the group consisting of —CH₃, $C_{2\,to\,4}$alkyl, halogen, hydroxyl, —OCH₃, —O$C_{2\,to\,4}$alkyl, ethynyl, —OCF₃, and —CF₃, more preferably one or more substituents independently selected from the group consisting of —CH₃, —CH₂CH₃, —OH, —CF₃, —OCF₃, ethynyl, and halogen, wherein halogen is preferably F or Cl or Br, most preferably independently selected from one or more substituents selected the group consisting of —CH₃, —CH₂CH₃, —CF₃, —OCF₃, ethynyl, and halogen, wherein halogen is preferably F or Cl or Br, and the furan ring may be optionally further substituted, preferably by one or more substituents, independently selected from —CH₃, $C_{2\,to\,4}$alkyl, halogen, —OCH₃, and —O$C_{2\,to\,4}$alkyl, more preferably by one or more substituents independently selected from —CH₃, $C_{2\,to\,4}$alkyl and halogen, most preferably by one or more —CH₃ substituents.

List 7

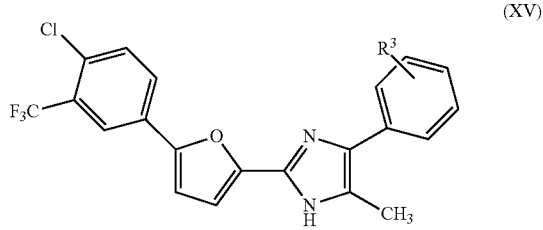

(XV)

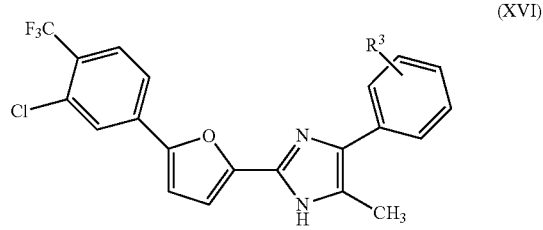

(XVI)

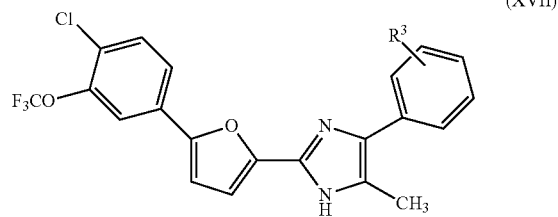

(XVII)

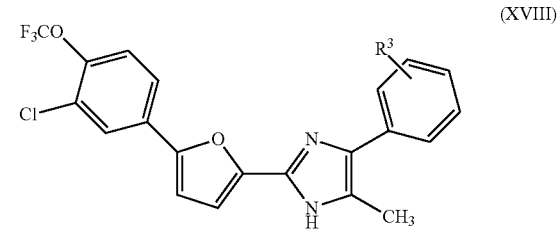

(XVIII)

In some embodiments, in the moieties of formula (I) represented by compounds (XV), (XVI), (XVII) and (XVIII) in List 7 R³ is H. In some embodiments, in the moieties of formula (I) represented by compounds (XV), (XVI), (XVII) and (XVIII) in List 7 R³ is halogen, preferably F or Cl or Br. In other embodiments, in the moieties of formula (I) represented by compounds (XV), (XVI), (XVII) and (XVIII) in List 7 R³ is —CF₃, —OCF₃, —CH₃, ethyl, or —C≡CH. It has been found that examples of such compounds which show excellent activity in the assays of the invention include formula (XV) in which R³ is para-Cl, formula (XV) in which R³ is meta-Cl, formula (XV) in which R³ is para-CH₃, formula (XVI) in which R³ is para-Cl, formula (XV) in which R³ is meta-Cl, formula (XVII) in which R³ is para-Cl, formula (XV) in which R³ is para-OCF₃, formula (XV) in which R³ is para-CF₃, formula (XV) in which R³ is para-C≡CH, formula (XV) in which R³ is ortho-CH₃, formula (XVIII) in which R³ is para-OCF₃, formula (XVIII) in which R³ is para-CF₃.

In a further embodiment of the present invention, the moieties of formula (I) are represented by the formulae of List 8, where R⁴, R⁵, R⁷ and R⁸ are independently selected from the group consisting of H, —CH₃, C₂ₜₒ₄alkyl, halogen, hydroxyl, —OCH₃, —OC₂ₜₒ₄alkyl, —CF₃, —OCF₃, —NH₂, —CH₂NH₂, —N(CH₃)₂, —NO₂, —CH₂OH, —CO₂CH₃, —CO₂C₂ₜₒ₄alkyl, —CO₂H, —N(alkyl)₂ where the two alkyl groups are independently selected from —CH₃ or C₂ₜₒ₄alkyl, —NH(alkyl) where the alkyl group is selected from —CH₃ or C₂ₜₒ₄alkyl, 4-morpholinyl, 1-piperidinyl, 4H-piperazinyl, 4-C₁ₜₒ₄alkyl-piperazinyl, and 4-C₃ₜₒ₆cycloalkyl-piperazinyl, preferably independently selected from the group consisting of H, —CH₃, C₂ₜₒ₄alkyl, iso-propyl, tert-butyl, halogen wherein halogen is preferably F or Cl or Br, hydroxyl, —OCH₃, —CF₃, —OCF₃, —N(CH₃)₂, —NO₂, and 4-methylpiperazinyl, more preferably independently selected from the group consisting of H, —CH₃, —CH₂CH₃, iso-propyl, —N(CH₃)₂, halogen wherein halogen is preferably F or Cl or Br, —OCH₃, —CF₃, and —OCF₃, and the furan ring may be optionally further substituted, preferably by one or more substituents independently selected from —CH₃, C₂ₜₒ₄alkyl, halogen, —OCH₃, and —OC₂ₜₒ₄alkyl, preferably by one or more substituents independently selected from —CH₃, C₂ₜₒ₄alkyl, and halogen, most preferably by one or more —CH₃ substituents.

List 8

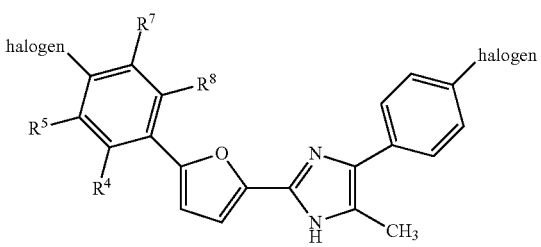

(XIX)

In some embodiments, in the formulae of List 8 one of R⁴, R⁵, R⁷ or R⁸ is —CF₃ or —OCF₃. In one aspect of the embodiment, one of R⁴, R⁵, R⁷ or R⁸ is —CF₃. In another aspect of the embodiment, one of R⁴, R⁵, R⁷ or R⁸ is —OCF₃. The two groups labeled "halogen" in formula (XIX), i.e. the groups corresponding respectively to an R⁶ substituent and an R³ substituent, are preferably independently selected from the group consisting of F, Cl, and Br. In some embodiments, the group labeled "halogen" in formula (XIX) which corresponds to an R⁶ substituent is Cl. In some embodiments, the group labeled "halogen" in formula (XIX) which corresponds to an R⁶ substituent is F. In some embodiments, the group labeled "halogen" in formula (XIX) which corresponds to an R⁶ substituent is Br. In some embodiments, the group labeled "halogen" in formula (XIX) which corresponds to an R³ substituent is Br. In some embodiments, the group labeled "halogen" in formula (XIX) which corresponds to an R³ substituent is Cl. In some embodiments, the group labeled "halogen" in formula (XIX) which corresponds to an R³ substituent is F. In some embodiments, the group labeled "halogen" in formula (XIX) which corresponds to an R⁶ substituent is Cl and the group labeled "halogen" in formula (XIX) which corresponds to an R³ substituent is Cl. In some embodiments, the group labeled "halogen" in formula (XIX) which corresponds to an R⁶ substituent is Cl and the group labeled "halogen" in formula (XIX) which corresponds to an R³ substituent is Br. In some embodiments, the group labeled "halogen" in formula (XIX) which corresponds to an R⁶ substituent is Cl and the group labeled "halogen" in formula (XIX) which corresponds to an R³ substituent is F. In some embodiments, the group labeled "halogen" in formula (XIX) which corresponds to an R⁶ substituent is F and the group labeled "halogen" in formula (XIX) which corresponds to an R³ substituent is Cl. In some embodiments, the group labeled "halogen" in formula (XIX) which corresponds to an R⁶ substituent is F and the group labeled "halogen" in formula (XIX) which corresponds to an R³ substituent is Br. In some embodiments, the group labeled "halogen" in formula (XIX) which corresponds to an R⁶ substituent is F and the group labeled "halogen" in formula (XIX) which corresponds to an R³ substituent is F. In some embodiments, the group labeled "halogen" in formula (XIX) which corresponds to an R⁶ substituent is Br and the group labeled "halogen" in formula (XIX) which corresponds to an R³ substituent is Cl. In some embodiments, the group labeled "halogen" in formula (XIX) which corresponds to an R⁶ substituent is Br and the group labeled "halogen" in formula (XIX) which corresponds to an R³ substituent is Br. In some embodiments, the group labeled "halogen" in formula (XIX) which corresponds to an R⁶ substituent is Br and the group labeled "halogen" in formula (XIX) which corresponds to an R³ substituent is F.

The compounds described in lists 7 and 8 may find particular use in the treatment of microbial infections caused by a wide spectrum of gram-positive bacteria including Enterococci, for example *Enterococcus faecium* or *Enterococcus faecalis*.

In some embodiments of the invention, the moiety of formula (I) is represented by the formula (XIXa) shown in List 9.

List 9

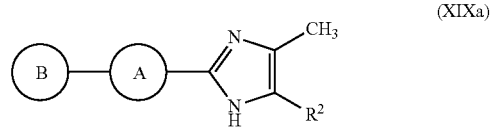

(XIXa)

In the moiety of List 9, group A and group B are as defined for formula (I) and R² is an alkyl group selected from the group consisting of C₃ₜₒ₆alkyl and C₃ₜₒ₆cycloalkyl, and is preferably selected from the group consisting of n-propyl, n-butyl, and iso-butyl. In some embodiments R² is n-propyl. In some embodiments R² is n-butyl. In some embodiments R² is iso-butyl.

In some embodiments of the invention in which R¹ is aryl, heteroaryl, or benzyl or benzyl substituted on the phenyl ring, and Y is C, R² is H.

In some embodiments of the invention in which R¹ is aryl, heteroaryl, or benzyl or benzyl substituted on the phenyl ring, and Y is C, R² is —CH₃.

In some embodiments of the invention in which $R^1$ is aryl, heteroaryl, or benzyl or benzyl substituted on the phenyl ring, and Y is C, $R^2$ is —CH$_2$N(CH$_3$)$_2$.

In some embodiments of the invention in which $R^1$ is aryl, heteroaryl, or benzyl or benzyl substituted on the phenyl ring, and Y is C, $R^2$ is halogen, in particular chlorine.

In some embodiments of the invention in which $R^2$ is aryl, heteroaryl, or benzyl or benzyl substituted on the phenyl ring, and Y is C, $R^1$ is H.

In some embodiments of the invention in which $R^2$ is aryl, heteroaryl, or benzyl or benzyl substituted on the phenyl ring, and Y is C, $R^1$ is —CH$_3$.

In some embodiments of the invention in which $R^2$ is aryl, heteroaryl, or benzyl or benzyl substituted on the phenyl ring, and Y is C, $R^1$ is —CH$_2$N(CH$_3$)$_2$.

In some embodiments of the invention in which $R^2$ is aryl, heteroaryl, or benzyl or benzyl substituted on the phenyl ring, and Y is C, $R^1$ is halogen, in particular chlorine.

In some embodiments of the invention, the group representing B in the moiety of formula (I) is a 2-chloro-4-trifluoromethylphenyl group. In some embodiments of the invention, the group representing B in the moiety of formula (I) is a 2-chloro-4-trifluoromethoxyphenyl group.

In some embodiments of the invention, the group representing B in the moiety of formula (I) is a 3-chloro-4-trifluoromethylphenyl group. In some embodiments of the invention, the group representing B in the moiety of formula (I) is a 3-chloro-4-trifluoromethoxyphenyl group.

In some embodiments of the invention, the group representing B in the moiety of formula (I) is a 4-chloro-3-trifluoromethylphenyl group. In some embodiments of the invention, the group representing B in the moiety of formula (I) is a 4-chloro-3-trifluoromethoxyphenyl group.

In some preferred embodiments of the invention, when the group representing A is a furan joined at the 2-position of the furan ring to the group representing B and joined at the 5-position of the furan ring to the 5-membered heterocyclic ring which is substituted with $R^1$ and $R^2$ (i.e. A is furan-2,5-diyl), the furan ring carries no further substituents, i.e. the furan moiety representing A comprises two unsubstituted positions on the furan ring.

In any of the formulae (IV) to (VIII) or in any of the formulae of lists 1 to 8, the moiety representing

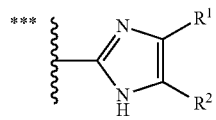

of formula (I), where *** is the point of connection to A, may be replaced with the moiety

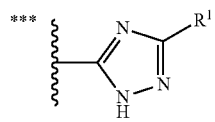

with $R^1$ being as defined for formula (I).

In a preferred embodiment, the compounds of the invention comprise at least one F atom. In some embodiments, the compounds of the invention comprise at least three F atoms. Further, the compounds of the invention may comprise at least one or more F atoms and/or Cl atoms. In some embodiments, the compounds of the invention comprise at least two Cl atoms. In some embodiments, the compounds of the invention comprise at least two O atoms. In some embodiments, the compounds of the invention comprise at least three N atoms. In some embodiments, the compounds of the invention comprise at least one —CH$_3$ group. In some embodiments, the compounds of the invention comprise at least one —CF$_3$ or —OCF$_3$ group. In some embodiments, the compounds of the invention comprise at least one —CF$_3$ or —OCF$_3$ group and at least one halogen atom. In some embodiments, the compounds of the invention comprise at least one —CF$_3$ or —OCF$_3$ group and at least one Cl atom. In some embodiments, the compounds of the invention comprise at least one —CF$_3$ or —OCF$_3$ group and at least one F atom. In some embodiments, the compounds of the invention comprise at least one —CF$_3$ or —OCF$_3$ group and at least one Br atom. In some embodiments, the compounds of the invention comprise at least one —CF$_3$ or —OCF$_3$ group and at least one —CH$_3$ group.

In some embodiments of the present invention, the number of carbon atoms in the group representing $R^1$ differs from the number of carbon atoms in the group representing $R^2$ by one carbon atom. In some embodiments of the present invention, the number of carbon atoms in the group representing $R^1$ differs from the number of carbon atoms in the group representing $R^2$ by two carbon atoms. In some embodiments of the present invention, the number of carbon atoms in the group representing $R^1$ differs from the number of carbon atoms in the group representing $R^2$ by three carbon atoms. In some embodiments of the present invention, the number of carbon atoms in the group representing $R^1$ differs from the number of carbon atoms in the group representing $R^2$ by four carbon atoms. In some embodiments of the present invention, the number of carbon atoms in the group representing $R^1$ differs from the number of carbon atoms in the group representing $R^2$ by five carbon atoms. In some embodiments of the present invention, the number of carbon atoms in the group representing $R^1$ differs from the number of carbon atoms in the group representing $R^2$ by six carbon atoms. In some embodiments of the present invention, the number of carbon atoms in the group representing $R^1$ differs from the number of carbon atoms in the group representing $R^2$ by seven carbon atoms. In some embodiments of the present invention, the number of carbon atoms in the group representing $R^1$ differs from the number of carbon atoms in the group representing $R^2$ by eight carbon atoms. In some embodiments of the present invention, the number of carbon atoms in the group representing $R^1$ differs from the number of carbon atoms in the group representing $R^2$ by nine carbon atoms. In some embodiments of the present invention, the number of carbon atoms in the group representing $R^1$ differs from the number of carbon atoms in the group representing $R^2$ by ten carbon atoms. In some embodiments of the present invention, the number of carbon atoms in the group representing $R^1$ differs from the number of carbon atoms in the group representing $R^2$ by eleven carbon atoms. In some embodiments of the present invention, the number of carbon atoms in the group representing $R^1$ differs from the number of carbon atoms in the group representing $R^2$ by twelve carbon atoms.

In the compounds of the present invention, $R^1$ and $R^2$ can be connected to form a four-, five- or six-membered non-aromatic carbocyclic ring thus providing a fused bicyclic moiety in which one or more of the carbon atoms of the ring comprising groups $R^1$ and $R^2$ is optionally replaced by a heteroatom selected from O, N, or S. Accordingly, fully aromatic bicycles, i.e. bicycles in which both rings are aromatic, do not fall under the present invention. For example, $R^1$ and $R^2$ cannot be connected to form a phenyl ring, thus giving rise to a benzimidazole.

The bond linking the ring bearing the substituents $R^1$ and $R^2$ of the compounds of the present invention to the rings represented by A is preferably a carbon-carbon (C—C) single bond.

In the present invention, A is aryl or heteroaryl. A is therefore an aromatic ring. "Aromatic" in the context of the present invention means that, at ambient (room) temperature (20° C.), the corresponding ring exists in the aromatic form (in the case of tautomers, in the aromatic tautomeric form) preferably to the degree of at least 10, 20, 30, 40, 50, 60, 70, 80, or 90%. Preferably, "aromatic" means that the corresponding ring exists at room temperature in the aromatic form to the degree of at least 95%, more preferably at least 99%, still more preferably at least 99.5% or at least 99.9%.

When the A ring is substituted in the compounds of the present invention, it is preferably not substituted with an acyl substituent, i.e. it is preferred that no atom of the A ring is directly bonded to a carbonyl group.

In the compounds of the present invention, the bond linking the groups corresponding to A and B in formula (I) is preferably a single covalent bond and may be, for example, a C—C single bond, a C—N single bond, or a N—C single bond.

It is preferred that $R^1$ and $R^2$ are not both aryl or both phenyl, e.g. if $R^1$ is phenyl, $R^2$ is preferably not phenyl or aryl. Preferably, if $R^1$ is unsubstituted phenyl, $R^2$ is not unsubstituted phenyl. Preferably, if $R^1$ is substituted phenyl, $R^2$ is not substituted phenyl. Preferably, if $R^1$ is substituted phenyl, $R^2$ is not unsubstituted phenyl. Preferably, if $R^1$ is unsubstituted phenyl, $R^2$ is not substituted phenyl. Preferably, if $R^1$ is substituted aryl, $R^2$ is not substituted aryl. Preferably, if $R^1$ is unsubstituted aryl, $R^2$ is not unsubstituted aryl. Preferably, if $R^1$ is substituted aryl, $R^2$ is not unsubstituted aryl. Preferably, if $R^1$ is unsubstituted aryl, $R^2$ is not substituted aryl.

$R^1$ and $R^2$ are preferably not both heteroaryl, i.e. if $R^1$ is heteroaryl, $R^2$ is preferably not heteroaryl. Preferably, if $R^1$ is unsubstituted heteroaryl, $R^2$ is not unsubstituted heteroaryl. Preferably, if $R^1$ is substituted heteroaryl, $R^2$ is not substituted heteroaryl. Preferably, if $R^1$ is substituted heteroaryl, $R^2$ is not unsubstituted heteroaryl. Preferably, if $R^1$ is unsubstituted heteroaryl, $R^2$ is not substituted heteroaryl.

$R^1$ and $R^2$ are preferably not both aromatic rings, e.g. if $R^1$ is aryl, $R^2$ is preferably not heteroaryl. Preferably, if $R^1$ is substituted or unsubstituted heteroaryl, $R^2$ is not substituted or unsubstituted aryl or phenyl. Preferably, if $R^1$ is substituted heteroaryl, $R^2$ is not substituted or unsubstituted aryl or phenyl. Preferably, if $R^1$ is unsubstituted heteroaryl, $R^2$ is not substituted or unsubstituted aryl or phenyl.

$R^1$ and $R^2$ are preferably not both benzyl optionally substituted on the phenyl ring, i.e. if $R^1$ is benzyl optionally substituted on the phenyl ring, $R^2$ is preferably not benzyl optionally substituted on the phenyl ring. Preferably, if $R^1$ is benzyl unsubstituted on the phenyl ring, $R^2$ is not benzyl unsubstituted on the phenyl ring. Preferably, if $R^1$ is benzyl substituted on the phenyl ring, $R^2$ is not benzyl substituted on the phenyl ring. Preferably, if $R^1$ is benzyl substituted on the phenyl ring, $R^2$ is not benzyl unsubstituted on the phenyl ring. Preferably, if $R^1$ is benzyl unsubstituted on the phenyl ring, $R^2$ is not benzyl substituted on the phenyl ring.

If one of $R^1$ or $R^2$ is benzyl optionally substituted on the phenyl ring, the other of $R^1$ or $R^2$ is preferably not substituted or unsubstituted phenyl. If one of $R^1$ or $R^2$ is benzyl optionally substituted on the phenyl ring, the other of $R^1$ or $R^2$ is preferably not substituted or unsubstituted aryl. If one of $R^1$ or $R^2$ is benzyl optionally substituted on the phenyl ring, the other of $R^1$ or $R^2$ is preferably not substituted or unsubstituted heteroaryl. If one of $R^1$ or $R^2$ is benzyl optionally substituted on the phenyl ring, the other of $R^1$ or $R^2$ is preferably not a substituted or unsubstituted aromatic group.

In the compounds of the present invention, if one of $R^1$ or $R^2$ is H, the other of $R^1$ or $R^2$ is preferably not $CH_3$, or $C_{2 to 6}$alkyl.

The imidazole/triazole ring (i.e. the ring substituted with $R^1$ and $R^2$) and the B ring of the compounds of the present invention preferably do not constitute substituents on the A ring of the compounds of the present invention exhibiting a relative 1,2-substitution pattern, i.e. they are preferably not respectively bonded to atoms of the A ring (irrespective of IUPAC numbering of the atoms of the given ring) which are directly adjacent to one another. Preferably the B ring and the imidazole ring constitute substituents exhibiting a relative 1,3-, preferably a relative 1,4-substitution pattern, e.g. in the case of A being a furan ring these substituents are present at the 4- and 2-, or 2- and 4-positions respectively, preferably at the 2- and 5-, or 5- and 2-positions of the furan ring.

When in the compounds of the present invention the A ring is unsubstituted or substituted pyrrazole, the A ring preferably does not constitute a pyrrazole ring with a free NH group, i.e. it is preferred that the valency of all N atoms in the pyrrazole ring is completely satisfied through bonding to non-hydrogen atoms.

When in the compounds of the present invention the A ring is unsubstituted or substituted pyrrazole, the A ring is preferably not directly joined to the group representing the B ring of the compounds of the present invention via a C-atom of the pyrrazole ring.

When in the compounds of the present invention the A ring is unsubstituted or substituted pyrrazole, the imidazole/triazole ring (i.e. the ring substituted with $R^1$ and $R^2$) and the group representing the B ring of the compounds of the present invention are preferably not joined to the pyrrazole at its 3- and 5-positions or 5- and 3-positions.

When in the compounds of the present invention the A ring is unsubstituted or substituted pyrrazole, the A ring is preferably not substituted with a hydroxyl group.

In the compounds of the present invention, the B ring is preferably not an unsubstituted 2-thiophene ring, more preferably not a 2-thiophene ring, still more preferably not an unsubstituted thiophene ring, still more preferred not a thiophene ring.

In the compounds of the present invention, the B ring is preferably not a 5-membered S-containing heteroaryl ring. In the compounds of the present invention, the group representing the B ring is preferably not a 5-membered heteroaryl ring containing only one heteroatom.

In the compounds of the present invention, the B ring is preferably not a 1-indolyl group, more preferably not a substituted 1-indolyl group.

In the compounds of the present invention, the B ring is preferably not a 1-indolyl group when the group representing the A ring is a 2,4-disubstituted thiazole. In the compounds of the present invention, the B ring is preferably not a 1-indolyl group when the group representing the A ring contains two heteroatoms.

In the compounds of the present invention, when one of $R^1$ or $R^2$ is H the group representing the B ring is preferably not a 1-indolyl group.

In the compounds of the present invention, when the A ring is a pyrrole ring it is preferably not directly substituted with both an O-atom and a N-atom. In the compounds of the present invention, when the A ring is a pyrrole ring it is preferably substituted with no more than one additional substituent. In the compounds of the present invention, when the A ring is a pyrrole ring it is preferably not a hydroxyl-substituted pyrrole ring. In the compounds of the present invention, when the A ring is a pyrrole ring it is preferably not a $NH_2$-substituted pyrrole ring.

In the compounds of the present invention, the A ring is preferably not substituted with an aromatic ring which is other than an aromatic ring belonging to B or the aromatic ring bearing the substituents $R^1$ and $R^2$.

In the compounds of the present invention, the A ring is preferably not a tetrasubstituted pyrrazole, more preferably not a tetrasubstituted ring.

When in the compounds of the present invention the A ring is an unsubstituted or substituted pyrrazole, the imidazole/triazole ring (i.e. the ring substituted with $R^1$ and $R^2$) and the B ring of the compounds of the present invention are preferably not respectively joined to the pyrrazole at its 1- and 3-positions or 3- and 1-positions.

In the compounds of the present invention, the A ring is preferably not an oxazole ring exhibiting substituents at both the 4- and 5-positions.

In the compounds of the present invention, when $R^1$ or $R^2$ is aryl, they are preferably selected from the group consisting of phenyl, naphthyl, anthracyl, and penanthracyl, where each of these groups can be substituted or unsubstituted. When $R^1$ or $R^2$ is aryl they are preferably substituted or unsubstituted phenyl.

When $R^1$ or $R^2$ is heteroaryl, they are preferably selected from the group consisting of 5-membered single ring heteroaryl, 6-membered single ring heteroaryl, and bicyclic fused ring heteroaryl.

In the compounds of the present invention, when the A ring is aryl it is preferably selected from the group consisting of phenyl, naphthyl, anthracyl, and penanthracyl, where each of these groups can be substituted or unsubstituted. When A is aryl it is preferably substituted or unsubstituted phenyl or naphthyl.

In the compounds of the present invention, when the A ring is heteroaryl, it is preferably selected from the group consisting of 5-membered (single ring) heteroaryl, 6-membered (single ring heteroaryl), and bicyclic fused ring heteroaryl. In the compounds of the present invention, when the A ring is heteroaryl, it is preferably 5-membered (single ring) heteroaryl.

In the compounds of the present invention, when the B ring is aryl, it is preferably selected from the group consisting of phenyl, naphthyl, anthracyl, and penanthracyl, where each of these groups can be substituted or unsubstituted. When B is aryl, it is preferably substituted or unsubstituted phenyl or naphthyl.

In the compounds of the present invention, when the B ring is heteroaryl, it is preferably selected from the group consisting of 5-membered (single ring) heteroaryl, 6-membered (single ring) heteroaryl, and bicyclic fused ring heteroaryl.

When B is bicyclic fused ring heteroaryl, it is preferably selected from the group consisting of indolyl (e.g. 1-, 2-, 3-, 4-, 5-, 6-, or 7-indolyl), benzofuranyl (e.g. 2-, 3-, 4-, 5-, 6-, or 7-benzofuranyl), indazolyl (e.g. 1-, 3-, 4-, 5-, 6-, or 7-indazolyl), oxindolyl (e.g. 1-, 3-, 4-, 5-, 6-, or 7-oxindolyl), benzimidazolyl (e.g. 1-, 2-, 4-, 5-, 6-, or 7-benzimidazolyl), benzothiophenyl (e.g. 2-, 3-, 4-, 5-, 6-, or 7-benzothiophenyl), benzoxazolyl (e.g. 2-, 4-, 5-, 6-, or 7-benzoxazolyl), benzo[d]thiazolyl (e.g. 2-, 4-, 5-, 6-, or 7-benzo[d]thiazolyl), quinolinyl (e.g. 2-, 3-, 4-, 5-, 6-, 7-, or 8-quinolinyl), isoquinolinyl (e.g. 1-, 3-, 4-, 5-, 6-, 7-, or 8-isoquinolinyl), coumarinyl (e.g. 3-, 4-, 5-, 6-, 7-, or 8-coumarinyl), purinyl (e.g. 2-, 6-, 8-, or 9-purinyl), 1,2-diazanaphthyl (e.g. 3-, 4-, 5-, 6-, 7-, 8-(1,2-diazanaphth)-yl), 1,3-diazanaphthyl (e.g. 2-, 4-, 5-, 6-, 7-, 8-(1,3-diazanaphth)-yl), 1,4-diazanaphthyl (e.g. 2-, 3-, 5-, 6-, 7-, 8-(1, 4-diazanaphth)-yl), 1,5-diazanaphthyl (e.g. 2-, 3-, 4-, 6-, 7-, 8-(1,5-diazanaphth)-yl), 1,6-diazanaphthyl (e.g. 2-, 3-, 4-, 5-, 7-, 8-(1,6-diazanaphth)-yl), 1,7-diazanaphthyl (e.g. 2-, 3-, 4-, 5-, 6-, 8-(1,7-diazanaphth)-yl), 1,8-diazanaphthyl (e.g. 2-, 3-, 4-, 5-, 6-, 7-(1,8-diazanaphth)-yl), 2,3-diazanaphthyl (e.g. 1-, 4-, 5-, 6-, 7-, 8-(2,3-diazanaphth)-yl), 2,6-diazanaphthyl (e.g. 1-, 3-, 4-, 5-, 7-, 8-(2,6-diazanaphth)-yl), and 2,7-diazanaphthyl (e.g. 1-, 3-, 4-, 5-, 6-, 8-(2,7-diazanaphth)-yl). More preferably when B is bicyclic fused ring heteroaryl, it is selected from the group consisting of indolyl (e.g. 1-, 2-, 3-, 4-, 5-, 6-, or 7-indolyl), benzofuranyl (e.g. 2-, 3-, 4-, 5-, 6-, or 7-benzofuranyl), indazolyl (e.g. 1-, 3-, 4-, 5-, 6-, or 7-indazolyl), and oxindolyl (e.g. 1-, 3-, 4-, 5-, 6-, or 7-oxindolyl).

In an exemplary aspect of the invention, when the groups described herein are said to be "substituted or unsubstituted", "optionally substituted", or "substituted", when substituted, they may be preferably substituted with one or more of any substituent. Examples of such substituents are those found in the exemplary compounds and embodiments disclosed herein, as well as, for example, halo (e.g., chloro, iodo, bromo, or fluoro); $C_{1- \text{ or } 2-8}$ alkyl; $C_{1- \text{ or } 2-8}$ alkyl substituted with one or more substituents independently selected from OH, $NH_2$, $NHCH_3$, $N(CH_3)_2$, $NH(C_{2-6}\text{alkyl})$, $N(C_{2-6}\text{alkyl})_2$, SH, $SCH_3$, $SC_{2-6}\text{alkyl}$, CN, $CONH_2$, $CO_2H$, $NO_2$, $SO_2H$, $SO_2CH_3$, and $SO_2\text{Aryl}$; $C_{2-8}$ alkenyl; $C_{2-8}$ alkynyl; hydroxyl; $C_{1- \text{ or } 2-8}$ alkoxyl; —$NH_2$; —$NHCH_3$; —$NHC_{2-6}$ alkyl; —$N(CH_3)_2$; —$N(C_{2-6}$ alkyl$)_2$; amino (primary, secondary, or tertiary); —$NO_2$; —SH; —$SCH_3$; —$SC_{2-6}$ alkyl; —C=NH; —C=$NCH_3$; —C=$NC_{2-6}$alkyl; —CN; —$CONH_2$; —$CONHCH_3$; —$CONHC_{2-6}$alkyl; —$CON(CH_3)_2$; —$CON(C_{2-6}$ alkyl$)_2$; phosphonato; —P(O)(OH)$_2$; —P(O)(OH)(OCH$_3$); —P(O)(OCH$_3$)$_2$; —P(O)(OH)(OC$_{2-6}$ alkyl); —P(O)(OC$_{2-6}$ alkyl)$_2$; —OP(O)(OH)$_2$; —OP(O)(OH)(OCH$_3$); —OP(O)(OCH$_3$)$_2$; —OP(O)(OH)(OC$_{2-6}$ alkyl); —OP(O)(OC$_{2-6}$ alkyl)$_2$; phosphine; —P(CH$_3$)$_2$; —P(C$_{2-6}$ alkyl)$_2$; —P(C$_{3-6}$ cycloalkyl)$_2$; —P(Aryl)$_2$; —P(Phenyl)$_2$; —P(Heteroaryl)$_2$; carboxyl; —CO$_2$H; carbamoyl; —OCONH$_2$; —OCONHCH$_3$; —OCON(CH$_3$)C$_{2-6}$ alkyl; —OCON(CH$_3$)C$_{3-6}$ cycloalkyl; —OCON(CH$_3$)Aryl; —OCON(CH$_3$)Phenyl; —OCON(CH$_3$)Heteroaryl; —OCON(CH$_3$)$_2$; —OCONHC$_{2-6}$ alkyl; —OCON(C$_{2-6}$ alkyl)C$_{3-6}$ cycloalkyl; —OCON(C$_{2-6}$ alkyl)Aryl; —OCON (C$_{2-6}$ alkyl)Phenyl; —OCON(C$_{2-6}$ alkyl)Heteroaryl; —OCON(C$_{2-6}$ alkyl)$_2$; —OCONHC$_{3-6}$ cycloalkyl; —OCON(C$_{3-6}$ cycloalkyl)Aryl; —OCON(C$_{3-6}$ cycloalkyl) Phenyl; —OCON(C$_{3-6}$ cycloalkyl)Heteroaryl; —OCON (C$_{3-6}$ cycloalkyl)$_2$; —OCONHAryl; —OCON(Aryl)Phenyl; —OCON(Aryl)Heteroaryl; —OCON(Aryl)$_2$; —OCONH-Phenyl; —OCON(Phenyl)Heteroaryl; —OCON(Phenyl)$_2$; —OCONHHeteroaryl; —OCON(Heteroaryl)$_2$; —OCON (CH$_3$)$_2$; —OCON(C$_{2-6}$ alkyl)$_2$; —OCONCH$_3$(C$_{2-6}$ alkyl); —NHCOOCH$_3$; —NHCOOC$_{2-6}$ alkyl; —NHCOOC$_{3-6}$cycloalkyl; —NHCOOAryl; —NHCOOPhenyl; —NHCOO (Heteroaryl); —N(CH$_3$)COOCH$_3$; —N(CH$_3$)COOC$_{2-6}$ alkyl; —N(CH$_3$)COOC$_{3-6}$cycloalkyl; —N(CH$_3$)COOAryl; —N(CH$_3$)COOPhenyl; —N(CH$_3$)COO(Heteroaryl); —N(C$_{2-6}$ alkyl)COOCH$_3$; —N(C$_{2-6}$ alkyl)COOC$_{2-6}$ alkyl; —N(C$_{2-6}$ alkyl)COOC$_{3-6}$cycloalkyl; —N(C$_{2-6}$ alkyl) COOAryl; —N(C$_{2-6}$ alkyl)COOPhenyl; —N(C$_{2-6}$ alkyl) COO(Heteroaryl); —N(COOC$_{3-6}$cycloalkyl)COOCH$_3$;

—N(COOC$_{3-6}$cycloalkyl)COOC$_{2-6}$ alkyl; —N(COOC$_{3-6}$cycloalkyl)COOC$_{3-6}$cycloalkyl; —N(COOC$_{3-6}$cycloalkyl)COOAryl; —N(COOC$_{3-6}$cycloalkyl)COOPhenyl; —N(COOC$_{3-6}$cycloalkyl)COO(Heteroaryl); —N(Aryl)COOCH$_3$; —N(Aryl)COOC$_{2-6}$ alkyl; —N(Aryl)COOC$_{3-6}$ cycloalkyl; —N(Aryl)COOAryl; —N(Aryl)COOPhenyl; —N(Aryl)COO(Heteroaryl); —N(Phenyl)COOCH$_3$; —N(Phenyl)COOC$_{2-6}$ alkyl; —N(Phenyl)COOC$_{3-6}$cycloalkyl; —N(Phenyl)COOAryl; —N(Phenyl)COOPhenyl; —N(Phenyl)COO(Heteroaryl); —N(Heteroaryl)COOCH$_3$; —N(Heteroaryl)COOC$_{2-6}$ alkyl; —N(Heteroaryl)COOC$_{3-6}$ cycloalkyl; —N(Heteroaryl)COOAryl; —N(Heteroaryl)COOPhenyl; —N(Heteroaryl)COO(Heteroaryl); —NCOOCH$_3$; —N(CH$_3$)COOC$_{2-6}$ alkyl; —N(C$_{2-6}$ alkyl)COOCH$_3$; —N(C$_{2-6}$ alkyl)COOC$_{2-6}$ alkyl; carbamate; acetal; urea; —NHCONH$_2$; —NHCONH(CH$_3$); NHCON(CH$_3$)$_2$; —NHCONH(C$_{2-6}$ alkyl); —NHCON(C$_{2-6}$ alkyl)$_2$; —NHCONHC$_{3-6}$ cycloalkyl; —NHCON(C$_{3-6}$ cycloalkyl)$_2$; —NHCONHAryl; —NHCON(Aryl)$_2$; —NHCONHPhenyl; —NHCON(Phenyl)$_2$; —NHCONHHeteroaryl; —NHCON(Heteroaryl)$_2$; —NHCON(CH$_3$)(C$_{2-6}$ alkyl); —NHCON(CH$_3$)(C$_{3-6}$ cycloalkyl); —NHCON(CH$_3$)(Aryl); —NHCON(CH$_3$)(Phenyl); —NHCON(CH$_3$)(Heteroaryl); —NHCON(C$_{2-6}$ alkyl)(C$_{3-6}$ cycloalkyl); —NHCON(C$_{2-6}$ alkyl)(Aryl); —NHCON(C$_{2-6}$ alkyl)(Phenyl); —NHCON(C$_{2-6}$ alkyl)(Heteroaryl); —NHCON(C$_{3-6}$ cycloalkyl)(Aryl); —NHCON(C$_{3-6}$ cycloalkyl)(Phenyl); —NHCON(C$_{3-6}$ cycloalkyl)(Heteroaryl); —NHCON(Aryl)(Phenyl); —NHCON(Aryl)(Heteroaryl); —NHCON(Phenyl)(Heteroaryl); —N(CH$_3$)CONH$_2$; —N(CH$_3$)CONH(CH$_3$); N(CH$_3$)CON(CH$_3$)$_2$; —N(CH$_3$)CONH(C$_{2-6}$ alkyl); —N(CH$_3$)CON(C$_{2-6}$ alkyl)$_2$; —N(CH$_3$)CONHC$_{3-6}$ cycloalkyl; —N(CH$_3$)CON(C$_{3-6}$ cycloalkyl)$_2$; —N(CH$_3$)CONHAryl; —N(CH$_3$)CON(Aryl)$_2$; —N(CH$_3$)CONHPhenyl; —N(CH$_3$)CON(Phenyl)$_2$; —N(CH$_3$)CONHHeteroaryl; —N(CH$_3$)CON(Heteroaryl)$_2$; —N(CH$_3$)CON(CH$_3$)(C$_{2-6}$ alkyl); —N(CH$_3$)CON(CH$_3$)(C$_{3-6}$ cycloalkyl); —N(CH$_3$)CON(CH$_3$)(Aryl); —N(CH$_3$)CON(CH$_3$)(Phenyl); —N(CH$_3$)CON(CH$_3$)(Heteroaryl); —N(CH$_3$)CON(C$_{2-6}$ alkyl)(C$_{3-6}$ cycloalkyl); —N(CH$_3$)CON(C$_{2-6}$ alkyl)(Aryl); —N(CH$_3$)CON(C$_{2-6}$ alkyl)(Phenyl); —N(CH$_3$)CON(C$_{2-6}$ alkyl)(Heteroaryl); —N(CH$_3$)CON(C$_{3-6}$ cycloalkyl)(Aryl); —N(CH$_3$)CON(C$_{3-6}$ cycloalkyl)(Phenyl); —N(CH$_3$)CON(C$_{3-6}$ cycloalkyl)(Heteroaryl); —N(CH$_3$)CON(Aryl)(Phenyl); —N(CH$_3$)CON(Aryl)(Heteroaryl); —N(CH$_3$)CON(Phenyl)(Heteroaryl); —N(C$_{2-6}$ alkyl)CONH$_2$; —N(C$_{2-6}$ alkyl)CONH(CH$_3$); N(C$_{2-6}$ alkyl)CON(CH$_3$)$_2$; —N(C$_{2-6}$ alkyl)CONH(C$_{2-6}$ alkyl); —N(C$_{2-6}$ alkyl)CON(C$_{2-6}$ alkyl)$_2$; —N(C$_{2-6}$ alkyl)CONHC$_{3-6}$ cycloalkyl; —N(C$_{2-6}$ alkyl)CON(C$_{3-6}$ cycloalkyl)$_2$; —N(C$_{2-6}$ alkyl)CONHAryl; —N(C$_{2-6}$ alkyl)CON(Aryl)$_2$; —N(C$_{2-6}$ alkyl)CONHPhenyl; —N(C$_{2-6}$ alkyl)CON(Phenyl)$_2$; —N(C$_{2-6}$ alkyl)CONHHeteroaryl; —N(C$_{2-6}$ alkyl)CON(Heteroaryl)$_2$; —N(C$_{2-6}$ alkyl)CON(CH$_3$)(C$_{2-6}$ alkyl); —N(C$_{2-6}$ alkyl)CON(CH$_3$)(C$_{3-6}$ cycloalkyl); —N(C$_{2-6}$ alkyl)CON(CH$_3$)(Aryl); —N(C$_{2-6}$ alkyl)CON(CH$_3$)(Phenyl); —N(C$_{2-6}$ alkyl)CON(CH$_3$)(Heteroaryl); —N(C$_{2-6}$ alkyl)CON(C$_{2-6}$ alkyl)(C$_{3-6}$ cycloalkyl); —N(C$_{2-6}$ alkyl)CON(C$_{2-6}$ alkyl)(Aryl); —N(C$_{2-6}$ alkyl)CON(C$_{2-6}$ alkyl)(Phenyl); —N(C$_{2-6}$ alkyl)CON(C$_{2-6}$ alkyl)(Heteroaryl); —N(C$_{2-6}$ alkyl)CON(C$_{3-6}$ cycloalkyl)(Aryl); —N(C$_{2-6}$ alkyl)CON(C$_{3-6}$ cycloalkyl)(Phenyl); —N(C$_{2-6}$ alkyl)CON(C$_{3-6}$ cycloalkyl)(Heteroaryl); —N(C$_{2-6}$ alkyl)CON(Aryl)(Phenyl); —N(C$_{2-6}$ alkyl)CON(Aryl)(Heteroaryl); —N(C$_{2-6}$ alkyl)CON(Phenyl)(Heteroaryl); —N(C$_{3-6}$ cycloalkyl)CONH$_2$; —N(C$_{3-6}$ cycloalkyl)CONH(CH$_3$); N(C$_{3-6}$ cycloalkyl)CON(CH$_3$)$_2$; —N(C$_{3-6}$ cycloalkyl)CONH(C$_{2-6}$ alkyl); —N(C$_{3-6}$ cycloalkyl)CON(C$_{2-6}$ alkyl)$_2$; —N(C$_{3-6}$ cycloalkyl)CONHC$_{3-6}$ cycloalkyl; —N(C$_{3-6}$ cycloalkyl)CON(C$_{3-6}$ cycloalkyl)$_2$; —N(C$_{3-6}$ cycloalkyl)CONHAryl; —N(C$_{3-6}$ cycloalkyl)CON(Aryl)$_2$; —N(C$_{3-6}$ cycloalkyl)CONHPhenyl; —N(C$_{3-6}$ cycloalkyl)CON(Phenyl)$_2$; —N(C$_{3-6}$ cycloalkyl)CONHHeteroaryl; —N(C$_{3-6}$ cycloalkyl)CON(Heteroaryl)$_2$; —N(C$_{3-6}$ cycloalkyl)CON(CH$_3$)(C$_{2-6}$ alkyl); —N(C$_{3-6}$ cycloalkyl)CON(CH$_3$)(C$_{3-6}$ cycloalkyl); —N(C$_{3-6}$ cycloalkyl)CON(CH$_3$)(Aryl); —N(C$_{3-6}$ cycloalkyl)CON(CH$_3$)(Phenyl); —N(C$_{3-6}$ cycloalkyl)CON(CH$_3$)(Heteroaryl); —N(C$_{3-6}$ cycloalkyl)CON(C$_{2-6}$ alkyl)(C$_{3-6}$ cycloalkyl); —N(C$_{3-6}$ cycloalkyl)CON(C$_{2-6}$ alkyl)(Aryl); —N(C$_{3-6}$ cycloalkyl)CON(C$_{2-6}$ alkyl)(Phenyl); —N(C$_{3-6}$ cycloalkyl)CON(C$_{2-6}$ alkyl)(Heteroaryl); —N(C$_{3-6}$ cycloalkyl)CON(C$_{3-6}$ cycloalkyl)(Aryl); —N(C$_{3-6}$ cycloalkyl)CON(C$_{3-6}$ cycloalkyl)(Phenyl); —N(C$_{3-6}$ cycloalkyl)CON(C$_{3-6}$ cycloalkyl)(Heteroaryl); —N(C$_{3-6}$ cycloalkyl)CON(Aryl)(Phenyl); —N(C$_{3-6}$ cycloalkyl)CON(Aryl)(Heteroaryl); —N(C$_{3-6}$ cycloalkyl)CON(Phenyl)(Heteroaryl); —N(Aryl)CONH$_2$; —N(Aryl)CONH(CH$_3$); N(Aryl)CON(CH$_3$)$_2$; —N(Aryl)CONH(C$_{2-6}$ alkyl); —N(Aryl)CON(C$_{2-6}$ alkyl)$_2$; —N(Aryl)CONHC$_{3-6}$ cycloalkyl; —N(Aryl)CON(C$_{3-6}$ cycloalkyl)$_2$; —N(Aryl)CONHAryl; —N(Aryl)CON(Aryl)$_2$; —N(Aryl)CONHPhenyl; —N(Aryl)CON(Phenyl)$_2$; —N(Aryl)CONHHeteroaryl; —N(Aryl)CON(Heteroaryl)$_2$; —N(Aryl)CON(CH$_3$)(C$_{2-6}$ alkyl); —N(Aryl)CON(CH$_3$)(C$_{3-6}$ cycloalkyl); —N(Aryl)CON(CH$_3$)(Aryl); —N(Aryl)CON(CH$_3$)(Phenyl); —N(Aryl)CON(CH$_3$)(Heteroaryl); —N(Aryl)CON(C$_{2-6}$ alkyl)(C$_{3-6}$ cycloalkyl); —N(Aryl)CON(C$_{2-6}$ alkyl)(Aryl); —N(Aryl)CON(C$_{2-6}$ alkyl)(Phenyl); —N(Aryl)CON(C$_{2-6}$ alkyl)(Heteroaryl); —N(Aryl)CON(C$_{3-6}$ cycloalkyl)(Aryl); —N(Aryl)CON(C$_{3-6}$ cycloalkyl)(Phenyl); —N(Aryl)CON(C$_{3-6}$ cycloalkyl)(Heteroaryl); —N(Aryl)CON(Aryl)(Phenyl); —N(Aryl)CON(Aryl)(Heteroaryl); —N(Aryl)CON(Phenyl)(Heteroaryl); —N(Phenyl)CONH$_2$; —N(Phenyl)CONH(CH$_3$); N(Phenyl)CON(CH$_3$)$_2$; —N(Phenyl)CONH(C$_{2-6}$ alkyl); —N(Phenyl)CON(C$_{2-6}$ alkyl)$_2$; —N(Phenyl)CONHC$_{3-6}$ cycloalkyl; —N(Phenyl)CON(C$_{3-6}$ cycloalkyl)$_2$; —N(Phenyl)CONHAryl; —N(Phenyl)CON(Aryl)$_2$; —N(Phenyl)CONHPhenyl; —N(Phenyl)CON(Phenyl)$_2$; —N(Phenyl)CONHHeteroaryl; —N(Phenyl)CON(Heteroaryl)$_2$; —N(Phenyl)CON(CH$_3$)(C$_{2-6}$ alkyl); —N(Phenyl)CON(CH$_3$)(C$_{3-6}$ cycloalkyl); —N(Phenyl)CON(CH$_3$)(Aryl); —N(Phenyl)CON(CH$_3$)(Phenyl); —N(Phenyl)CON(CH$_3$)(Heteroaryl); —N(Phenyl)CON(C$_{2-6}$ alkyl)(C$_{3-6}$ cycloalkyl); —N(Phenyl)CON(C$_{2-6}$ alkyl)(Aryl); —N(Phenyl)CON(C$_{2-6}$ alkyl)(Phenyl); —N(Phenyl)CON(C$_{2-6}$ alkyl)(Heteroaryl); —N(Phenyl)CON(C$_{3-6}$ cycloalkyl)(Aryl); —N(Phenyl)CON(C$_{3-6}$ cycloalkyl)(Phenyl); —N(Phenyl)CON(C$_{3-6}$ cycloalkyl)(Heteroaryl); —N(Phenyl)CON(Aryl)(Phenyl); —N(Phenyl)CON(Aryl)(Heteroaryl); —N(Phenyl)CON(Phenyl)(Heteroaryl); —N(Heteroaryl)CONH$_2$; —N(Heteroaryl)CONH(CH$_3$); N(Heteroaryl)CON(CH$_3$)$_2$; —N(Heteroaryl)CONH(C$_{2-6}$ alkyl); —N(Heteroaryl)CON(C$_{2-6}$ alkyl)$_2$; —N(Heteroaryl)CONHC$_{3-6}$ cycloalkyl; —N(Heteroaryl)CON(C$_{3-6}$ cycloalkyl)$_2$; —N(Heteroaryl)CONHAryl; —N(Heteroaryl)CON(Aryl)$_2$; —N(Heteroaryl)CONHPhenyl; —N(Heteroaryl)CON(Phenyl)$_2$; —N(Heteroaryl)CONHHeteroaryl; —N(Heteroaryl)CON(Heteroaryl)$_2$; —N(Heteroaryl)CON(CH$_3$)(C$_{2-6}$ alkyl); —N(Heteroaryl)CON(CH$_3$)(C$_{3-6}$ cycloalkyl); —N(Heteroaryl)CON(CH$_3$)(Aryl); —N(Heteroaryl)CON(CH$_3$)(Phenyl); —N(Heteroaryl)CON(CH$_3$)(Heteroaryl); —N(Heteroaryl)CON(C$_{2-6}$ alkyl)(C$_{3-6}$ cycloalkyl); —N(Heteroaryl)CON(C$_{2-6}$ alkyl)(Aryl); —N(Heteroaryl)CON(C$_{2-6}$ alkyl)(Phenyl); —N(Heteroaryl)CON(C$_{2-6}$ alkyl)

(Heteroaryl); —N(Heteroaryl)CON(C$_{3-6}$ cycloalkyl)(Aryl); —N(Heteroaryl)CON(C$_{3-6}$ cycloalkyl)(Phenyl); —N(Heteroaryl)CON(C$_{3-6}$ cycloalkyl)(Heteroaryl); —N(Heteroaryl)CON(Aryl)(Phenyl); —N(Heteroaryl)CON(Aryl)(Heteroaryl); —N(Heteroaryl)CON(Phenyl)(Heteroaryl); —NHCONH(CH$_3$); —NHCON(CH$_3$)$_2$; —NHCONH(C$_{2-6}$ alkyl); —NHCON(C$_{2-6}$alkyl)$_2$; —NHCON(CH$_3$)(C$_{2-6}$ alkyl); —N(C$_{2-6}$ alkyl)CONH$_2$; —N(C$_{2-6}$ alkyl)CONH(CH$_3$); —N(C$_{2-6}$ alkyl)CON(CH$_3$)$_2$; —N(C$_{2-6}$ alkyl)CONH(C$_{2-6}$ alkyl); —N(C$_{2-6}$ alkyl)CON(C$_{2-6}$ alkyl)$_2$; —N(C$_{2-6}$ alkyl)CON(CH$_3$)(C$_{2-6}$ alkyl); thiocarbonyl; —C(S)CH$_3$; —C(S)C$_{2-6}$ alkyl; —C(S)C$_{3-6}$ cycloalkyl; —C(S)Aryl; —C(S)Phenyl; —C(S)Heteroaryl; sulfonyl; —SO$_2$CH$_3$; —SO$_2$C$_{2-6}$ alkyl; —SO$_2$C$_{3-6}$ cycloalkyl; —SO$_2$Aryl; —SO$_2$Ph; —SO$_2$Heteroaryl; sulfinyl; —SOCH$_3$; —SOC$_{2-6}$ alkyl; —SOC$_{3-6}$ cycloalkyl; —SOAryl; —SOPh; —SOHeteroaryl; sulfate; —OSO$_2$CH$_3$; —OSO$_2$C$_{2-6}$ alkyl; —OSO$_2$C$_{3-6}$ cycloalkyl; —OSO$_2$Aryl; —OSO$_2$Phenyl; —OSO$_2$Heteroaryl; sulfonamide; —SO$_2$NH$_2$; —SO$_2$NHCH$_3$; —SO$_2$NHC$_{2-6}$ alkyl; SO$_2$NHC$_{3-6}$ cycloalkyl; —SO$_2$NHAryl; —SO$_2$NHPh; —SO$_2$NHHeteroaryl; —SO$_2$N(CH$_3$)$_2$; —SO$_2$N(C$_{2-6}$ alkyl)$_2$; —SO$_2$N(C$_{3-6}$ cycloalkyl)$_2$; —SO$_2$N(Aryl)$_2$; —SO$_2$N(Ph)$_2$; —SO$_2$N(Heteroaryl)$_2$; —SO$_2$N(CH$_3$)(C$_{2-6}$ alkyl); —SO$_2$N(CH$_3$)(C$_{3-6}$ cycloalkyl); —SO$_2$N(CH$_3$)(Aryl); —SO$_2$N(CH$_3$)(Phenyl); —SO$_2$N(CH$_3$)(Heteroaryl); —SO$_2$N(C$_{2-6}$ alkyl)(C$_{3-6}$ cycloalkyl); —SO$_2$N(C$_{2-6}$ alkyl)(Aryl); —SO$_2$N(C$_{2-6}$ alkyl)(Phenyl); —SO$_2$N(C$_{2-6}$ alkyl)(Heteroaryl); —SO$_2$N(C$_{3-6}$ cycloalkyl)(Aryl); —SO$_2$N(C$_{3-6}$ cycloalkyl)(Phenyl); —SO$_2$N(C$_{3-6}$ cycloalkyl)(Heteroaryl); —SO$_2$N(Aryl)(Phenyl); —SO$_2$N(Aryl)(Heteroaryl); —SO$_2$N(Phenyl)(heteroaryl); —NHSO$_2$CH$_3$; —NHSO$_2$C$_{2-6}$ alkyl; —NHSO$_2$C$_{3-6}$ cycloalkyl; —NHSO$_2$Aryl; —NHSO$_2$Phenyl; —NHSO$_2$Heteroaryl; —N(CH$_3$)SO$_2$CH$_3$; —N(CH$_3$)SO$_2$C$_{2-6}$ alkyl; —N(CH$_3$)SO$_2$C$_{3-6}$ cycloalkyl; —N(CH$_3$)SO$_2$Aryl; —N(CH$_3$)SO$_2$Phenyl; —N(CH$_3$)SO$_2$Heteroaryl; —N(C$_{2-6}$ alkyl)SO$_2$CH$_3$; —N(C$_{2-6}$ alkyl)SO$_2$C$_{2-6}$ alkyl; —N(C$_{2-6}$ alkyl)SO$_2$C$_{3-6}$ cycloalkyl —N(C$_{2-6}$ alkyl)SO$_2$Aryl; —N(C$_{2-6}$ alkyl)SO$_2$Phenyl; —N(C$_{2-6}$ alkyl)SO$_2$Heteroaryl; —N(C$_{3-6}$ cycloalkyl)SO$_2$CH$_3$; —N(C$_{3-6}$ cycloalkyl)SO$_2$C$_{2-6}$ alkyl; —N(C$_{3-6}$ cycloalkyl)SO$_2$C$_{3-6}$ cycloalkyl —N(C$_{3-6}$ cycloalkyl)SO$_2$Aryl; —N(C$_{3-6}$ cycloalkyl)SO$_2$Phenyl; —N(C$_{3-6}$ cycloalkyl)SO$_2$Heteroaryl; —N(Aryl)SO$_2$CH$_3$; —N(Aryl)SO$_2$C$_{2-6}$ alkyl; N(Aryl)SO$_2$C$_{3-6}$ cycloalkyl; —N(Aryl)SO$_2$Aryl; —N(Aryl)SO$_2$Phenyl; —N(Aryl)SO$_2$Heteroaryl —N(Phenyl)SO$_2$CH$_3$; —N(Phenyl)SO$_2$C$_{2-6}$ alkyl; —N(Phenyl)SO$_2$C$_{3-6}$ cycloalkyl; —N(Phenyl)SO$_2$Aryl; —N(Phenyl)SO$_2$Phenyl; —N(Phenyl)SO$_2$Heteroaryl; —N(Heteroaryl)SO$_2$CH$_3$; —N(Heteroaryl)SO$_2$C$_{2-6}$ alkyl; —N(Heteroaryl)SO$_2$C$_{3-6}$ cycloalkyl; —N(Heteroaryl)SO$_2$Aryl; —N(Heteroaryl)SO$_2$Phenyl; —N(Heteroaryl)SO$_2$Heteroaryl; oxime; =NOH; =NOCH$_3$; =NOC$_{2-6}$alkyl; =NOC$_{3-6}$cycloalkyl; =NOAryl; =NOPhenyl; =NOHeteroaryl; —CH=NOH; —CH=NOCH$_3$; —CH=NOC$_{2-6}$alkyl; —CH=NOC$_{3-6}$cycloalkyl; —CH=NOAryl; —CH=NOPhenyl; —CH=NOHeteroaryl; —C(CH$_3$)=NOH; —C(CH$_3$)=NOCH$_3$; —C(CH$_3$)=NOC$_{2-6}$alkyl; —C(CH$_3$)=NOC$_{3-6}$cycloalkyl; —C(CH$_3$)=NOAryl; —C(CH$_3$)=NOPhenyl; —C(CH$_3$)=NOHeteroaryl; —C(C$_{2-6}$alkyl)=NOH; —C(C$_{2-6}$alkyl)=NOCH$_3$; —C(C$_{2-6}$alkyl)=NOC$_{2-6}$alkyl; —C(C$_{2-6}$alkyl)=NOC$_{3-6}$cycloalkyl; —C(C$_{2-6}$alkyl)=NOAryl; —C(C$_{2-6}$alkyl)=NOPhenyl; —C(C$_{2-6}$alkyl)=NOHeteroaryl; —C(C$_{3-6}$cycloalkyl)=NOH; —C(C$_{3-6}$cycloalkyl)=NOCH$_3$; —C(C$_{3-6}$cycloalkyl)=NOC$_{2-6}$alkyl; —C(C$_{3-6}$cycloalkyl)=NOC$_{3-6}$cycloalkyl; —C(C$_{3-6}$cycloalkyl)=NOAryl; —C(C$_{3-6}$cycloalkyl)=NOPhenyl; —C(C$_{3-6}$cycloalkyl)=NOHeteroaryl; —C(Aryl)=NOH; —C(Aryl)=NOCH$_3$; —C(Aryl)=NOC$_{2-6}$alkyl; —C(Aryl)=NOC$_{3-6}$cycloalkyl; —C(Aryl)=NOAryl; —C(Aryl)=NOPhenyl; —C(Aryl)=NOHeteroaryl; —C(Phenyl)=NOH; —C(Phenyl)=NOCH$_3$; —C(Phenyl)=NOC$_{2-6}$alkyl; —C(Phenyl)=NOC$_{3-6}$cycloalkyl; —C(Phenyl)=NOAryl; —C(Phenyl)=NOPhenyl; —C(Phenyl)=NOHeteroaryl; —C(Heteroaryl)=NOH; —C(Heteroaryl)=NOCH$_3$; —C(Heteroaryl)=NOC$_{2-6}$alkyl; —C(Heteroaryl)=NOC$_{3-6}$cycloalkyl; —C(Heteroaryl)=NOAryl; —C(Heteroaryl)=NOPhenyl; —C(Heteroaryl)=NOHeteroaryl; —ON=CH(CH$_3$); —ON=CH(C$_{2-6}$ alkyl); —ON=CH(C$_{3-6}$cycloalkyl); —ON=CH(Aryl); —ON=CH(Phenyl); —ON=CH(heteroaryl); —ON=C(CH$_3$)$_2$; —ON=C(CH$_3$)(C$_{2-6}$alkyl); —ON=C(CH$_3$)(C$_{3-6}$cycloalkyl); —ON=C(CH$_3$)(Aryl); —ON=C(CH$_3$)(Phenyl); —ON=C(CH$_3$)(heteroaryl); —ON=C(C$_{2-6}$alkyl)$_2$; —ON=C(C$_{2-6}$alkyl) (C$_{3-6}$cycloalkyl); —ON=C(C$_{2-6}$alkyl)(Aryl); —ON=C(C$_{2-6}$alkyl)(Phenyl); —ON=C(C$_{2-6}$alkyl)(Heteroaryl); —ON=C(C$_{3-6}$cycloalkyl)$_2$; —ON=C(C$_{3-6}$cycloalkyl)(Aryl); —ON=C(C$_{3-6}$cycloalkyl)(Phenyl); —ON=C(C$_{3-6}$cycloalkyl)(Heteroaryl); —ON=C(Aryl)$_2$; —ON=C(Aryl)(Phenyl); —ON=C(Aryl)(Heteroaryl); —ON=C(Phenyl)$_2$; —ON=C(Phenyl)(Heteroaryl); —ON=C(Heteroaryl)$_2$; imine; =NH; =NCH$_3$; =NC$_{2-6}$alkyl; =NC$_{3-6}$cycloalkyl; =NAryl; =NPhenyl; =NHeteroaryl; —CH=NH; —CH=NCH$_3$; —CH=NC$_{2-6}$alkyl; —CH=NC$_{3-6}$cycloalkyl; —CH=NAryl; —CH=NPhenyl; —CH=NHeteroaryl; —C(CH$_3$)=NH; —C(CH$_3$)=NCH$_3$; —C(CH$_3$)=NC$_{2-6}$alkyl; —C(CH$_3$)=NC$_{3-6}$cycloalkyl; —C(CH$_3$)=NAryl; —C(CH$_3$)=NPhenyl; —C(CH$_3$)=NHeteroaryl; —C(C$_{2-6}$alkyl)=NH; —C(C$_{2-6}$alkyl)=NCH$_3$; —C(C$_{2-6}$alkyl)=NC$_{2-6}$alkyl; —C(C$_{2-6}$alkyl)=NC$_{3-6}$cycloalkyl; —C(C$_{2-6}$alkyl)=NAryl; —C(C$_{2-6}$alkyl)=NPhenyl; —C(C$_{2-6}$alkyl)=NHeteroaryl; —C(C$_{3-6}$cycloalkyl)=NH; —C(C$_{3-6}$cycloalkyl)=NCH$_3$; —C(C$_{3-6}$cycloalkyl)=NC$_{2-6}$alkyl; —C(C$_{3-6}$cycloalkyl)=NC$_{3-6}$cycloalkyl; —C(C$_{3-6}$cycloalkyl)=NAryl; —C(C$_{3-6}$cycloalkyl)=NPhenyl; —C(C$_{3-6}$cycloalkyl)=NHeteroaryl; —C(Aryl)=NH; —C(Aryl)=NCH$_3$; —C(Aryl)=NC$_{2-6}$alkyl; —C(Aryl)=NC$_{3-6}$cycloalkyl; —C(Aryl)=NAryl; —C(Aryl)=NPhenyl; —C(Aryl)=NHeteroaryl; —C(Phenyl)=NH; —C(Phenyl)=NCH$_3$; —C(Phenyl)=NC$_{2-6}$alkyl; —C(Phenyl)=NC$_{3-6}$cycloalkyl; —C(Phenyl)=NAryl; —C(Phenyl)=NPhenyl; —C(Phenyl)=NHeteroaryl; —C(Heteroaryl)=NH; —C(Heteroaryl)=NCH$_3$; —C(Heteroaryl)=NC$_{2-6}$alkyl; —C(Heteroaryl)=NC$_{3-6}$cycloalkyl; —C(Heteroaryl)=NAryl; —C(Heteroaryl)=NPhenyl; —C(Heteroaryl)=NHeteroaryl; —N=CH(CH$_3$); —N=CH(C$_{2-6}$alkyl); —N=CH(C$_{3-6}$cycloalkyl); —N=CH(Aryl); —N=CH(Phenyl); —N=CH(heteroaryl); —N=C(CH$_3$)$_2$; —N=C(CH$_3$)(C$_{2-6}$alkyl); —N=C(CH$_3$)(C$_{3-6}$cycloalkyl); —N=C(CH$_3$)(Aryl); —N=C(CH$_3$)(Phenyl); —N=C(CH$_3$)(heteroaryl); —N=C(C$_{2-6}$alkyl)$_2$; —N=C(C$_{2-6}$alkyl) (C$_{3-6}$cycloalkyl); —N=C(C$_{2-6}$alkyl)(Aryl); —N=C(C$_{2-6}$alkyl)(Phenyl); —N=C(C$_{2-6}$alkyl)(Heteroaryl); —N=C(C$_{3-6}$cycloalkyl)$_2$; —N=C(C$_{3-6}$cycloalkyl)(Aryl); —N=C(C$_{3-6}$cycloalkyl)(Phenyl); —N=C(C$_{3-6}$cycloalkyl)(Heteroaryl); —N=C(Aryl)$_2$; —N=C(Aryl)(Phenyl); —N=C(Aryl)(Heteroaryl); —N=C(Phenyl)$_2$; —N=C(Phenyl)(Heteroaryl); —N=C(Heteroaryl)$_2$; ketone; acetyl; —C(O)CH$_3$; —C(O)C$_{2-6}$alkyl; —C(O)C$_{3-6}$cycloalkyl; —C(O)Aryl; —C(O)Phenyl; —C(O)Heteroaryl; —CH$_2$C(O)CH$_3$; —CH$_2$C(O)C$_{2-6}$alkyl; —CH$_2$C(O)C$_{3-6}$cycloalkyl; —CH$_2$C(O)Aryl;

—CH₂C(O)Phenyl; —CH₂C(O)Heteroaryl; —C₂₋₆alkyl C(O)C₂₋₆alkyl; —C₂₋₆alkylC(O)C₃₋₆cycloalkyl; —C₂₋₆alkyl C(O)Aryl; —C₂₋₆alkylC(O)Phenyl; —C₂₋₆alkylC(O)Heteroaryl; —C(O)CH₂CH₃; —C(O)CH₂C₂₋₆alkyl; —C(O)CH₂C₃₋₆cycloalkyl; —C(O)CH₂Aryl; —C(O)CH₂Phenyl; —C(O)CH₂Heteroaryl; —C(O)C₂₋₆alkylCH₃; —C(O)C₂₋₆alkylC₂₋₆alkyl; —C(O)C₂₋₆alkyC₃₋₆cycloalkyl; —C(O)C₂₋₆alkylAryl; —C(O)C₂₋₆alkylPhenyl; —C(O)C₂₋₆alkyl Heteroaryl; aldehyde; —CHO; —CH₂CHO; —C₂₋₆alkylCHO; ester; —CO₂CH₃; —CO₂C₂₋₆alkyl; —CO₂C₃₋₆cycloalkyl; —CO₂Aryl; —CO₂Phenyl; —CO₂Heteroaryl; reverse ester; acetoxy; —OCOCH₃; —OCOC₂₋₆alkyl; —OCOC₃₋₆cycloalkyl; —OCOAryl; —OCOPhenyl; —OCOHeteroaryl; oxygen (=O); hydrazinyl; —NHNH₂; —N(CH₃)NH₂; —N(C₂₋₆alkyl)NH₂; —N(C₃₋₆cycloalkyl)NH₂; —N(Aryl)NH₂; —N(Phenyl)NH₂; —N(Heteroaryl)NH₂; —N(COCH₃)NH₂; —N(COC₂₋₆alkyl)NH₂; —N(COC₃₋₆cycloalkyl)NH₂; —N(COAryl)NH₂; —N(COPhenyl)NH₂; —N(COHeteroaryl)NH₂; —NHNH(CH₃); —NHNH(C₂₋₆alkyl); —NHNH(C₃₋₆cycloalkyl); —NHNH(Aryl); —NHNH(Phenyl); —NHNH(Heteroaryl); —NHNH(COCH₃); —NHNH(COC₂₋₆alkyl); —NHNH(COC₃₋₆cycloalkyl); —NHNH(COAryl); —NHNH(COPhenyl); —NHNH(COHeteroaryl); —N(CH₃)NH(CH₃); —N(CH₃)NH(C₂₋₆alkyl); —N(CH₃)NH(C₃₋₆cycloalkyl); —N(CH₃)NH(Aryl); —N(CH₃)NH(Phenyl); —N(CH₃)NH(Heteroaryl); —N(CH₃)NH(COCH₃); —N(CH₃)NH(COC₂₋₆alkyl); —N(CH₃)NH(COC₃₋₆cycloalkyl); —N(CH₃)NH(COAryl); —N(CH₃)NH(COPhenyl); —N(CH₃)NH(COHeteroaryl); —N(C₂₋₆alkyl)NH(CH₃); —N(C₂₋₆alkyl)NH(C₂₋₆alkyl); —N(C₂₋₆alkyl)NH(C₃₋₆cycloalkyl); —N(C₂₋₆alkyl)NH(Aryl); —N(C₂₋₆alkyl)NH(Phenyl); —N(C₂₋₆alkyl)NH(Heteroaryl); —N(C₂₋₆alkyl)NH(COCH₃); —N(C₂₋₆alkyl)NH(COC₂₋₆alkyl); —N(C₂₋₆alkyl)NH(COC₃₋₆cycloalkyl); —N(C₂₋₆alkyl)NH(COAryl); —N(C₂₋₆alkyl)NH(COPhenyl); —N(C₂₋₆alkyl)NH(COHeteroaryl); —N(C₃₋₆cycloalkyl)NH(CH₃); —N(C₃₋₆cycloalkyl)NH(C₂₋₆alkyl); —N(C₃₋₆cycloalkyl)NH(C₃₋₆cycloalkyl); —N(C₃₋₆cycloalkyl)NH(Aryl); —N(C₃₋₆cycloalkyl)NH(Phenyl); —N(C₃₋₆cycloalkyl)NH(Heteroaryl); —N(C₃₋₆cycloalkyl)NH(COCH₃); —N(C₃₋₆cycloalkyl)NH(COC₂₋₆alkyl); —N(C₃₋₆cycloalkyl)NH(COC₃₋₆cycloalkyl); —N(C₃₋₆cycloalkyl)NH(COAryl); —N(C₃₋₆cycloalkyl)NH(COPhenyl); —N(C₃₋₆cycloalkyl)NH(COHeteroaryl); —N(Aryl)NH(CH₃); —N(Aryl)NH(C₂₋₆alkyl); —N(Aryl)NH(C₃₋₆cycloalkyl); —N(Aryl)NH(Aryl); —N(Aryl)NH(Phenyl); —N(Aryl)NH(Heteroaryl); —N(Aryl)NH(COCH₃); —N(Aryl)NH(COC₂₋₆alkyl); —N(Aryl)NH(COC₃₋₆cycloalkyl); —N(Aryl)NH(COAryl); —N(Aryl)NH(COPhenyl); —N(Aryl)NH(COHeteroaryl); —N(Phenyl)NH(CH₃); —N(Phenyl)NH(C₂₋₆alkyl); —N(Phenyl)NH(C₃₋₆cycloalkyl); —N(Phenyl)NH(Aryl); —N(Phenyl)NH(Phenyl); —N(Phenyl)NH(Heteroaryl); —N(Phenyl)NH(COCH₃); —N(Phenyl)NH(COC₂₋₆alkyl); —N(Phenyl)NH(COC₃₋₆cycloalkyl); —N(Phenyl)NH(COAryl); —N(Phenyl)NH(COPhenyl); —N(Phenyl)NH(COHeteroaryl); —N(Heteroaryl)NH(CH₃); —N(Heteroaryl)NH(C₂₋₆alkyl); —N(Heteroaryl)NH(C₃₋₆cycloalkyl); —N(Heteroaryl)NH(Aryl); —N(Heteroaryl)NH(Phenyl); —N(Heteroaryl)NH(Heteroaryl); —N(Heteroaryl)NH(COCH₃); —N(Heteroaryl)NH(COC₂₋₆alkyl); —N(Heteroaryl)NH(COC₃₋₆cycloalkyl); —N(Heteroaryl)NH(COAryl); —N(Heteroaryl)NH(COPhenyl); —N(Heteroaryl)NH(COHeteroaryl); —N(COCH₃)NH(CH₃); —N(COCH₃)NH(C₂₋₆alkyl); —N(COCH₃)NH(C₃₋₆cycloalkyl); —N(COCH₃)NH(Aryl); —N(COCH₃)NH(Phenyl); —N(COCH₃)NH(Heteroaryl); —N(COCH₃)NH(COCH₃); —N(COCH₃)NH(COC₂₋₆alkyl); —N(COCH₃)NH(COC₃₋₆cycloalkyl); —N(COCH₃)NH(COAryl); —N(COCH₃)NH(COPhenyl); —N(COCH₃)NH(COHeteroaryl); —N(COC₂₋₆alkyl)NH(CH₃); —N(COC₂₋₆alkyl)NH(C₂₋₆alkyl); —N(COC₂₋₆alkyl)NH(C₃₋₆cycloalkyl); —N(COC₂₋₆alkyl)NH(Aryl); —N(COC₂₋₆alkyl)NH(Phenyl); —N(COC₂₋₆alkyl)NH(Heteroaryl); —N(COC₂₋₆alkyl)NH(COCH₃); —N(COC₂₋₆alkyl)NH(COC₂₋₆alkyl); —N(COC₂₋₆alkyl)NH(COC₃₋₆cycloalkyl); —N(COC₂₋₆alkyl)NH(COAryl); —N(COC₂₋₆alkyl)NH(COPhenyl); —N(COC₂₋₆alkyl)NH(COHeteroaryl); —N(COC₃₋₆cycloalkyl)NH(CH₃); —N(COC₃₋₆cycloalkyl)NH(C₂₋₆alkyl); —N(COC₃₋₆cycloalkyl)NH(C₃₋₆cycloalkyl); —N(COC₃₋₆cycloalkyl)NH(Aryl); —N(COC₃₋₆cycloalkyl)NH(Phenyl); —N(COC₃₋₆cycloalkyl)NH(Heteroaryl); —N(COC₃₋₆cycloalkyl)NH(COCH₃); —N(COC₃₋₆cycloalkyl)NH(COC₂₋₆alkyl); —N(COC₃₋₆cycloalkyl)NH(COC₃₋₆cycloalkyl); —N(COC₃₋₆cycloalkyl)NH(COAryl); —N(COC₃₋₆cycloalkyl)NH(COPhenyl); —N(COC₃₋₆cycloalkyl)NH(COHeteroaryl); —N(COAryl)NH(CH₃); —N(COAryl)NH(C₂₋₆alkyl); —N(COAryl)NH(C₃₋₆cycloalkyl); —N(COAryl)NH(Aryl); —N(COAryl)NH(Phenyl); —N(COAryl)NH(Heteroaryl); —N(COAryl)NH(COCH₃); —N(COAryl)NH(COC₂₋₆alkyl); —N(COAryl)NH(COC₃₋₆cycloalkyl); —N(COAryl)NH(COAryl); —N(COAryl)NH(COPhenyl); —N(COAryl)NH(COHeteroaryl); —N(COPhenyl)NH(CH₃); —N(COPhenyl)NH(C₂₋₆alkyl); —N(COPhenyl)NH(C₃₋₆cycloalkyl); —N(COPhenyl)NH(Aryl); —N(COPhenyl)NH(Phenyl); —N(COPhenyl)NH(Heteroaryl); —N(COPhenyl)NH(COCH₃); —N(COPhenyl)NH(COC₂₋₆alkyl); —N(COPhenyl)NH(COC₃₋₆cycloalkyl); —N(COPhenyl)NH(COAryl); —N(COPhenyl)NH(COPhenyl); —N(COPhenyl)NH(COHeteroaryl); —N(COHeteroaryl)NH(CH₃); —N(COHeteroaryl)NH(C₂₋₆alkyl); —N(COHeteroaryl)NH(C₃₋₆cycloalkyl); —N(COHeteroaryl)NH(Aryl); —N(COHeteroaryl)NH(Phenyl); —N(COHeteroaryl)NH(Heteroaryl); —N(COHeteroaryl)NH(COCH₃); —N(COHeteroaryl)NH(COC₂₋₆alkyl); —N(COHeteroaryl)NH(COC₃₋₆cycloalkyl); —N(COHeteroaryl)NH(COAryl); —N(COHeteroaryl)NH(COPhenyl); —N(COHeteroaryl)NH(COHeteroaryl); —NHN(CH₃)₂; —NHN(CH₃)(C₂₋₆alkyl); —NHN(CH₃)(C₃₋₆cycloalkyl); —NHN(CH₃)(Aryl); —NHN(CH₃)(Phenyl); —NHN(CH₃)(Heteroaryl); —NHN(CH₃)(COCH₃); —NHN(CH₃)(COC₂₋₆alkyl); —NHN(CH₃)(COC₃₋₆cycloalkyl); —NHN(CH₃)(COAryl); —NHN(CH₃)(COPhenyl); —NHN(CH₃)(COHeteroaryl); —NHN(C₂₋₆alkyl)₂; —NHN(C₂₋₆alkyl)(C₃₋₆cycloalkyl); —NHN(C₂₋₆alkyl)(Aryl); —NHN(C₂₋₆alkyl)(Phenyl); —NHN(C₂₋₆alkyl)(Heteroaryl); —NHN(C₂₋₆alkyl)(COCH₃); —NHN(C₂₋₆alkyl)(COC₂₋₆alkyl); —NHN(C₂₋₆alkyl)(COC₃₋₆cycloalkyl); —NHN(C₂₋₆alkyl)(COAryl); —NHN(C₂₋₆alkyl)(COPhenyl); —NHN(C₂₋₆alkyl)(COHeteroaryl); —NHN(C₃₋₆cycloalkyl)₂; —NHN(C₃₋₆cycloalkyl)(Aryl); —NHN(C₃₋₆cycloalkyl)(Phenyl); —NHN(C₃₋₆cycloalkyl)(Heteroaryl); —NHN(C₃₋₆cycloalkyl)(COCH₃); —NHN(C₃₋₆cycloalkyl)(COC₂₋₆alkyl); —NHN(C₃₋₆cycloalkyl)(COC₃₋₆cycloalkyl); —NHN(C₃₋₆cycloalkyl)(COAryl); —NHN(C₃₋₆cycloalkyl)(COPhenyl); —NHN(C₃₋₆cycloalkyl)(COHeteroaryl); —NHN(Ary)₂; —NHN(Aryl)(Phenyl); —NHN(Ary)(Heteroaryl); —NHN(Aryl)(COCH₃); —NHN(Aryl)(COC₂₋₆alkyl); —NHN(Aryl)(COC₃₋₆cycloalkyl); —NHN(Aryl)(COAryl); —NHN(Aryl)(COPhenyl); —NHN(Ary)(COHeteroaryl); —NHN(Phenyl)₂; —NHN(Phenyl)(Heteroaryl); —NHN (Phenyl)(COCH₃); —NHN(Phenyl)(COC₂₋₆alkyl); —NHN(Phenyl)(COC₃₋₆cycloalkyl); —NHN(Phenyl)(COAryl); —NHN(Phenyl)(COPhenyl); —NHN(Phenyl)(COHeteroaryl); —NHN(Heteroaryl)₂; —NHN(Heteroaryl)(COCH₃); —NHN(Heteroaryl)(COC₂₋₆alkyl); —NHN(Heteroaryl)(COC₃₋₆cycloalkyl); —NHN(Heteroaryl)(COAryl); —NHN(Heteroaryl)(COPhenyl); —NHN(Heteroaryl)(COHeteroaryl); —NHN(COCH₃)₂; —NHN(COCH₃)(COC₂₋₆alkyl); —NHN(COCH₃)(COC₃₋₆cycloalkyl); —NHN(COCH₃)(COAryl); —NHN(COCH₃)(COPhenyl); —NHN(COCH₃)(COHeteroaryl); —NHN(COC₂₋₆alkyl)₂; —NHN(COC₂₋₆alkyl)(COC₃₋₆cycloalkyl); —NHN(COC₂₋₆alkyl)(COAryl); —NHN(COC₂₋₆alkyl)(COPhenyl); —NHN(COC₂₋₆alkyl)(COHeteroaryl); —NHN(COC₃₋₆cycloalkyl)₂; —NHN(COC₃₋₆cycloalkyl)(COAryl); —NHN(COC₃₋₆cycloalkyl)(COPhenyl); —NHN(COC₃₋₆cycloalkyl)(COHeteroaryl); —NHN(COAryl)₂; —NHN(COAryl)(COPhenyl); —NHN(COAryl)(COHeteroaryl); —NHN(COPhenyl)₂; —NHN(COPhenyl)(COHeteroaryl); —NHN(COHeteroaryl)₂; —N(CH₃)N(CH₃)₂; —N(CH₃)N(CH₃)(C₂₋₆alkyl); —N(CH₃)N(CH₃)(C₃₋₆cycloalkyl); —N(CH₃)N(CH₃)(Aryl); —N(CH₃)N(CH₃)(Phenyl); —N(CH₃)N(CH₃)(Heteroaryl); —N(CH₃)N(CH₃)(COCH₃); —N(CH₃)N(CH₃)(COC₂₋₆alkyl); —N(CH₃)N(CH₃)(COC₃₋₆cycloalkyl); —N(CH₃)N(CH₃)(COAryl); —N(CH₃)N(CH₃)(COPhenyl); —N(CH₃)N(CH₃)(COHeteroaryl); —N(CH₃)N(C₂₋₆alkyl)₂; —N(CH₃)N(C₂₋₆alkyl)(C₃₋₆cycloalkyl); —N(CH₃)N(C₂₋₆alkyl)(Aryl); —N(CH₃)N(C₂₋₆alkyl)(Phenyl); —N(CH₃)N(C₂₋₆alkyl)(Heteroaryl); —N(CH₃)N(C₂₋₆alkyl)(COCH₃); —N(CH₃)N(C₂₋₆alkyl)(COC₂₋₆alkyl); —N(CH₃)N(C₂₋₆alkyl)(COC₃₋₆cycloalkyl); —N(CH₃)N(C₂₋₆alkyl)(COAryl); —N(CH₃)N(C₂₋₆alkyl)(COPhenyl); —N(CH₃)N(C₂₋₆alkyl)(COHeteroaryl); —N(CH₃)N(C₃₋₆cycloalkyl)₂; —N(CH₃)N(C₃₋₆cycloalkyl)(Aryl); —N(CH₃)N(C₃₋₆cycloalkyl)(Phenyl); —N(CH₃)N(C₃₋₆cycloalkyl)(Heteroaryl); —N(CH₃)N(C₃₋₆cycloalkyl)(COCH₃); —N(CH₃)N(C₃₋₆cycloalkyl)(COC₂₋₆alkyl); —N(CH₃)N(C₃₋₆cycloalkyl)(COC₃₋₆cycloalkyl); —N(CH₃)N(C₃₋₆cycloalkyl)(COAryl); —N(CH₃)N(C₃₋₆cycloalkyl)(COPhenyl); —N(CH₃)N(C₃₋₆cycloalkyl)(COHeteroaryl); —N(CH₃)N(Aryl)₂; —N(CH₃)N(Aryl)(Phenyl); —N(CH₃)N(Aryl)(Heteroaryl); —N(CH₃)N(Aryl)(COCH₃); —N(CH₃)N(Aryl)(COC₂₋₆alkyl); —N(CH₃)N(Aryl)(COC₃₋₆cycloalkyl); —N(CH₃)N(Aryl)(COAryl); —N(CH₃)N(Aryl)(COPhenyl); —N(CH₃)N(Aryl)(COHeteroaryl); —N(CH₃)N(Phenyl)₂; —N(CH₃)N(Phenyl)(Heteroaryl); —N(CH₃)N(Phenyl)(COCH₃); —N(CH₃)N(Phenyl)(COC₂₋₆alkyl); —N(CH₃)N(Phenyl)(COC₃₋₆cycloalkyl); —N(CH₃)N(Phenyl)(COAryl); —N(CH₃)N(Phenyl)(COPhenyl); —N(CH₃)N(Phenyl)(COHeteroaryl); —N(CH₃)N(Heteroaryl)₂; —N(CH₃)N(Heteroaryl)(COCH₃); —N(CH₃)N(Heteroaryl)(COC₂₋₆alkyl); —N(CH₃)N(Heteroaryl)(COC₃₋₆cycloalkyl); —N(CH₃)N(Heteroaryl)(COAryl); —N(CH₃)N(Heteroaryl)(COPhenyl); —N(CH₃)N(Heteroaryl)(COHeteroaryl); —N(CH₃)N(COCH₃)₂; —N(CH₃)N(COCH₃)(COC₂₋₆alkyl); —N(CH₃)N(COCH₃)(COC₃₋₆cycloalkyl); —N(CH₃)N(COCH₃)(COAryl); —N(CH₃)N(COCH₃)(COPhenyl); —N(CH₃)N(COCH₃)(COHeteroaryl); —N(CH₃)N(COC₂₋₆alkyl)₂; —N(CH₃)N(COC₂₋₆alkyl)(COC₃₋₆cycloalkyl); —N(CH₃)N(COC₂₋₆alkyl)(COAryl); —N(CH₃)N(COC₂₋₆alkyl)(COPhenyl); —N(CH₃)N(COC₂₋₆alkyl)(COHeteroaryl); —N(CH₃)N(COC₃₋₆cycloalkyl)₂; —N(CH₃)N(COC₃₋₆cycloalkyl)(COAryl); —N(CH₃)N(COC₃₋₆cycloalkyl)(COPhenyl); —N(CH₃)N(COC₃₋₆cycloalkyl)(COHeteroaryl); —N(CH₃)N(COAryl)₂; —N(CH₃)N(COAryl)(OAryl)(COPhenyl); —N(CH₃)N(COAryl)(COHeteroaryl); —N(CH₃)N(COPhenyl)₂; —N(CH₃)N(COPhenyl)(COHeteroaryl); —N(CH₃)N(COHeteroaryl)₂; —N(Phenyl)N(CH₃)₂; —N(Phenyl)N(CH₃)(C₂₋₆alkyl); —N(Phenyl)N(CH₃)(C₃₋₆cycloalkyl); —N(Phenyl)N(CH₃)(Aryl); —N(Phenyl)N(CH₃)(Phenyl); —N(Phenyl)N(CH₃)(Heteroaryl); —N(Phenyl)N(CH₃)(COCH₃); —N(Phenyl)N(CH₃)(COC₂₋₆alkyl); —N(Phenyl)N(CH₃)(COC₃₋₆cycloalkyl); —N(Phenyl)N(CH₃)(COAryl); —N(Phenyl)N(CH₃)(COPhenyl); —N(Phenyl)N(CH₃)(COHeteroaryl); —N(Phenyl)N(C₂₋₆alkyl)₂; —N(Phenyl)N(C₂₋₆alkyl)(C₃₋₆cycloalkyl); —N(Phenyl)N(C₂₋₆alkyl)(Aryl); —N(Phenyl)N(C₂₋₆alkyl)(Phenyl); —N(Phenyl)N(C₂₋₆alkyl)(Heteroaryl); —N(Phenyl)N(C₂₋₆alkyl)(COCH₃); —N(Phenyl)N(C₂₋₆alkyl)(COC₂₋₆alkyl); —N(Phenyl)N(C₂₋₆alkyl)(COC₃₋₆cycloalkyl); —N(Phenyl)N(C₂₋₆alkyl)(COAryl); —N(Phenyl)N(C₂₋₆alkyl)(COPhenyl); —N(Phenyl)N(C₂₋₆alkyl)(COHeteroaryl); —N(Phenyl)N(C₃₋₆cycloalkyl)₂; —N(Phenyl)N(C₃₋₆cycloalkyl)(Aryl); —N(Phenyl)N(C₃₋₆cycloalkyl)(Phenyl); —N(Phenyl)N(C₃₋₆cycloalkyl)(Heteroaryl); —N(Phenyl)N(C₃₋₆cycloalkyl)(COCH₃); —N(Phenyl)N(C₃₋₆cycloalkyl)(COC₂₋₆alkyl); —N(Phenyl)N(C₃₋₆cycloalkyl)(COC₃₋₆cycloalkyl); —N(Phenyl)N(C₃₋₆cycloalkyl)(COAryl); —N(Phenyl)N(C₃₋₆cycloalkyl)(COPhenyl); —N(Phenyl)N(C₃₋₆cycloalkyl)(COHeteroaryl); —N(Phenyl)N(Aryl)₂; —N(Phenyl)N(Aryl)(Phenyl); —N(Phenyl)N(Aryl)(Heteroaryl); —N(Phenyl)N(Aryl)(COCH₃); —N(Phenyl)N(Aryl)(COC₂₋₆alkyl); —N(Phenyl)N(Aryl)(COC₃₋₆cycloalkyl); —N(Phenyl)N(Aryl)(COAryl); —N(Phenyl)N(Aryl)(COPhenyl); —N(Phenyl)N(Aryl)(COHeteroaryl); —N(Phenyl)N(Phenyl)₂; —N(Phenyl)N(Phenyl)(Heteroaryl); —N(Phenyl)N(Phenyl)(COCH₃); —N(Phenyl)N(Phenyl)(COC₂₋₆alkyl); —N(Phenyl)N(Phenyl)(COC₃₋₆cycloalkyl); —N(Phenyl)N(Phenyl)(COAryl); —N(Phenyl)N(Phenyl)(COPhenyl); —N(Phenyl)N(Phenyl)(COHeteroaryl); —N(Phenyl)N(Heteroaryl)₂; —N(Phenyl)N(Heteroaryl)(COCH₃); —N(Phenyl)N(Heteroaryl)(COC₂₋₆alkyl); —N(Phenyl)N(Heteroaryl)(COC₃₋₆cycloalkyl); —N(Phenyl)N(Heteroaryl)(COAryl); —N(Phenyl)N(Heteroaryl)(COPhenyl); —N(Phenyl)N(Heteroaryl)(COHeteroaryl); —N(Phenyl)N(COCH₃)₂; —N(Phenyl)N(COCH₃)(COC₂₋₆alkyl); —N(Phenyl)N(COCH₃)(COC₃₋₆cycloalkyl); —N(Phenyl)N(COCH₃)(COAryl); —N(Phenyl)N(COCH₃)(COPhenyl); —N(Phenyl)N(COCH₃)(COHeteroaryl); —N(Phenyl)N(COC₂₋₆alkyl)₂; —N(Phenyl)N(COC₂₋₆alkyl)(COC₃₋₆cycloalkyl); —N(Phenyl)N(COC₂₋₆alkyl(COAryl); —N(Phenyl)N(COC₂₋₆alkyl)(COPhenyl); —N(Phenyl)N(COC₂₋₆alkyl)(COHeteroaryl); —N(Phenyl)N(COC₃₋₆cycloalkyl)₂; —N(Phenyl)N(COC₃₋₆cycloalkyl)(COAryl); —N(Phenyl)N(COC₃₋₆cycloalkyl)(COPhenyl); —N(Phenyl)N(COC₃₋₆cycloalkyl)(COHeteroaryl); —N(Phenyl)N(COAryl)₂; —N(Phenyl)N(COAryl)(COPhenyl); —N(Phenyl)N(COAryl)(COHeteroaryl); —N(Phenyl)N(COPhenyl)₂; —N(Phenyl)N(COPhenyl)(COHeteroaryl); —N(Phenyl)N(COHeteroaryl)₂; hydrazonyl; =NNH₂; =NNH(CH₃); =NNH(C₂₋₆alkyl); =NNH(C₃₋₆cycloalkyl); =NNH(Aryl); =NNH(Phenyl); =NNH(Heteroaryl); =NNH(COCH₃); =NNH(COC₂₋₆alkyl); =NNH(COC₃₋₆cycloalkyl); =NNH(COAryl); =NNH(COPhenyl); =NNH(COHeteroaryl); =NN(CH₃)₂; =NN(CH₃)(C₂₋₆alkyl); =NN(CH₃)(C₃₋₆cycloalkyl); =NN(CH₃)(Aryl); =NN(CH₃)(Phenyl); =NN(CH₃)(Heteroaryl); =NN(CH₃)(COCH₃); =NN(CH₃)(COC₂₋₆alkyl); =NN(CH₃)(COC₃₋₆cycloalkyl); =NN(CH₃)(COAryl); =NN(CH₃)(COPhenyl); =NN(CH₃)(COHeteroaryl); =NN(C₂₋₆alkyl)₂; =NN(C₂₋₆alkyl)(C₃₋₆cycloalkyl); =NN(C₂₋₆alkyl)(Aryl); =NN(C₂₋₆alkyl)(Phenyl); =NN(C₂₋₆alkyl)(Heteroaryl); =NN (C₂₋₆alkyl)(COCH₃); =NN(C₂₋₆alkyl)(COC₂₋₆alkyl); =NN(C₂₋₆alkyl)(COC₃₋₆cycloalkyl); =NN(C₂₋₆alkyl) (COAryl); =NN(C₂₋₆alkyl)(COPhenyl); =NN(C₂₋₆alkyl) (COHeteroaryl); =NN(C₃₋₆cycloalkyl)₂; =NN(C₃₋₆cycloalkyl)(Aryl); =NN(C₃₋₆cycloalkyl)(Phenyl); =NN(C₃₋₆ cycloalkyl)(Heteroaryl); =NN(C₃₋₆cycloalkyl)(COCH₃); =NN(C₃₋₆cycloalkyl)(COC₂₋₆alkyl); =NN(C₃₋₆cycloalkyl)(COC₃₋₆cycloalkyl); =NN(C₃₋₆cycloalkyl) (COAryl); =NN(C₃₋₆cycloalkyl)(COPhenyl); =NN(C₃₋₆ cycloalkyl)(COHeteroaryl); =NN(Aryl)₂; =NN(Aryl) (Phenyl); =NN(Aryl)(Heteroaryl); =NN(Aryl)(COCH₃); =NN(Aryl)(COC₂₋₆alkyl); =NN(Aryl)(COC₃₋₆cycloalkyl); =NN(Aryl)(COAryl); =NN(Aryl)(COPhenyl); =NN(Aryl)(COHeteroaryl); =NN(Phenyl)₂; =NN(Phenyl)(Heteroaryl); =NN(Phenyl)(COCH₃); =NN(Phenyl) (COC₂₋₆alkyl); =NN(Phenyl)(COC₃₋₆cycloalkyl); =NN (Phenyl)(COAryl); =NN(Phenyl)(COPhenyl); =NN (Phenyl)(COHeteroaryl); =NN(Heteroaryl)₂; =NN (Heteroaryl)(COCH₃); =NN(Heteroaryl)(COC₂₋₆alkyl); =NN(Heteroaryl)(COC₃₋₆cycloalkyl); =NN(Heteroaryl) (COAryl); =NN(Heteroaryl)(COPhenyl); =NN(Heteroaryl)(COHeteroaryl); =NN(COCH₃)₂; =NN(COCH₃) (COC₂₋₆alkyl); =NN(COCH₃)(COC₃₋₆cycloalkyl); =NN (COCH₃)(COAryl); =NN(COCH₃)(COPhenyl); =NN (COCH₃)(COHeteroaryl); =NN(COC₂₋₆alkyl)₂; =NN (COC₂₋₆alkyl)(COC₃₋₆cycloalkyl); =NN(COC₂₋₆alkyl) (COAryl); =NN(COC₂₋₆alkyl)(COPhenyl); =NN(COC₂₋₆ alkyl)(COHeteroaryl); =NN(COC₃₋₆cycloalkyl)₂; =NN (COC₃₋₆cycloalkyl)(COAryl); =NN(COC₃₋₆cycloalkyl) (COPhenyl); =NN(COC₃₋₆cycloalkyl)(COHeteroaryl); =NN(COAryl)₂; =NN(COAryl)(COPhenyl); =NN (COAryl)(COHeteroaryl); =NN(COPhenyl)₂; =NN(COPhenyl)(COHeteroaryl); =NN(COHeteroaryl)₂; haloalkyl (e.g., trifluoromethyl, difluoromethyl, fluoromethyl); substituted aminoacyl and aminoalkyl; carbocyclic C₃₋₈ cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, furanyl, or thiazinyl); carbocyclic or heterocyclic, monocyclic or fused or non-fused polycyclic aryl (e.g., phenyl, naphthyl, pyrrolyl, indolyl, furanyl, thienyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothienyl, or benzofuranyl); —O-aryl; aryl; aryl-C₁₋ or ₂₋₆alkyl; alkoxy; —OCH₃; —OC₂₋₆alkyl; —OC₃₋₆cycloalkyl; —OPhenyl; —OPhenyl-C₁₋ or ₂₋₆alkyl; —OHeteroaryl; —CO₂CH₃; —CONH₂; —OCH₂CONH₂; —NH₂; —N(C₁₋₄alkyl)₂; amido; —NHC(O)CH₃; —NHC(O)C₂₋₆alkyl; —NHC(O)C₃₋₆cycloalkyl; —NHC(O)Aryl; —NHC(O)Phenyl; —NHC(O)Heteroaryl; —N(CH₃)C(O)CH₃; —N(CH₃)C(O)C₂₋₆alkyl; —N(CH₃)C(O)C₃₋₆cycloalkyl; —N(CH₃)C(O)Aryl; —N(CH₃)C(O)Phenyl; —N(CH₃)C(O)Heteroaryl; —N(C₂₋₆alkyl)C(O)CH₃; —N(C₂₋₆alkyl)C(O)C₂₋₆alkyl; —N(C₂₋₆alkyl)C(O)C₃₋₆cycloalkyl; —N(C₂₋₆alkyl)C(O)Aryl; —N(C₂₋₆alkyl)C(O)Phenyl; —N(C₂₋₆alkyl)C(O)Heteroaryl; —N(C₃₋₆cycloalkyl)C(O)CH₃; —N(C₃₋₆cycloalkyl)C(O)C₂₋₆alkyl; —N(C₃₋₆cycloalkyl)C(O)C₃₋₆cycloalkyl; —N(C₃₋₆cycloalkyl)C(O)Aryl; —N(C₃₋₆cycloalkyl)C(O)Phenyl; —N(C₃₋₆cycloalkyl)C(O)Heteroaryl; —N(Aryl)C(O)CH₃; —N(Aryl)C(O)C₂₋₆alkyl; —N(Aryl)C(O)C₃₋₆cycloalkyl; —N(Aryl)C(O)Aryl; —N(Aryl)C(O)Phenyl; —N(Aryl)C(O)Heteroaryl; —N(Phenyl)C(O)CH₃; —N(Phenyl)C(O)C₂₋₆alkyl; —N(Phenyl)C(O)C₃₋₆cycloalkyl; —N(Phenyl)C(O)Aryl; —N(Phenyl)C(O)Phenyl; —N(Phenyl)C(O)Heteroaryl; —N(Heteroaryl)C(O)CH₃; —N(Heteroaryl)C(O)C₂₋₆alkyl; —N(Heteroaryl)C(O)C₃₋₆cycloalkyl; —N(Heteroaryl)C(O)Aryl; —N(Heteroaryl)C(O)Phenyl; —N(Heteroaryl)C(O)Heteroaryl; guanidyl; amidinyl; —SO₂NH₂; —OCHF₂; —CF₃; —OCF₃; and such moieties may also be optionally substituted by a fused-ring structure or bridge, for example —OCH₂O— or —O—C₁₋ or ₂₋₆alkylene-O—. These substituents may optionally be further substituted with a substituent selected from such groups.

Preferably, when the structural moiety of formula (I) has the structure depicted in formula (III 3e), the ring corresponding to the A-ring of formula (I) (in this case the pyrrole ring) may be optionally substituted, and when the pyrrole ring is substituted it is substituted by one or more substituents independently selected from —CH₃, C₂to₄alkyl, halogen, —OCH₃, and —OC₂to₄alkyl.

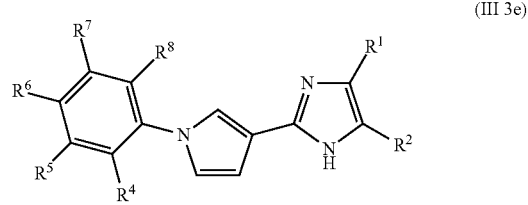

(III 3e)

Therein, R¹ and R² are as defined for formula (I) and R⁴ to R⁸ are independently selected from the group consisting of H, —CH₃, C₂to₄alkyl, halogen, hydroxyl, —OCH₃, —OC₂to₄alkyl, —CF₃, —OCF₃, —NH₂, —CH₂NH₂, —N(CH₃)₂, —NO₂, —CH₂OH, —CO₂CH₃, —CO₂C₂to₄alkyl, —CO₂H, —N(alkyl)₂ where the two alkyl groups are independently selected from —CH₃ or C₂to₄alkyl, —NH(alkyl) where the alkyl group is selected from —CH₃ or C₂to₄alkyl, 4-morpholinyl, 1-piperidinyl, 4H-piperazinyl, 4-C₁to₄alkyl-piperazinyl, and 4-C₃to₆cycloalkyl-piperazinyl.

When R¹ or R² is aryl, phenyl, heteroaryl, or benzyl optionally substituted on the phenyl ring, they may be substituted with one or more of the substituents as described elsewhere herein. Other examples of R¹ or R² groups according to the present invention include phenyl substituted with a substituent selected from the group consisting of phenyl, substituted phenyl, —CH₂CF₃, —CH₂OCF₃, —CHF₂, piperazinyl, N-Methyl-piperazinyl, N-acyl-piperazinyl for example N-acetyl-piperazinyl, N-sulfonyl-piperazinyl for example N-methylsulfonyl-piperazinyl or N-phenylsulfonyl-piperazinyl, morpholinyl, —NHCOC₁₋ or ₂to₆alkyl, —NHCOC₁₋ or ₂to₈hydrocarbon and —NHCO(CH₂)₄C≡CH, where said substituent is present at the position of the phenyl ring para to the point of connection of the phenyl ring to the ring of the compounds of the invention which bears the R¹ and R² groups. Other examples of R¹ or R² groups according to the present invention include phenyl substituted with a substituent selected from the group consisting of phenyl, substituted phenyl, —CH₂CF₃, —CH₂OCF₃, —CHF₂, piperazinyl, N-Methyl-piperazinyl, N-acyl-piperazinyl for example N-acetyl-piperazinyl, N-sulfonyl-piperazinyl for example N-methylsulfonyl-piperazinyl or N-phenylsulfonyl-piperazinyl, morpholinyl, —NHCOC₁₋ or ₂to₆alkyl, —NHCOC₁₋ or ₂to₈hydrocarbon and —NHCO(CH₂)₄C≡CH, where said substituent is present at the position of the phenyl ring meta to the point of connection of the phenyl ring to the ring of the compounds of the invention which bears the R¹ and R² groups. Other examples of R¹ or R² groups according to the present invention include phenyl substituted with a substituent selected from the group consisting of phenyl, substituted phenyl, —CH$_2$CF$_3$, —CH$_2$OCF$_3$, —CHF$_2$, piperazinyl, N-Methyl-piperazinyl, N-acyl-piperazinyl for example N-acetyl-piperazinyl, N-sulfonyl-piperazinyl for example N-methylsulfonyl-piperazinyl or N-phenylsulfonyl-piperazinyl, morpholinyl, —NHCOC$_{1\text{- or }2to6}$alkyl, —NHCOC$_{1\text{- or }2to8}$hydrocarbon and —NHCO(CH$_2$)$_4$C≡CH, where said substituent is present at the position of the phenyl ring ortho to the point of connection of the phenyl ring to the ring of the compounds of the invention which bears the R$^1$ and R$^2$ groups. In each the above examples, the phenyl ring which is substituted in either the ortho, meta, or para position with the listed substituents may be replaced with a heteroaryl ring (for example a pyridyl or pyrimidyl ring) substituted in said ortho, meta or para position with the listed substituents, a benzyl group whereby the phenyl ring of the benzyl group is substituted in said ortho, meta or para position with the listed substituents, or aryl substituted in said ortho, meta or para position with the listed substituents.

Preferably in the present invention, when R$^1$ or R$^2$ is heteroaryl it is optionally substituted 6-membered heteroaryl, for example optionally substituted pyridinyl (pyridyl), pyridazinyl, pyrimidinyl, pyrazinyl, triazinyl, most preferably optionally substituted pyridinyl (pyridyl) or pyrimidinyl. These rings are optionally substituted with one or more substituents, suitable substituents being described elsewhere herein, in particular with one or more substituents corresponding to those described as being preferred for R$^1$ or R$^2$ in the compounds of formula (I) when R$^1$ or R$^2$ is (optionally) substituted aryl or phenyl.

In one embodiment of the present invention, one of R$^1$ or R$^2$ is —CH$_3$. In one embodiment of the present invention, one of R$^1$ or R$^2$ is —H. In one embodiment of the present invention, one of R$^1$ or R$^2$ is —CH$_2$N(CH$_3$)$_2$. In one embodiment of the present invention, one of R$^1$ or R$^2$ is halogen, preferably Cl.

In a preferred embodiment of the present invention, the compounds comprising or consisting of the moieties of the invention are selected from the group consisting of 1
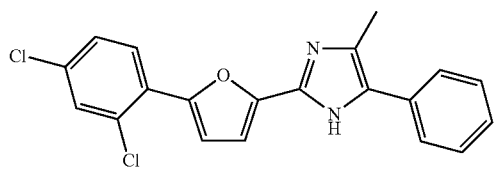

2
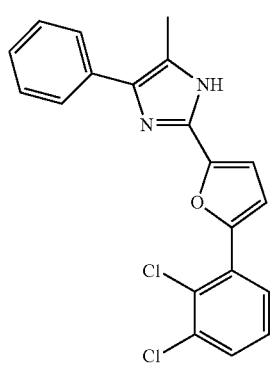

3
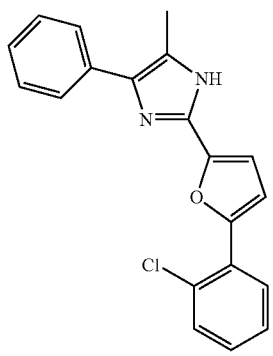

4
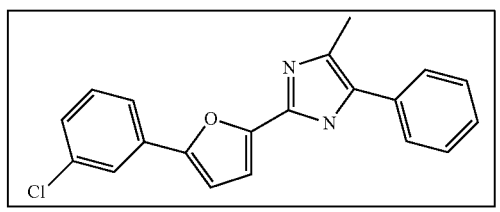

5
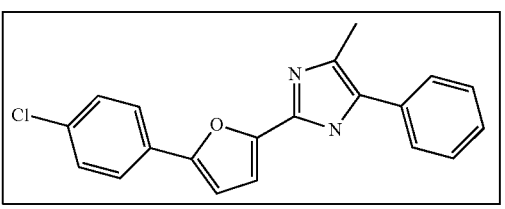

6
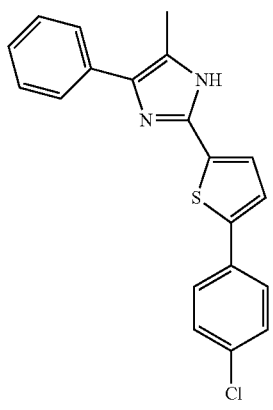

7
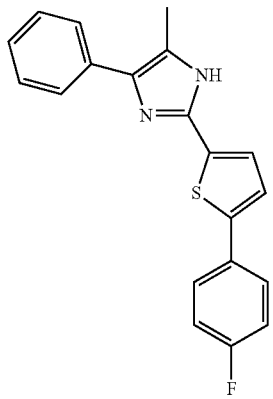

8
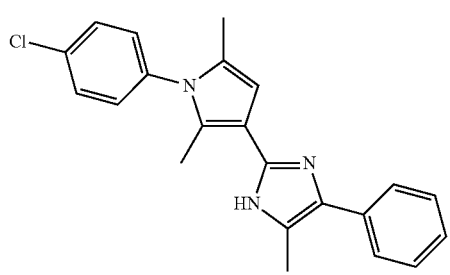
9
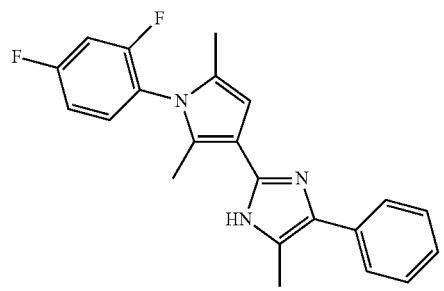
10
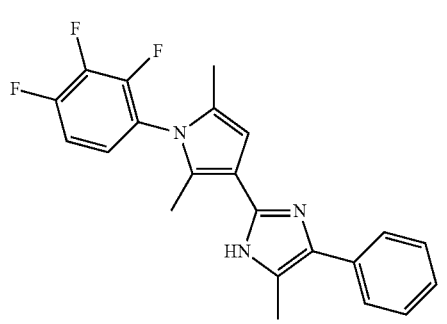
11
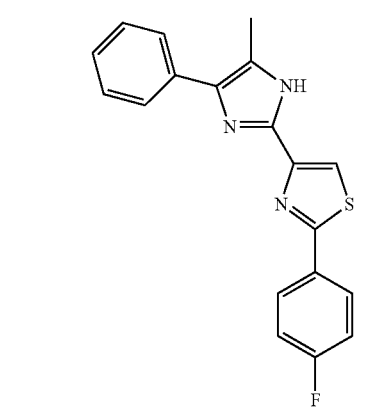
12
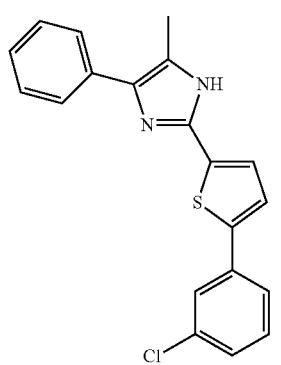
13
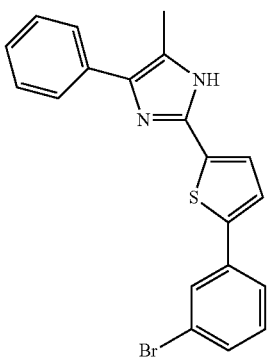
14
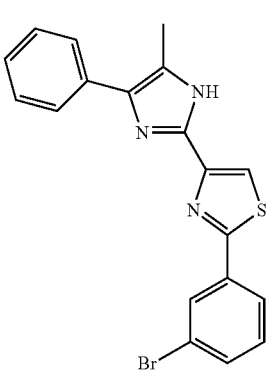
15
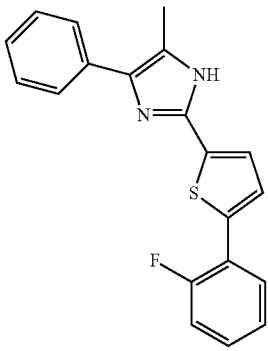
16
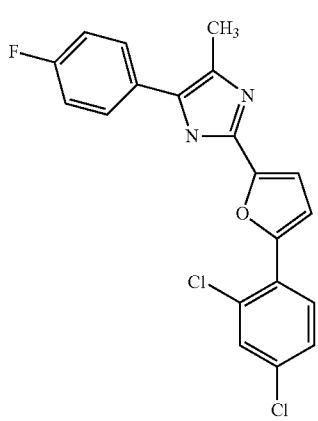

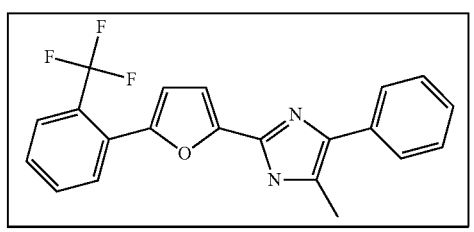
17
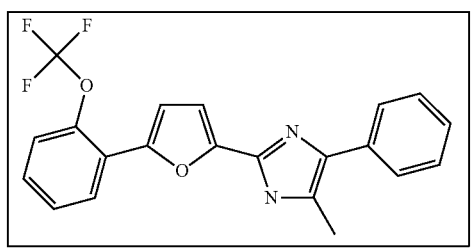
18
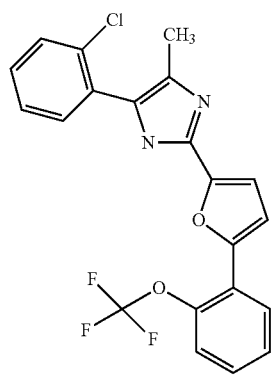
19
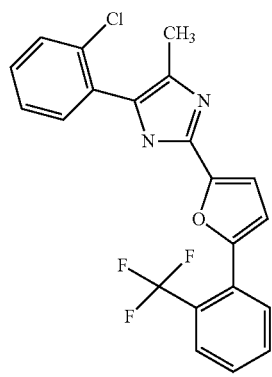
20
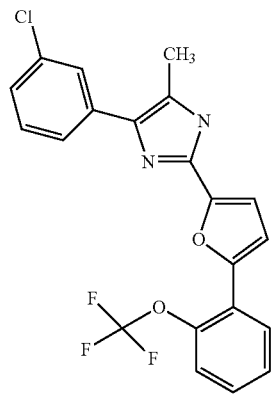
21
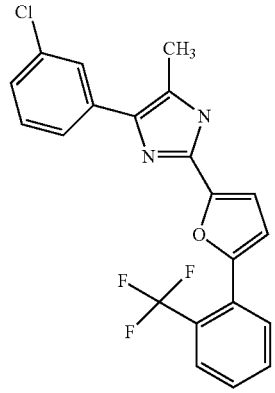
22
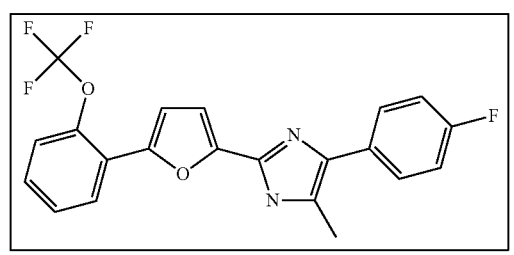
23
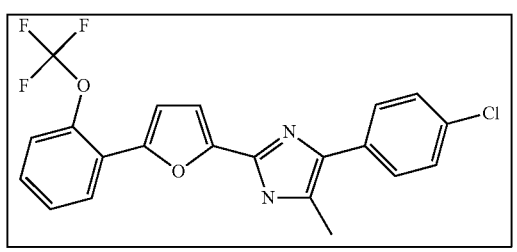
24
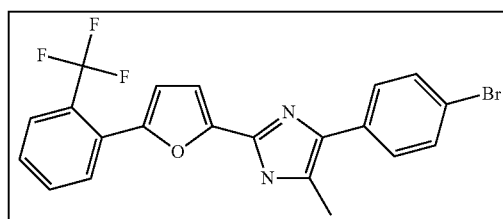
25
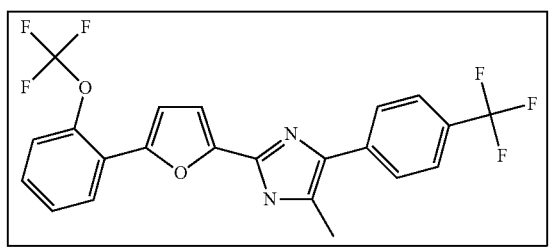
26

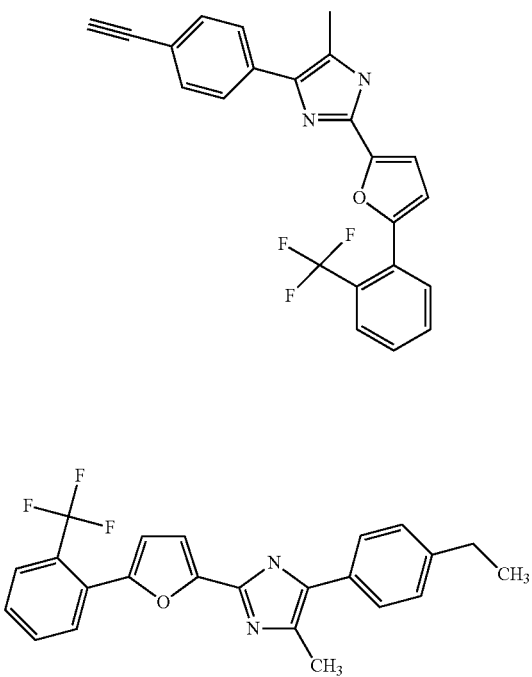
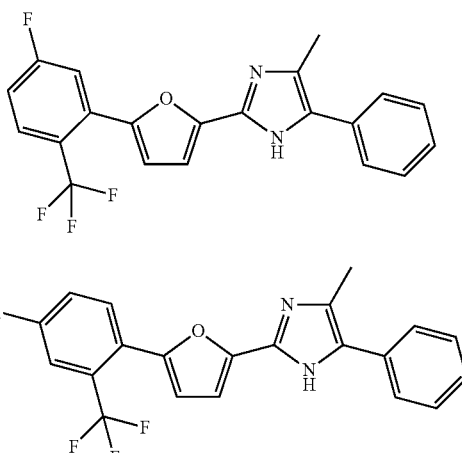
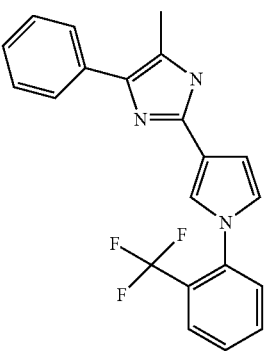
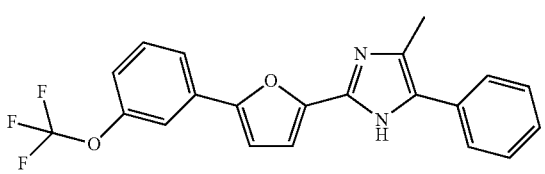
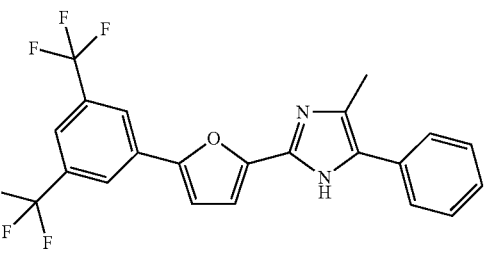
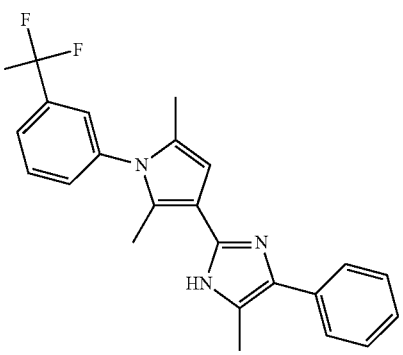
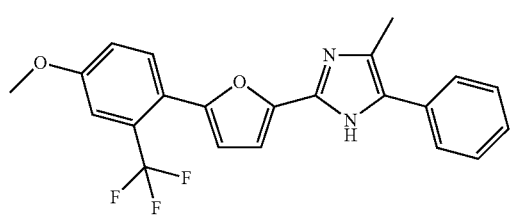

37
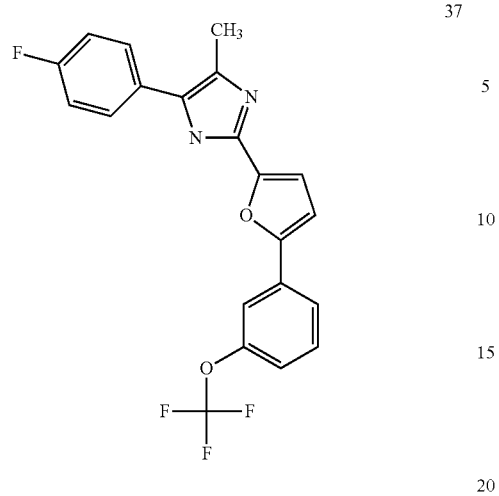
38
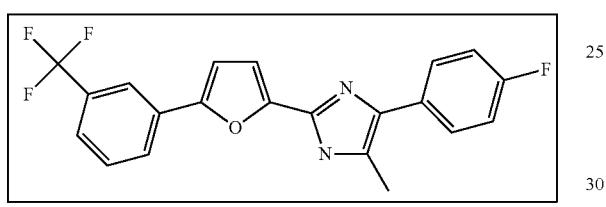
39
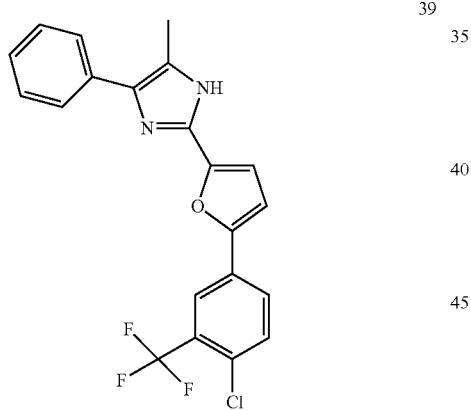
40
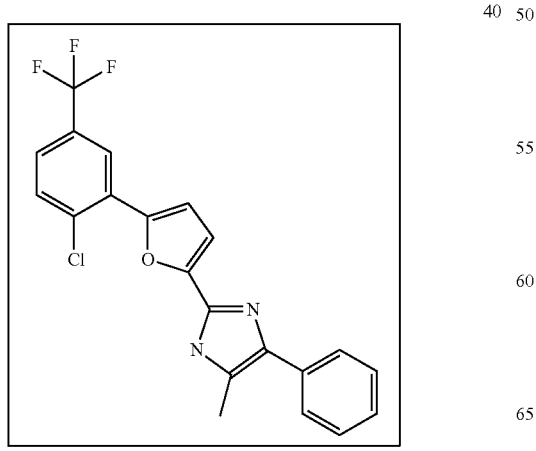
41
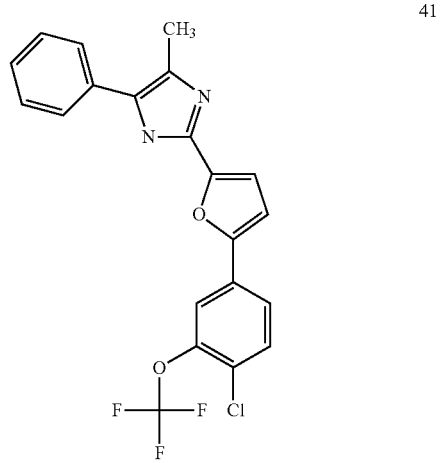
42
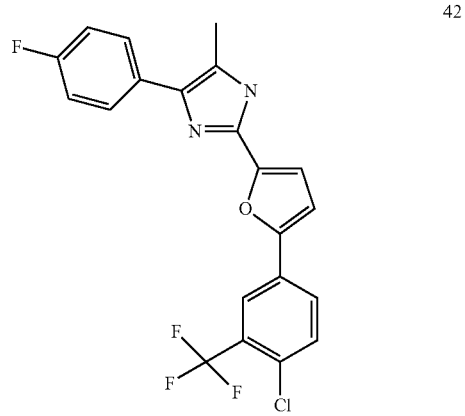
43
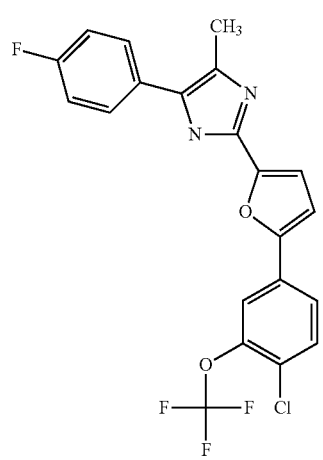

44
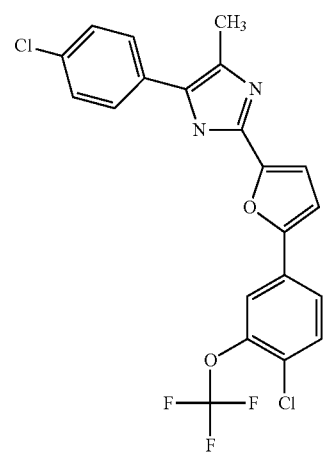
45
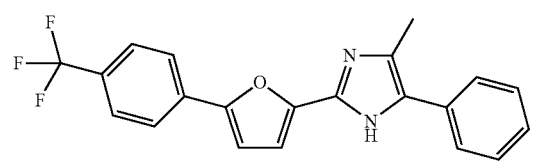
46
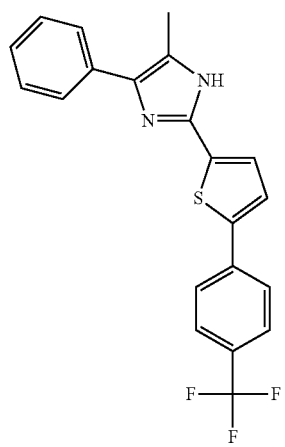
47
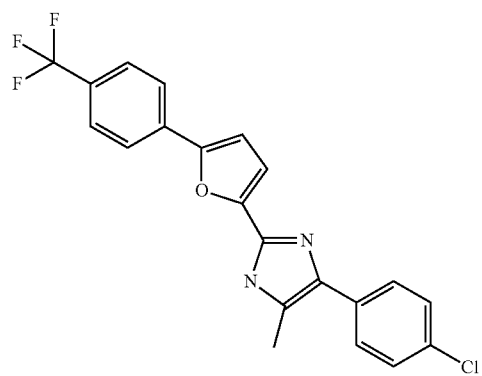
48
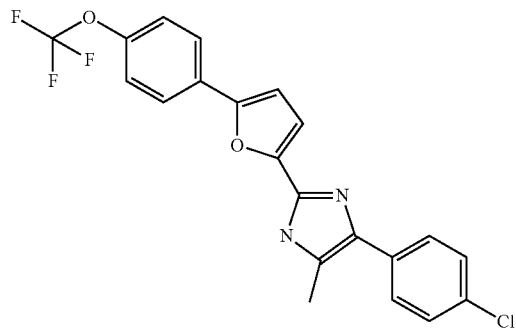
49
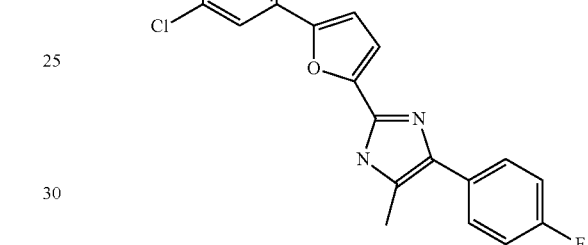
50
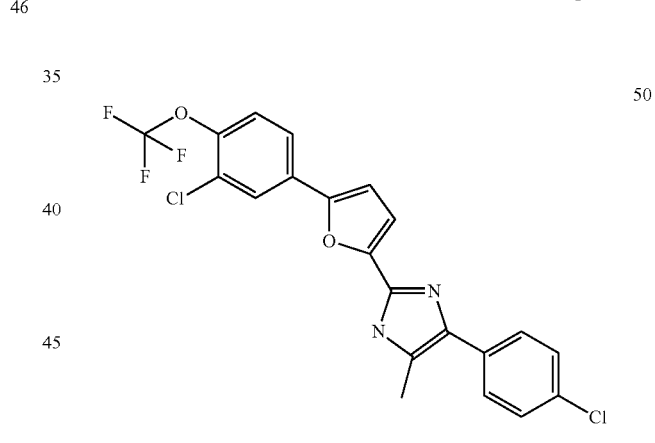
51
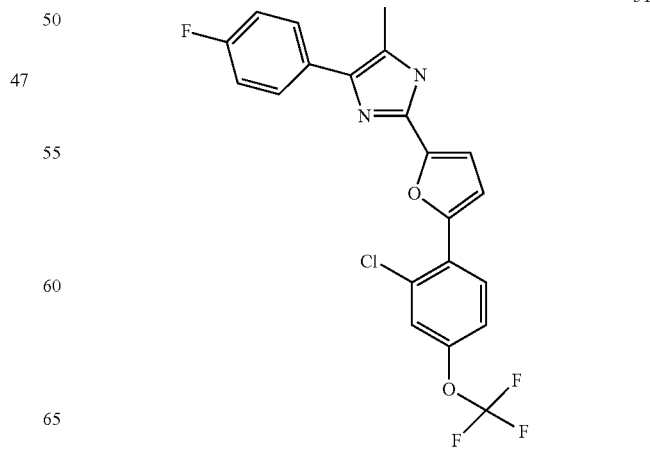

52
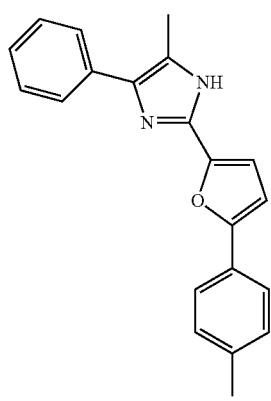
53
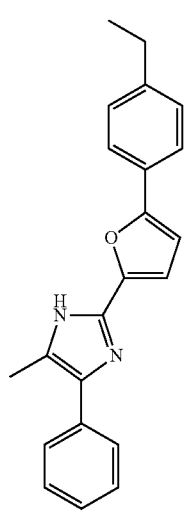
54
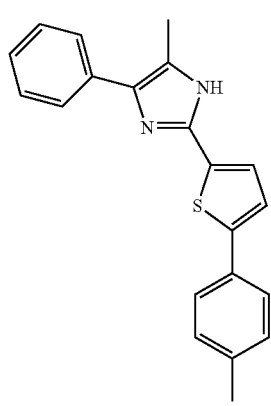
55
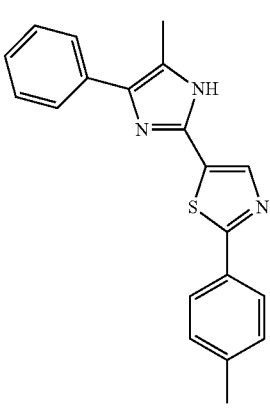
56
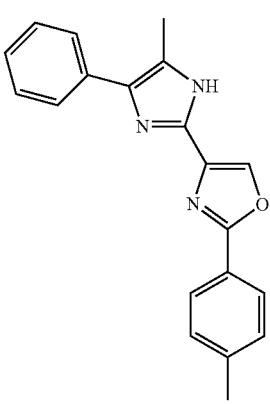
57

| | |
|---|---|
| 58 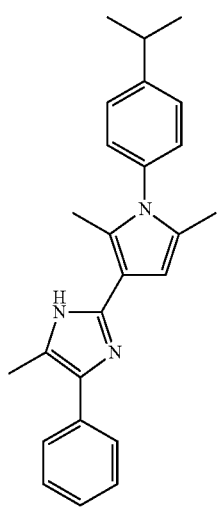 | 63 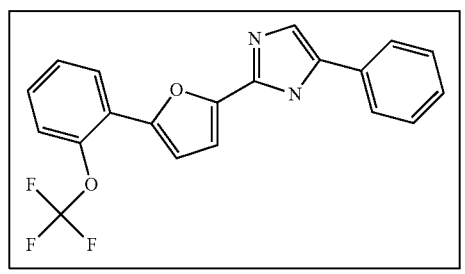 |
| 59 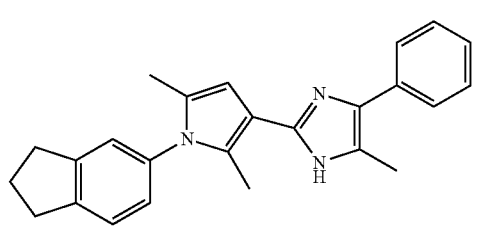 | 64 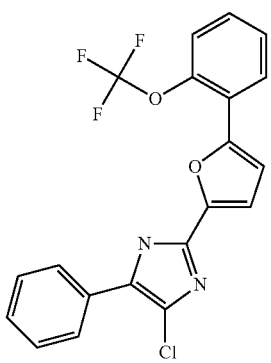 |
| 60 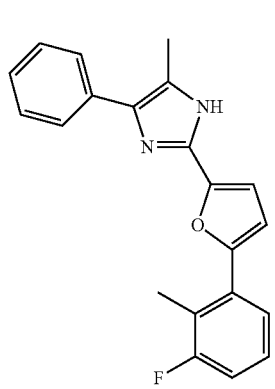 | 65 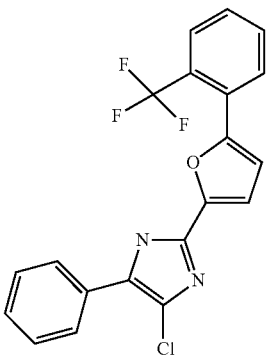 |
| 61 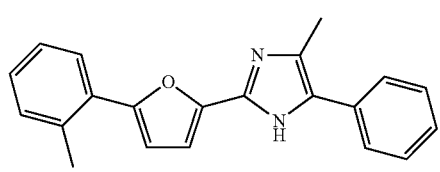 62 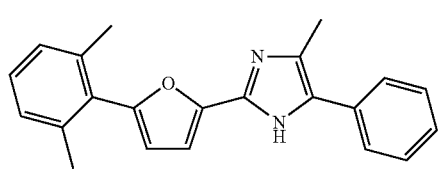 | 66 |

-continued

67
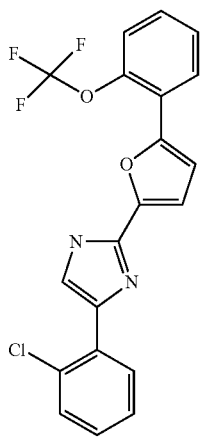

68
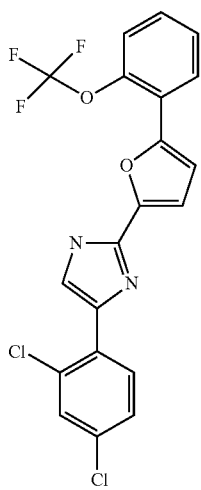

69
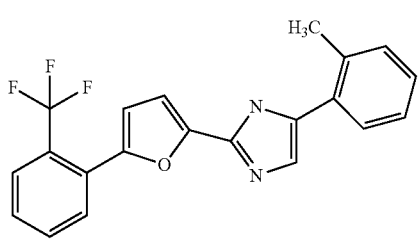

70
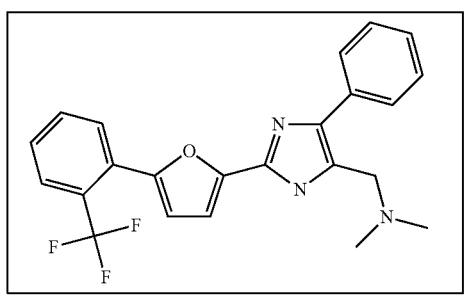

71
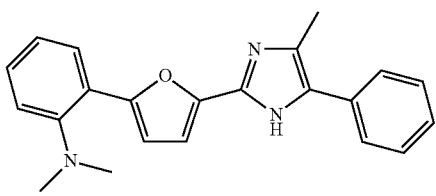

-continued

72
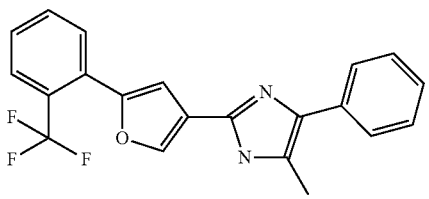

73
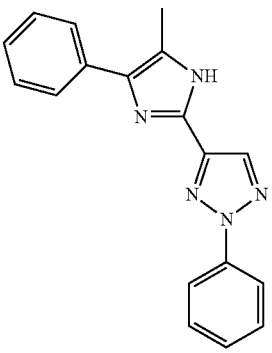

74
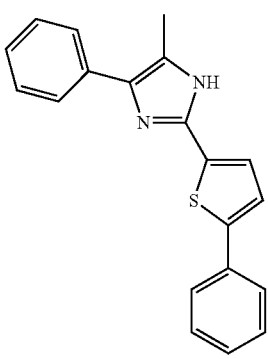

The proviso that at least one of R¹ or R² in the moieties of formulae (I), (VII) and (VII) possesses 3 or more carbon atoms is non-essential for anti-microbial activity. In the case that the compounds of the invention are directed to use in the treatment of microbial infection, either or both of R¹ or R² may possess less than 3 carbon atoms, for example both R¹ and R² can be a methyl group.

The present invention is also directed towards processes or methods for making the compounds of the invention. Accordingly, the processes for the production of the compounds of the invention and intermediates thereto as outlined under Methods A to I in the Examples Section hereinafter are also included as further aspects of the present invention. Any novel intermediates as defined in the Schemes, Lists, Examples or Methods herein are also included within the scope of the invention.

Other compounds of formula (I) may be prepared by methods analogous to those described in the Examples section or by methods known per se. Further details for the preparation of the compounds of formula (I) are found in the Examples.

The compounds of formula (I) may be prepared singly or as compound libraries comprising at least 2, for example, 5 to 1,000, compounds and more preferably 10 to 100 compounds of formula (I). Compound libraries may be prepared by a combinatorial "split and mix" approach or by multiple parallel synthesis using either solution or solid phase chemistry, using procedures to those skilled in the art.

During the synthesis of the compounds of formula (I), labile functional groups in the intermediate compounds, e.g. hydroxyl, carboxy and amino groups, may be protected. The protecting groups may be removed at any stage in the synthesis of the compounds of formula (I) or may be present on the final compound of formula (I). A comprehensive discussion of the ways in which various labile functional groups may be protected and methods for cleaving the resulting derivatives is given in, for example, Protective groups in Organic Chemisty, T. W. Greene and P. G. M Wuts, (1991) Wiley-Interscience, New York, $2^{nd}$ edition.

The preferred groups for variables recited herein in relation to the compounds of formula (I) also apply to the intermediate compounds.

The present invention relates to a compound comprising or consisting of the structural moiety of formula (I) or a pharmaceutically-acceptable salt of said compound. In some embodiments, the moiety of formula (I) may be the only moiety comprised in the structure of the compound of the invention.

While the preferred groups for each variable have generally been listed above separately for each variable, preferred compounds of this invention include those in which several or each variable in formula (I) is selected from the preferred groups for each variable. Therefore, this invention is intended to include all combinations of preferred listed groups.

Representative compounds of the invention which may be mentioned are those provided in the Examples as the free base or a pharmaceutically acceptable salt thereof. The molecular weight of the compounds of the invention is preferably less than 800 g/mol, more preferably less than 600 g/mol.

As used throughout herein, unless stated otherwise, "alkyl" means carbon chains which may be linear (straight chain) or branched. Examples of, for example, $C_{2\,to\,4}$alkyl groups include ethyl, n-propyl, isopropyl, n-, iso-, sec- and tert-butyl. As used throughout herein, unless stated otherwise, "cycloalkyl" means rings of which the atoms forming the ring itself are exclusively carbon atoms. The term "halogen" as used throughout herein means, unless otherwise stated, F, Cl, Br or I. As used herein, the term "halogen" preferably means F, Cl or Br. As used throughout herein, the term "heteroaryl" rings means 5- or 6-membered unsubstituted or substituted N-containing heteroaryl rings containing up to 2 additional heteroatoms independently selected from N, O and S. Examples of such heteroaryl rings are pyrrolyl, pyrazolyl, imidazolyl, oxazolyl, isoxazolyl, thiazolyl, isothiazolyl, triazolyl, oxadiazolyl, thiadiazolyl, pyridinyl, pyridazinyl, pyrimidinyl, pyrazinyl, triazinyl, indolyl. The term "aryl" as used throughout herein may refer to unsubstituted aryl and/or substituted aryl. Compounds described throughout herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The present invention includes all stereoisomers of the compounds of the invention and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

In an exemplary aspect of the invention, an "aryl" group is preferably an unsaturated aromatic carbocyclic group of from 6 to 14 carbon atoms having a single ring (e.g., phenyl) or multiple condensed rings (e.g., naphthyl or anthryl). Particular aryls include phenyl, biphenyl, naphthyl and the like.

In an exemplary aspect of the invention, a "heteroaryl" or "heteroaromatic" ring/group is preferably an aryl ring system having one to four heteroatoms (e.g., O, S, N, or combinations thereof) as ring atoms in a heteroaromatic ring system, wherein the remainder of the atoms are carbon atoms. The heteroaryl moiety preferably may consist of a single or fused ring system. A typical single heteroaryl ring in this sense is a 5- to 6-membered ring containing one to four, preferably one to three or one to two heteroatoms selected from oxygen, sulfur and nitrogen and a typical fused heteroaryl ring system is a 9- to 10-membered ring system containing one to four heteroatoms selected from oxygen, sulfur and nitrogen. Examples of 5-membered (single ring) heteroaryl include pyrrolyl, furanyl, thienyl, imidazolyl, pyrazolyl, oxazolyl, isoxazolyl, thiazolyl, isothiazolyl, triazolyl, furazanyl, oxadiazolyl, thiadiazolyl, dithiazolyl, and tetrazolyl. Examples of 6-membered (single ring) heteroaryl include pyridyl, pyrazinyl, pyrimidyl, pyridazinyl, triazinyl, and tetrazinyl. Examples of fused heteroaryl ring systems include indolyl, oxindolyl, indazolyl, coumarinyl, 1H-indolyl, 1H-indazolyl, benzo[d]thiazolyl, benzofuranyl, purinyl, benzimidazolyl, quinolinyl, isoquinolinyl, benzothiophenyl, benzoxazolyl, 1,2-diazanaphthyl, 1,3-diazanaphthyl, 1,4-diazanaphthyl, 1,5-diazanaphthyl, 1,6-diazanaphthyl, 1,7-diazanaphthyl, 1,8-diazanaphthyl, 2,3-diazanaphthyl, 2,6-diazanaphthyl, and 2,7-diazanaphthyl. The heteroaryl group may preferably be attached to the chemical entity or moiety of the compounds of the invention to which they are bonded by any one of the atoms within the aromatic ring system (e.g., imidazol-1-yl, imidazol-2-yl, imidazol-4-yl, imidazol-5-yl, pyrid-2-yl, pyrid-3-yl, pyrid-4-yl, pyrid-5-yl, or pyrid-6-yl). In one embodiment, the heteroaryl group is a 5- to 10-membered heteroaryl group.

Examples of 5-membered (single ring) heteroaryl include pyrrolyl (e.g. 1-, 2-, 3-, 4-, or 5-pyrrolyl), furanyl (e.g. 2-, 3-, 4-, or 5-furanyl), thienyl (e.g. 2-, 3-, 4-, or 5-thienyl), imidazolyl (e.g. 1-, 2-, 4-, or 5-imidazolyl), pyrazolyl (e.g. 1-, 3-, 4-, or 5-pyrazolyl), oxazolyl (e.g. 2-, 4-, or 5-oxazolyl), isoxazolyl (e.g. 3-, 4-, or 5-isoxazolyl), thiazolyl (e.g. 2-, 4-, or 5-thiazolyl), isothiazolyl (e.g. 3-, 4-, or 5-isothiazolyl), triazolyl (e.g. 4-, or 5-(1H-1,2,3-triazol)-yl; 4-, or 5-(2H-1,2,3-triazol)-yl; 3-, or 5-(1H-1,2,4-triazol)-yl; 3-, or 5-(4H-1,2,4-triazol)-yl), furazanyl (e.g. 3-, or 4-furazanyl), oxadiazolyl (e.g. 3-, or 4-(1,2,5-oxadiazol)-yl; 3-, or 5-(1,2,4-oxadiazol)-yl; 4-, or 5-(1,2,3-oxadiazol)-yl; 2-, or 5-(1,3,4-oxadiazol)-yl), thiadiazolyl (e.g. 3-, or 4-(1,2,5-thiadiazol)-yl; 3-, or 5-(1,2,4-thiadiazol)-yl; 4-, or 5-(1,2,3-thiadiazol)-yl; 2-, or 5-(1,3,4-thiadiazol)-yl), and tetrazolyl (e.g. 1-, or 5-(1H-tetrazolyl); 1-, or 4-(2H-tetrazolyl).

Examples of 6-membered (single ring) heteroaryl include pyridyl (e.g. 2-, 3-, 4-, 5- or 6-pyridyl), pyrazinyl (e.g. 2-, 3-, 5- or 6-pyrazinyl), pyrimidyl (e.g. 2-, 4-, 5- or 6-pyrimidyl), pyridazinyl (e.g. 3-, 4-, 5- or 6-pyridazinyl), triazinyl (e.g. 4-, or 5-, or 6-(1,2,3-triazin)-yl; 3-, or 5-, or 6-(1,2,4-triazin)-yl; 2-, or 4-, or 6-(1,3,5-triazin)-yl).

Examples of bicyclic fused ring heteroaryl include indolyl (e.g. 1-, 2-, 3-, 4-, 5-, 6-, or 7-indolyl), benzofuranyl (e.g. 2-, 3-, 4-, 5-, 6-, or 7-benzofuranyl), indazolyl (e.g. 1-, 3-, 4-, 5-, 6-, or 7-indazolyl), oxindolyl (e.g. 1-, 3-, 4-, 5-, 6-, or 7-oxindolyl), benzimidazolyl (e.g. 1-, 2-, 4-, 5-, 6-, or 7-benzimidazolyl), benzothiophenyl (e.g. 2-, 3-, 4-, 5-, 6-, or 7-benzothiophenyl), benzoxazolyl (e.g. 2-, 4-, 5-, 6-, or 7-benzoxazolyl), benzo[d]thiazolyl (e.g. 2-, 4-, 5-, 6-, or 7-benzo[d]thiazolyl), quinolinyl (e.g. 2-, 3-, 4-, 5-, 6-, 7-, or 8-quinolinyl), isoquinolinyl (e.g. 1-, 3-, 4-, 5-, 6-, 7-, or 8-isoquinolinyl), coumarinyl (e.g. 3-, 4-, 5-, 6-, 7-, or 8-coumarinyl), purinyl (e.g. 2-, 6-, 8-, or 9-purinyl), 1,2-diazanaphthyl (e.g. 3-, 4-, 5-, 6-, 7-, 8-(1,2-diazanaphth)-yl), 1,3-diazanaphthyl (e.g. 2-, 4-, 5-, 6-, 7-, 8-(1,3-diazanaphth)-yl), 1,4-diazanaphthyl (e.g. 2-, 3-, 5-, 6-, 7-, 8-(1,4-diazanaphth)-yl), 1,5-diazanaphthyl (e.g. 2-, 3-, 4-, 6-, 7-, 8-(1,5-diazanaphth)-yl), 1,6-diazanaphthyl (e.g. 2-, 3-, 4-, 5-, 7-, 8-(1,6-diazanaphth)-yl), 1,7-diazanaphthyl (e.g. 2-, 3-, 4-, 5-, 6-, 8-(1,7-diazanaphth)-yl), 1,8-diazanaphthyl (e.g. 2-, 3-, 4-, 5-, 6-, 7-(1,8-diazanaphth)-yl), 2,3-diazanaphthyl (e.g. 1-, 4-, 5-, 6-, 7-, 8-(2,3-diazanaphth)-yl), 2,6-diazanaphthyl (e.g. 1-, 3-, 4-, 5-, 7-, 8-(2,6-diazanaphth)-yl), and 2,7-diazanaphthyl (e.g. 1-, 3-, 4-, 5-, 6-, 8-(2,7-diazanaphth)-yl). More preferably when B is bicyclic fused ring heteroaryl, it is selected from the group consisting of indolyl (e.g. 1-, 2-, 3-, 4-, 5-, 6-, or 7-indolyl), benzofuranyl (e.g. 2-, 3-, 4-, 5-, 6-, or 7-benzofuranyl), indazolyl (e.g. 1-, 3-, 4-, 5-, 6-, or 7-indazolyl), and oxindolyl (e.g. 1-, 3-, 4-, 5-, 6-, or 7-oxindolyl).

In an exemplary aspect of the invention, $C_{3-6}$cycloalkyl may be selected from cyclopropyl, cyclobutyl, cyclopentyl, and cyclohexyl. In one exemplary aspect of the invention, $C_{3-6}$cycloalkyl may be selected from cyclopropyl, cyclobutyl, cyclopentyl, and cyclohexyl, whereby the cycloalkyl ring is a substituent on an atom and is attached to said atom by a single covalent bond. In one exemplary aspect of the invention, $C_{3-6}$cycloalkyl may be selected from cyclopropyl, cyclobutyl, cyclopentyl, and cyclohexyl, whereby the cycloalkyl ring is a substituent on an atom and is attached to said atom by a double covalent bond. In one exemplary aspect of the invention, $C_{3-6}$cycloalykl may be selected from cyclopropyl, cyclobutyl, cyclopentyl, and cyclohexyl, whereby the cycloalkyl ring is a substituent on an atom and constitutes a spiro substituent on said atom, i.e. two atoms of the cycloalkyl ring are directly and independently bonded to said atom.

When a tautomer of the compound of the invention exists, the present invention includes any possible tautomers and pharmaceutically acceptable salts thereof, and mixtures thereof, except where specifically drawn or stated otherwise.

When the compound of the invention and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (both cupric and cuprous), ferric, ferrous, lithium, magnesium, potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Since the compounds of the invention are intended for pharmaceutical use they are preferably provided in substantially pure form, for example at least 60% pure, more suitably at least 75% pure, especially at least 98% pure (% are on a weight for weight basis).

The invention also provides a compound comprising the moiety of the invention, or a pharmaceutically acceptable salt thereof, for use as a pharmaceutical. The invention also provides a pharmaceutical composition comprising a compound comprising the moiety of the invention, in combination with a pharmaceutically acceptable carrier.

Preferably the composition is comprised of a pharmaceutically acceptable carrier and a non-toxic therapeutically effective amount of a compound of the invention, or a pharmaceutically acceptable salt thereof.

Moreover, the invention also provides a pharmaceutical composition for use in the treatment of disease by modulating microbial activity, resulting in the prophylactic or therapeutic treatment of microbial infection, comprising a pharmaceutically acceptable carrier and a non-toxic therapeutically effective amount of compound comprising the moiety of the invention, or a pharmaceutically acceptable salt thereof.

The pharmaceutical compositions may optionally comprise other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds of the invention, or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous).

Thus, the pharmaceutical compositions can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound of the invention, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation. The compounds of the invention, or pharmaceutically acceptable salts thereof, can also be included in pharmaceutical compositions in combination with one or more other therapeutically active compounds. The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof. Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, using a compound of the invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, or pharmaceutically acceptable salts thereof, may also be prepared in powder or liquid concentrate form. Generally, dosage levels on the order of 0.01 mg/kg to about 150 mg/kg of body weight per day are useful in the treatment of the above-indicated conditions, or alternatively about 0.5 mg to about 7 g per patient per day. For example, microbial infection may be effectively treated by the administration of from about 0.01 to 50 mg of the compound per kilogram of body weight per day, or alternatively about 0.5 mg to about 3.5 g per patient per day. It is understood, however, that the specific dose level for any particular patient will depend upon a variety of factors including the age, body weight, general health, sex, diet, time of administration, route of administration, rate of excretion, drug combination and the severity of the particular disease undergoing therapy.

The invention also provides a compound of the invention, or a pharmaceutically acceptable salt thereof, for treating a medical condition, in particular for treating microbial infection and/or infectious diseases. Examples of medical conditions or diseases which may be treated by the compounds or pharmaceutical compositions of the invention include respiratory tract infections, complicated skin and soft tissue infections, complicated intra-abdominal infections, community acquired pneumonia, hospital-acquired pneumonia, ventilator-associated pneumonia, urinary tract infections, bacterial meningitis, infective endocarditis, sepsis, osteomyelitis, septic arthritis, septicemia, anthrax, osteomyelitis, tuberculosis, leprosy, necrotizing fasciitis, scarlet fever, rheumatic fever, postpartum fever, and streptococcal toxic shock syndrome, and additional nosocomial infections, for example infections caused from the use of intravascular catheters.

The invention also provides a method for the treatment of a disease or condition in which microbes play a role, said method comprising a step of administering to a subject in need thereof an effective amount of a compound of the invention, said subject being a mammal, in particular a human.

The invention also provides a method for the treatment of microbial infection, said method comprising a step of administering to a subject in need thereof an effective amount of a compound of the invention, said subject being a mammal, in particular a human.

The compounds of the invention may show activity against, and thus be used in the treatment of microbial infections caused by gram-positive bacteria or gram-negative bacteria. The compounds of the invention are preferably used in the treatment of microbial infections caused by gram-positive bacteria, in particular by one or more gram-positive bacterial species selected from the list consisting of Streptococci, Staphylococci, Bacilli, Enterococci and Mycobacteria. In some embodiments, the compounds of the invention are used in the treatment of microbial infections caused by *Streptococcus pneumoniae*. In some embodiments, the compounds of the invention are used in the treatment of microbial infections caused by *Staphylococcus aureus*. In some embodiments, the compounds of the invention are used in the treatment of microbial infections caused by methicillin-resistant *Staphylococcus aureus*. In some embodiments, the compounds of the invention are used in the treatment of microbial infections caused by *Staphylococcus epidermidis*. In some embodiments, the compounds of the invention are used in the treatment of microbial infections caused by Bacilli as exemplified by the activity against *Bacillus subtilis*. In some embodiments, the compounds of the invention are used in the treatment of microbial infections caused by *Enterococcus faecium*. In some embodiments, the compounds of the invention are used in the treatment of microbial infections caused by *Enterococcus faecalis*. In some embodiments, the compounds of the invention are used in the treatment of microbial infections caused by Mycobacteria as exemplified in the activity against *Mycobacterium smegmatis*. In some embodiments, the compounds of the invention are used in the treatment of microbial infections caused by one or more of these organisms.

The compounds of the present invention are preferably used in the treatment of microbial diseases caused by bacteria which exhibit resistance to existing antibiotics, in particular Staphylococci, Streptococci and Enterococci which exhibit resistance to one or more antibiotics. Preferred compounds of the invention exhibit activity against, and may thus be used in the treatment of microbial infections caused by, methicillin-resistant *Staphylococcus aureus*, still more preferably against methicillin-resistant *Staphylococcus aureus* which show resistance to other antibiotics, for example to other beta-lactam antibiotics, to macrolide antibiotics, to quinolones, or to cephalosporins, or to so-called antibiotics of "last resort" e.g. daptomycin, vancomycin, or linezolid, as well as to novel antibacterial agents such as moenomycin and platensimycin. It has been found that the compounds of the invention may be at least tenfold more potent against methicillin-resistant *Staphylococcus aureus* which is also resistant to daptomycin (daptomycin-resistant MRSA) than against daptomycin-sensitive strains. The compounds of the invention may thus exhibit advantageous properties for the treatment of infections caused by or caused at least in part by staphylococci resistant to daptomycin. Preferred compounds of the invention exhibit activity against, and may thus be used in the treatment of microbial infections caused by penicillin-resistant *Streptococcus pneumoniae* or erythromycin-resistant *Streptococcus pneumoniae* or tetracycline-resistant *Streptococcus pneumoniae* or penicillin-, erythromycin-, and tetracycline-resistant *Streptococcus pneumoniae*. The compounds of the invention may thus be used as antibiotics.

Generally, the compounds of the invention, in particular the preferred compounds of the invention, exhibit a therapeutic window for anti-microbial activity over toxicity to healthy human cells.

The invention also provides the use of a compound of the invention, or a pharmaceutically acceptable salt thereof, in the manufacture of a medicament for the treatment of a condition as defined above. In the methods of the invention the term "treatment" includes both therapeutic and prophylactic treatment.

The compounds of the invention may exhibit advantageous properties compared to known compounds or combination therapies for the treatment of microbial infection. The compounds of the invention, or pharmaceutically acceptable salts thereof, may be administered alone or in combination with one or more other therapeutically active compounds. The other therapeutically active compounds may be for the treatment of the same disease or condition as the compounds of the invention or a different disease or condition, for example in their use in immunocompromised patients. In a preferred embodiment the treatment consists of combining a compound of the invention with platensimycin. The therapeutically active compounds may be administered simultaneously, sequentially or separately.

The compounds of the invention may be administered with other active compounds for the treatment of microbial infection, for example together with penicillins, cephalosporins, polymyxins, rifamycins, quinolones, sulfonamides, macrolide antibiotics, lincosamides, tetracyclines, aminoglycosides, cyclic lipopeptides (such as daptomycin), glycylcyclines, oxazolidinones (such as linezolid). Inhibitors of bacterial efflux pumps, such as the AcrAB-TolC pump or the CmeABC efflux pump, may also be administered simultaneously, sequentially or separately with the compounds of the invention.

Combination therapy comprising the administration of a compound of the invention, or a pharmaceutically acceptable salt thereof, and at least one other agent, for example another agent for the treatment of microbial infection, represents a further aspect of the invention.

The present invention also provides a method for the treatment of microbial infection in a mammal, such as a human, which method comprises administering an effective amount of a compound of the invention, or a pharmaceutically acceptable salt thereof, and another agent, for example another agent for the treatment of microbial infection, to a mammal in need thereof.

The invention also provides the use of a compound of the invention, or a pharmaceutically acceptable salt thereof, and another agent for the treatment of microbial infection.

The invention also provides the use of a compound of the invention, or a pharmaceutically acceptable salt thereof, in the manufacture of a medicament for use in combination with another agent, for the treatment of microbial infection.

The compound of the invention, or a pharmaceutically acceptable salt thereof, and the other agent(s) may be co-administered or administered sequentially or separately.

Co-administration includes administration of a formulation which includes both the compound of the invention, or a pharmaceutically acceptable salt thereof, and the other agent(s), or the simultaneous or separate administration of different formulations of each agent. Where the pharmacological profiles of the compound of the invention, or a pharmaceutically acceptable salt thereof, and the other agent(s) allow it, co-administration of the two agents may be preferred. The invention also provides the use of a compound of the invention, or a pharmaceutically acceptable salt thereof, and another agent in the manufacture of a medicament for the treatment of microbial infection.

The invention also provides a pharmaceutical composition comprising a compound of the invention, or a pharmaceutically acceptable salt thereof, and another anti-microbial agent, and a pharmaceutically acceptable carrier.

When described herein that the compounds of the invention may be used in the treatment of microbial infection, it is to be understood that they may also be used in the treatment of a disorder, affliction or illness caused at least in part by microbial infection. As used herein throughout, the term "microbial infection" is to be understood to preferably mean "bacterial infection.

The invention also encompasses the use of such compositions in the methods described above.

The antibacterial activity of compounds of the invention against methicillin-resistant *Staphylococcus aureus* (MRSA) can be amplified by interfering with bacterial lipid biosynthesis.

Thus, synergistic activity with platensimycin, an inhibitor of bacterial lipid biosynthesis, is observed for compounds of the invention. This synergistic activity is determined from the fractional inhibitory concentration (FIC) indexes (FICi). An FIC is obtained by dividing the MIC of the compound when used in combination by the MIC when used alone, i.e. when using compounds A and B in combination $FIC_A = MIC_{A\ in\ combination}/MIC_{A\ alone}$ and $FIC_B = MIC_{B\ in\ combination}/MIC_{B\ alone}$. FICi is the sum of the two FIC values for each compound; that is, $FICi = FIC_A + FIC_B$. If the $FICi \leq 0.5$, then the interaction of the two compounds is defined as a synergistic interaction. Particularly preferred compounds of the invention for achieving synergistic activity against methicillin-resistant *Staphylococcus aureus* (MRSA) through their use in combination with platensimycin are compounds 2, 6, 19, 25, 26, 48, 50, 43, 44, 49, 64, 65, and 68, most preferably compounds 2, 6, 19, 25, 26, 48, and 50.

This same phenomenon is also observed in cells in which bacterial lipid biosynthesis is impacted, for example, by their being at least partially resistant to daptomycin. Here, the compounds of the invention may be at least tenfold more potent against MRSA strains in which bacterial lipid biosynthesis is impacted by their resistance to daptomycin than against the parental MRSA strain without daptomycin resistance. In this respect, compounds 2, 6, 19, 25, 26, 48, 50, 43, 44, 49, 64, 65, and 68 are particularly preferred.

Accordingly, in a preferred embodiment at least one compound of the invention is combined with at least one inhibitor of bacterial lipid synthesis, preferably with at least platensimycin. In a preferred embodiment the compounds of the invention are used in treatments which consist of combining the activity of a compound of the invention with the activity of platensimycin. This combination may be achieved through the dosing each of these compounds (compound of the invention and at least one inhibitor of bacterial lipid synthesis) separately or by dosing them together in a single dosage form. The compounds may be co-administered, administered sequentially or administered entirely separately. The combination dosed in any of these manners may be used in the treatment of microbial infection and/or a disorder, affliction or illness caused at least in part by microbial infection, in particular where said microbial infection is a bacterial infection, in particular a bacterial infection caused at least in part by methicillin-resistant *Staphylococcus aureus*.

In a preferred embodiment, the compounds of the invention may be used in the treatment of microbial infection and/or a disorder, affliction or illness caused at least in part by microbial infection, said microbial infection being a bacterial infection caused at least in part by bacteria in which bacterial lipid synthesis is negatively impacted, in particular daptomycin-resistant methicillin-resistant *Staphylococcus aureus*.

In a preferred embodiment, the compounds of the invention may be used in the treatment of microbial infection and/or a disorder, affliction or illness caused at least in part by microbial infection, in particular where said microbial infection is a bacterial infection, in particular a bacterial infection caused at least in part by daptomycin-resistant MRSA. Preferred compounds are compounds 2, 6, 19, 25, 26, 48, 50, 43, 44, 49, 64, 65, and 68 or combinations thereof, with compounds 2, 6, 19, 25, 26, 48, and 50 or combinations thereof being most preferred.

The compounds of the invention may be used in the treatment of microbial infection and/or a disorder, affliction or illness caused by or at least in part by microbial infection, said microbial infection being a bacterial infection caused by or at least in part by bacteria in which bacterial lipid synthesis is negatively impacted, in particular daptomycin-resistant methicillin-resistant *Staphylococcus aureus*. Preferred compounds are compounds 2, 6, 19, 25, 26, 48, 50, 43, 44, 49, 64, 65, and 68 or combinations thereof, with compounds 2, 6, 19, 25, 26, 48, and 50 or combinations thereof being most preferred.

A preferred embodiment relates to a combination of at least one compound of the invention and at least one inhibitor of bacterial lipid biosynthesis, in particular platensimycin, for use in the treatment of microbial infection and/or a disorder, affliction or illness caused by or at least in part by microbial infection, in particular where said microbial infection is a bacterial infection, in particular a bacterial infection caused by or at least in part by methicillin-resistant *Staphylococcus aureus*. Preferred compounds of the invention are compounds 2, 6, 19, 25, 26, 48, 50, 43, 44, 49, 64, 65, and 68 or combinations thereof, with compounds 2, 6, 19, 25, 26, 48, and 50 or combinations thereof being most preferred. In a further aspect, the combination of at least one compound of the invention and at least one inhibitor of bacterial lipid biosynthesis, in particular platensimycin, is provided by combining the two active agents in a single formulation before dosing or by dosing the two active agents separately. Accordingly, the present invention also relates to a composition comprising (i) at least one compound according to the invention, in particular at least one compound selected from compounds 2, 6, 19, 25, 26, 48, 43, 44, 49, 50, 64, 65 and 68, preferably at least one compound selected from compounds 2, 6, 19, 25, 26, 48 and 50, and (ii) at least one inhibitor of bacterial lipid biosynthesis, in particular platensimycin.

In a preferred embodiment, the compounds of the invention may be used in the treatment of daptomycin-resistant MRSA.

In another preferred embodiment, the infection may be caused by or at least in part caused by staphylococci resistant to daptomycin, in particular by daptomycin-resistant MRSA A further aspect of the present invention relates to a kit comprising a first composition and a second composition, said first composition comprising at least one compound of the invention and said second composition comprising at least one inhibitor of bacterial lipid biosynthesis, in particular platensimycin, wherein said first and second compositions are physically separate from each other.

All publications, including, but not limited to, patents and patent application cited in this specification, are herein incorporated by reference as if each individual publication were specifically and individually indicated to be incorporated by reference herein as fully set forth. The invention will now be described by reference to the following examples which are for illustrative purposes and are not to be construed as a limitation of the scope of the present invention.

All measurements and determinations have been carried out at room temperature (20° C.) unless otherwise stated.

EXAMPLES

Materials and Methods

Column chromatography was carried out on commercially available silica gel (loose or pre-packed cartridges) unless otherwise stated.

NMR data were obtained in the specified solvent and using the following machines:

NMR data for compounds synthesised using synthetic Methods A or B were obtained using a Brucker 400 MHz Ultrashield spectrometer. NMR data for compounds synthesised using synthetic Method C were obtained using a Bruker AVANCE III HD Spectrometer. NMR data for compounds synthesised using synthetic Methods D or E were obtained using a Bruker Avance III 600 NMR spectrometer or Bruker Avance DPX300 NMR spectrometer. NMR data for compounds synthesised using synthetic Methods F to I were obtained using a Varian INOVA Plus (400 MHz) spectrometer or Bruker Avance (500 MHz) spectrometer.

LCMS data were obtained and HPLC analysis carried out using one or more of the following methods:

LCMS Procedure #1:

Mobile phases: 10 mM ammonium formate in 9:1 (v/v) water:methanol at pH 8 (A) & 10 mM ammonium formate in methanol (B). Chromatography uses a Variant Pursuit C18 column (2.0×20.0 mm, 5 μm, flow rate=0.8 ml/min). Total run time: 5 min.

Gradient Elution:

| Time (min) | A(%, v/v) | B(%, v/v) |
| --- | --- | --- |
| 0 | 100 | 0 |
| 0.2 | 100 | 0 |
| 2.7 | 0 | 100 |
| 4.4 | 0 | 100 |
| 5 | 100 | 0 |

The system used was the Waters 2795/Micromass Platform. UV detection was at 180 to 500 nm (diode array detection). The mass spectra were obtained using an electrospray ionization source in the positive (ES<+>) mode.

For clarity, in the above table for LCMS procedure #1 in which the details of the gradient elution are outlined, the presented data should be understood to mean the following: Between 0 min and 0.2 min 100% of eluent A was employed. From 0.2 to 2.7 min the eluent mixture was gradually changed (gradient) such that at 2.7 min an eluent composition of 100% eluent B was reached. Between 2.7 min and 4.4 min the eluent composition was held at 100% eluent B. From 4.4 to 5.0 min the eluent mixture was gradually changed such that at 5.0 min an eluent composition of 100% eluent A was reached. In all other LCMS and HPLC procedures described herein in which 'gradient elution' is employed, the information provided in the respective tables corresponding to the 'gradient elution' table of LCMS procedure #1 should be interpreted/understood analogously.

LCMS Procedure #2:

Solvents: acetonitrile (Far UV grade) with 0.1% (v/v) formic acid and water (high purity via PureLab Option unit) with 0.1% formic acid. Column: Phenomenex Luna 5 μm, C18, 100×4.6 mm (plus guard cartridge). Flow rate: 2 ml/min. Total run time: 6 min.

Mobile phases: water/formic acid (A) & acetonitrile/formic acid (B); gradient elution:

| Time (min) | A(%, v/v) | B(%, v/v) |
| --- | --- | --- |
| 0.00 | 95 | 5 |
| 3.50 | 5 | 95 |
| 5.50 | 5 | 95 |
| 5.60 | 95 | 5 |
| 6.50 | 95 | 5 |

UV detection was via HP or Waters DAD. Start range 210 nm, end range 400 nm; range interval 4.0 nm. Other wavelength traces extracted from the DAD data. Optional ELS detection was done using Polymer Labs ELS-1000.

The mass spectra were obtained using an ESCI (combined electrospray/APCI ionization source) in ES+, ES−, APCI+ & APCI− modes.

LCMS Procedure #3:

Solvents: acetonitrile (Far UV grade), and water (high purity via PureLab Option unit) with 10 mM ammonium bicarbonate (ammonium hydrogen carbonate). Column: Waters Xterra-MS 5 μm, C18, 100×4.6 mm. Flow rate: 2 ml/min. Total run time: 6 min.

Mobile phases: water/bicarbonate (A) & acetonitrile (B); gradient elution:

| Time (min) | A(%, v/v) | B(%, v/v) |
| --- | --- | --- |
| 0.00 | 95 | 5 |
| 0.50 | 95 | 5 |
| 4.00 | 5 | 95 |
| 5.50 | 5 | 95 |
| 5.60 | 95 | 5 |
| 6.50 | 95 | 5 |

UV detection was done via HP or Waters DAD. Start range 210 nm, end range 400 (nm); range interval 4.0 nm. Other wavelength traces extracted from the DAD data. Optional ELS detection was done using Polymer Labs ELS-1000.

The mass spectra were obtained using an ESCI (combined electrospray/APCI ionization source) in ES+, ES−, APCI+ & APCI− modes.

HPLC Procedure #4:

Solvents: Acetonitrile (Far UV grade) with 0.1% (v/v) formic acid and water (high purity via PureLab Ultra unit) with 0.1% (v/v) formic acid. Column: Supelco, Ascentis® Express C18 or Hichrom Halo C18, 2.7 m C18, 150×4.6 mm. Flow rate: 1 ml/min. Total run time: 16 min.

Mobile phases: water/formic acid (A) & acetonitrile/formic acid (B); gradient elution:

| Time (min) | A(%, v/v) | B(%, v/v) |
|---|---|---|
| 0.00 | 96 | 4 |
| 3.00 | 96 | 4 |
| 9.00 | 0 | 100 |
| 13.6 | 0 | 100 |
| 13.7 | 96 | 4 |
| 15 | 96 | 4 |

Instrument: Agilent 1100, Binary Pump, Agilent Sampler and Agilent DAD detector. Diode array detection: (300 nm, band width 200 nm; Ref. 450 nm, band width 100 nm).

HPLC Procedure #5:

Solvents: as for HPLC procedure #4, Column: Hichrom ACE 3 μm C18-AR mixed mode column 100×4.6 mm. Flow rate: 1 ml/min. Total run time: 20 min.

Mobile phases: water/formic acid (A) & acetonitrile/formic acid (B); gradient elution:

| Time (min) | A(%, v/v) | B(%, v/v) |
|---|---|---|
| 0.00 | 98 | 2 |
| 3.00 | 98 | 2 |
| 12.00 | 0 | 100 |
| 15.4 | 0 | 100 |
| 15.5 | 98 | 2 |
| 17 | 98 | 2 |

Instrument and detection were as for HPLC procedure #4.

HPLC Procedure #6:

Solvents: 100% Acetonitrile (Far UV grade), and water (High purity via PureLab Ultra unit) with 10 mM ammonium bicarbonate. Column: Hichrom, ACE Excel 3 μm SuperC18, 150×4.6 mm. Flow rate: 1 ml/min. Total run time: 16 min.

Mobile phases: 10 mM ammonium bicarbonate in water (A) & 100% acetonitrile (B); gradient elution:

| Time (min) | A(%, v/v) | B(%, v/v) |
|---|---|---|
| 0.00 | 95.5 | 4.5 |
| 3.00 | 95.5 | 4.4 |
| 9.00 | 0 | 100 |
| 13.6 | 0 | 100 |
| 13.7 | 95.5 | 4.5 |
| 15 | 95.5 | 4.5 |

Instrument and detection were as for HPLC procedure #4.

LCMS Procedure #7:

Solvents were acetonitrile (Far UV grade) with 0.1% (v/v) formic acid (A) and water (high purity via PureLab Option unit) with 0.1% formic acid (B). The column was a Supelco Ascentis Express C18-2.7 μm column of 4.6×30 mm, used at a flow rate of 3 ml/min. Gradient elution was as follows (% are v/v): 0 min—100% B, 0% A; 0.01 min—100% B, 0% A; 1.5 min—0% B, 100% A; 2.2 min—0% B, 100% A; 2.21 min—100% B, 0% A.

UV detection was done via Shimadzu VP HPLC systems with diode array UV-VIS detector. Start range 210 nm, end range 400 (nm); range interval 4.0 nm. The mass spectra were obtained using electrospray ionization (ESI) in either the ES or ES-mode; scan range was m/z 80-1000.

LCMS Procedure #8:

Mobile phases were acetonitrile with 0.1% (v/v) formic acid (A) and water with 0.1% formic acid (B). The column was Waters SunFire C18, 3.5 μm, 2.1×50 mm. Flow rate: 0.5 ml/min. Total run time: 22 min.

Gradient Elution:

| Time (min) | A(%, v/v) | B(%, v/v) |
|---|---|---|
| 0.00 | 95.0 | 5.0 |
| 3.00 | 95.0 | 5.0 |
| 17.50 | 5.0 | 95.0 |
| 19.00 | 5.0 | 95.0 |
| 19.50 | 95.0 | 5.0 |
| 20.00 | 95.0 | 5.0 |

UV detection was done via HP or Waters DAD. Start range 210 nm, end range 400 (nm); range interval 4.0 nm. The mass spectra were obtained using an ESCI (combined electrospray/APCI ionization source) in ES+ and ES− modes.

LCMS Procedure #9:

Mobile phases were as for procedure #8. The column was Acquity UPLC BEH C18 (50 mm×2.1 mm, 1.7 μm packing diameter). Total run time: 13 min.

Gradient Elution:

| Time (min) | Flow Rate (ml/min) | % (v/v)A | %(v/v)B |
|---|---|---|---|
| 0 | 0.9 | 95 | 5 |
| 1.50 | 0.9 | 95 | 5 |
| 8.75 | 0.9 | 20 | 80 |
| 9.50 | 0.9 | 10 | 90 |
| 9.80 | 0.9 | 10 | 90 |
| 12.00 | 0.05 | 95 | 5 |

The UV detection was a summed signal from wavelength of 210 nm to 350 nm. The mass spectra were obtained using alternate—scan positive and negative Electrospray (ES+/ES−).

Preparative HPLC Procedure #10:

Mobile phases were a mixture of water: methanol 9:1 (v/v) containing 0.1% (v/v) NH$_3$ (A) and methanol with 0.1% (v/v) NH$_3$ (B). The column was an Interchim Puriflash C18 HP 30 μm, 6 g column. Flow rate: 7 ml/min. Total run time: 25 min.

Gradient Elution:

| Time (min) | % A | % B |
|---|---|---|
| 0 | 100 | 0 |
| 3 | 100 | 0 |
| 10 | 0 | 100 |
| 25 | 0 | 100 |

UV detection was done at 385 nm

Preparative HPLC Procedure #11:

Compounds were purified via reverse phase HPLC using a Gilson preparative HPLC system (322 pump; 156 UV/VIS detector; GX281 liquid handler). The GX281 liquid handler acted as both auto-sampler and fraction collector. The column is either a Waters Sunfire OBD column (10 μm; 19×150 mm) for acidic conditions or a Waters Xbridge OBD column (5 μm; 19×100 mm) for basic conditions. The gradient used is 95% water & 5% acetonitrile for 1 min to 5% water & 95% acetonitrile over 5 min, then held at 5% water & 95% acetonitrile for 4 min. The solvent mixture is then returned to the initial conditions over 3 min. For elution under acidic conditions, the solvents contain 0.1% (v/v) formic acid, whilst for elution under obtain basic conditions the solvents contain 10 mM ammonium bicarbonate. A flow rate of 20 ml/min is used. To decide which conditions are best, compounds are screened analytically prior to purification, whereby each sample is run under both acidic and basic conditions (0.5 μl injection, 5/95 gradient for 5 minutes). The purification is controlled by Trilution® software through monitoring at 260 nm and 230 nm. Collected fractions are analyzed by UPLC (Waters Acquity with SQD mass spectrometer). The fractions containing the desired product are concentrated and lyophilized by vacuum centrifugation (Genevac) or lyophilized separately using a Virtis freeze-drier.

Where necessary, the standard gradient may be amended for challenging separations.

Preparative HPLC Procedure #12:

Mobile phases were 10 mM ammonium bicarbonate adjusted to pH=10 with ammonia (A) and acetonitrile (B). The column was an Xbridge Prep. MS C18 OBD column (5 μm; 150×30 mm). The following gradient was used:

| Time (min) | % A | % B (v/v) |
| --- | --- | --- |
| 0 | 97 | 3 |
| 1 | 97 | 3 |
| 30 | 0 | 100 |
| 35 | 0 | 100 |

The flow rate was 50 ml/min; stop-time was 35 min. UV detection was a summed signal from a wavelength of 210 to 600 nm.

Abbreviations and Acronyms

AcOH: Acetic acid;
AcOEt: Ethyl acetate;
ADDP: Azodicarboxylic dipiperidine;
APCI: Atmospheric Pressure Chemical Ionization;
BA: Butylamine;
CDI: 1,1'-Carbonyldiimidazole;
$CH_2Cl_2$: Dichloromethane;
$CHCl_3$: Chloroform;
CsF: Cesium fluoride;
DBU: 1,8-Diazabicyclo[5.4.0]undec-7-ene;
DCM: Dichloromethane;
DEA: Diethylamine;
DIPE: Diisopropyl ether;
DIPEA: N,N-Diisopropylethylamine;
DMAP: Dimethylpyridin-4-ylamine;
DME: Dimethoxyethane;
DMF: Dimethylformamide;
DMSO: Dimethyl sulfoxide;
EDCI: (3-Dimethylaminopropyl)ethylcarbodiimide hydrochloride;
ESCI: Multi-Mode Ionization Source combining high-speed switching between electrospray ionization (ESI) and Atmospheric Pressure Chemical Ionization (APCI);
$Et_2O$: Diethyl ether;
$Et_3N$: Triethylamine;
EtOH: Ethanol;
EtOAc: Ethyl Acetate;
eq: molar equivalents
h: hour(s);
HCHO: formaldehyde;
HCl: Hydrochloric acid;
$HCO_2H$: Formic acid;
$H_2O$: Water;
HOBt: 1-Hydroxybenzotriazole monohydrate;
HPLC: High performance liquid chromatography;
IH: Isohexane;
IMS: Industrial methylated spirit;
IPA: Isopropyl alcohol;
KOH: Potassium hydroxide
$K_3PO_4$: Tripotassium phosphate;
LAH: Lithium aluminium hydride;
LCMS: liquid chromatography plus mass spectrometry;
M: Molar;
MDR: multi drug resistant;
MeCN: Acetonitrile;
MeOH: Methanol;
$MgSO_4$: Magnesium sulfate;
MIC: Minimal Inhibitory Concentration;
MIC100: minimal concentration to obtain 100% inhibition of bacterial growth;
MIC50: minimal concentration to obtain 50% inhibition of bacterial growth;
min: minutes;
mmol: millimoles;
μM: micro-molar;
MRSA: methicillin-resistant *Staphylococcus aureus;*
MSSA: methicillin-sensitive *Staphylococcus aureus;*
MTBE: Methyl-tert-butyl ether;
$Na_2CO_3$: Sodium carbonate;
$NaHCO_3$: Sodium hydrogen carbonate;
NaOH: Sodium hydroxide;
$NaNO_2$: sodium nitrite;
$Na_2SO_4$: Sodium sulfate;
NH4Cl: Ammonium chloride;
$NH_4HCO_3$: Ammonium bicarbonate;
$NH_4OH$: Ammonium hydroxide;
NMR: nuclear magnetic resonance;
Pd: Palladium;
$Pd^0$: Any palladium species where palladium is in the 'zero oxidation state';
$Pd(OAc)_2$: Palladium(II) acetate;
$Pd(PPh_3)$: Palladium tetrakis(triphenylphosphine);
$Pd(dppf)Cl_2 \cdot CH_2Cl_2$: [1,1'-Bis(diphenylphosphino)ferrocene]dichloropalladium(II), complex with dichloromethane;
$PPh_3$: Triphenylphosphine;
RT: Retention time;
r.t.: Room temperature (20° C.);
sat: saturated;
SCX: Strong Cation Exchange resin;
$SiO_2$: Silica gel;
SM: starting material;
THF: Tetrahydrofuran;
TFA: Trifluoroacetic acid;
$TiCl_3$: Titanium (III) chloride;
TLC: thin layer chromatography;
TSB: Tryptic soy broth;
TsOH: p-Toluenesulfonic acid monohydrate;
UPLC: ultra-high performance liquid chromatography;
UV: ultraviolet.

General Synthetic Routes

The compounds of the present invention may be made using at least one of the following synthetic routes and, in some instances, may be successfully synthesized via more than one or using a combination of more than one of the following synthetic routes. For each of the Methods listed below which do not relate to the synthesis of a specific single compound but instead to the synthesis of compounds which remain, to some extent, generic, e.g. a generic group such as $R^1$, $R^2$, A, B etc remains in the structure, the specified absolute and molar quantities, concentrations, reaction temperatures, reaction times and purification procedures etc serve to provide an indication of typical reaction conditions/procedures used in the synthesis of compounds of their respective generic class. Specific compounds made according to such a 'generic' Method may have been made on a different scale to that described for the 'generic' Method. In such cases, the relative molar equivalents of starting materials and reagents, reaction concentrations and temperatures are the same as those described in the 'generic' Method. In certain cases, such absolute and molar quantities, concentrations, reaction temperatures, reaction times and purification procedures etc may be altered for the synthesis of given compounds of the class, as would be standard laboratory practice for the skilled person.

The conditions described for general transformations which are common to/present within more than one Method may be transferable between Methods. For example, if more than one Method contains a description of the reaction of an aldehyde with a dicarbonyl compound in the presence of a source of ammonia such to furnish an imidazole-containing compound, if these respective Methods describe differing conditions for this general transformation then their respective conditions may also be applicable to the other Method(s) which also describe(s) this general transformation.

All reactions have been carried out at room temperature (20° C.) unless otherwise stated.

Method A (General Procedure for the Synthesis of the Imidazoles in One Step):

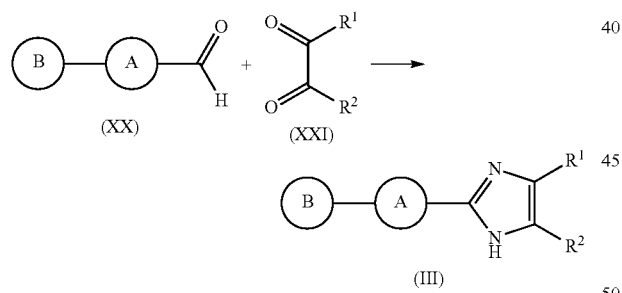

Compounds of Formula (III) may be made through the reaction of an aldehyde of formula (XX) with a dicarbonyl compound of formula (XXI) in the presence of a source of ammonia preferably under standard conditions such as heating in a solvent, for example an alcoholic solvent.

Aldehydes of formula (XX) are generally commercially available (for example from, inter alia, Sigma-Aldrich (St. Louis, Mo., USA), Alfa Aesar (Schiltigheim, France), Acros Organics (Geel, Belgium), Key Organics (Camelford, UK), Matrix Scientific (Columbia, S.C., USA), Fluorochem (Hadfield, Derbyshire, UK) and Enamine (Kiev, Ukraine)) but, when they are not commercially available, they may also be made by at least one of a number of standard methods known to the person skilled in the art such as, for example, reduction of the corresponding nitrile or acid or ester, reaction of an appropriate organometallic or metallated species with N,N-dimethylformamide, general carbonylation methods known to the skilled person etc. Aldehydes of formula (XX) may also be made by further methods such as, for example, those outlined herein under the corresponding reaction step in Method D (step 1), in Method H or by any number of the steps (as required depending on the available starting material) leading to such aldehydes in Method E herein.

Dicarbonyl compounds of formula (XXI) can either be purchased from commercial suppliers (for example, inter alia, Sigma-Aldrich (St. Louis, Mo., USA), Alfa Aesar (Schiltigheim, France), Acros Organics (Geel, Belgium), Key Organics (Camelford, UK), Matrix Scientific (Columbia, S.C., USA), Fluorochem (Hadfield, Derbyshire, UK) and Enamine (Kiev, Ukraine)) or made by at least one of a number of standard methods known to the person skilled in the art such as, for example, by selenium-dioxide-mediated oxidation of the appropriate substrate as described in Rabjohn, N. Org. React, 1976, 44, 261, or by the method outlined herein below under Method F.

An example of the use of Method A in the synthesis of 2-furanylimidazole compounds of the invention is

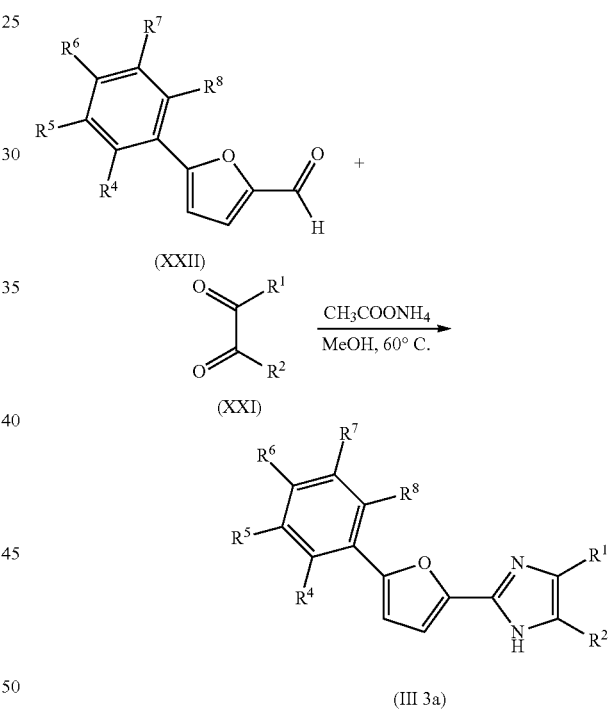

To the diketone (XXI) (1 eq) dissolved in methanol (0.1 M) was added a solution of aldehyde (XXII) (1 eq) dissolved in methanol (0.1 M). Eight equivalents of ammonium acetate dissolved in methanol (0.8 M) were added. The mixture was stirred at 60° C. for two hours. The solvent was evaporated and the residue was dissolved in ethyl acetate and washed twice with $Na_2CO_3$ 0.1 M, then with water. The organic layer was evaporated and the compound (III 3a) was purified on C18 with a semi-automated system in a $H_2O$/MeOH gradient using preparative HPLC Procedure 10 (yield 70 to 90%).

By means of example, compound 23 below was synthesized in 70% yield from 1-(4-Fluorophenyl)propane-1,2-dione monohydrate (commercially available from, inter alia, Fluorochem (Hadfield, Derbyshire, UK)) and 5-[2-(trifluoromethoxy)phenyl]-2-furaldehyde (commercially available from, inter alia, Fluorochem (Hadfield, Derbyshire, UK)) using 0.1 mmol of the aldehyde SM using the conditions outlined above.

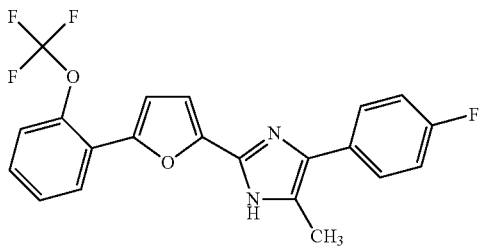

23

4-(4-Fluoro-phenyl)-5-methyl-2-[5-(2-trifluoromethoxy-phenyl)-furan-2-yl]-1H-imidazole 23

$^1$H NMR (400 MHz, DMSO-d$_6$): δ 2.49 (3H, s, CH$_3$), 6.98 (1H, d, J=3.2 Hz, furan), 7.02 (1H, d, J=3.2 Hz, furan), 7.27 (2H, m, F-phenyl), 7.50 (2H, m, OCF$_3$-phenyl), 7.58 (1H, m, OCF$_3$-phenyl), 7.73 (2H, m, F-phenyl), 8.21 (1H, d, J=8.0 Hz, OCF$_3$-phenyl); LC-MS procedure 1 (electrospray positive ion mode): m/z 403 (M+H)$^+$.

Further compounds of the invention made by the above-outlined procedure are outlined herein below. Reactions were performed using 0.1 mmol of the appropriate starting aldehyde:

Compound 18 was synthesized in 66% yield from 1-Phenyl-1,2-propanedione (commercially available from, inter alia, Sigma-Aldrich) and 5-[2-(trifluoromethoxy)phenyl]-2-furaldehyde (commercially available from, inter alia, Fluorochem (Hadfield, Derbyshire, UK)).

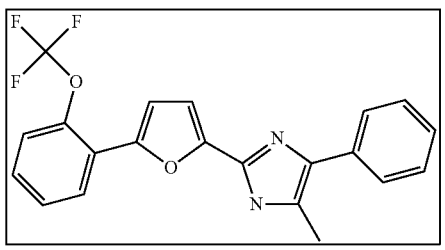

18

Compound 5 was synthesized in 73% yield from 1-Phenyl-1,2-propanedione (commercially available from, inter alia, Sigma-Aldrich) and 5-(4-Chlorophenyl)furfural (commercially available from, inter alia, Sigma-Aldrich).

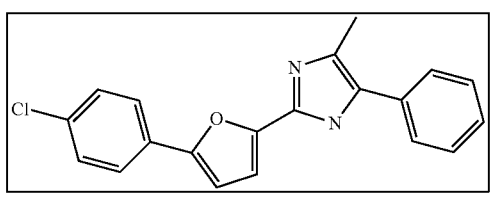

5

Compound 17 was synthesized in 59% yield from 1-Phenyl-1,2-propanedione (commercially available from, inter alia, Sigma-Aldrich) and 5-[2-(Trifluoromethyl)phenyl]furfural (commercially available from, inter alia, Sigma-Aldrich).

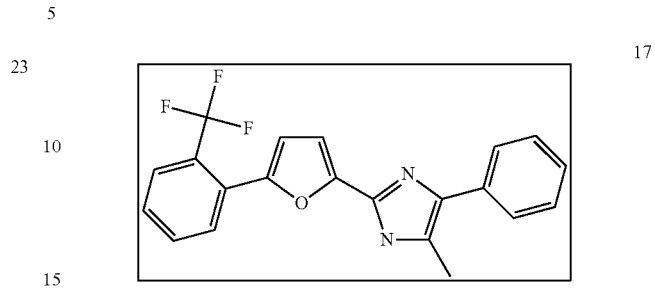

17

Compound 63 was synthesized in 53% yield from Phenylglyoxal (commercially available from, inter alia, Sigma-Aldrich) and 5-[2-(trifluoromethoxy)phenyl]-2-furaldehyde (commercially available from, inter alia, Fluorochem (Hadfield, Derbyshire, UK)).

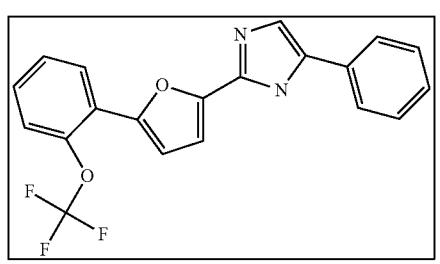

63

Compound 25 was synthesized in 59% yield from 1-(4-bromophenyl)-1,2-propanedione (commercially available from, inter alia, Chembridge) and 5-[2-(Trifluoromethyl)phenyl]furfural (commercially available from, inter alia, Sigma-Aldrich).

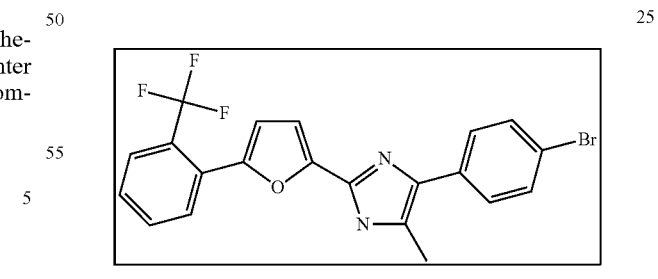

25

Compound 24 was synthesized in 71% yield from 1-(4-Chlorophenyl)propane-1,2-dione (commercially available from, inter alia, Fluorochem (Hadfield, Derbyshire, UK)) and 5-[2-(trifluoromethoxy)phenyl]-2-furaldehyde (commercially available from, inter alia, Fluorochem (Hadfield, Derbyshire, UK)).

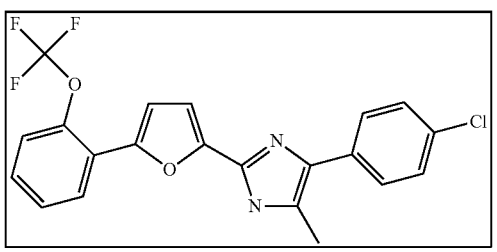

24

Compound 26 was synthesized in 49% yield from 1-(4-Trifluoromethylphenyl)-1,2-propanedione monohydrate (commercially available from, inter alia, Fluorochem (Hadfield, Derbyshire, UK)) and 5-[2-(trifluoromethoxy)phenyl]-2-furaldehyde (commercially available from, inter alia, Fluorochem (Hadfield, Derbyshire, UK)).

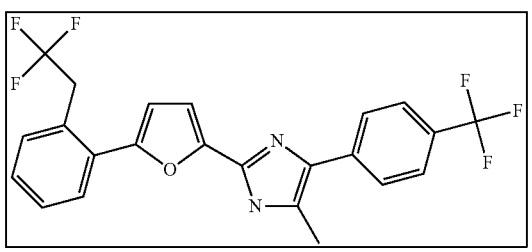

26

Compound 38 was synthesized in 59% yield from 1-(4-Fluorophenyl)propane-1,2-dione monohydrate (commercially available from, inter alia, Fluorochem (Hadfield, Derbyshire, UK)) and 5-[3-(Trifluoromethyl)phenyl]furfural (commercially available from, inter alia, Sigma-Aldrich).

38

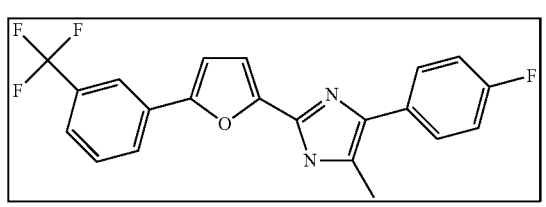

Compound 4 was synthesized in 85% yield from 1-Phenyl-1,2-propanedione (commercially available from, inter alia, Sigma-Aldrich) and 5-(3-Chlorophenyl)furfural (commercially available from, inter alia, Sigma-Aldrich).

4

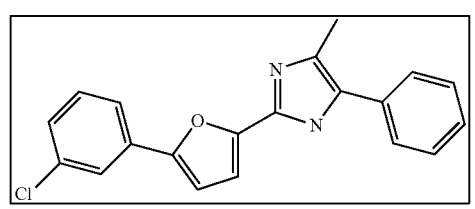

Compound 29 was synthesized in 67% yield from 1-(4-Bromophenyl)propane-1,2-dione (commercially available from, inter alia, Otava Chemicals (Vaughan, Ontario, Canada)) and 5-[2-(trifluoromethoxy)phenyl]-2-furaldehyde (commercially available from, inter alia, Acros Organics) using 0.1 mmol of the aldehyde SM using the conditions outlined above.

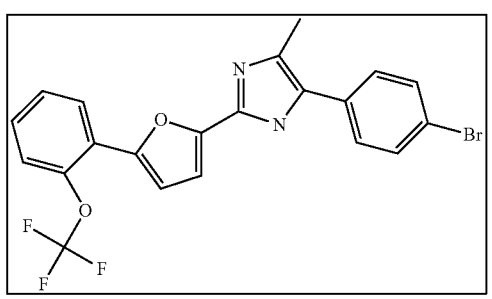

29

Compound 28 was synthesized in 70% yield from 1-(4-Ethyl-phenyl)-propane-1,2-dione obtained by oxidation with sodium nitrite of 1-(4-Ethyl-phenyl)-propan-1-one (commercially available from, inter alia, Enamine) and 5-[2-(trifluoromethyl)phenyl]-2-furaldehyde (commercially available from, inter alia, Sigma Aldrich) using 0.1 mmol of the aldehyde SM using the conditions outlined above.

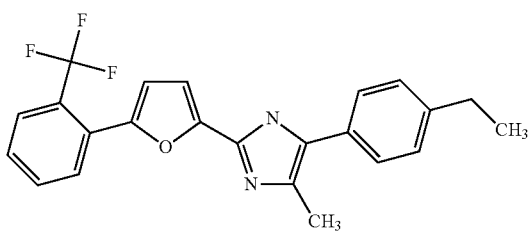

28

Compound 40 was synthesized in 88% yield from 1-(phenyl)-propane-1,2-dione monohydrate (commercially available from, inter alia, Sigma-Aldrich) and 5-[3-(Trifluoromethyl-5-chloro)phenyl]furfural (commercially available from Sigma-Aldrich).

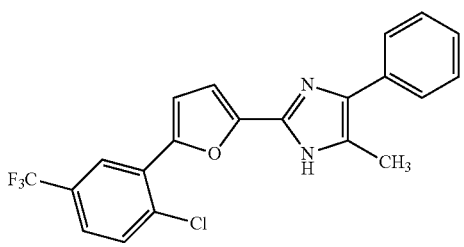

40

Compound 70 was obtained as follows: 100 mg of the imidazole intermediate (4-phenyl-2-[5-(2-trifluoromethylphenyl)-furan-2-yl]-1H-imidazole 123, synthesized in 52% yield according to the methods detailed above) was dissolved in 2.5 mL of N,N-Dimethylformamide, and 2.5 mL of water and excess formaldehyde (500 μL of a 37% solution in water) and KOH (1 g) were added.

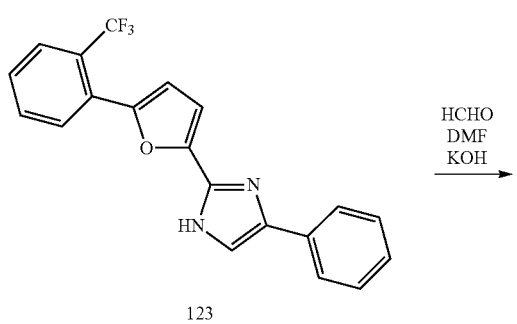

123

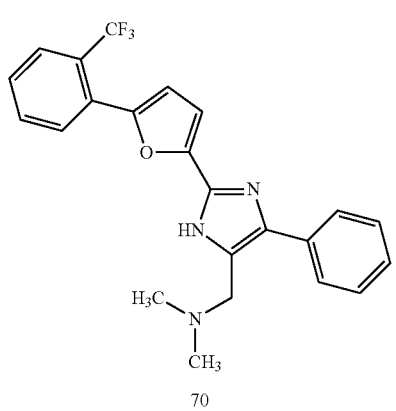

70

The reaction mixture was heated at 80° C. for 1 hour. The solvent was evaporated and the residue was purified on C18 with a semi-automated system in a H$_2$O:MeOH gradient using preparative HPLC Procedure 10, affording compound 70, below in 70% yield.

70

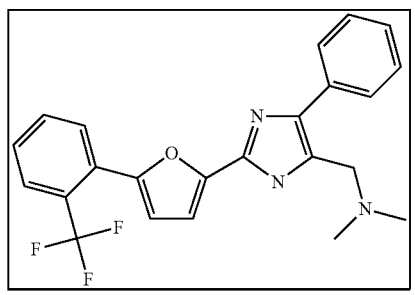

Method B (General Procedure for the Synthesis of the Imidazoles in Three Steps):

Step 1:

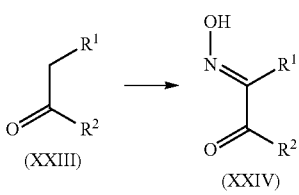

or

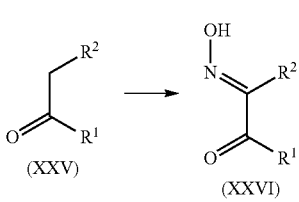

Compounds of formula (XXIV) or (XXVI) may be made by reacting, respectively, compounds of formula (XXIII) or (XXV) with NaNO$_2$ preferably under standards conditions such as in an ethereal solvent, e.g. tetrahydrofuran, at ambient (room) temperature.

The requisite carbonyl starting materials can generally be purchased from commercial suppliers such as, for example, Matrix Scientific, Columbia, S.C., USA or other suppliers. When these starting materials are not commercially available they may also be made by at least one of a number of standard methods known to the person skilled in the art for making carbonyl compounds such as, for example, reduction of the corresponding nitrile or acid or ester, reaction of an appropriate organometallic or metallated species with the appropriate carboxylic acid, ester or Weinreb amide, Friedel-Kraft acylation chemistry, etc.

Step 2:

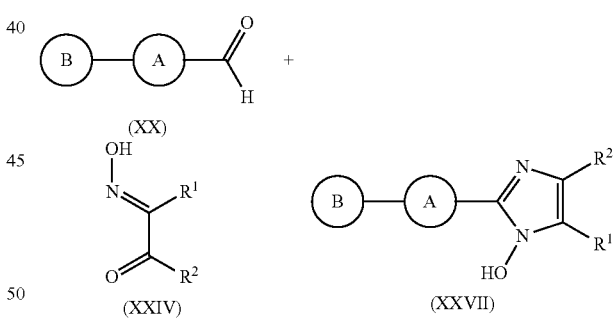

Compounds of formula (XXVII) or (XXVIII) may be made by reacting, respectively, the compounds formula (XXIV) or (XXVI) from Step 1 with an aldehyde of formula (XX) in the presence of a source of ammonia preferably under standard conditions, for example in an alcoholic solvent with heating.

Aldehydes of formula (XX) are generally commercially available (for example from, inter alia, Sigma-Aldrich (St. Louis, Mo., USA), Alfa Aesar (Schiltigheim, France), Acros Organics (Geel, Belgium), Key Organics (Camelford, UK), Matrix Scientific (Columbia, S.C., USA), Fluorochem (Hadfield, Derbyshire, UK) and Enamine (Kiev, Ukraine)) but, when they are not commercially available, they may also be made by at least one of a number of standard methods known to the person skilled in the art such as, for example, reduction of the corresponding nitrile or acid or ester, reaction of an appropriate organometallic or metallated species with N,N-dimethylformamide, general carbonylation methods known to the skilled person etc. Aldehydes of formula (XX) may also be made by further methods such as, for example, those outlined herein under the corresponding reaction step in Method D (step 1), in Method H or by any number of the steps (as required depending on the available starting material) leading to such aldehydes in Method E herein.

Step 3:

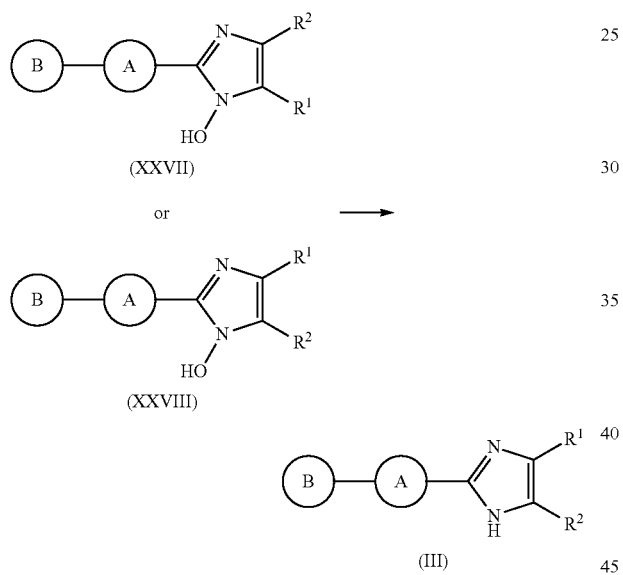

Compounds of formula (III) may be respectively generated from compounds of formula (XXVII) or (XXVIII) preferably through standard reduction conditions such as heating in a solvent, for example a dipolar aprotic solvent such as DMF, in the presence of TiCl$_3$.

An example of the use of Method B in the synthesis of 2-furanylimidazole compounds of the invention is:

Step 1: Oxidation of the Ketone to Obtain the Keto-Oxime:

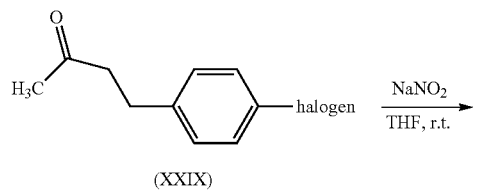

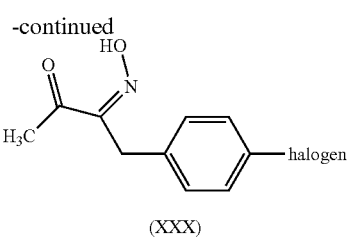

A suspension of the starting ketone (XXIX) (5 mmol) and NaNO$_2$ (345 mg, 5 mmol) in THF (10 mL) was cooled to 0° C. Concentrated HCl (6.5 mL) was added to the mixture in such a way that the temperature did not exceed 10° C. In order to avoid the evolution of nitrous gases the acid was added via a needle that was immersed into the reaction mixture. After the addition the cooling bath was removed, and the suspension turned slowly yellow. The progress of the reaction was monitored by HPLC and TLC. Water (50 mL) was added to the reaction mixture that was poured into a separatory funnel with AcOEt (50 mL).

The organic layer was separated and was washed with a saturated aqueous solution of NaHCO$_3$ (50 mL) and with brine (50 mL), dried over MgSO$_4$, filtered and concentrated under reduced pressure. The residue was purified by filtration over a pad of silica gel using dichloromethane as the eluent to obtain pure keto-oximes (XXX) (yield 45 to 65%).

Step 2: Synthesis of the Hydroxyimidazole

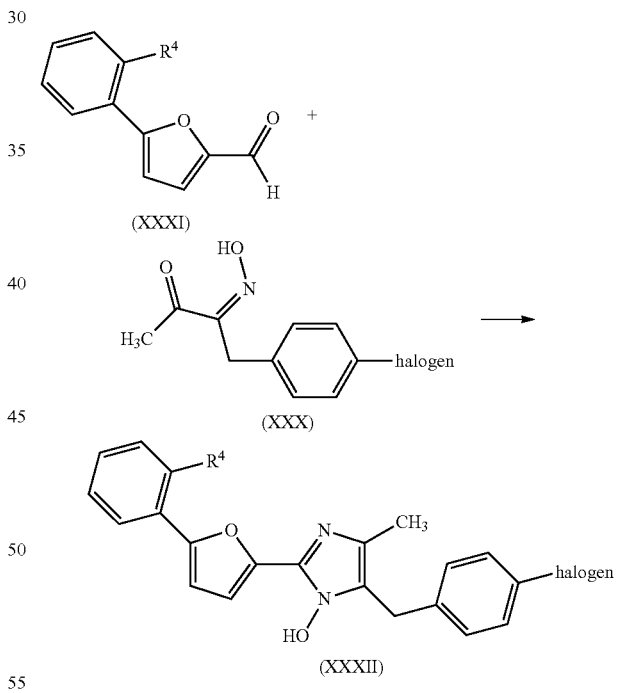

To the keto-oxime (XXX) (1 eq) dissolved in methanol (0.1 M) was added a solution of aldehyde (XXXI) (1 eq) dissolved in methanol (0.1 M). Eight equivalents of ammonium acetate dissolved in methanol (0.8 M) were added. The mixture was stirred at 60° C. for eight hours. The solvent was evaporated and the residue was dissolved in ethyl acetate, and washed twice with Na$_2$CO$_3$ 0.1 M, then with water. The organic layer was evaporated and the compound (XXXII) was purified on C18 with a semi-automated system in a H$_2$O/MeOH gradient using preparative HPLC Procedure 10 (yield 55 to 75%).

Step 3: Reduction of the Hydroxyl-Imidazole

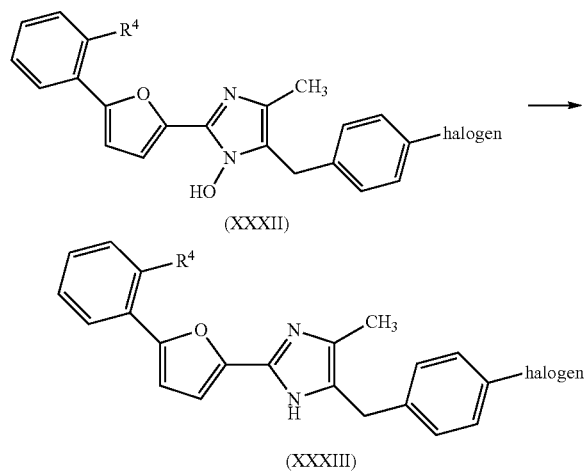

The hydroxyl-imidazole (XXXII) (100 mg) was dissolved in 4 mL of N,N-dimethylformamide and 1 mL of a solution of $TiCl_3$ 20% in 2 N HCl was added. The mixture was heated at 60° C. for two hours. The solvent was evaporated and the compound (XXXIII) was purified on C18 with a semi-automated system in a $H_2O$/MeOH gradient using preparative HPLC Procedure 10 (yield 75 to 95%).

Depending on the exact structure of the hydroxyimidazole, 100 mg constitutes differing molar quantities. Within the scope of the subject-matter claimed, however, this difference in molar quantities was insignificant in respect of this experimental procedure and, for every 100 mg of hydroximidazole starting material used, 4 ml of N,N-dimethylformamide and 1 mL of a solution of $TiCl_3$ 20% in 2 N HCl were used.

Further compounds of the invention made by the above-outlined procedure are outlined herein below (reaction scale may vary between Examples but the relative quantities of starting materials and reagents as well as concentrations were consistent with the above-outlined method):

By means of example, compound 30 below was synthesized in 53% yield over 3 steps from 4-(4-Bromophenyl)-2-butanone (commercially available from, inter alia, Matrix Scientific (Columbia, S.C., USA)) and 5-[2-(trifluoromethoxy)phenyl]-2-furaldehyde (commercially available from, inter alia, Fluorochem (Hadfield, Derbyshire, UK)) using the conditions outlined above.

Step 1:
Using 4-(4-Bromophenyl)-2-butanone (commercially available from, inter alia, Matrix Scientific (Columbia, S.C., USA)) as the starting material.

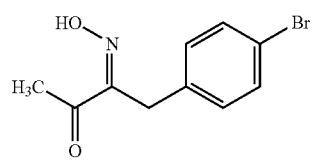

1-(4-Bromo-phenyl)-butane-2,3-dione 2-oxime 124

$^1$H NMR (400 MHz, DMSO-$d_6$): δ 2.33 (3H, s, $CH_3$), 3.73 (2H, s, $CH_2$) 7.11 (2H, d, J=8.4 Hz, Br-phenyl), 7.44 (2H, d, J=8.4 Hz, Br-phenyl).

Step 2:
Using 5-[2-(trifluoromethoxy)phenyl]-2-furaldehyde (commercially available from, inter alia, Fluorochem (Hadfield, Derbyshire, UK)) as the reaction partner.

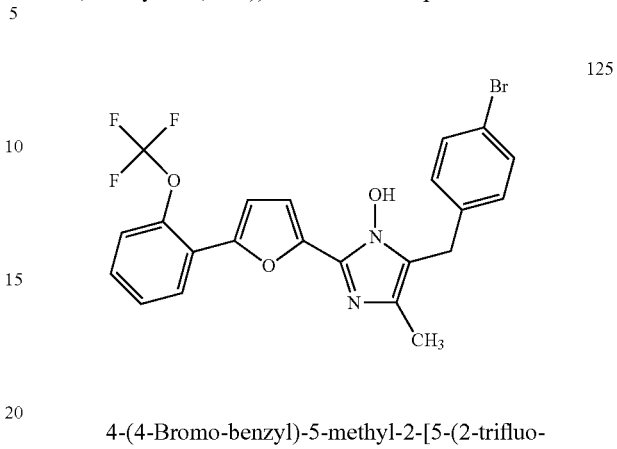

4-(4-Bromo-benzyl)-5-methyl-2-[5-(2-trifluoromethoxy-phenyl)-furan-2-yl]-imidazol-1-ol 125

$^1$H NMR (400 MHz, DMSO-$d_6$): δ 2.05 (3H, s, $CH_3$), 3.79 (2H, s, $CH_2$), 6.88 (1H, d, J=3.2 Hz, furan), 6.99 (1H, d, J=3.2 Hz, furan), 7.13 (2H, d, J=8.0 Hz, Br-phenyl), 7.42 (2H, d, J=8.0 Hz, Br-phenyl), 7.46 (3H, m, $OCF_3$-phenyl), 8.01 (1H, d, J=6.8 Hz, $OCF_3$-phenyl); LC-MS procedure 1 (electrospray positive ion mode): m/z 476, 478 (M+H)$^+$.

Step 3:

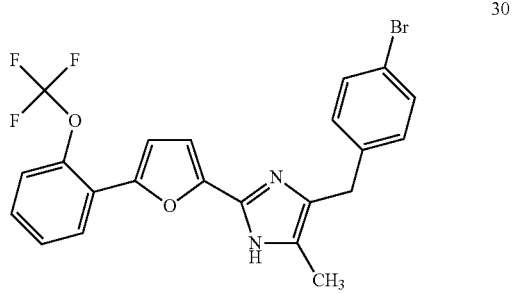 [SMILES: Cc1[nH]c(-c2ccc(-c3ccccc3OC(F)(F)F)o2)nc1Cc1ccc(Br)cc1]

4-(4-Bromo-benzyl)-5-methyl-2-[5-(2-trifluoromethoxy-phenyl)-furan-2-yl]-1H-imidazole 30

$^1$H NMR (400 MHz, DMSO-$d_6$): δ 2.45 (3H, s, $CH_3$), 3.95 (2H, s, $CH_2$), 6.99 (1H, d, J=3.6 Hz, furan), 7.17 (1H, d, J=3.6 Hz, furan), 7.23 (2H, d, J=8.4 Hz, Br-phenyl), 7.40 (2H, m, $OCF_3$-phenyl), 7.46 (2H, d, J=8.4 Hz, Br-phenyl), 7.53 (1H, m, $OCF_3$-phenyl), 8.22 (1H, d, J=8.0 Hz, $OCF_3$-phenyl); LC-MS procedure 1 (electrospray positive ion mode): m/z 477, 479 (M+H)$^+$.

Method C (General Procedure for the Synthesis of the Imidazoles in Two Steps):
Step 1:

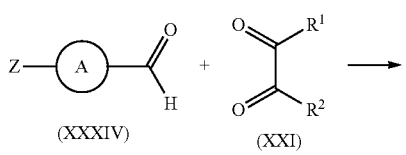

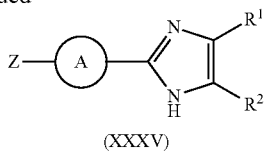

(XXXV)

where Z is selected from the group consisting of Cl, Br, I and triflate

Compounds of formula (XXXV) can be made through reaction of aldehydes of formula (XXXIV) with dicarbonyl compounds of formula (XXI) in the presence of a source of ammonia preferably under standard conditions such as heating in a solvent, for example an alcoholic solvent. Aldehydes of formula (XXXIV) can generally be purchased from commercial suppliers (e.g. Sigma-Aldrich, Apollo Scientific, CombiBlocks (San Diego, USA) etc) but, in instances where aldehydes of formula (XXXIV) are not commercially available, they may also be made by at least one of a number of standard methods known to the person skilled in the art such as, for example, reduction of the corresponding nitrile or acid or ester, reaction of an appropriate organometallic or metallated species with N,N-dimethylformamide, general carbonylation methods known to the skilled person etc. Dicarbonyl compounds of formula (XXI) can either be purchased from commercial suppliers (e.g. Sigma-Aldrich etc) or made by at least one of a number of standard methods known to the person skilled in the art such as, for example, by selenium-dioxide-mediated oxidation of the appropriate substrate as described in Rabjohn, N. *Org. React*, 1976, 44, 261, or by the method outlined below under Method F.

Step 2:

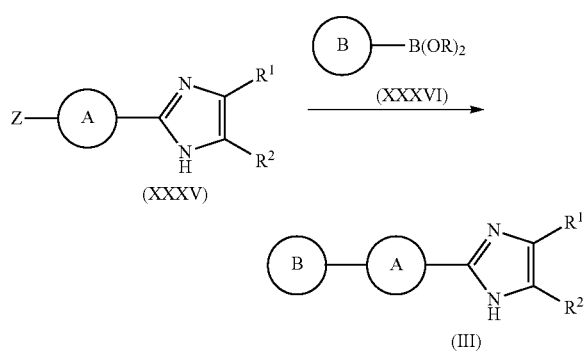

where Z is selected from the group consisting of Cl, Br, I and triflate

Compounds of formula (III) can be made, respectively, through the reaction of compounds of formula (XXXV) with boronic acids or boronic esters of formula (XXXVI) preferably under standard Suzuki coupling conditions such as reaction with a source of Pd⁰ such as Pd(OAc)₂ reduced in situ using, for example, PPh₃, and a base such as CsF in a suitable solvent such as DMF. Heating may also be employed in the reaction. Boronic acids or boronic esters of formula (XXXVI) can generally be purchased from commercial suppliers (e.g. CombiBlocks (San Diego, USA), San Diego, USA) but, in instances where boronic acids or boronic esters of formula (XXXVI) are not commercially available, they may also be made by at least one of a number of standard methods known to the person skilled in the art such as, for example, the reaction of an appropriate organometallic species, e.g. an organolithium or Grignard species, with a borate ester followed by an optional hydrolysis of the product borate ester, cross-coupling of an appropriate halide with a diboronyl ester or diboronic acid, transmetallation of an appropriate stannane with boron tribromide followed by hydrolysis to the corresponding boronic acid, etc.

An example of the use of Method C in the synthesis of 2-furanylimidazole compounds of the invention is as follows (1-phenylpropane-1,2-dione is commercially available from, inter alia, Sigma-Aldrich and 5-bromo-2-furaldehyde is commercially available from, inter alia, Sigma-Aldrich):

Step 1:

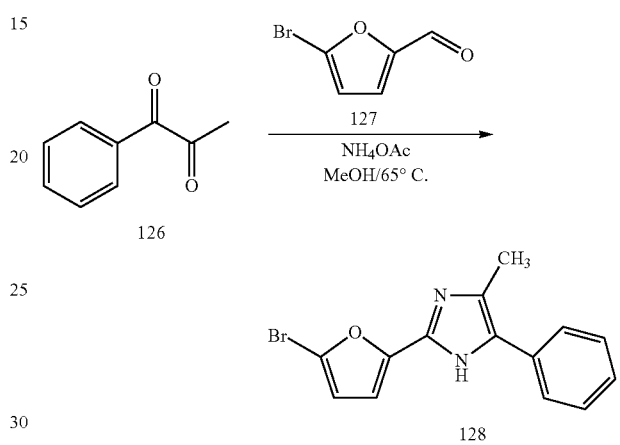

Into a solution of 1-phenylpropane-1,2-dione 126 (4.03 g, 27.2 mmol, 1.0 equiv.) in methanol (60 mL) was added 5-bromo-2-furaldehyde 127 (4.76 g, 27.2 mmol, 1.0 equiv.) followed by ammonium acetate (16.8 g, 217.0 mmol, 8.0 equiv.) and the reaction stirred at 65° C. for 2 h. The mixture was cooled, concentrated in vacuo, diluted with water (150 mL) and extracted with dichloromethane (2×100 mL; 1×50 mL). The combined organic phases were washed with water (100 mL), passed through a phase separating frit and concentrated in vacuo. The desired product 128 was isolated after column chromatography on silica eluting with mixtures of iso-hexane/ethyl acetate.

Yield: 6.58 g (80%); ¹H NMR (CDCl₃, 400 MHz): δ 7.57 (d, 2H, J=7.3 Hz), 7.42 (dd, 2H, J=7.7, 7.7 Hz), 7.29 (dd, 1H, J=7.5, 7.5 Hz), 6.86 (d, 1H, J=3.3 Hz), 6.41 (d, 1H, J=3.3 Hz), 2.47 (s, 3H).

In the above-outlined reaction of Step 1, either of the starting materials (diketone or aldehyde) may be replaced by analogous starting materials containing corresponding functionality (e.g. the diketone with alternative diketones and the aromatic aldehyde with alternative aromatic aldehydes) in the same molar ratios to yield the analogous reaction product. For example, the diketone compound used can be other than an aryl diketone.

Step 2:

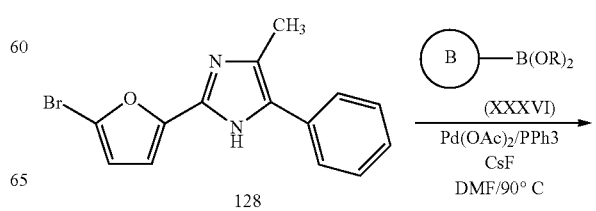

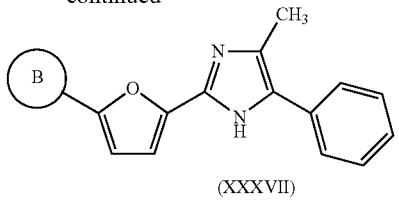

(XXXVII)

Stock solutions of intermediate 128 (0.29 M in deoxygenated DMF), Pd(OAc)₂ (0.045 M in deoxygenated DMF), PPh₃ (0.14 M in deoxygenated DMF) and CsF (1.73 M in deoxygenated H₂O) were prepared. Each reaction vessel was charged with intermediate 3 (750 μL, 0.22 mmol, 1.0 equiv.), boronic acid/boronate ester (XXXVI) (0.30 mmol, 1.4 equiv.), PPh₃ (200 μL, 0.03 mmol, 12 mol %), and CsF (375 μL, 0.65 mmol, 3.0 equiv.). The solution was sparged with nitrogen, Pd(OAc)₂ (200 μL, 4 mol %) added, the tubes flushed with nitrogen, sealed and stirred at 90° C. for 16 h. The reactions were cooled and diluted with water/brine (5 mL; 2:3) and ethyl acetate (3 mL). The mixture was agitated in the reaction tube with a plastic pipette and the ethyl acetate layer separated. Centrifugation was used to improve partition where poor phase separation occurred. Additional aliquots of ethyl acetate (2×2.0 mL) were added and the procedure repeated. The combined ethyl acetate extracts were concentrated in vacuo using a Genevac, the residue dissolved in DMSO (1.5 mL) and purified by reversed phase preparative HPLC using preparative HPLC Procedure 11.

By means of example, the following compounds were synthesized by the method outlined above (replacing the starting materials described therein with the appropriate analogues) and purified using preparative HPLC Procedure 11.

Compound 1 below was synthesized in 37% yield over 2 steps from 5-bromo-2-furaldehyde (commercially available from, inter alia, Sigma-Aldrich) and 1-phenylpropane-1,2-dione (also known as Phenyl-1,2-propanedione and commercially available from, inter alia, Sigma-Aldrich) followed by reaction in step 2 with 2,4-dichlorophenylboronic acid (commercially available from CombiBlocks (San Diego, USA)) using the conditions outlined above.

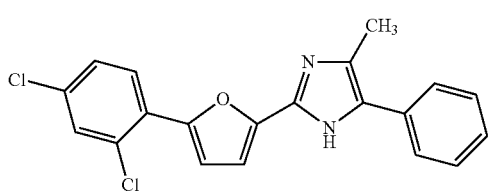

1

¹H NMR (DMSO-d6, 400 MHz): δ 12.75 (s, 1H), 8.23 (d, 1H, J=8.6 Hz), 7.81 (d, 1H, J=2.3 Hz), 7.75 (d, 1H, J=7.3 Hz), 7.69-7.64 (m, 2H), 7.64-7.57 (m, 1H), 7.49 (dd, 1H, J=7.6, 7.6 Hz), 7.40 (d, 1H, J=3.5 Hz), 7.32 (dd, 1H, J=7.2, 7.2 Hz), 7.07 (d, 1H, J=3.5 Hz), 2.53 (s, 3H); MS (ESI+): m/z 369 (MH+; ³⁵Cl); Purity: 94.7%; RT: 4.11 min.

Compound 17 below was synthesized in 35% yield over 2 steps from 5-bromo-2-furaldehyde (commercially available from, inter alia, Sigma-Aldrich) and 1-phenylpropane-1,2-dione (also known as Phenyl-1,2-propanedione and commercially available from, inter alia, Sigma-Aldrich) followed by reaction in step 2 with 2-(trifluoromethyl)phenylboronic acid (commercially available from CombiBlocks (San Diego, USA)) using the conditions outlined above.

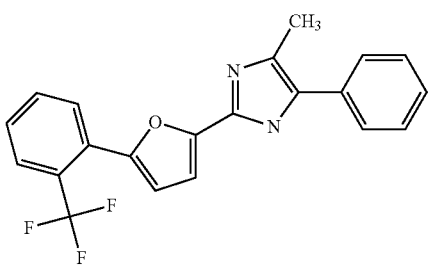

17

Compound 31 below was synthesized in 52% yield over 2 steps from 5-bromo-2-furaldehyde (commercially available from, inter alia, Sigma-Aldrich) and 1-phenylpropane-1,2-dione (also known as Phenyl-1,2-propanedione and commercially available from, inter alia, Sigma-Aldrich) followed by reaction in step 2 with 4-methoxy-2-(trifluoromethyl)phenylboronic acid (commercially available from CombiBlocks (San Diego, USA)) using the conditions outlined above.

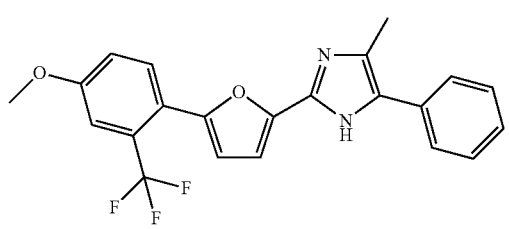

31

Compound 31a below was synthesized in 6% yield over 2 steps from 5-bromo-2-furaldehyde (commercially available from, inter alia, Sigma-Aldrich) and 1-phenylpropane-1,2-dione (also known as Phenyl-1,2-propanedione and commercially available from, inter alia, Sigma-Aldrich) followed by reaction in step 2 with 5-fluoro-2-(trifluoromethyl)phenylboronic acid (commercially available from CombiBlocks (San Diego, USA)) using the conditions outlined above.

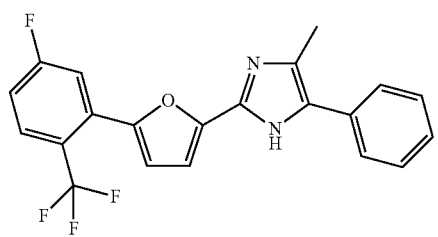

31a

Compound 32 below was synthesized in 6% yield over 2 steps from 5-bromo-2-furaldehyde (commercially available from, inter alia, Sigma-Aldrich) and 1-phenylpropane-1,2-dione (also known as Phenyl-1,2-propanedione and commercially available from, inter alia, Sigma-Aldrich) followed by reaction in step 2 with 4-chloro-2-

(trifluoromethyl)phenylboronic acid (commercially available from CombiBlocks (San Diego, USA)) using the conditions outlined above.

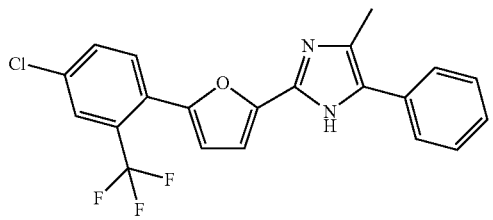

32

Compound 34 below was synthesized in 41% yield over 2 steps from 5-bromo-2-furaldehyde (commercially available from, inter alia, Sigma-Aldrich) and 1-phenylpropane-1,2-dione (also known as Phenyl-1,2-propanedione and commercially available from, inter alia, Sigma-Aldrich) followed by reaction in step 2 with 3-(trifluoromethoxy) phenylboronic acid (commercially available from Combi-Blocks (San Diego, USA)) using the conditions outlined above.

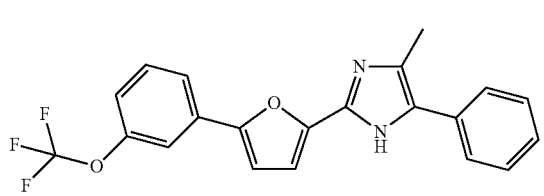

34

Compound 35 below was synthesized in 44% yield over 2 steps from 5-bromo-2-furaldehyde (commercially available from, inter alia, Sigma-Aldrich) and 1-phenylpropane-1,2-dione (also known as Phenyl-1,2-propanedione and commercially available from, inter alia, Sigma-Aldrich) followed by reaction in step 2 with 3, 5-bis(trifluoromethyl) phenylboronic acid (commercially available from Combi-Blocks (San Diego, USA)) using the conditions outlined above.

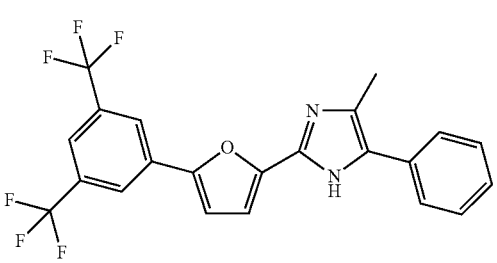

35

Compound 45 below was synthesized in 60% yield over 2 steps from 5-bromo-2-furaldehyde (commercially available from, inter alia, Sigma-Aldrich) and 1-phenylpropane-1,2-dione (also known as Phenyl-1,2-propanedione and commercially available from, inter alia, Sigma-Aldrich) followed by reaction in step 2 with 4-(trifluoromethyl) phenylboronic acid (commercially available from Combi-Blocks (San Diego, USA)) using the conditions outlined above.

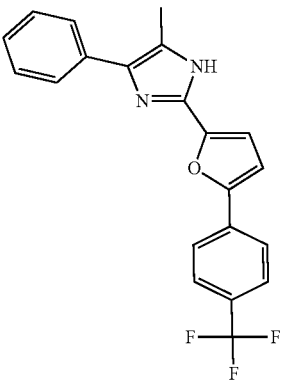

45

Compound 61 below was synthesized in 59% yield over 2 steps from 5-bromo-2-furaldehyde (commercially available from, inter alia, Sigma-Aldrich) and 1-phenylpropane-1,2-dione (also known as Phenyl-1,2-propanedione and commercially available from, inter alia, Sigma-Aldrich) followed by reaction in step 2 with o-tolylboronic acid (commercially available from CombiBlocks (San Diego, USA)) using the conditions outlined above.

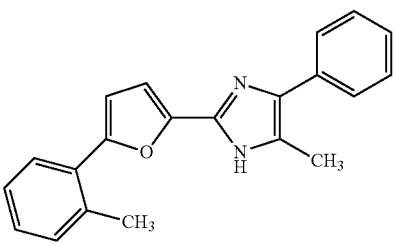

61

Compound 62 below was synthesized in 11% yield over 2 steps from 5-bromo-2-furaldehyde (commercially available from, inter alia, Sigma-Aldrich) and 1-phenylpropane-1,2-dione (also known as Phenyl-1,2-propanedione and commercially available from, inter alia, Sigma-Aldrich) followed by reaction in step 2 with 2,6-dimethylphenylboronic acid (commercially available from CombiBlocks (San Diego, USA)) using the conditions outlined above.

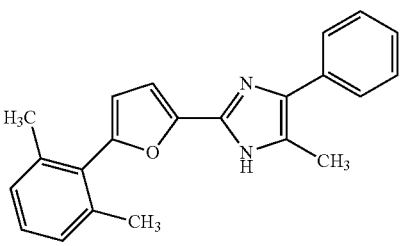

62

Compound 71, below, was synthesized in 40% yield over 2 steps from 5-bromo-2-furaldehyde (commercially available from, inter alia, Sigma-Aldrich) and 1-phenylpropane-1,2-dione (also known as Phenyl-1,2-propanedione and commercially available from, inter alia, Sigma-Aldrich) followed by reaction in step 2 with 2-(dimethylamino)

phenylboronic acid (commercially available from Combi-Blocks (San Diego, USA)) using the conditions outlined above.

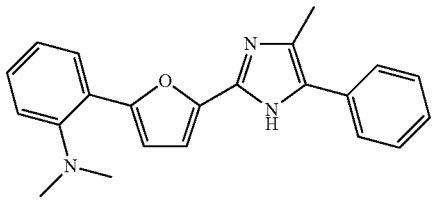

71

Method D (General Procedure for the Synthesis of the Imidazoles in Two Steps):

Step 1:

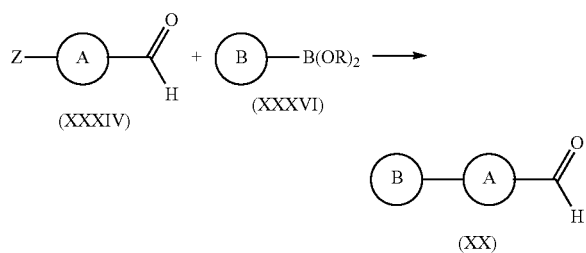

where Z is selected from the group consisting of Cl, Br, I and triflate

Compounds of formula (XX) can be made by reaction of compounds of formula (XXXIV) with compounds of formula (XXXVI) in the presence of a source of Pd⁰ and a base preferably under standard Suzuki reaction conditions. Exemplary reaction conditions are (i) the reaction of the above compounds with Pd(PPh)$_3$ and 2M aqueous Na$_2$CO$_3$ solution in a solvent mixture of toluene/ethanol and (ii) the reaction of the above compounds with Pd(dppf)Cl$_2$•CH$_2$Cl$_2$ and K$_3$PO$_4$ in a solvent mixture of DME/water. Aldehydes of formula (XXXIV) can generally be purchased from commercial suppliers but, in instances where aldehydes of formula (XXXIV) are not commercially available, they may also be made by at least one of a number of standard methods known to the person skilled in the art such as, for example, reduction of the corresponding nitrile or acid or ester, reaction of an appropriate organometallic or metallated species with N,N-dimethylformamide, general carbonylation methods known to the skilled person etc. Boronic acids or boronic esters of formula (XXXVI) can generally be purchased from commercial suppliers (e.g. CombiBlocks (San Diego, USA), San Diego, USA) but, in instances where boronic acids or boronic esters of formula (XXXVI) are not commercially available, they may also be made by at least one of a number of standard methods known to the person skilled in the art such as, for example, the reaction of an appropriate organometallic species, e.g. an organolithium or Grignard species, with a borate ester followed by an optional hydrolysis of the product borate ester, cross-coupling of an appropriate halide with a diboronyl ester or diboronic acid, transmetallation of an appropriate stannane with boron tribromide followed by hydrolysis to the corresponding boronic acid, etc.

Step 2:

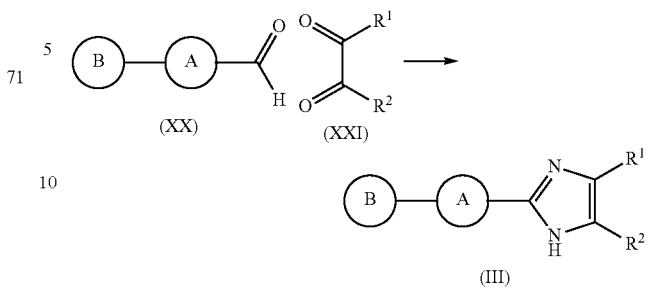

Compounds of Formula (III) may be made through the reaction of an aldehyde of formula (XX) with a dicarbonyl compound of formula (XXI) in the presence of a source of ammonia preferably under standard conditions such as heating in a solvent, for example an alcoholic solvent. Exemplary reaction conditions are (i) the reaction of the above compounds with ammonium acetate in either glacial acetic acid or methanol and using a reaction temperature from 25 to 70° C.

Dicarbonyl compounds of formula (XXI) can either be purchased from commercial suppliers (for example, inter alia, Sigma-Aldrich (St. Louis, Mo., USA), Alfa Aesar (Schiltigheim, France), Acros Organics (Geel, Belgium), Key Organics (Camelford, UK), Matrix Scientific (Columbia, S.C., USA), Fluorochem (Hadfield, Derbyshire, UK) and Enamine (Kiev, Ukraine)) or made by at least one of a number of standard methods known to the person skilled in the art such as, for example, by selenium-dioxide-mediated oxidation of the appropriate substrate as described in Rabjohn, N. *Org. React,* 1976, 44, 261, or by the method outlined herein below under Method F.

By means of example, the following compounds were synthesized using Method D by means of the following specific reaction conditions:

Step 1—Suzuki Reaction: General Procedure

A mixture of the aldehyde (XXXIV) (0.523 mmol), the appropriate boronic acid or ester (XXXVI) (0.628 mmol), toluene (10 mL), EtOH (2.6 mL) and a 2 M aq. Na$_2$CO$_3$ solution (15.4 mL) was degassed by bubbling argon for 30 min. Then, Pd(PPh$_3$)$_4$ (36 mg, 0.0314 mmol) was added and the mixture was stirred overnight at 80° C.

The reaction mixture was diluted with water (30 mL) and extracted with EtOAc (4×10 mL). Organic layers were combined and the solvent evaporated to yield the crude product.

The crude product was purified by flash chromatography (SiO$_2$ column 10 g—eluents n-Hexane/EtOAc=3/1). The appropriate fractions were combined and the solvent evaporated to yield the desired purified aldehyde (XX) compound.

Step 2—Imidazole Formation: General Procedure

The product aldehyde (XX) from step 1 (0.382 mmol), NH$_4$OAc (294 mg, 3.82 mmol) and the appropriate dicarbonyl compound (XXI) (0.382 mmol) were combined and dissolved in 3.9 mL MeOH and heated at 60° C. overnight.

The solvent of the reaction mixture was evaporated to get the crude material which was purified by preparative HPLC Procedure #12. The appropriate fractions were combined and lyophilized overnight giving the desired final product (III).

Further compounds of the invention made by the above-outlined procedure are outlined herein below:

Compound 115 was synthesized in 24% yield over 2 steps through reaction in Step 1 of 5-Bromo-4-methyl-thiophene- 2-carbaldehyde (purchased from CombiBlocks (San Diego, USA)) and 2-[2-(Trifluoromethyl)phenyl]-4,4,5,5-tetramethyl-1,3,2-dioxaborolane (commercially available from, inter alia, TCI (TOKYO, JAPAN) Chemicals) followed by reaction in Step 2 with 2,3-Hexanedione (commercially available from multiple suppliers including, inter alia, Sigma-Aldrich) using the conditions outlined above.

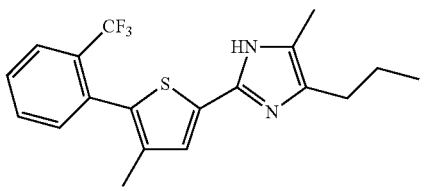

115

Compound 113 was synthesized in 29% yield over 2 steps through reaction in Step 1 of 5-Bromo-thiophene-3-carbaldehyde (purchased from CombiBlocks (San Diego, USA)) and 2-[2-(Trifluoromethyl)phenyl]-4,4,5,5-tetramethyl-1,3,2-dioxaborolane (commercially available from, inter alia, TCI (TOKYO, JAPAN) Chemicals) followed by reaction in Step 2 with 2,3-Hexanedione (commercially available from multiple suppliers including, inter alia, Sigma-Aldrich) using the conditions outlined above.

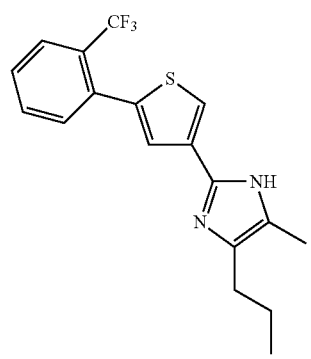

113

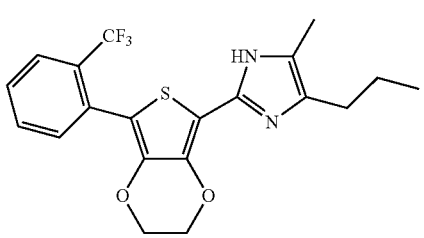

114

Compound 114 was synthesized in 36% yield over 2 steps through reaction in Step 1 of 7-Bromo-2,3-dihydro-thieno[3,4-b][1,4]-dioxine-5-carbaldehyde (purchased from Bepharm, Shanghai, China) and 2-[2-(Trifluoromethyl)phenyl]-4,4,5,5-tetramethyl-1,3,2-dioxaborolane (commercially available from, inter alia, TCI (TOKYO, JAPAN) Chemicals) followed by reaction in Step 2 with 2,3-Hexanedione (commercially available from multiple suppliers including, inter alia, Sigma-Aldrich) using the conditions outlined above.

Method E (General Procedure for the Synthesis of the Imidazoles):

Compounds of formula (III) can be made through the reaction of aldehydes of formula (XX) with dicarbonyl compounds of formula (XXI) in the presence of a source of ammonia preferably under standard conditions such as heating in a solvent, for example an alcoholic solvent. Exemplary reaction conditions are (i) the reaction of the above compounds with ammonium acetate in either glacial acetic acid or methanol and using a reaction temperature from 25 to 70° C.

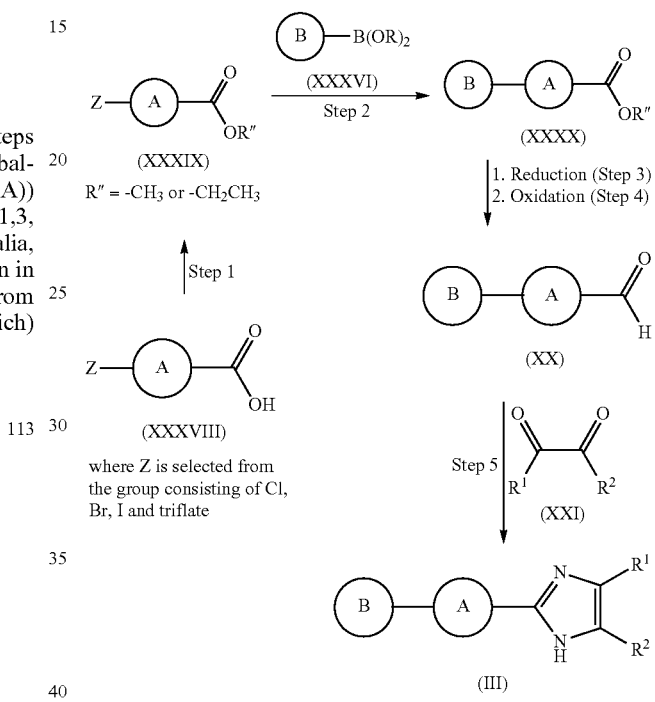

R″ = -CH$_3$ or -CH$_2$CH$_3$ where Z is selected from the group consisting of Cl, Br, I and triflate Aldehydes of formula (XX) may be generated from esters of formula (XXXX) via a two step reduction/oxidation process preferably under standard conditions such as reduction of the ester group with a standard reducing agent (for example LiAlH$_4$ in diethyl ether) and oxidation of the resultant alcohol with a standard oxidizing agent for alcohol to aldehyde transformations (for example Dess-Martin Periodinane in CH$_2$Cl$_2$). Esters of formula (XXXX) can be made through Suzuki cross-coupling reaction of esters of formula (XXXIX) with boronic acids or boronic esters of formula (XXXVI) preferably under standard Suzuki reaction conditions such as those mentioned in Method C above and esters of formula (XXXIX) can, in turn, be made from acids of formula (XXXVIII) preferably under standard esterification conditions such as reaction with SOCl$_2$ in methanol at ambient (room) temperature for 16 h. In addition to —CH$_3$, or —CH$_2$CH$_3$, R″ may be also be C$_{3 to 6}$alkyl. Steps 3 and 4 may be replaced by a single reduction step such to reduce ester (XXXX) directly to aldehyde (XX) using conditions known to the person skilled in the art.

An example of the use of Method E in the synthesis of 2-furanylimidazole compounds of the invention is

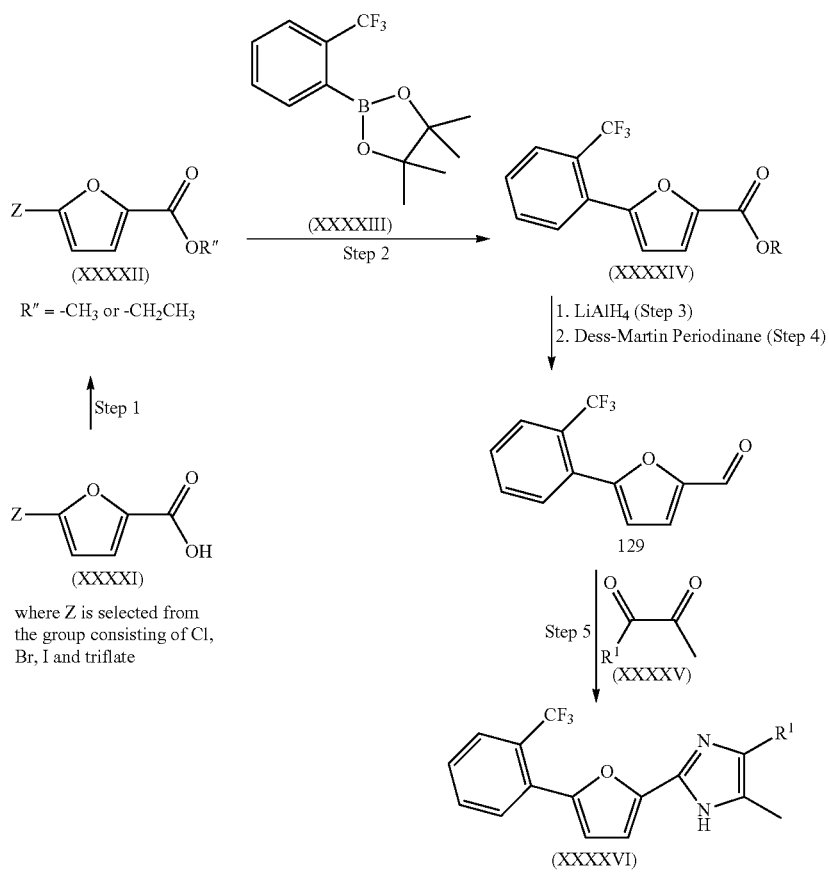

By means of example, the following compounds were synthesized using Method E by means of the following specific reaction conditions:

Step 1—Esterification: General Procedure

To a solution of the starting carboxylic acid (XXXVIII) (3.141 mmol) in MeOH or EtOH (24 mL) was added thionyl chloride (1.13 mL). The reaction mixture was stirred at room temperature overnight.

The reaction mixture was evaporated. The crude product was re-dissolved in DCM (10 mL) and the solvent evaporated again. This procedure was repeated 3 times to get the desired product (XXXIX) (either ethyl ester or methyl ester depending on solvent used).

Appropriate carboxylic acid starting materials (XXXVIII) are generally commercially from suppliers such as, inter alia, Apollo Scientific, Manchester, UK. In instances where the appropriate starting carboxylic acids (XXXVIII) are not commercially available, they may also be made by at least one of a number of standard methods known to the person skilled in the art such as, for example, hydrolysis of the corresponding nitrile or ester, reaction of an appropriate organometallic or metallated species with $CO_2$ or a $CO_2$ analogue, general carboxylation methods known to the skilled person etc.

Step 2—Suzuki Reaction: General Procedure

A mixture of the ester (XXXIX) from Step 1 (0.523 mmol), the appropriate the appropriate boronic acid or ester (XXXVI) (0.628 mmol), toluene (10 mL), EtOH (2.6 mL) and a 2 M aq. $Na_2CO_3$ solution (15.4 mL) was degassed by bubbling argon for 30 min. Then, $Pd(PPh_3)_4$ (36 mg, 0.0314 mmol) was added and the mixture was stirred overnight at 80° C.

The reaction mixture was diluted with water (30 mL) and extracted with EtOAc (4×10 mL). Organic layers were combined and the solvent evaporated to yield the crude product.

The crude product was purified by flash chromatography ($SiO_2$ column 10 g—eluents n-Hexane/EtOAc=3/1). The appropriate fractions were combined and the solvent evaporated to yield the desired purified compound (XXXX).

Appropriate boronic acids or boronic esters of formula (XXXVI) can generally be purchased from commercial suppliers (e.g. CombiBlocks (San Diego, USA), San Diego, USA) but, in instances where boronic acids or boronic esters of formula (XXXVI) are not commercially available, they may also be made by at least one of a number of standard methods known to the person skilled in the art such as, for example, the reaction of an appropriate organometallic species, e.g. an organolithium or Grignard species, with a borate ester followed by an optional hydrolysis of the product borate ester, cross-coupling of an appropriate halide with a diboronyl ester or diboronic acid, transmetallation of an appropriate stannane with boron tribromide followed by hydrolysis to the corresponding boronic acid, etc.

Step 3—Reduction: General Procedure

To a cooled solution of $LiAlH_4$ (114 mg) in diethyl ether (2.7 mL) at 0° C. was added dropwise a solution of the carboxylic acid ester (XXXX) from step 2 (1.003 mmol) in diethyl ether (2.7 mL). The reaction mixture was stirred at 0° C. for 1 hr.

The reaction mixture was slowly added to cooled water (50 mL) and extracted with EtOAc (5×30 mL). Organic layers were combined and evaporated to yield the desired product Step 4—Oxidation: General Procedure To a solution of the product alcohol from step 3 (0.136 mmol) in DCM (2.5 mL) was added Dess-Martin periodane (115 mg) at 0° C. The reaction mixture was stirred at room temperature for 30 min.

The reaction mixture was filtered through celite and the solvent was evaporated. The residue was dissolved in EtOAc (50 mL) and washed with sat. NaHCO₃ solution (8×30 mL). The combined organic layers were evaporated to yield the desired product (XX).

Step 5—Imidazole Formation: General Procedure

The aldehyde (XX) from step 4 (0.382 mmol), NH₄OAc (294 mg, 3.82 mmol) and the appropriate dione (XXI) (0.382 mmol) were combined and dissolved in 3.9 mL MeOH and heated at 60° C. overnight.

The solvent of the reaction mixture was evaporated to get the crude material which was purified by preparative HPLC Procedure #12. The appropriate fractions were combined and lyophilized overnight giving the desired final product (III).

Appropriate diones (XXI) can either be purchased from commercial suppliers (for example, inter alia, Sigma-Aldrich (St. Louis, Mo., USA), Alfa Aesar (Schiltigheim, France), Acros Organics (Geel, Belgium), Key Organics (Camelford, UK), Matrix Scientific (Columbia, S.C., USA), Fluorochem (Hadfield, Derbyshire, UK) and Enamine (Kiev, Ukraine)) or made by at least one of a number of standard methods known to the person skilled in the art such as, for example, by selenium-dioxide-mediated oxidation of the appropriate substrate as described in Rabjohn, N. *Org. React,* 1976, 44, 261, or by the method outlined herein below under Method F.

Further compounds of the invention made by the above-outlined procedure are outlined herein below:

Compound 72 was synthesized in 18% yield over 5 steps from 5-Bromo-furan-3-carboxylic acid (purchased from Apollo Scientific, Manchester UK) using the conditions outlined above. 2-[2-(Trifluoromethyl)phenyl]-4,4,5,5-tetramethyl-1,3,2-dioxaborolane was used as the appropriate boronic ester in step 2 (commercially available from, inter alia, TCI (TOKYO, JAPAN) Chemicals and CombiBlocks (San Diego, USA)). In step 5, 1-Phenyl-1,2-propanedione was used as the appropriate dione (commercially available from, inter alia, Sigma-Aldrich).

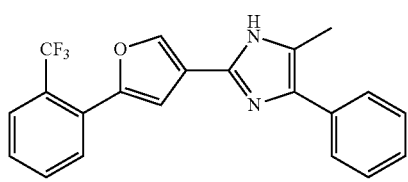

72

Compound 112 was synthesized in 22% yield over 5 steps from 5-Bromo-furan-3-carboxylic acid (purchased from Apollo Scientific) using the conditions outlined above. 2-[2-(Trifluoromethyl)phenyl]-4,4,5,5-tetramethyl-1,3,2-dioxaborolane was used as the appropriate boronic ester in step 2 (commercially available from, inter alia, TCI (TOKYO, JAPAN) Chemicals). In step 5, 2,3-Hexanedione was used as the appropriate dione (commercially available from multiple suppliers including, inter alia, Sigma-Aldrich).

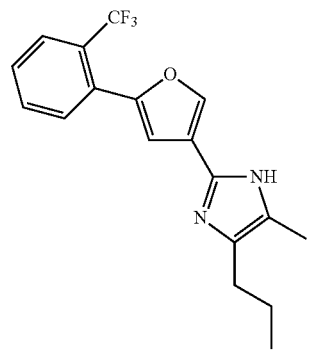

112

Method F (General Procedure for the Synthesis of the Dicarbonyl Compounds and their Subsequent Conversion to Imidazoles):

When one of $R^1$ or $R^2$ in a compound of the present invention is an unsubstituted or substituted phenyl ring and the other is a methyl group, when compounds of formula (L) are not commercially available they may be made via the following process. This general procedure may also be useful in some instances for the synthesis of non-aryl-ring-containing dicarbonyl compounds.

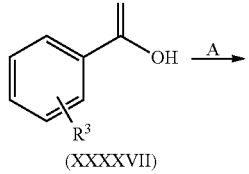

(XXXXVII)

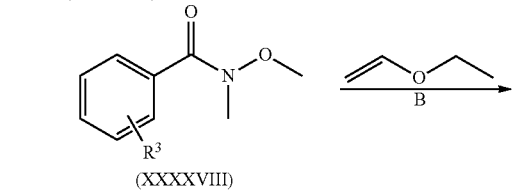

(XXXXVIII)

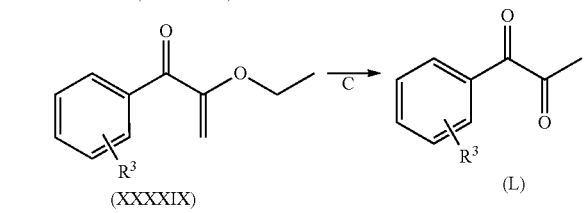

(XXXXIX)            (L)

Diketo compounds of formula (L) may be made from vinyl ether compounds of formula (XXXXIX) preferably under standard conditions ether hydrolysis conditions such as treatment with aqueous acid, for example hydrochloric acid. Vinyl ether compounds of formula (XXXXIX) may be made via reaction of Weinreb amides of formula (XXXXVIII) preferably under standard anionic conditions such as reaction of the Weinreb amide of formula (XXXXVIII) with the corresponding metalated, for example lithiated, vinyl ether, i.e. through reaction with the vinyl anion. Weinreb amides of formula (XXXXVIII) may be made from acids of formula (XXXXVII) preferably under standard conditions such as amide coupling of N,O-dimethylhydroxylamine hydrochloride and acids of formula (XXXXVII) using a standard amide coupling agent such as CDI and a base, for example an organic base such as triethylamine, in an appropriate solvent such as CH$_2$Cl$_2$.

Carboxylic acid starting materials of formula (XXXXVII) can generally be purchased from commercial suppliers (e.g. Sigma-Aldrich, Apollo Scientifc, CombiBlocks (San Diego, USA), Enamine (Kiev, Ukraine) etc). In instances where the appropriate starting carboxylic acids (XXXXVII) are not commercially available, they may also be made by at least one of a number of standard methods known to the person skilled in the art such as, for example, hydrolysis of the corresponding nitrile or ester, reaction of an appropriate organometallic or metallated species with CO$_2$ or a CO$_2$ analogue, general carboxylation methods known to the skilled person etc.

Exemplary general experimental protocols for the above reaction scheme are provided as follows:

Step A:

To a suspension of corresponding acid (XXXXVII) (64 mmol) in DCM (150 mL) CDI (1,1'-Carbonyldiimidazole) (11 g, 68 mmol) was added in several portions under cooling with ice-bath, and the resulting mixture was stirred until the evolution of gas was ceased. Freshly distilled Et$_3$N(14 mL, 100 mmol) followed by N,O-dimethylhydroxylamine hydrochloride (6.8 g, 70 mmol) were added, and the resulting mixture was stirred for 16 h. The organic solution was washed with water (2×30 mL), 2N HCl solution, dried and evaporated. An average yield of (XXXXVIII) was 75-80%.

Step B:

To a degassed solution of ethyl vinyl ether (9 mL, 94 mmol) in THF (300 mL) t-BuLi (31 mL, 1.6M in pentane, 50 mmol) was added drop by drop maintaining the temperature below −65° C. The above obtained solution was warmed up to 0° C. during 1 h, stirred for 10 min, cooled to −65° C., and treated with a solution of (XXXXVIII) (50 mmol) in THF (100 mL). The mixture was stirred overnight without cooling, neutralized with a saturated NH$_4$Cl solution (500 mL), and extracted with MTBE (3×50 mL). The combined organic layers were washed with water (3×20 mL), dried and concentrated to afford pure (XXXXIX) as a dark oily residue which was immediately used in the next step.

Step C:

A solution of intermediate (XXXXIX) in a mixture of MeOH (100 mL) and HCl (2N, 50 mL) was refluxed overnight. Then it was cooled, concentrated, and aqueous phase was extracted with DCM (2×50 mL). The combined organic layers were washed with water (1×20 mL), aqueous solution of sodium bicarbonate, dried, and concentrated. The yield of (L) was 30-40% over 2 steps. The dicarbonyl compounds of formula (L) obtained from step C may then be employed to make the compounds of the invention via one of the methods listed herein which utilizes dicarbonyl compounds in the synthesis of compounds of the invention. An example of such a reaction is provided in Step D below.

Step D:

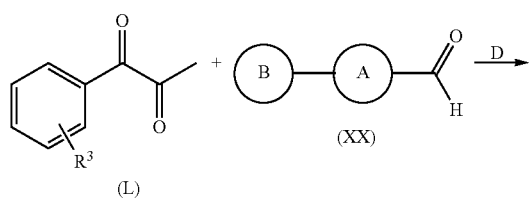

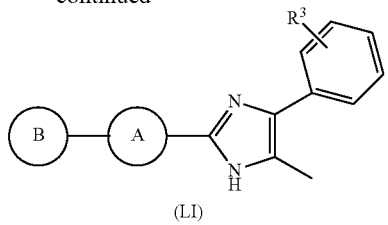

Imidazole compounds of formula (LI) may be made through the reaction of an aldehyde of formula (XX) with a dicarbonyl compound of formula (L) in the presence of a source of ammonia preferably under standard conditions such as heating in a solvent, for example an acidic solvent such as acetic acid. The following outlines an exemplary general procedure for this transformation:

A mixture of aldehyde (XX) (5.5 mmol), dicarbonyl intermediate from step C (L) (5.5 mmol) and ammonium acetate (6 g, 52 mmol) in HOAc (50 mL) was refluxed for 16 h. Then it was evaporated to dryness, and residue was dissolved in EtOAc. The resulting solution was washed with water, sodium bicarbonate, dried over sodium sulfate, and concentrated. The crude material was purified by column chromatography (silica gel, MTBE-hexane).

Aldehydes of formula (XX) are generally commercially available (for example from, inter alia, Sigma-Aldrich (St. Louis, Mo., USA), Alfa Aesar (Schiltigheim, France), Acros Organics (Geel, Belgium), Key Organics (Camelford, UK), Matrix Scientific (Columbia, S.C., USA), Fluorochem (Hadfield, Derbyshire, UK) and Enamine (Kiev, Ukraine)) but, when they are not commercially available, they may also be made by at least one of a number of standard methods known to the person skilled in the art such as, for example, reduction of the corresponding nitrile or acid or ester, reaction of an appropriate organometallic or metallated species with N,N-dimethylformamide, general carbonylation methods known to the skilled person etc. Aldehydes of formula (XX) may also be made by further methods such as, for example, those outlined herein under the corresponding reaction step in Method D (step 1), in Method H or by any number of the steps (as required depending on the available starting material) leading to such aldehydes in Method E herein.

Examples of the invention can be made according to the above-outlined steps A to D where, although the absolute quantities of starting materials, reactants and reagents used therein may deviate from those outlined above for steps A to D, within any given step the relative molar quantities of starting materials, reactants and reagents as well as concentrations are consistent with those stipulated in steps A to D above.

By means of example, the following compounds of the invention were made according to Method F as outlined above.

Compound 60 below was synthesized in 7% yield (yield for step D) from 1-Phenyl-1,2-propanedione (commercially available from, inter alia, Sigma-Aldrich) and 5-(3-fluoro-2-methylphenyl)furan-2-carbaldehyde (commercially available from Enamine (Kiev, Ukraine)) using 5.5 mmol of the aldehyde SM using the conditions outlined above.

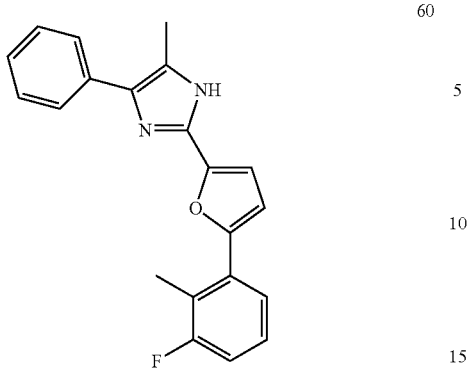

60

Compound 39 below was synthesized in 56% yield (yield for step D) from 1-Phenyl-1,2-propanedione (commercially available from, inter alia, Sigma-Aldrich) and 5-[4-chloro-3-(trifluoromethyl)phenyl]furan-2-carbaldehyde (commercially available from Enamine (Kiev, Ukraine)) using 5.5 mmol of the aldehyde SM using the conditions outlined above.

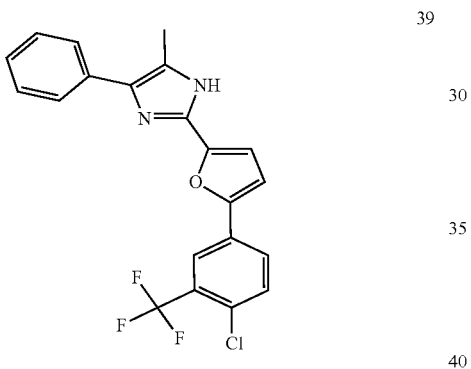

39

Compound 3 below was synthesized in 7% yield (yield for step D) from 1-Phenyl-1,2-propanedione (commercially available from, inter alia, Sigma-Aldrich) and 5-(2-Chlorophenyl)furfural (commercially available from, inter alia, Sigma-Aldrich) using 5.5 mmol of the aldehyde SM using the conditions outlined above.

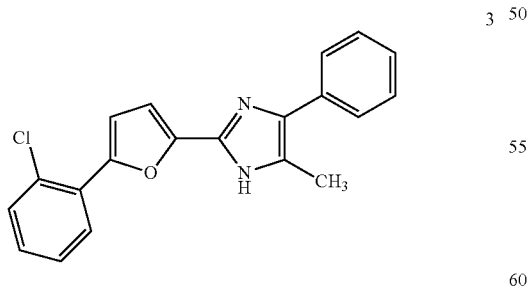

3

Compound 45 below was synthesized in 91% yield (yield for step D) from 1-Phenyl-1,2-propanedione (commercially available from, inter alia, Sigma-Aldrich) and 5-[4-(trifluoromethyl)phenyl]furan-2-carbaldehyde (commercially available from Enamine (Kiev, Ukraine)) using 5.5 mmol of the aldehyde SM using the conditions outlined above.

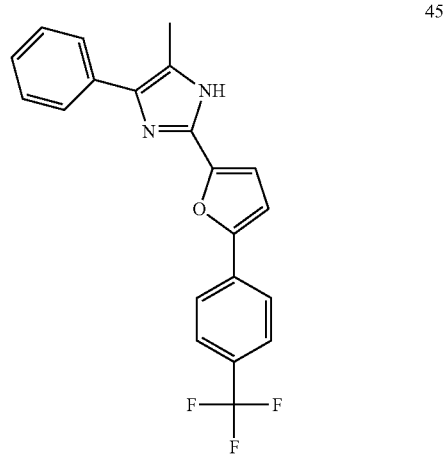 [SMILES: Cc1[nH]c(-c2ccc(-c3ccc(C(F)(F)F)cc3)o2)nc1-c1ccccc1]

45

Compound 2 below was synthesized in 93% yield (yield for step D) from 1-Phenyl-1,2-propanedione (commercially available from, inter alia, Sigma-Aldrich) and 5-(2,3-dichlorophenyl)furan-2-carbaldehyde (commercially available from Enamine (Kiev, Ukraine)) using 5.5 mmol of the aldehyde SM using the conditions outlined above.

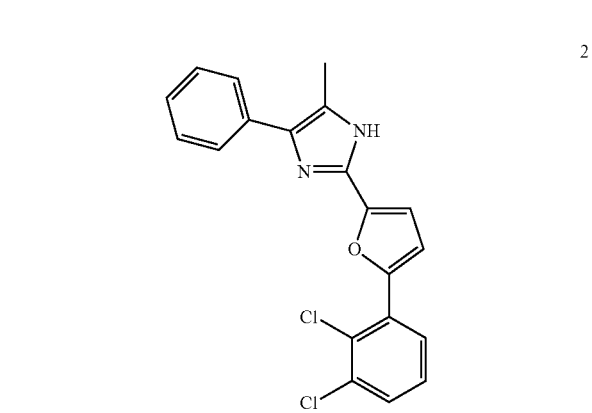 [SMILES: Cc1[nH]c(-c2ccc(-c3cccc(Cl)c3Cl)o2)nc1-c1ccccc1]

2

Compound 57 below was synthesized in 68% yield (yield for step D) from 1-Phenyl-1,2-propanedione (commercially available from, inter alia, Sigma-Aldrich) and 2-(4-methylphenyl)-1,3-oxazole-4-carbaldehyde (commercially available from Enamine (Kiev, Ukraine)) using 5.5 mmol of the aldehyde SM using the conditions outlined above.

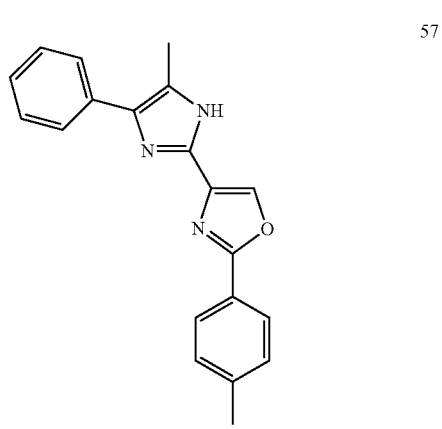 [SMILES: Cc1ccc(-c2nc(-c3nc(-c4ccccc4)c(C)[nH]3)cs2)cc1]

57

Compound 8 below was synthesized in 14% yield (yield for step D) from 1-Phenyl-1,2-propanedione (commercially available from, inter alia, Sigma-Aldrich) and 2,5-dimethyl-1-(4-methylphenyl)-1H-pyrrole-3-carbaldehyde (commercially available from Enamine (Kiev, Ukraine)) using 5.5 mmol of the aldehyde SM using the conditions outlined above.

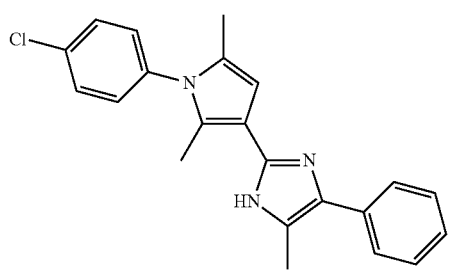

8

Compound 11 below was synthesized in 96% yield (yield for step D) from 1-Phenyl-1,2-propanedione (commercially available from, inter alia, Sigma-Aldrich) and 2-(4-methylphenyl)-1,3-thiazole-4-carbaldehyde (commercially available from Enamine (Kiev, Ukraine)) using 5.5 mmol of the aldehyde SM using the conditions outlined above.

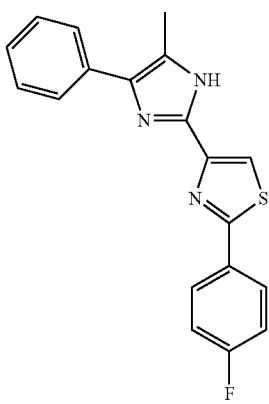

11

Compound 73 below was synthesized in 31% yield (yield for step D) from 1-Phenyl-1,2-propanedione (commercially available from, inter alia, Sigma-Aldrich) and 2-phenyl-2H-1,2,3-triazole-4-carbaldehyde (commercially available from Enamine (Kiev, Ukraine)) using 5.5 mmol of the aldehyde SM using the conditions outlined above.

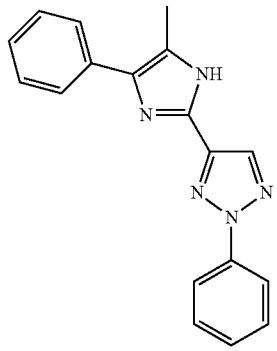

73

Compound 14 below was synthesized from 1-Phenyl-1,2-propanedione (commercially available from, inter alia, Sigma-Aldrich) and 2-(3-bromophenyl)-1,3-thiazole-4-carbaldehyde (commercially available from Enamine (Kiev, Ukraine)) using 5.5 mmol of the aldehyde SM using the conditions outlined above.

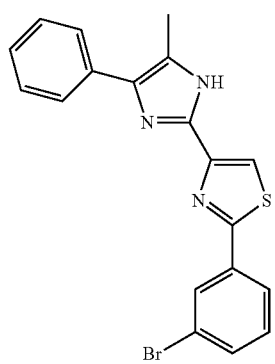

14

Compound 56 below was synthesized in 24% yield (yield for step D) from 1-Phenyl-1,2-propanedione (commercially available from, inter alia, Sigma-Aldrich) and 2-(4-methylphenyl)-1,3-thiazole-4-carbaldehyde (commercially available from Enamine (Kiev, Ukraine)) using 5.5 mmol of the aldehyde SM using the conditions outlined above.

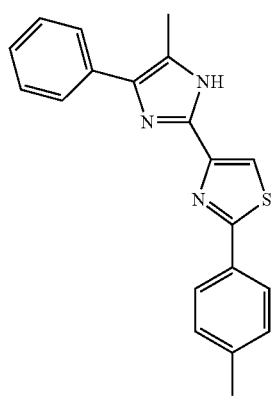

56

Compound 58 below was synthesized from 1-Phenyl-1,2-propanedione (commercially available from, inter alia, Sigma-Aldrich) and 2,5-dimethyl-1-[4-(propan-2-yl)phenyl]-1H-pyrrole-3-carbaldehyde (commercially available from Enamine (Kiev, Ukraine)) using 5.5 mmol of the aldehyde SM using the conditions outlined above.

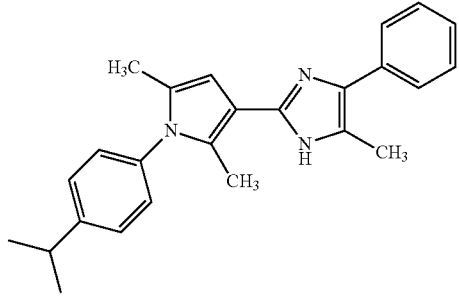

58

Compound 36 below was synthesized in 32% yield (yield for step D) from 1-Phenyl-1,2-propanedione (commercially available from, inter alia, Sigma-Aldrich) and 2,5-dimethyl-1-[3-(trifluoromethyl)phenyl]-1H-pyrrole-3-carbaldehyde (commercially available from Enamine (Kiev, Ukraine)) using 5.5 mmol of the aldehyde SM using the conditions outlined above.

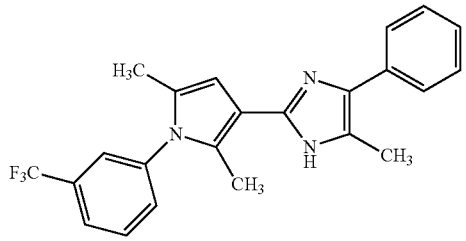

36

Compound 59 below was synthesized in 16% yield (yield for step D) from 1-Phenyl-1,2-propanedione (commercially available from, inter alia, Sigma-Aldrich) and 1-(2,3-dihydro-1H-inden-5-yl)-2,5-dimethyl-1H-pyrrole-3-carbaldehyde (commercially available from Enamine (Kiev, Ukraine)) using 5.5 mmol of the aldehyde SM using the conditions outlined above.

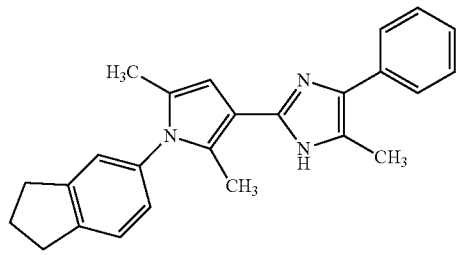

59

Compound 52 below was synthesized in 43% yield (yield for step D) from 1-Phenyl-1,2-propanedione (commercially available from, inter alia, Sigma-Aldrich) and 5-(4-methylphenyl)furan-2-carbaldehyde (commercially available from Enamine (Kiev, Ukraine)) using 5.5 mmol of the aldehyde SM using the conditions outlined above.

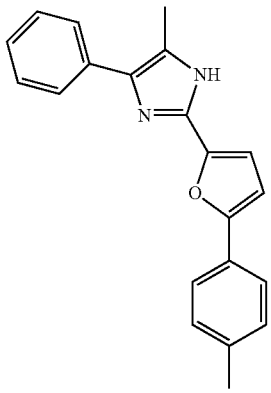

52

Compound 54 below was synthesized in 25% yield (yield for step D) from 1-Phenyl-1,2-propanedione (commercially available from, inter alia, Sigma-Aldrich) and 5-(p-tolyl)thiophene-2-carbaldehyde (commercially available from Enamine (Kiev, Ukraine)) using 5.5 mmol of the aldehyde SM using the conditions outlined above.

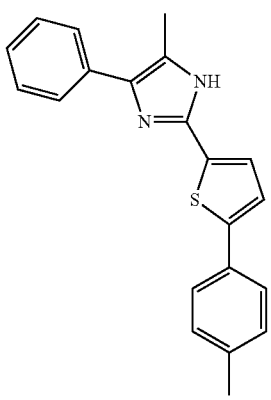

54

Compound 7 below was synthesized in 21% yield (yield for step D) from 1-Phenyl-1,2-propanedione (commercially available from, inter alia, Sigma-Aldrich) and 5-(4-fluorophenyl)thiophene-2-carbaldehyde (commercially available from Enamine (Kiev, Ukraine)) using 5.5 mmol of the aldehyde SM using the conditions outlined above.

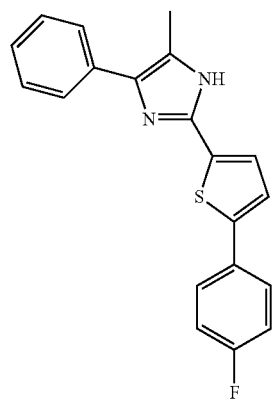

7

Compound 15 below was synthesized from 1-Phenyl-1,2-propanedione (commercially available from, inter alia, Sigma-Aldrich) and 5-(2-fluorophenyl)thiophene-2-carbaldehyde (commercially available from Enamine (Kiev, Ukraine)) using 5.5 mmol of the aldehyde SM using the conditions outlined above.

15

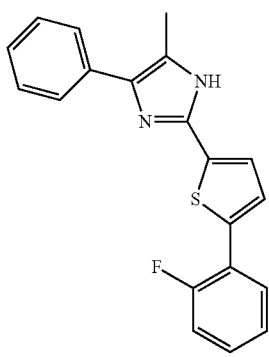

Compound 46 below was synthesized in 45% yield (yield for step D) from 1-Phenyl-1,2-propanedione (commercially available from, inter alia, Sigma-Aldrich) and 5-[4-(trifluoromethyl)phenyl]thiophene-2-carbaldehyde (commercially available from Enamine (Kiev, Ukraine)) using 5.5 mmol of the aldehyde SM using the conditions outlined above.

46

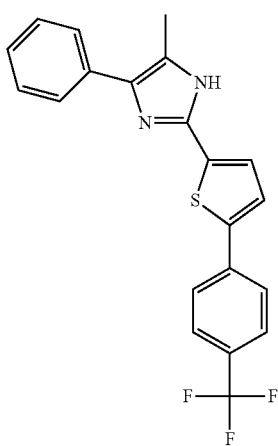

Compound 6 below was synthesized in 47% yield (yield for step D) from 1-Phenyl-1,2-propanedione (commercially available from, inter alia, Sigma-Aldrich) and 5-(4-chlorophenyl)thiophene-2-carbaldehyde (commercially available from Enamine (Kiev, Ukraine)) using 5.5 mmol of the aldehyde SM using the conditions outlined above.

6

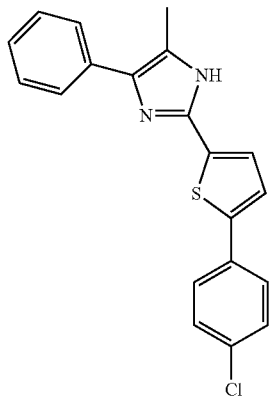

Compound 10 below was synthesized in 11% yield (yield for step D) from 1-Phenyl-1,2-propanedione (commercially available from, inter alia, Sigma-Aldrich) and 2,5-dimethyl-1-(2,3,4-trifluorophenyl)-1H-pyrrole-3-carbaldehyde (commercially available from Enamine (Kiev, Ukraine)) using 5.5 mmol of the aldehyde SM using the conditions outlined above.

10

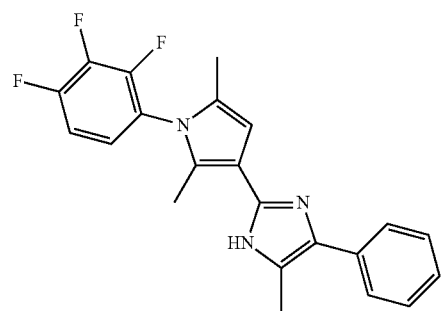

Compound 55 below was synthesized from 1-Phenyl-1,2-propanedione (commercially available from, inter alia, Sigma-Aldrich) and 2-(4-methylphenyl)-1,3-thiazole-5-carbaldehyde (commercially available from Enamine (Kiev, Ukraine)) using 5.5 mmol of the aldehyde SM using the conditions outlined above.

55

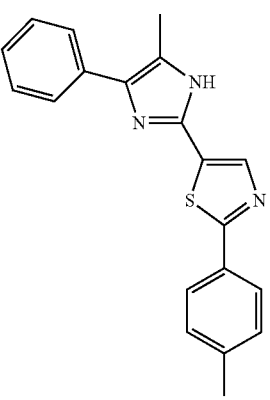

Compound 12 below was synthesized in 58% yield (yield for step D) from 1-Phenyl-1,2-propanedione (commercially available from, inter alia, Sigma-Aldrich) and 5-(3-chlorophenyl)thiophene-2-carbaldehyde (commercially available from Enamine (Kiev, Ukraine)) using 5.5 mmol of the aldehyde SM using the conditions outlined above.

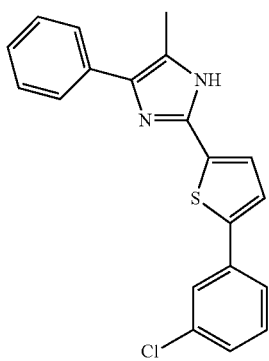

12

Compound 33 below was synthesized in 7% yield (yield for final step) from 1-Phenyl-1,2-propanedione (commercially available from, inter alia, Sigma-Aldrich) and 1-(2-trifluoromethylphenyl)-1H-pyrrole-3-carbaldehyde using 5.5 mmol of the aldehyde SM using the conditions outlined above.

1-(2-trifluoromethylphenyl)-1H-pyrrole-3-carbaldehyde was not commercially available but instead synthesized through arylation of 1H-pyrrole-3-carbaldehyde (commercially available from Sigma, Enamine (Kiev, Ukraine) etc.) with 2-Bromobenzotrifluoride (commercially available from Sigma, Enamine (Kiev, Ukraine) etc.) as follows:

A mixture of 1H-pyrrole-3-carbaldehyde (50 mmol), 2-Bromobenzotrifluoride (50 mmol) and potassium carbonate (50 mmol) in DMF (25 mL) was stirred at 80° C. until reaction complete by TLC analysis. The mixture was treated with water and extracted with DCM. The organics were washed with brine, dried, and concentrated. The resultant solids were recrystallized from 2-propanol to yield 1-(2-trifluoromethylphenyl)-1H-pyrrole-3-carbaldehyde in 80-85% purity which was used in the next steps without further purification.

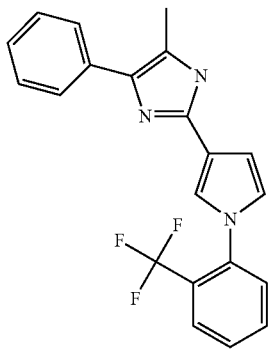

33

Compound 42 below was synthesized in 45% yield (yield for step D) from 4-fluorobenzoic acid (commercially available from, inter alia, Enamine (Kiev, Ukraine)) and 5-[4-chloro-3-(trifluoromethyl)phenyl]furan-2-carbaldehyde (commercially available from Enamine (Kiev, Ukraine)) using 5.5 mmol of the aldehyde SM using the conditions outlined above.

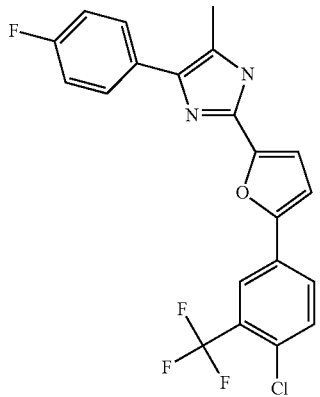

42

Compound 27 below was synthesized in 23% yield (yield for step D) from 4-Ethynylbenzoic acid (commercially available from, inter alia, Sigma-Aldrich (St. Louis, Mo., USA)) and 5-[2-(Trifluoromethyl)phenyl]furfural (commercially available from, inter alia, Sigma-Aldrich (St. Louis, Mo., USA)) using 5.5 mmol of the aldehyde SM using the conditions outlined above.

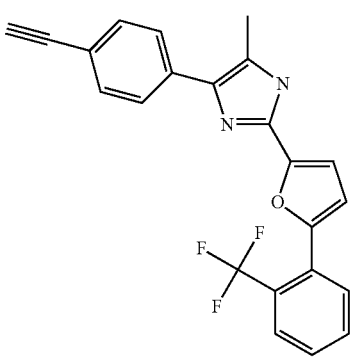

27

Compound 13 below was synthesized in 29% yield (yield for step D) from 1-Phenyl-1,2-propanedione (commercially available from, inter alia, Sigma-Aldrich) and 5-(3-bromophenyl)thiophene-2-carbaldehyde (commercially available from Enamine (Kiev, Ukraine)) using 5.5 mmol of the aldehyde SM using the conditions outlined above.

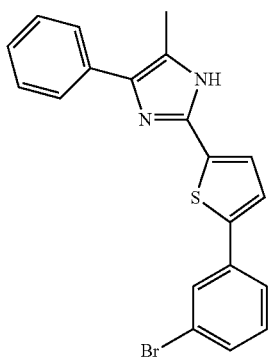

13

Compound 9 below was synthesized in 46% yield (yield for step D) from 1-Phenyl-1,2-propanedione (commercially available from, inter alia, Sigma-Aldrich) and 2,5-dimethyl-1-(2,4-difluorophenyl)-1H-pyrrole-3-carbaldehyde (commercially available from Enamine (Kiev, Ukraine)) using 5.5 mmol of the aldehyde SM using the conditions outlined above.

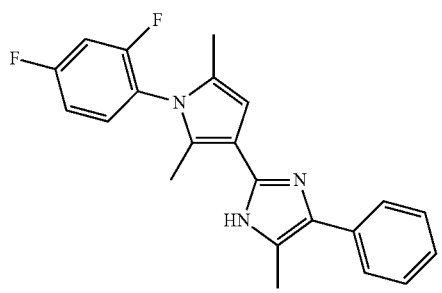

9

Compound 53 below was synthesized in 81% yield (yield for step D) from 1-Phenyl-1,2-propanedione (commercially available from, inter alia, Sigma-Aldrich) and 5-(4-ethylphenyl)furan-2-carbaldehyde (commercially available from Enamine (Kiev, Ukraine)) using 5.5 mmol of the aldehyde SM using the conditions outlined above.

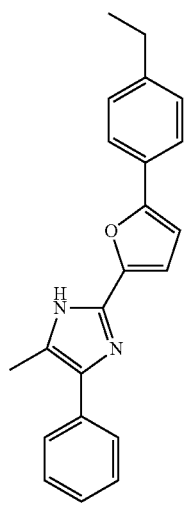

53

Compound 74 below was synthesized in 62% yield (yield for step D) from 1-Phenyl-1,2-propanedione (commercially available from, inter alia, Sigma-Aldrich) and 5-phenylthiophene-2-carbaldehyde (commercially available from Enamine (Kiev, Ukraine)) using 5.5 mmol of the aldehyde SM using the conditions outlined above.

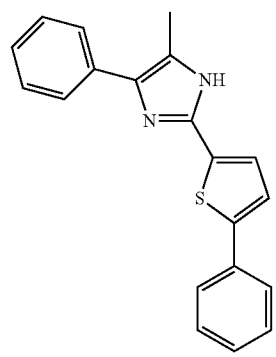

74

By means of example, the following compounds of the invention were made according to Method F as outlined above wherein the aldehyde starting material required in step D was synthesized in accordance with Method H of the present application.

Compound 19 below was synthesized in 20% yield (yield for step D of Method F) from 2-chlorobenzoic acid (commercially available from, inter alia, Enamine (Kiev, Ukraine)) and 5-[2-(trifluoromethoxy)phenyl]furan-2-carbaldehyde using 5.5 mmol using the conditions outlined above. 5-[2-(trifluoromethoxy)phenyl]furan-2-carbaldehyde was made from [2-(trifluoromethoxy)phenyl]boronic acid (commercially available from Enamine (Kiev, Ukraine)) and 5-bromofuran-2-carbaldehyde (commercially available from Enamine (Kiev, Ukraine)) using Method H of the present invention.

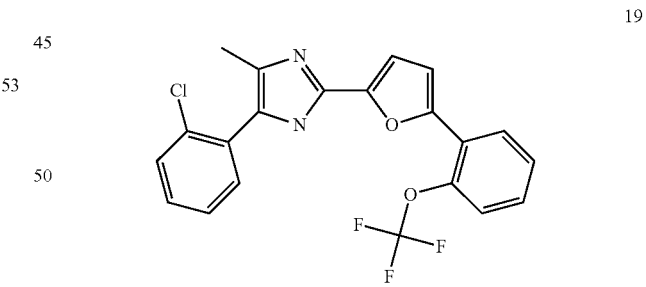

19

Compound 20 below was synthesized in 16% yield (yield for step D of Method F) from 2-chlorobenzoic acid (commercially available from, inter alia, Enamine (Kiev, Ukraine)) and 5-[2-(trifluoromethyl)phenyl]furan-2-carbaldehyde using 5.5 mmol of the aldehyde SM using the conditions outlined above. 5-[2-(trifluoromethyl)phenyl]furan-2-carbaldehyde was made from [2-(trifluoromethyl)phenyl]boronic acid (commercially available from Enamine (Kiev, Ukraine)) and 5-bromofuran-2-carbaldehyde (commercially available from Enamine (Kiev, Ukraine)) using Method H of the present invention.

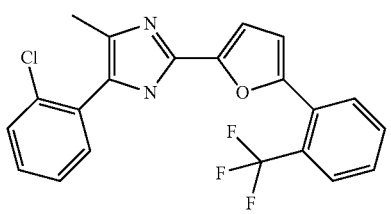

20

Compound 21 below was synthesized in 23% yield (yield for step D of Method F) from 3-chlorobenzoic acid (commercially available from, inter alia, Enamine (Kiev, Ukraine)) and 5-[2-(trifluoromethoxy)phenyl]furan-2-carbaldehyde using 5.5 mmol of the aldehyde using the conditions outlined above. 5-[2-(trifluoromethoxy)phenyl]furan-2-carbaldehyde was made from [2-(trifluoromethoxy)phenyl]boronic acid (commercially available from Enamine (Kiev, Ukraine)) and 5-bromofuran-2-carbaldehyde (commercially available from ENAMINE (KIEV, UKRAINE)) using Method H of the present invention.

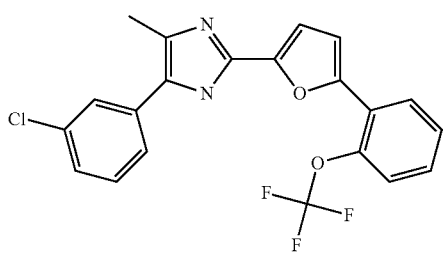

21

Compound 22 below was synthesized in 21% yield (yield for step D of Method F) from 3-chlorobenzoic acid (commercially available from, inter alia, Enamine (Kiev, Ukraine)) and 5-[2-(trifluoromethyl)phenyl]furan-2-carbaldehyde using 5.5 mmol of the aldehyde SM using the conditions outlined above. 5-[2-(trifluoromethyl)phenyl]furan-2-carbaldehyde was made from [2-(trifluoromethyl)phenyl]boronic acid (commercially available from Enamine (Kiev, Ukraine)) and 5-bromofuran-2-carbaldehyde (commercially available from Enamine (Kiev, Ukraine)) using Method H of the present invention.

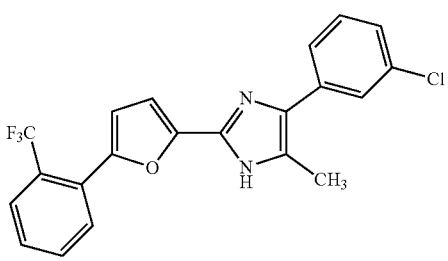

22

Compound 37 below was synthesized in 37% yield (yield for step D) from 4-fluorobenzoic acid (commercially available from, inter alia, Enamine (Kiev, Ukraine)) and 5-[3-(trifluoromethoxy)phenyl]furan-2-carbaldehyde using 5.5 mmol of the aldehyde SM using the conditions outlined above. 5-[3-(trifluoromethoxy)phenyl]furan-2-carbaldehyde was made from (5-formylfuran-2-yl)boronic acid (commercially available from TCI (TOKYO, JAPAN)) and 3-(Trifluoromethoxy)iodobenzene (commercially available from Enamine (Kiev, Ukraine)) using Method H of the present invention.

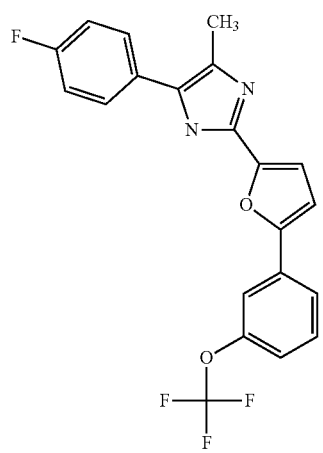

37

Compound 44 below was synthesized in 42% yield (yield for step D of Method F) from 4-chlorobenzoic acid (commercially available from, inter alia, Enamine (Kiev, Ukraine)) and 5-[4-chloro-3-(trifluoromethoxy)phenyl]furan-2-carbaldehyde using 5.5 mmol of the aldehyde SM using the conditions outlined above. 5-[4-chloro-3-(trifluoromethoxy)phenyl]furan-2-carbaldehyde was made from (5-formylfuran-2-yl)boronic acid (commercially available from TCI (TOKYO, JAPAN)) and 4-bromo-1-chloro-2-(trifluoromethoxy)benzene (commercially available from Fluorochem (Hadfield, Derbyshire, UK)) using Method H of the present invention.

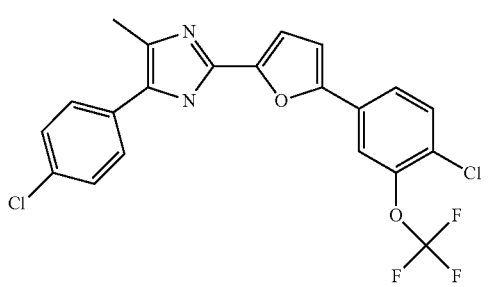

44

Compound 16 below was synthesized in 27% yield (yield for step D) from 4-fluorobenzoic acid (commercially available from, inter alia, Enamine (Kiev, Ukraine)) and 5-(2,4-dichlorophenyl)furan-2-carbaldehyde using 5.5 mmol of the aldehyde SM using the conditions outlined above. 5-(2,4-dichlorophenyl)furan-2-carbaldehyde was made from (2,4-dichlorophenyl)boronic acid (commercially available from Enamine (Kiev, Ukraine)) and 5-bromofuran-2-carbaldehyde (commercially available from Enamine (Kiev, Ukraine)) using Method H of the present invention.

16

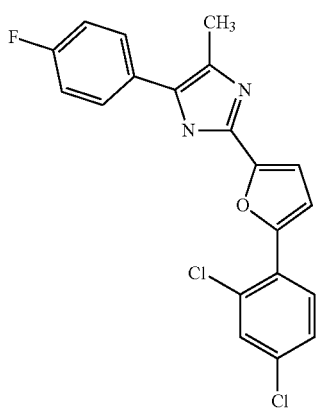

Compound 47 below was synthesized in 16% yield (yield for step D of Method F) from 4-chlorobenzoic acid (commercially available from, inter alia, Enamine (Kiev, Ukraine)) and 5-[4-(trifluoromethyl)phenyl]furan-2-carbaldehyde using 5.5 mmol of the aldehyde SM using the conditions outlined above. 5-[4-(trifluoromethyl)phenyl]furan-2-carbaldehyde was made from (5-formylfuran-2-yl)boronic acid (commercially available from TCI (TOKYO, JAPAN)) and 1-bromo-4-(trifluoromethyl)benzene (commercially available from Sigma-Aldrich (St. Louis, Mo., USA)) using Method H of the present invention.

47

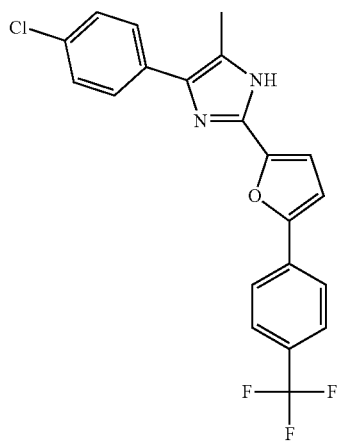

Compound 48 below was synthesized in 61% yield (yield for step D of Method F) from 4-chlorobenzoic acid (commercially available from, inter alia, Enamine (Kiev, Ukraine)) and 5-[4-(trifluoromethoxy)phenyl]furan-2-carbaldehyde using 5.5 mmol of the aldehyde SM using the conditions outlined above. 5-[4-(trifluoromethoxy)phenyl]furan-2-carbaldehyde was made from (5-formylfuran-2-yl)boronic acid (commercially available from TCI (TOKYO, JAPAN)) and 1-bromo-4-(trifluoromethoxy)benzene (commercially available from ENAMINE (KIEV, UKRAINE)) using Method H of the present invention.

48

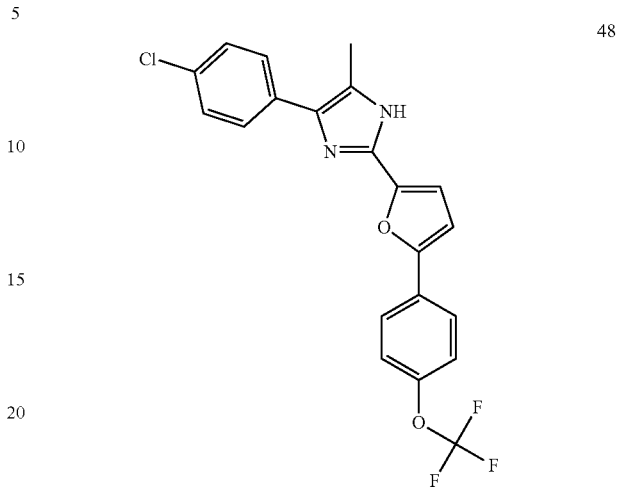

Compound 43 below was synthesized in 35% yield (yield for step D) from 4-fluorobenzoic acid (commercially available from, inter alia, Enamine (Kiev, Ukraine)) and 5-[4-chloro-3-(trifluoromethoxy)phenyl]furan-2-carbaldehyde using 5.5 mmol of the aldehyde SM using the conditions outlined above. 5-[4-chloro-3-(trifluoromethoxy)phenyl]furan-2-carbaldehyde was made from (5-formylfuran-2-yl)boronic acid (commercially available from TCI (TOKYO, JAPAN)) and 4-bromo-1-chloro-2-(trifluoromethoxy)benzene (commercially available from Fluorochem (Hadfield, Derbyshire, UK)) using Method H of the present invention.

43

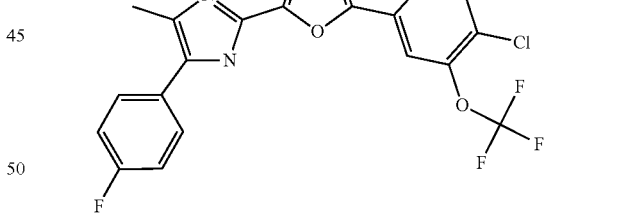

Compound 41 below was synthesized in 40% yield (yield for step D) from 1-Phenyl-1,2-propanedione (commercially available from, inter alia, Sigma-Aldrich (St. Louis, Mo., USA)) and 5-[4-chloro-3-(trifluoromethoxy)phenyl]furan-2-carbaldehyde using 5.5 mmol of the aldehyde SM using the conditions outlined above. 5-[4-chloro-3-(trifluoromethoxy)phenyl]furan-2-carbaldehyde was made from (5-formylfuran-2-yl)boronic acid (commercially available from TCI (TOKYO, JAPAN)) and 4-bromo-1-chloro-2-(trifluoromethoxy)benzene (commercially available from Fluorochem (Hadfield, Derbyshire, UK)) using Method H of the present invention.

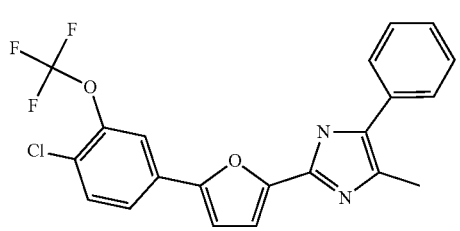

41

Compound 51 below was synthesized from 4-fluorobenzoic acid (commercially available from, inter alia, Enamine (Kiev, Ukraine)) and 5-(2-chloro-4-(trifluoromethoxy)phenyl)furan-2-carbaldehyde using 5.5 mmol of the aldehyde SM using the conditions outlined above. 5-(2-chloro-4-(trifluoromethoxy)phenyl)furan-2-carbaldehyde was made from (5-formylfuran-2-yl)boronic acid (commercially available from TCI (TOKYO, JAPAN)) and 1-Bromo-2-chloro-4-(trifluoromethoxy)benzene (commercially available from Enamine (Kiev, Ukraine)) using Method H of the present invention.

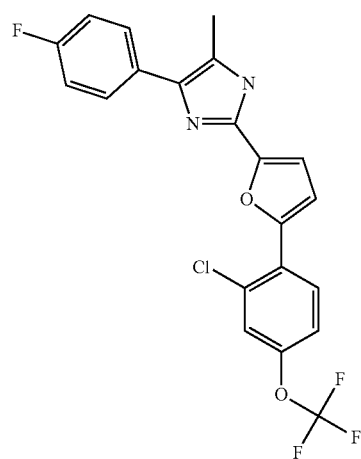

51

Compound 49 below was synthesized in from 4-fluorobenzoic acid (commercially available from, inter alia, Enamine (Kiev, Ukraine)) and 5-(3-chloro-4-(trifluoromethyl)phenyl)furan-2-carbaldehyde using 5.5 mmol of the aldehyde SM using the conditions outlined above. 5-(3-chloro-4-(trifluoromethyl)phenyl)furan-2-carbaldehyde was made from (5-formylfuran-2-yl)boronic acid (commercially available from TCI (TOKYO, JAPAN)) and 4-bromo-2-chloro-1-(trifluoromethyl)benzene (commercially available from TCI (TOKYO, JAPAN)) using Method H of the present invention.

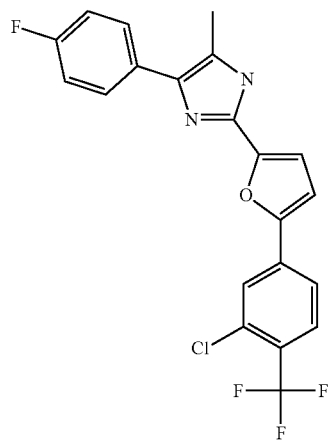

49

Compound 50 below was synthesized from 4-chlorobenzoic acid (commercially available from, inter alia, Enamine (Kiev, Ukraine)) and 5-(3-chloro-4-(trifluoromethoxy)phenyl)furan-2-carbaldehyde using 5.5 mmol of the aldehyde SM using the conditions outlined above. 5-(3-chloro-4-(trifluoromethoxy)phenyl)furan-2-carbaldehyde was made from (5-formylfuran-2-yl)boronic acid (commercially available from TCI (TOKYO, JAPAN)) and 4-bromo-2-chloro-1-(trifluoromethoxy)benzene (commercially available from Fluorochem (Hadfield, Derbyshire, UK)) using Method H of the present invention.

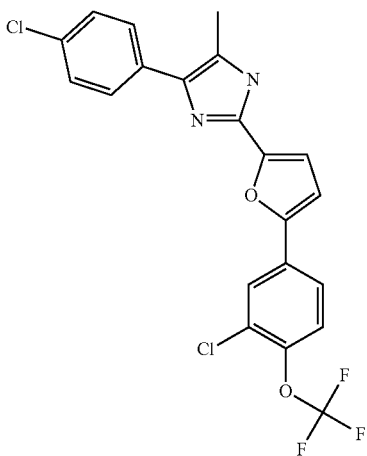

50

Method G (General Procedure for the Synthesis of the Imidazoles):

In certain cases where one of $R^1$ or $R^2$ in a compound of the present invention is H and the other is an unsubstituted or substituted phenyl ring, compounds of the present invention may be made via the following process.

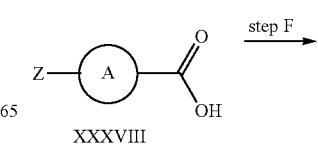

XXXVIII

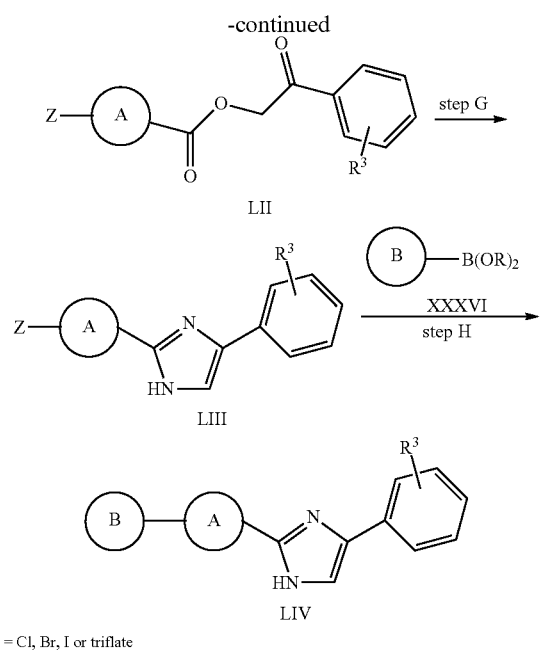

Z = Cl, Br, I or triflate

Compounds of formula (LIV) may be made through Suzuki coupling reaction of a boronic acid/ester of formula (XXXVI) with an imidazole of formula (LIII) preferably via standard Suzuki reaction conditions such as those described in Step 2 of Method C hereinabove. Imidazoles of formula (LIII) may be made through cyclization of dicarbonyl compounds of formula (LII) in the presence of a source of ammonia, for example ammonium acetate, preferably using standard cond H is for such cyclizations such as heating over a prolonged period in a high boiling solvent, for example xylene, with a system designed to remove any water generated, for example a Dean-Stark apparatus. Dicarbonyl compounds of formula (LII) may be made from acids of formula (XXXVIII) preferably through standard alkylation reaction with the appropriate 1-arylethanone which is furnished with an appropriate leaving group, for example a bromine atom, at the alkyl position adjacent to the ketone. Such conditions may involve initially forming the anion of the acid of formula (XXXVIII) preferably under standard conditions such as stirring with base in an appropriate solvent followed by reaction of the resultant carboxylate salt with the appropriate alkylating agent, for example a 2-bromo-1-arylethanone.

Carboxylic acid starting materials of formula (XXXVIII) can generally be purchased from commercial suppliers (e.g. Sigma-Aldrich (St. Louis, Mo., USA), Apollo Scientifc, CombiBlocks (San Diego, USA), Enamine (Kiev, Ukraine) etc). In instances where the appropriate starting carboxylic acids (XXXVIII) are not commercially available, they may also be made by at least one of a number of standard methods known to the person skilled in the art such as, for example, hydrolysis of the corresponding nitrile or ester, reaction of an appropriate organometallic or metallated species with $CO_2$ or a $CO_2$ analogue, general carboxylation methods known to the skilled person etc.

Boronic acids or boronic esters of formula (XXXVI) can generally be purchased from commercial suppliers (e.g. CombiBlocks (San Diego, USA)) but, in instances where boronic acids or boronic esters of formula (XXXVI) are not commercially available, they may also be made by at least one of a number of standard methods known to the person skilled in the art such as, for example, the reaction of an appropriate organometallic species, e.g. an organolithium or Grignard species, with a borate ester followed by an optional hydrolysis of the product borate ester, cross-coupling of an appropriate halide with a diboronyl ester or diboronic acid, transmetallation of an appropriate stannane with boron tribromide followed by hydrolysis to the corresponding boronic acid, etc.

The appropriate alkylating agents, for example a 2-halo-1-arylethanones can generally be purchased from commercial suppliers (e.g. Enamine (Kiev, Ukraine), Alfa Aesar (Schiltigheim, France) and others) but, in instances where 2-halo-1-arylethanones are not commercially available, they may also be made by at least one of a number of standard methods known to the person skilled in the art such as, for example, Friedel-Krafts acylation reaction of the appropriate aryl ring with a haloacetyl halide preferably under standard conditions, or halogenation of the methyl group of an appropriate acetophenone preferably under standard conditions.

A general example of the use of Method G to furnish compounds of the invention is as follows

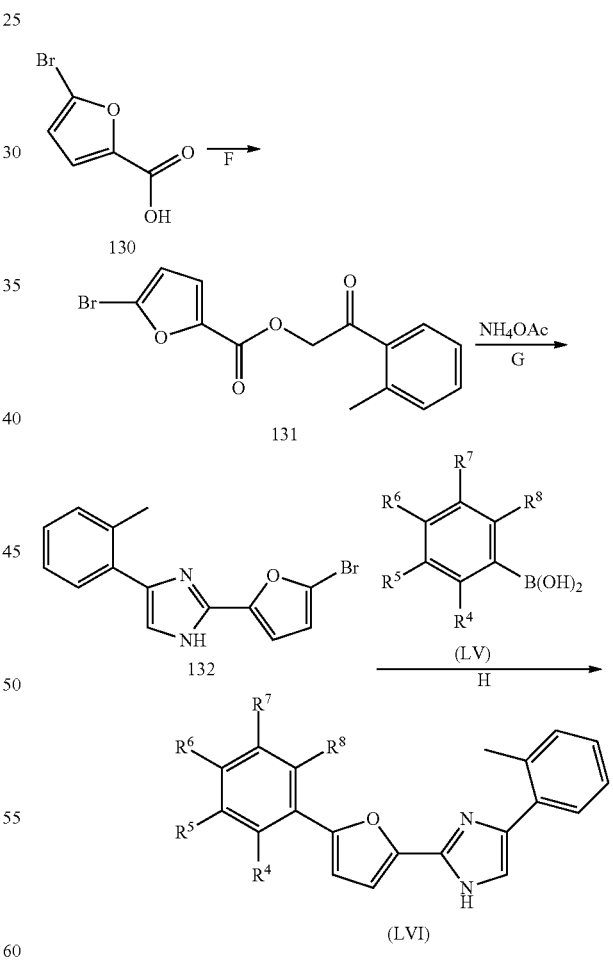

Step F:

A solution of 5-bromo-furane-2-carboxylic acid 130 (5 g, 26 mmol) in EtOH (200 mL) was combined with potassium carbonate (3.5 g, 27.8 mmol). The resulting suspension was stirred for 30 min, evaporated to dryness, and solids were suspended in MeCN (300 mL). To a stirred suspension 2-bromo-1-(o-tolyl)ethanone (3.48 g, 26 mmol) was added in one portion, and resulting system was stirred for 24 h at room temperature. The reaction mixture was filtered, evaporated to dryness, and used as is in the next step.

Step G:

To a solution of compound 131 obtained from step F (8 g, 24.7 mmol) in xylene (600 mL) ammonium acetate (39 g, 50.6 mmol) was added, and the resulting mixture was refluxed for 1 week with Dean-Stark trap. During this week additional portions of ammonium acetate (3×20 g) were added each 2 days. After cooling down to r.t. the mixture was diluted with EtOAc (500 mL). The organic layer was washed with water, saturated NaHCO$_3$ solution, brine, dried, and concentrated. The residue was purified by column chromatography (silica gel, MTBE/hexane) to obtain pure derivative 132 (900 mg, 2.97 mmol, 12% yield).

Step H:

A round-bottomed flask was charged with compound 132 obtained from step G (250 mg, 825 μmol), the appropriate boronic acid (LV) (900 μmol), sodium carbonate (190 mg, 1.8 mmol), Pd(dppf)$_2$ (5 mol %, 30 mg), DME (40 mL), and water (10 mL). The reaction mixture was stirred at 80° C. for 16 h and then diluted with EtOAc. The organic phase was washed with water, brine, dried, and evaporated. The residue was purified by flash column chromatography on silica gel (MTBE-hexane). Yield of (LVI) 10 to 50%.

Examples of the invention may be made according to the above-outlined steps F to H where, although the absolute quantities of starting materials, reactants and reagents used therein may deviate from those outlined above for steps F to H, within any given step the relative molar quantities of starting materials, reactants and reagents as well as concentrations are consistent with those stipulated in steps F to H above.

By means of example, the following compounds of the invention were made according to Method G as outlined above.

Compound 66 below was synthesized in 15% yield (yield for final step) from 2-bromo-1-(o-tolyl)ethanone (commercially available from Enamine (Kiev, Ukraine)) and 5-bromo-furan-2-carboxylic acid (commercially available from Enamine (Kiev, Ukraine)) using 26 mmol of the acid SM followed by reaction in step H with (2-(trifluoromethoxy)phenyl)boronic acid (commercially available from Enamine (Kiev, Ukraine)) using the conditions outlined above.

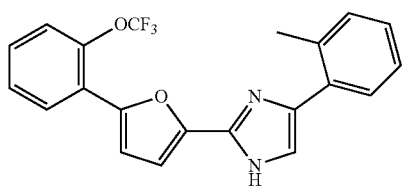

66

Compound 69 below was synthesized in 35% yield (yield for final step) from 2-bromo-1-(o-tolyl)ethanone (commercially available from Enamine (Kiev, Ukraine)) and 5-bromo-furan-2-carboxylic acid (commercially available from Enamine (Kiev, Ukraine)) using 26 mmol of the acid SM followed by reaction in step H with (2-(trifluoromethyl) phenyl)boronic acid (commercially available from Enamine (Kiev, Ukraine)) using the conditions outlined above.

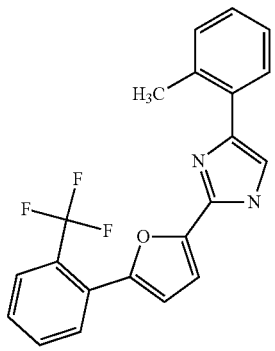

69

It is also possible that compounds of the present invention be synthesized using only parts of the chemistry of Method G. In such cases, the structures of the starting materials vary slightly from those depicted in the general scheme for Method G shown above. For example, in cases where an appropriate carboxylic acid starting material in which z does not represent Cl, Br, I or triflate but instead already the desired 'B' group to be present in the final compound is available, the final step (step H) of Method G may not be necessary to access the compounds of the invention. In such a case, however, steps F and G of Method G may still be employed to convert the appropriate carboxylic acid starting material into a compound of the invention through reaction with the appropriate reaction partner in step F followed by closure of the imidazole ring in step G.

By means of example, the following compounds were synthesized by such a process in which step H of method G was not necessary as the structural element which step H would have been intended to have introduced (the 'B' group) was already present in the starting carboxylic acid (i.e. 'z' in the starting acid is represented by the 'B' group and not by Cl, Br, I, or triflate):

Compound 67 below was synthesized in from 2-bromo-1-(2-chlorophenyl)ethan-1-one (commercially available from Enamine (Kiev, Ukraine)) and 5-[(2-(trifluoromethoxy)phenyl)furan]-2-carboxylic acid (commercially available from Enamine (Kiev, Ukraine)) using 26 mmol of the acid SM using the conditions outlined above.

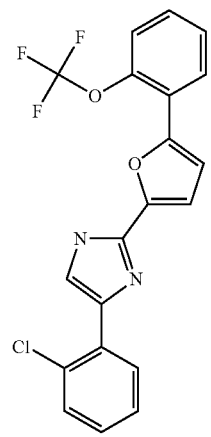

67

Compound 68 below was synthesized in from 2-bromo-1-(2,4-dichlorophenyl)ethanone (commercially available from Sigma-Aldrich (St. Louis, Mo., USA)) and 5-(2-(trifluoromethoxy)phenyl)furan-2-carboxylic acid (commercially available from Enamine (Kiev, Ukraine)) using 26 mmol of the acid SM using the conditions outlined above.

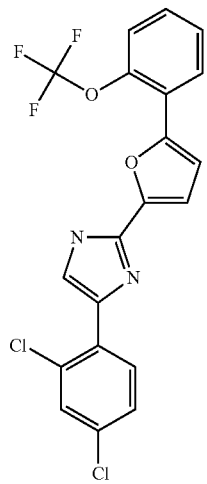

68

Method H (Alternative Procedure for the Synthesis of Compounds of Formula (XX)):

An alternative procedure for the synthesis of aldehydes of formula XX is outlined below. Aldehydes of formula XX made via this method may then be used in any of the Methods listed herein which use aldehydes of formula XX to synthesise the compounds of the invention.

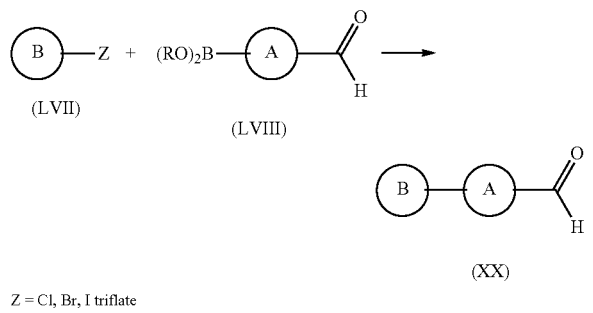

Z = Cl, Br, I triflate

Aldehydes of formula (XX) may be made via Suzuki cross-coupling reaction of aldehydes of formula (LVIII) and compounds of formula (LVII) preferably under standard Suzuki reaction conditions such as those outlined in Method C above.

Aldehydes of formula (LVIII) are generally commercially available from supplier such as, for example, Enamine (Kiev, Ukraine) or Sigma-Aldrich (St. Louis, Mo., USA) but in instances where aldehydes of formula (LVIII) are not commercially available they may be made by at least one of a number of standard methods known to the person skilled in the art such as, for example, reduction of the corresponding nitrile or acid or ester, reaction of an appropriate organometallic or metallated species with N,N-dimethylformamide, general carbonylation methods known to the skilled person etc. Alternatively, in some instances the boronic ester/acid functionality may be introduced into an appropriate starting material to deliver aldehydes of formula (LVIII) by at least one of a number of standard methods known to the person skilled in the art such as, for example, cross-coupling of an appropriate halide with a diboronyl ester or diboronic acid.

Aryl halides or triflates of formula (LVII) are generally commercially available from supplier such as, for example, Enamine (Kiev, Ukraine), Sigma-Aldrich (St. Louis, Mo., USA), Apollo Scientifc etc but in instances where aryl halides or triflates of formula (LVII) are not commercially available they may be made by at least one of a number of standard methods known to the person skilled in the art such as, for example, electrophilic aromatic substitution reaction with an electrophilic source of the desired halogen or, in the case of triflates, reaction of the corresponding hydroxyl compound with triflic anhydride.

Examples of aldehydes of formula (XX) made by this method include

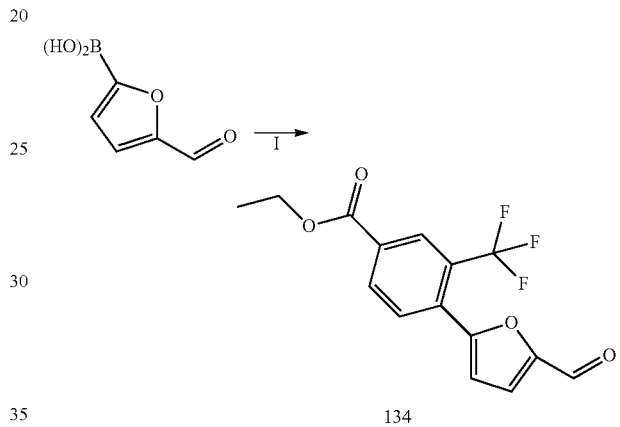

134

Step I:

A glass vial with magnetic stir bar was charged with ethyl 4-bromo-3-(trifluoromethyl)benzoate (5.94 g, 20 mmol), Pd(PPh$_3$)$_4$ (600 mg), dimethoxyethane (40 mL), sodium carbonate (4.25 g, 40 mmol), and water (20 mL). The vial was filled with argon, capped, and stirred for 15 min. Then it was opened and solution of (5-formylfuran-2-yl)boronic acid 133 (3.5 g, 25 mmol) in ethanol (40 mL) was added. The vial was filled with argon, capped, and heated at 90° C. for 7 h under stirring. The reaction mixture was cooled to room temperature and filtered through celite pad. The pad was washed several times with DCM. The filtrate was dried over sodium sulfate and concentrated. A crude material 134 was used in the next step without further purification.

Aldehydes of formula (XX) may also be made according to the above-outlined procedure where, although the absolute quantities of starting materials, reactants and reagents used therein may deviate from those in the above-outlined procedure, within any given step the relative molar quantities of starting materials, reactants and reagents as well as concentrations are consistent with those stipulated in the above-outlined procedure.

Method I (Synthesis of Compounds of the Invention where One of R$^1$ or R$^2$ is Cl):

In certain cases where one of R$^1$ or R$^2$ in a compound of the present invention is Cl and the other is an unsubstituted or substituted phenyl ring, the compounds of the present invention may be made via the following process.

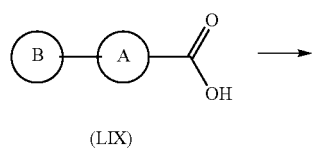

(LIX)

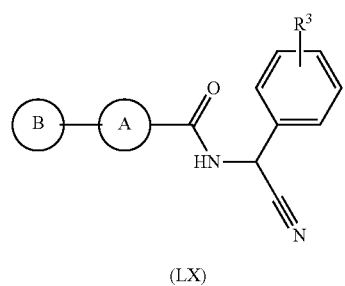

(LX)

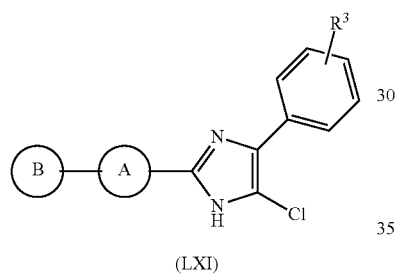

(LXI)

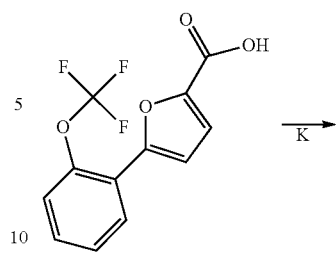

135

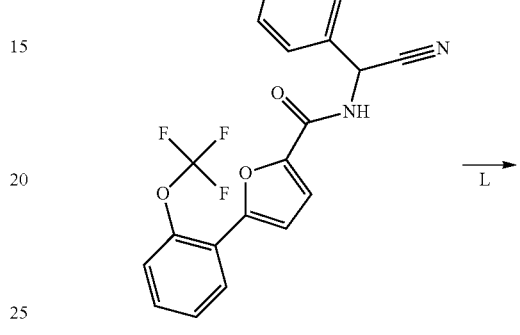

136

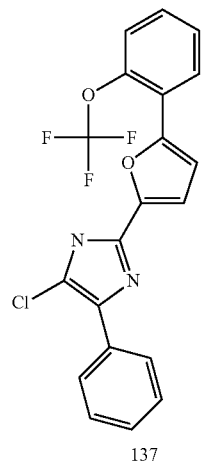

137

Chloroimidazoles of formula (LXI) can be made from via cyclisation of amides of formula (LX) preferably using standard conditions for such transformations, for example reaction with $PPh_3$, $CCl_4$ and a base, for example an organic base such as DIPEA. Amides of formula (LX) can be made from acids of formula (LIX) preferably via standard amide coupling conditions with the appropriate aminoacetonitrile, for example using an amide coupling agent such as CDI in a suitable solvent such as $CH_2Cl_2$.

Carboxylic acids of formula (LIX) are generally commercially available from supplier such as, for example, Enamine (Kiev, Ukraine) or Sigma-Aldrich (St. Louis, Mo., USA) but in instances where carboxylic acids of formula (LIX) are not commercially available they may be made by at least one of a number of standard methods known to the person skilled in the art such as, for example, hydrolysis of the corresponding nitrile or ester, or oxidation of the corresponding aldehyde, the synthesis for which is outlined in numerous locations throughout the present document including, for example, in Method H.

Aminoacetonitriles are generally commercially available from supplier such as, for example, Enamine (Kiev, Ukraine) or Sigma-Aldrich (St. Louis, Mo., USA) but in instances where aminoacetonitriles are not commercially available they may be made by at least one of a number of standard methods known to the person skilled in the art such as, for example, the method outlined in U.S. Pat. No. 5,332,825.

Step K:

A round-bottomed flask was charged with solution of compound 135 (272 mg, 1.0 mmol) in THF (20 mL). To a stirred solution a CDI (1,1'-Carbonyldiimidazole) (177 mg, 1.1 mmol) was added in one portion, and stirring was continued for 1 h. Then 2-amino-2-phenylacetonitrile (commercially available from, inter alia, Bepharm and Ukrorgsyntez Ltd.) (132 mg, 1.0 mmol) was added in one portion, and stirring was continued for 24 h. Then solution was concentrated, a residue was suspended in DCM (25 mL). The suspension was washed with water, and organic phase was separated and dried over sodium sulfate. The volatiles were evaporated to afford of the target material 136 in 159 mg (0.41 mmol, 41%) yield.

Step L:

A round-bottomed flask was charged with compound 136 from step K (159 mg, 0.42 mmol), $PPh_3$ (275 mg, 1.05 mmol), DIPEA (173 mg, 1.34 mmol), and $CCl_4$. The reaction mixture was refluxed for 12 h, cooled to r.t, and washed with water (2×50 mL). The organic layer was dried over sodium sulfate and concentrated. A crude residue (100 mg)

was purified by column chromatography on silica gel (hexane with MTBE). The yield of compound 137 was 25 mg.

Examples of compounds of the invention which have been made using Method I include Compound 64 below was synthesized in from 5-(2-(trifluoromethoxy)phenyl)furan-2-carboxylic acid (commercially available from Enamine (Kiev, Ukraine)) and 2-amino-2-phenylacetonitrile (commercially available from Enamine (Kiev, Ukraine)) using 2.0 mmol of the acid SM using the conditions outlined above.

64

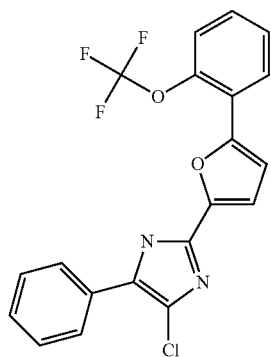

Compound 65 below was synthesized in 9% yield 5-(2-(trifluoromethyl)phenyl)furan-2-carboxylic acid (commercially available from Enamine (Kiev, Ukraine)) and 2-amino-2-phenylacetonitrile (commercially available from, inter alia, Bepharm (Shanghai, China and Ukrorgsyntez Ltd (Kiev, Ukraine)) using 2.0 mmol of the acid SM using the conditions outlined above.

65

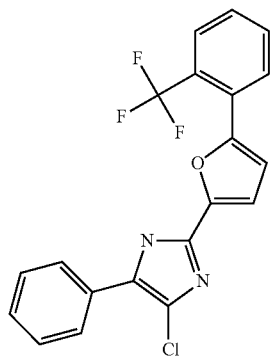

Biological Materials

The following bacterial strains were obtained from the American Type Culture Collection (Manassas, Va.; USA): *Enterococcus faecium* (strain designation AGR15, ATCCBAA-2127™), *Streptococcus pneumoniae* (Chester, ATCC49619™), *Bacillus subtilis* (Marburg strain, ATCC6051™), *Enterococcus faecalis* (ATCC29212™), *Staphylococcus epidermidis* (PCI 1200, ATCC12228™), *Mycobacterium smegmatis* (mc(2)155, ATCC®700084™), vancomycin-resistant *Enterococcus faecium* (ATCC51559), vancomycin-resistant *Enterococcus faecalis* (ATCC51575), and the penicillin-, erythromycin- and tetracycline-resistant *Streptococcus pneumoniae* (ATCC 700677), called herein ARSP. The methicillin-resistant *Staphylococcus aureus* MRSA (COL) strain (Gill S R et al. 2005, J Bacteriol. 187(7):2426-38) is available at the Culture Collection of Switzerland (CCOS 461) and so is the methicillin-sensitive *Staphylococcus aureus* MSSA (Newman) strain (Duthie E S et al. 1952, J. Gen. Microbiol. 695-107) as CCOS 199. The *Escherichia coli* (*E. coli*) TolC mutant strain ΔtolC (K12 b3035 TolC; JW5503) was obtained from GE Healthcare Dharmacon. Bacterial strains were stored in media (see below) supplemented with 50% glycerol at −80° C.

The antibiotic-resistant strains linezolid-resistant *Staphylococcus aureus*, vancomycin-resistant *Staphylococcus aureus*, daptomycin-resistant *Staphylococcus aureus*, moenomycin-resistant *Staphylococcus aureus*, and platensimycin-resistant *Staphylococcus aureus* were produced by serial-passage mutagenesis of the methicillin-resistant *Staphylococcus aureus* (MRSA, COL) in the presence of the relevant antibiotic using a published method (Friedman L et al. 2006, Antimicrob. Agents Chemother. 50:2137-2145). Specifically, standard MIC assays (see below) were performed for 24 h at 37° C. on day 1 (generation I) with antibiotics at concentrations as follows: linezolid: 0 μM-29.6 μM; vancomycin: 0 μM-6.7 μM; daptomycin: 0 μM-6.2 μM; platensimycin: 0 μM-22.6 μM, and platencin 0 μM-23.5 μM). The bacteria from cultures with the highest antibiotics concentrations that were still able to support staphylococcal growth were subsequently used as the inoculum (diluted 1:1000 in fresh tryptic soy broth (TSB; details below)) for a subsequent series of incubation at 37° C. under MIC-assay conditions (generation II; passage I) in TSB supplemented again with increasing concentrations of reference compounds. Serially repeated selection procedures were done in this manner until a stable antibiotic-resistant *Staphylococcus aureus* mutant was generated. The levels of resistance were determined by the broth microdilution minimal inhibitory concentration (MIC) Assay (detailed below).

Thus for linezolid 25 passages were needed to obtain a strain resistant to 7.5 μg/ml of linezolid (MIC 7.5 μg/ml for the resistant strain); for vancomycin 25 passages (MIC of 20 μg/ml for the resistant strain); for daptomycin 15 passages (MIC >50 μg/ml for the resistant strain); for platensimycin 2 passages (MIC >10 μg/ml for the resistant strain). Resistant clones were taken from the relevant microtiter plate positions, and streaked out to obtain single colonies on TSB agar. The levels of resistance were then confirmed by a standard MIC procedure (detailed below).

Strains of MRSA (COL) resistant to triclosan or moenomycin were generated on plates of TSB-agar incubated at 37° C. with 4 μg/ml of triclosan or 0.3 μg/ml of moenomycin. This resulted in resistant strains with MIC values of >20 μg/ml for triclosan and of >10 μg/ml for moenomycin. Strains were stored in TSB medium supplemented with 50% glycerol at −80° C.

The bacterial strains *Staphylococcus aureus* MRSA (COL), the antibiotics-resistant MRSA strains (with resistance against linezolid, daptomycin, triclosan, vancomycin, platensimcyin, or moenomycin), *Staphylococcus aureus* MSSA (Newman), *Staphylococcus epidermidis, Bacillus subtilis, Enterococcus faecalis*, and *Enterococcus faecium* were grown and tested in Mueller-Hinton Broth (Becton Dickinson Biosciences; #211443) or tryptic soy broth medium (Becton Dickinson Biosciences; #211822. For testing of daptomycin, the medium was supplemented with 75 mg/L of $CaCl_2 \cdot 2H_2O$. *Streptococcus pneumoniae* was grown in brain-heart broth (Merck, #1.10493) in a 5% $CO_2$ atmosphere. *Mycobacterium smegmatis* was grown in Middlebrook 7H9 broth (Becton Dickinson Biosciences, #271310) in a 5% $CO_2$ atmosphere at 37° C. *E. coli* ΔtolC was grown in in standard nutrient-rich Miller's Luria broth medium (Sigma-Aldrich; L3522).

Human hepatocytes (HepaRG™ cells) were obtained from Life Technologies, and were cultivated in William's E Medium (Gibco, Life Technologies; A12176-01) supplemented with 1× GlutaMAX™ plus 1× HepaRG™ General Purpose Medium Supplement in 25 cm² or 75 cm² flasks (TPP, Trasadingen, Switzerland) at 37° C. at 5% $CO_2$. Human keratinocytes (HaCaT cells; Boukamp P et al., 1988, J Cell Biol 106:761-771) were propagated in Epilife Medium (Gibco, Life Technologies; MEPICF) combined with CaCl2, 1×-growth-supplement containing penicillin and streptomycin (Gibco, Life Technologies). For sub-culturing, cells were split at a ratio of 1:4 to 1:8. For cryopreservation, cells were frozen down in 10% DMSO in liquid nitrogen.

Sources of the commercially available antibiotic substances are: linezolid (Santa Cruz Biotechnology, Inc.; sc-207827), triclosan (Calbiochem; 647950), vancomycin (Sigma-Aldrich®; 861987); moenomycin (Santa Cruz; sc-362031), daptomycin (Sigma-Aldrich®; D2446), and platensimycin (Calbiochem #528244).

Biological Tests

The broth microdilution Minimal Inhibitory Concentration (MIC) Assay was used to determine antibacterial activities of compounds. Compounds used for biological tests were stored at −20° C. as powders. Stock solutions (10-50 mM) of these test compounds were prepared in 100% DMSO (D2438, Sigma-Aldrich (St. Louis, Mo., USA)), and stored at −20° C. Broth microdilution MIC testing was performed according to the protocols listed in NCCLS M7-A6 (National Committee for Clinical Laboratory Standards, NCCLS. 2003: Methods for dilution antimicrobial susceptibility tests for bacteria that grow aerobically. Approved standard, 6th ed. NCCLS document M7-A6, NCCLS, Wayne, Pa., USA) with adaptations as described below. Briefly, eleven two-fold dilutions of the compounds under study in the range from 0 µM to 200 µM (i.e., 0 µM, 0.4 µM, 0.78 µM, 1.56 µM, 3.12 µM, 6.25 µM, 12.5 µM, 25 µM, 50 µM, 100 µM, 200 µM) were prepared as 100× concentrated stocks dissolved in 100% sterile DMSO. Of each, 1 µl was added to a single well of a sterile 96-well microtiter plate (#163320, ThermoScientific) and then filled-up with 100 µl of medium containing approximately $10^5$ bacteria (corresponding to a 1:1000 dilution of a stationary overnight culture in fresh medium). MRSA-COL, MSSA-Newman, S. epidermidis, B. subtilis, E. faecalis, and E. faecium were propagated in TSB broth (all at 37° C.). S. pneumonia was incubated in brain-heart broth a 37° C. with 5% $CO_2$, and E. coli ΔtolC in nutrient-rich Miller's Luria broth. For M. smegmatis, MIC assays were performed in a twofold scaled-up volume in order to account for eventual evaporation of Middlebrook 7H9 broth given the prolonged incubation time of 3 days at 37° C. in a 5% $CO_2$ incubator. In all experiments, the DMSO concentration was kept at 1%. Following rotational incubation at 200 rpm for 24 hours, plates were assayed visually and the optical density (OD600), which measures bacterial cell growth and proliferation, measured via a multimode reader (GloMax® Multi Detection Platform, Promega Corporation, Madison, Wis., USA). Growth was defined as turbidity achieving a minimum OD600 of <0.1; MIC values (in µg/ml) are concentrations preventing bacterial growth 100% (MIC100) unless indicated otherwise.

MIC values thus obtained for reference antibiotics were consistent with the values published by the British Society for Antimicrobial Chemotherapy (as published in BSAC Methods for Antimicrobial Susceptibility Testing (Version 12 May 2013, available at http://bsac.org.uk/wp-content/uploads/2012/02/Version-12 Apr. 2013_final.pdf.) and in the scientific literature.

Combinations of antibacterial compounds were assessed for cooperative interactions in checkerboard broth microdilution setups wherein two-dimensional titration matrices enable the calculation of so-called fractional inhibitory concentration (FIC) indexes, termed FICi (Odds F. C. 2003: Synergy, antagonism, and what the chequerboard puts between them. Journal of Antimicrobial Chemotherapy 52:1; Drago, L. et al. 2007: In vitro evaluation of antibiotics' combinations for empirical therapy of suspected methicillin resistant Staphylococcus aureus severe respiratory infections. BMC Infectious Diseases 7:111). To this end, the wells of a 96-well flat-bottom polystyrene microtiter plate were inoculated with $10^6$ cfu/ml S. aureus strain MRSA-COL in standard tryptic soy broth (TSB) culture medium, and challenged with serially-diluted compounds at concentrations bracketing the pre-determined MIC values. A 90° angle rotated pipetting-scheme was used to provide all possible dose combinations of two compounds under study. Specifically, compounds in the range of 0, 0.78, 1.56, 3.12, 6.25, 12.5, 25, 50, 100, and 200 µM (vertical columns) were examined for possible potentiating effects on horizontal rows of arrayed platensimycin concentrations. Optical density ($OD_{600}$) was then measured within technical replicates after a 24-hour incubation period at 37° C. The FIC was determined for each individual substance by dividing the MIC-value of the compound when used in combination by the MIC when used alone, i.e., $FIC_A=MIC_{A\ in\ combination}/MIC_{A\ alone}$ and $FIC_B=MIC_{B\ in\ combination}/MIC_{B\ alone}$. FICi was then quantified as the sum of the two FIC values for each drug present in the well; that is, $FICi=FIC_A+FIC_B$. Arbitrary thresholds of ≤0.5; >0.5 to ≤1.0; >1 to ≤4, and >4.0 were lastly used to score synergistic, additive (combined effect equal to the sum of the individual components), indifferent (neutral) or antagonistic (adverse interaction) effects within paired compound combinations, respectively.

Human cytotoxicity assays in vitro were done as described in "Guidance Document on Using In Vitro Data to Estimate In Vivo Starting Doses for Acute Toxicity Based on Recommendations" available at www.epa.gov/hpv/pubs/general/nih2001b.pdf. Briefly, human hepatocytes or human keratinocytes (HaCaTs) were seeded into sterile black clear-bottomed polystyrene Corning® CellBind® 96-well plates at a density of 20,000 cells/well after calculating cell numbers from trypsinized samples in a classical Neubauer Improved haemocytometer. The cells were grown for 24 h at 37° C. in a 5% $CO_2$ atmosphere in Epilife medium (keratinocytes) or William's E medium (hepatocytes). After a 24 h recovery period, media were removed from the wells by aspiration. The cells were then immediately exposed to the respective test compounds or reference antibiotics (prepared in advance in 100 µl of the same media) for 24 h 37° C. with 5% $CO_2$. The concentration range tested extended from 0.1 µM to 100 µM (0.1 µM, 1 µM, 5 µM, 10 µM, 25 µM, 50 µM, 75 µM, 100 µM) and was formulated as a 100× concentrated stock each, resulting in a final constant DMSO concentration of 1% per 100 µl sample volume. Test series were performed in triplicates each, and additionally included a vehicle reference (DMSO only) plus a further internal control for evaluating overall assay performance. Also, cells were visually examined under a light microscope for any morphological abnormalities relative to the untreated cells. Subsequently, cell viability as indicator of potential cytotoxicity was measured by applying the CellTiter-Glo® luminescent cell proliferation assay (G755A, Promega, Madison, Wis., USA). This method permits the determination of the number of viable cells in culture based on quantitation of the ATP present, which denotes the presence of metabolically active cells (Crouch, S. P. et al. 1993, J. Immunol. Methods 160, 81-8). To this end, 100 µl (equal to the volume of culture medium) of the kit-provided CellTiter-Glo® reagent (reconstituted by transferring the thawed CellTiter-Glo® buffer to the lyophilized enzyme and substrate mixture) was directly added to each well with a repetitive dispensing pipette. Contents were then mixed for 2 min at room temperature on an orbital minishaker (IKA® MS3 digital) at 450 rpm to induce efficient cell lysis, and then further incubated for 10 min at room temperature for stabilization of the resultant luminescent signal. Luminescence was recorded using a compatible multimode reader (GloMax® Multi Detection Platform, Promega Corporation, Madison, Wis., USA) with its embedded, preset CellTiter-Glo® parameters (integration time of 0.5 sec). Output values were expressed as percent cell viability compared to vehicle (DMSO) control, and EC50 values calculated from the dose-response curves via nonlinear regression (Graphpad Prism Software Inc., La Jolla, Calif., USA).

Biological Results

Example A

Representative compounds of the present invention, their synthetic routes and analytical characterizations are listed in Table AA. These compounds were tested for antibacterial activity against *Streptococcus pneumoniae, Staphylococcus aureus* MSSA (Newman) and *Staphylococcus aureus* MRSA (COL) according to the MIC procedure described in Biological Tests. The results are also listed in Table AA. With respect to streptococci (e.g. *Streptococcus pneumonia*), "4" indicates that the compound has an MIC of 1 µg/ml or less for preventing streptococcal growth 100% (MIC100). With respect to staphylococci (e.g. *Staphylococcus aureus* MSSA (Newman) and *Staphylococcus aureus* MRSA (COL)), "4" indicates that the compound has an MIC of ≥1 µg/ml to 3 µg/ml for preventing staphylococcal growth 100% (MIC100). For streptococci, the notation "3" indicates that the compound has an MIC100 of 2-5 µg/ml, whilst for staphylococci the notation "3" indicates that the compound has an MIC100 of 3-10 µg/ml. For streptococci, the notation "2" indicates that the compound has an MIC100 of 6-10 µg/ml, whilst for staphylococci the notation "2" indicates that the compound has an MIC100 of 11-201 µg/ml. For streptococci, the notation "1" indicates that the compound has an MIC100 of 11-201 µg/ml or an MIC50 of <10 µg/ml, whilst for staphylococci the notation "1" indicates that the compound has an MIC100 of 20-50 µg/ml or an MIC50 of <10 µg/ml. The compounds show activity against *Streptococcus pneumoniae* or *Staphylococcus aureus*, or both. "Inactive" means that no antibacterial activities were observed at a concentration of 200 µg/ml.

Example B

Compounds represented in Table AA were tested for cytotoxicity in vitro against human hepatocytes and human keratinocytes according to the cytotoxicity assay described in Biological Tests. A hepatocyte cytotoxicity score of 4 was assigned to compounds inhibiting cell viability 50% or more at concentrations of 10 µM or less. The hepatocyte cytotoxicity score of 3 was assigned to compounds causing at least 80% inhibition of viability at 25 µM, of 2 to compounds showing toxicity at 25 µM, but causing less than 20% inhibition of viability, of 1 to compounds not causing a loss of viability at concentrations between 25 and 50 µM, and of 0 to compounds without signs of cell viability loss at concentrations of 50 µM or higher. A keratinocyte cytotoxicity score of 4 was assigned to compounds inhibiting cell viability 50% or more at concentrations of 5 µM or less. The keratinocytes cytotoxicity score 3 was used for compounds causing more than 50% inhibition of cell viability at 10 µM; 2 for compounds causing >50% inhibition of cell viability at 25 µM; 1 for compounds causing less than 50% inhibition of cell viability at 50 µM, and 0 for compounds not causing loss of cell viability at concentrations of 50 µM or higher. Compounds with cytotoxicity scores of less than 4 in either keratinocytes or hepatocytes, or both, are preferred, and were tested against a panel of bacteria, including bacterial strains with resistance to antibiotics obtained as described in Biological Materials. Results are shown in Table BB. With respect to streptococci, "4" indicates that the compound has an MIC of 1 µg/ml or less for preventing streptococcal growth 100% (MIC100). With respect to the other bacteria, "4" indicates that the compound has an MIC of ≥1 µg/ml to 3 µg/ml for preventing bacterial growth 100% (MIC100). For streptococci, the notation "3" indicates that the compound has an MIC100 of 2-5 µg/ml, whilst for the other bacteria the notation "3" indicates that the compound has an MIC100 of 3-10 µg/ml. For streptococci, the notation "2" indicates that the compound has an MIC100 of 6-10 µg/ml, whilst for the other bacteria the notation "2" indicates that the compound has an MIC100 of 11-201 µg/ml. For streptococci, the notation "1" indicates that the compound has an MIC100 of 11-201 µg/ml or an MIC50 of <10 µg/ml, whilst for other the bacteria the notation "1" indicates that the compound has an MIC100 of 20-50 µg/ml or an MIC50 of <10 µg/ml.

In Table BB, when in a cell of the table a label of a particular bacterial species, e.g. MSSA as the label for multi-drug resistant *Staphylococcus aureus* MSSA, does not fit onto one line of the cell, and thus the letters MSSA are divided over two or more lines of the cell, the letters on one line of a given cell are not to be read in isolation but instead in combination with the letters on the remaining lines of the cell. A cell thus displaying "MS" on one line and "SA" on a second line of the same cell of the table is to be understood to refer to a single bacterial species, in this case "MSSA", and is in no way related to, for example, the bacteria labeled simply "MS", i.e. *Mycobacterium smegmatis*.

In one aspect, the invention thus provides a method for inhibiting the growth of microorganisms, preferably bacteria, comprising contacting said organisms with a compound of the invention, preferably a compound represented in Table BB, under conditions permitting entry of the compound into said microorganism. This method involves contacting a microbial cell with a therapeutically-effective amount of compound(s) of the invention, preferably of compounds represented in Table BB, in vivo or in vitro.

In some embodiments, the invention provides a method for treating an infection, especially infections caused by gram-positive bacteria, in a subject with a therapeutically-effective amount of a compound of the invention.

In a preferred embodiment, the bacterial infection is caused by gram-positive bacteria, e.g. selected from staphylococci, streptococci, enterococci, bacilli, and mycobacteria.

In a preferred embodiment, the bacterial infection is caused by gram-positive bacteria resistant against beta-lactam antibiotics such as methicillin. In another preferred embodiment the bacterial infection is caused by gram-positive bacteria resistant against other or additional antibiotics such as daptomycin, vancomycin, linezolid, triclosan, moenomycin or platensimycin. In a preferred embodiment the infection is caused by staphylococci or streptococci resistant to beta-lactam antibiotics. In another preferred embodiment the infection is caused by multi-drug resistant bacteria, such as staphylococci resistant to beta-lactam antibiotics and at least one other antibiotic substance, e.g. selected from daptomycin, vancomycin, linezolid, triclosan, moenomycin or platensimycin. In a further preferred embodiment the infection is caused by enterococci resistant to vancomycin. In another preferred embodiment the infection is caused by multi-drug resistant streptococci, such as streptococci resistant against penicillins and erythromycin and/or tetracyclines.

In a further aspect the present invention provides a compound for use in the preparation of a medicament for the treatment of microbial diseases, for example of diseases caused by bacteria, e.g. selected from staphylococci, streptococci, enterococci, bacilli, and mycobacteria. In a further aspect the present invention provides a compound for use in the preparation of a medicament for the treatment of diseases caused by bacteria resistant to antibiotics, such as beta-lactam antibiotics, daptomycin, vancomycin, linezolid, triclosan, moenomycin or platensimycin, or resistant against beta-lactam antibiotics, erythromycin or tetracyclines, and in addition to daptomycin, vancomycin, linezolid, triclosan, moenomycin or platensimycin.

The compounds of the invention may thus be used as antibiotics. The invention also provides a method for the treatment of additional diseases or conditions in which microbes play a role, for example in treatments of infections in immune-compromised hosts, including for example subjects infected with HIV or having AIDS, said method comprising a step of administering to a subject in need thereof an effective amount of a compound of the invention, said subject being a mammal, in particular a human.

The invention thus also provides a method for the treatment of microbial infection, said method comprising a step of administering to a subject in need thereof an effective amount of a compound of the invention, said subject being a mammal, in particular a human.

The present invention provides a method of treating or preventing a bacterial infection in a subject, or a disorder related to a bacterial infection in a subject, comprising the step of administering a therapeutically-effective amount of a pharmaceutical composition comprising a compound of the invention to a subject in need thereof. The subject is preferably selected from the group consisting of a human, an animal, a cell culture, and a plant, more preferably from the group consisting of a human and an animal, and is most preferably a human. The bacterial infection may be caused by a Gram-positive bacterial species. The bacterial species may be a bacterial species which exhibits resistance to antibiotics. In some embodiments, the bacterial species is selected from the group consisting of Streptococci, Staphylococci, Bacilli, Enterococci and Mycobacteria. In such cases, Streptococci may be *Streptococcus pneumonia*, Staphylococci may be *Staphylococcus aureus*, Staphylococci may be methicillin-resistant *Staphylococcus aureus*, Staphylococci may be *Staphylococcus epidermidis*, Bacilli may be *Bacillus subtilis*, Enterococci may be *Enterococcus faecium*, Enterococci may be *Enterococcus faecalis*, and Mycobacteria may be *Mycobacterium smegmatis*. In some embodiments, the compounds of the invention are used in the treatment of microbial infections caused by one or more of these organisms. Bacterial species which exhibit resistance to antibiotics may include, for example, daptomycin-resistant *Staphylococcus aureus*, daptomycin-resistant *Enterococcus faecium*, daptomycin-resistant *Enterococcus faecalis*, and methicillin-resistant *Staphylococcus aureus*. Antibiotics to which the bacterial species may exhibit resistance include, for example, vancomycin, methicillin, glycopeptide antibiotics, penicillin, and daptomycin. In some embodiments, the bacterial infection or disorder related to a bacterial infection may involve a mixture of bacterial species, optionally a mixture of bacterial species comprising at least one bacterial species which exhibits resistant to antibiotics, said species optionally being at least one of the antibiotic-resistant species listed hereinabove and/or optionally exhibiting resistance to one of the antibiotics listed hereinabove. The bacterial species may be an antibiotic-resistant Gram-positive bacterial species, including, for example, multidrug-resistant streptococci, multidrug-resistant staphylococci, or multidrug-resistant enterococci, or a mixture of bacterial species comprising at least one of these antibiotic-resistant bacterial species.

In the present invention, the antibiotic-resistant bacteria against which the compounds of the invention show activity do not exhibit resistance to the compounds and/or compositions of the invention.

As used throughout herein, the term "microbial" is to be understood to preferably mean "bacterial". Accordingly, as used throughout herein, the term "antimicrobial" is to be understood to preferably mean "antibacterial", and the term "microbial infection" is to be understood to preferably mean "bacterial infection". "Infections" described throughout herein are preferably "bacterial infections".

The methods of the invention may further comprise the step of co-administering more than one compound of the invention to a subject in need thereof. This may be performed in one single dosage form or in separate dosage forms for simultaneous, separate or sequential use in the prevention or treatment of bacterial infections. The methods of the invention my further comprise the step of co-administering an antimicrobial agent other than a compound of the invention to a subject in need thereof. This may be performed in one single dosage form or in separate dosage forms for simultaneous, separate or sequential use in the prevention or treatment of bacterial infections.

A further aspect of the invention thus relates to methods for preventing, inhibiting, or stopping the growth of bacteria on such surfaces involving the step of applying at least one compound of the invention directly or indirectly and in either pure form or in an alternative form, such as those disclosed herein, to said surface. Compounds of the invention may thus be formulated as an antiseptic, disinfectant or antimicrobial agent and used, for example, in one or more of the methods disclosed herein.

In some embodiments, a compound of the invention is provided for use in the treatment of microbial infection and/or a disorder, affliction or illness caused at least in part by microbial infection, in particular where said microbial infection is a bacterial infection and especially a bacterial infection caused at least in part by one or more Gram-positive bacterial species, especially wherein said one or more Gram-positive bacterial species include Gram-positive bacterial species resistant to existing antibiotics, including in particular multidrug-resistant streptococci, multidrug-resistant staphylococci, or multidrug-resistant enterococci. Said microbial or bacterial infections may include mixed infections involving both Gram-positive bacterial species resistant to and Gram-positive bacterial species sensitive to existing antibiotics and/or a mixture of bacterial species comprising at least one bacterial species which exhibits resistance to existing antibiotics. In some of these embodiments, said existing antibiotics are preferably selected from one or more members of the group of antibiotics consisting of cephalosporins, quinolones, macrolides, vancomycin, daptomycin, linezolid, moenomycin, platensimycin, and beta-lactam antibiotics including penicillins.

The terms "existing antibiotics" and "existing therapies" may be understood to refer to agents and therapies which were known in the art on 4 Dec. 2014 to have antibiotic activity and/or to be applicable to/used in the treatment of microbial infection and/or a disorder, affliction or illness caused at least in part by microbial infection, in particular where said microbial infection is a bacterial infection and especially a bacterial infection caused at least in part by one or more Gram-positive bacterial species. They may be understood to refer in particular to antibiotic agents or therapies which had been authorized and/or marketed in a country or region at or before that time or which were known in the art at that time to be in clinical development, pre-clinical development or pre-clinical research. Antibiotics may be understood to constitute a therapy for microbial infections, disorders, afflictions and illnesses in this sense. Antibiotic activity in this sense may be understood to be as defined elsewhere herein.

It has surprisingly also been found that the compounds of the invention are also effective in and thus may find use in preventing, inhibiting, or stopping the growth of bacteria on surfaces. Such surfaces may constitute hard surfaces such as, for example, floors, worktops, bathroom surfaces, glass surfaces, crockery, cutlery, pots, pans, devices such as household devices or medical devices including contact lenses, or soft surfaces, such as, for example, skin, hair, clothing, contact lenses and the like. The compounds of the invention may thus be formulated and used as antiseptics, disinfectants, etc and/or used as components, additives or preservatives for medical/surgical devices, disinfectants, soaps, shampoos, hand washes, denitrifiers, household cleaning formulations, detergents for laundry and dishes, in wash and treatment solutions for topical use, instruments and devices including contact lenses, and in other disinfecting and antibacterial applications.

A further embodiment of the invention thus relates to the use of the compounds of the invention in preventing, inhibiting, or stopping the growth of bacteria on surfaces, said surfaces including both hard surfaces such as floors, worktops, bathroom surfaces, glass surfaces, crockery, cutlery, pots, pans, surfaces of devices such as household devices or medical devices including contact lenses, and soft surfaces such as skin, hair, clothing, contact lenses and the like.

In one embodiment (E1), the present invention relates to a compound comprising or consisting of the structural moiety of formula (I) or a pharmaceutically-acceptable salt of said compound, for use as a medicament

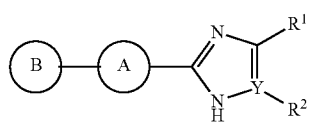

(I)

wherein
(i) Y is C or N;
(ii) $R^1$ and $R^2$ are independently selected from the group consisting of:
H, —$CH_3$, $C_{2 to 6}$alkyl, $C_{3 to 6}$cycloalkyl, halogen, —$(CH_2)_n$N$(CH_3)_2$ where n is an integer from 1 to 3, benzyl optionally substituted on the phenyl ring, heteroaryl, and aryl,
with the proviso that at least one of $R^1$ or $R^2$ possesses 3 or more carbon atoms;
or
$R^1$ and $R^2$ are connected to form a four-, five- or six-membered non-aromatic carbocyclic ring thus providing a fused bicyclic moiety in which one or more of the carbon atoms of the ring comprising groups $R^1$ and $R^2$ is optionally replaced by a heteroatom selected from O, N, or S, and where one or more of the atoms of the ring comprising groups $R^1$ and $R^2$ is optionally substituted with one or more substituents independently selected from the group consisting of —$CH_3$, $C_{2 to 4}$alkyl, halogen, hydroxyl, —$OCH_3$, —$OC_{2 to 4}$alkyl, ethynyl, —$OCF_3$, and —$CF_3$;
with the proviso for all of the above-mentioned alternatives that when:
Y is N, $R^2$ represents a lone pair of electrons belonging to the N atom; and
(iii) A is aryl or heteroaryl; and
(iv) B is aryl, heteroaryl, a bicyclic system comprising at least one aromatic ring, or styryl.

A further embodiment (E2) relates to a compound for use as in embodiment (E1), wherein A is 5-membered heteroaryl.

A further embodiment (E3) relates to compound for use as in either of embodiments (E1) or (E2), wherein A is selected from the group consisting of

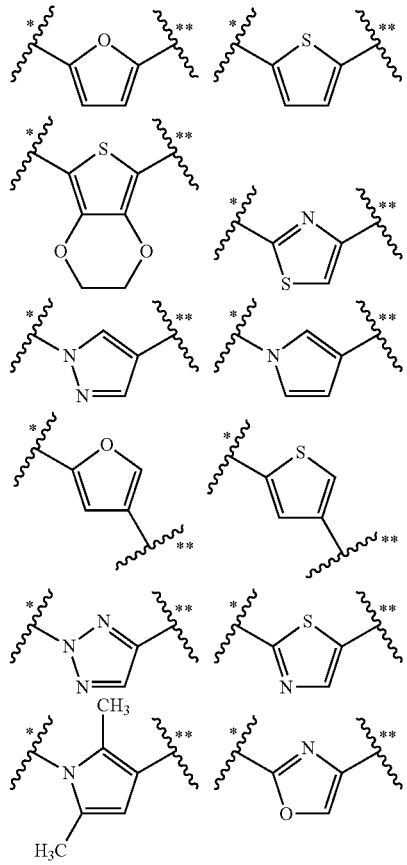

where * is the point of connection to the correspondingly-labeled atom of B and ** is the point of connection to the correspondingly-labeled atom of

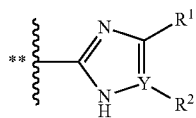

and wherein the aromatic ring of A is optionally substituted; and/or wherein B is selected from the group consisting of

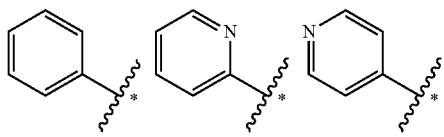

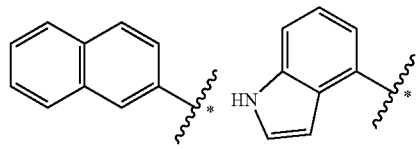

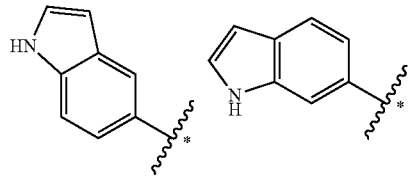

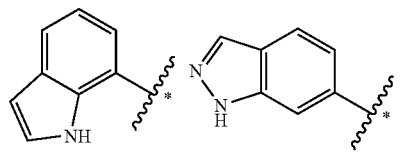

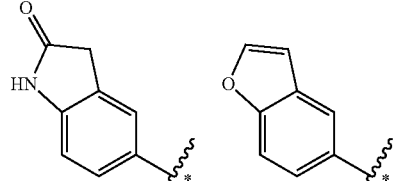

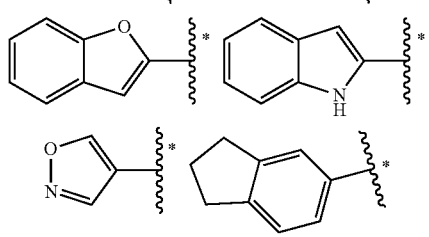

where * is the point of connection to the correspondingly-labeled atom of A; and wherein B is optionally substituted.

A further embodiment (E4) relates to a compound for use according to any of embodiments (E1) to (E3), wherein group A is selected from the formulae

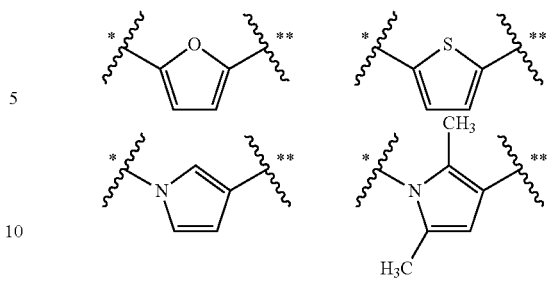

and is preferably

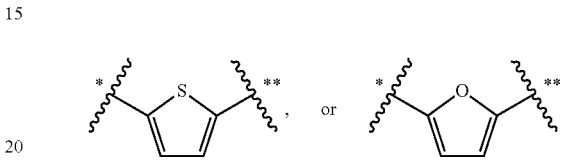

wherein * and ** are as defined above.

A further embodiment (E5) relates to a compound for use according to any of embodiments (E1) to (E4), wherein the aromatic ring of A is substituted by one or more substituents independently selected from —$CH_3$, $C_{2to4}$alkyl, halogen, —$OCH_3$, and —$OC_{2to4}$ alkyl, preferably substituted by one or more substituents independently selected from —$CH_3$, $C_{2to4}$alkyl, and halogen, most preferably by one or more —$CH_3$ substituents.

A further embodiment (E6) relates to a compound for use according to any of embodiments (E1) to (E5), wherein B is an unsubstituted phenyl ring or a substituted phenyl ring.

A further embodiment (E7) relates to a compound for use according to any of embodiments (E1) to (E6), wherein B is a phenyl ring optionally substituted with one or more substituents independently selected from the group consisting of —$CH_3$, $C_{2to4}$alkyl, halogen, hydroxyl, —$OCH_3$, —$OC_{2to4}$alkyl, —$CF_3$, —$OCF_3$, —$NH_2$, —$CH_2NH_2$, —$N(CH_3)_2$, —$NO_2$, —$CH_2OH$, —$CO_2CH_3$, —$CO_2C_{2to4}$alkyl, —$CO_2H$, —$N(alkyl)_2$ where the two alkyl groups are independently selected from —$CH_3$ or $C_{2to4}$alkyl, —NH(alkyl) where the alkyl group is selected from —$CH_3$ or $C_{2to4}$alkyl, 4-morpholinyl, 1-piperidinyl, 4H-piperazinyl, 4-$C_{1to4}$alkyl-piperazinyl, and 4-$C_{3to6}$cycloalkyl-piperazinyl, preferably independently selected from the group consisting of H, —$CH_3$, $C_{2to4}$alkyl, iso-propyl, tert-butyl, halogen wherein halogen is preferably F or Cl or Br, hydroxyl, —$OCH_3$, —$CF_3$, —$OCF_3$, —$N(CH_3)_2$, —$NO_2$, and 4-methylpiperazinyl, more preferably independently selected from the group consisting of H, —$CH_3$, —$CH_2CH_3$, iso-propyl, —$N(CH_3)_2$, halogen wherein halogen is preferably F or Cl or Br, —$OCH_3$, —$CF_3$, and —$OCF_3$.

A further embodiment (E8) relates to a compound for use according to any of embodiments (E1) to (E5), wherein B is a ring other than an unsubstituted or substituted phenyl ring and B is substituted or unsubstituted.

A further embodiment (E9) relates to a compound for use according to any of embodiments (E1) to (E5) or (E8), wherein B is a ring other than an unsubstituted or substituted phenyl ring and is optionally substituted with one or more substituents independently selected from the group consisting of —$CH_3$, $C_{2to4}$alkyl, halogen wherein halogen is preferably F or Cl or Br, hydroxyl, —$OCH_3$, —$OC_{2to4}$alkyl, —$CF_3$, —$OCF_3$, —$CO_2CH_3$, —$CO_2C_{2to4}$alkyl, and —CO$_2$H, more preferably selected from the group consisting of —CH$_3$, —CF$_3$, —OCF$_3$ and halogen, wherein halogen is preferably F or Cl or Br.

A further embodiment (E10) relates to a compound for use according to any of embodiments (E1) to (E9), wherein one of R$^1$ or R$^2$ is substituted or unsubstituted phenyl.

A further embodiment (E11) relates to a compound for use according to any of embodiments (E1) to (E10), wherein one of R$^1$ or R$^2$ is phenyl substituted with one or more substituents independently selected from the group consisting of —CH$_3$, C$_{2to4}$alkyl, halogen, hydroxyl, —OCH$_3$, —OC$_{2to4}$alkyl, ethynyl, —OCF$_3$, and —CF$_3$, more preferably with one or more substituents independently selected from the group consisting of —CH$_3$, —CH$_2$CH$_3$, —OH, —CF$_3$, —OCF$_3$, ethynyl, and halogen, wherein halogen is preferably F or Cl or Br, most preferably with one or more substituents independently selected from the group consisting of —CH$_3$, —CH$_2$CH$_3$, —CF$_3$, —OCF$_3$, ethynyl, and halogen, wherein halogen is preferably F or Cl or Br.

A further embodiment (E12) relates to a compound for use according to any of embodiments (E1) to (E11), wherein one of R$^1$ or R$^2$ is H, or halogen in particular where halogen is chlorine, or most preferably —CH$_3$.

A further embodiment (E13) relates to a compound for use according to any of embodiments (E1) to (E12), wherein Y is C.

A further embodiment (E14) relates to a compound as defined in any of embodiments (E1) to (E13) for use in the treatment of microbial infection and/or a disorder, affliction or illness caused at least in part by microbial infection, in particular where said microbial infection is a bacterial infection and especially a bacterial infection caused at least in part by one or more Gram-positive bacterial species, especially wherein said one or more Gram-positive bacterial species include Gram-positive bacterial species resistant to existing antibiotics, including in particular multidrug-resistant streptococci, multidrug-resistant staphylococci, or multidrug-resistant enterococci, wherein said microbial infections may include mixed infections involving both Gram-positive bacterial species resistant to and Gram-positive bacterial species sensitive to existing antibiotics and/or a mixture of bacterial species comprising at least one bacterial species which exhibits resistance to existing therapies; and wherein said existing antibiotics are preferably selected from one or more members of the group of antibiotics consisting of cephalosporins, quinolones, macrolides, vancomycin, daptomycin, linezolid, moenomycin, platensimycin, and beta-lactam antibiotics including penicillins.

A further embodiment (E15) relates to a compound as defined in any of embodiments (E1) to (E14) for use as an antibiotic in the treatment of bacterial infection and/or a disorder, affliction or illness caused at least in part by bacterial infection, said bacterial infection being preferably selected from one or more infections and infectious diseases from the list of including respiratory tract infections, complicated skin and soft tissue infections, complicated intra-abdominal infections, community acquired pneumonia, hospital-acquired pneumonia, ventilator-associated pneumonia, urinary tract infections, bacterial meningitis, infective endocarditis, sepsis, osteomyelitis, septic arthritis, septicemia, anthrax, osteomyelitis, tuberculosis, leprosy, necrotizing fasciitis, scarlet fever, rheumatic fever, postpartum fever, and streptococcal toxic shock syndrome, and additional nosocomial infections, for example infections caused from the use of intravascular catheters.

A further embodiment (E16) relates to a pharmaceutical composition comprising the compound according to any one of embodiments (E1) to (E15) and a pharmaceutically acceptable carrier.

TABLE AA

Compounds of the invention, synthesis, characterization, and antibacterial properties

| Compound Number | Structure | Synthetic route (yield) | NMR | LC/MS | Antibacterial activity | | |
|---|---|---|---|---|---|---|---|
| | | | | | Streptococcus pneumoniae | Staphylococcus aureus (MSSA) | Staphylococcus aureus (MRSA) |
| 63 | 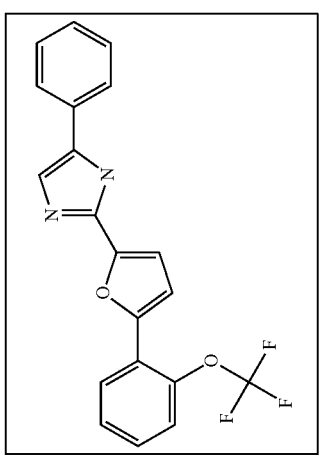 | A (53%) | | Procedure 1, RT = 2.91 min. Purity 97%. Electrospray positive ion mode: m/z 371 (M + H)+. | 3 | 3 | 3 |
| 75 | 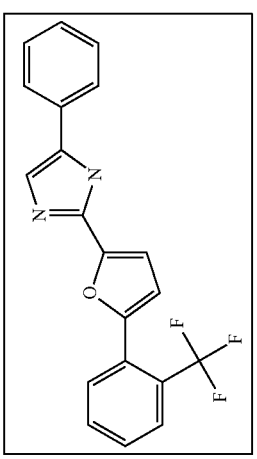 | A (34%) | | Procedure 1, RT = 2.79 min. Purity 95%; Electrospray positive ion mode: m/z 355 (M + H)+. | 3 | 2 | |

TABLE AA-continued

Compounds of the invention, synthesis, characterization, and antibacterial properties

| Compound Number | Structure | Synthetic route (yield) | Analytics | | Antibacterial activity | | |
|---|---|---|---|---|---|---|---|
| | | | NMR | LC/MS | Streptococcus pneumoniae | Staphylococcus aureus (MSSA) | Staphylococcus aureus (MRSA) |
| 18 | 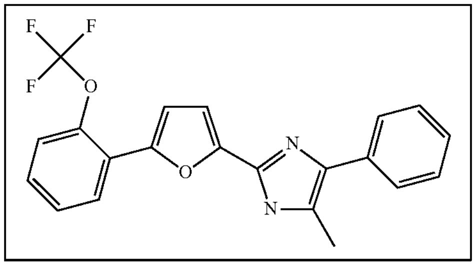 [SMILES: Cc1[nH]c(-c2ccc(-c3ccccc3OC(F)(F)F)o2)nc1-c1ccccc1] | A (66%) | $^1$H NMR (400 MHz, DMSO-d$_6$): δ 2.51 (3H, s, CH$_3$), 6.99 (1H, d, J = 3.2 Hz, furan), 7.03 (1H, d, J = 3.2 Hz, furan), 7.28 (1H, m, OCF$_3$-phenyl), 7.45 (5H, m, phenyl), 7.70 (2H, m, OCF$_3$-phenyl), 8.22 (1H, d, J = 6.8 Hz, OCF$_3$-phenyl) | Procedure 1, RT = 3.06 min. Purity 92%. Electrospray positive ion mode: m/z 385 (M + H)+. | 3 | 4 | 3 |
| 17 | 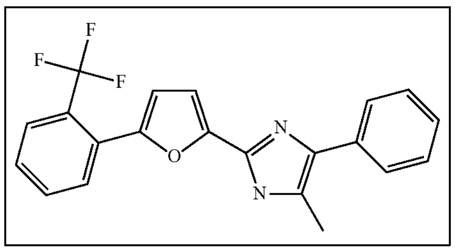 [SMILES: Cc1[nH]c(-c2ccc(-c3ccccc3C(F)(F)F)o2)nc1-c1ccccc1] | A (59%) | $^1$H NMR (400 MHz, acetone-d$_6$): δ 2.52 (3H, s, CH$_3$), 6.91 (1H, d, J = 3.2 Hz, furan), 7.01 (1H, d, J = 3.2 Hz, furan), 7.26 (1H, m, CF$_3$-phenyl), 7.42 (2H, m, phenyl), 7.60 (1H, m, CF$_3$-phenyl), 7.77 (3H, m, phenyl), 7.87 (1H, d, J = 8.0 Hz, CF$_3$-phenyl), 7.98 (1H, d, J = 8.0 Hz, CF$_3$-phenyl) | Procedure 1, RT = 2.91 min. Purity 99%. Electrospray positive ion mode: m/z 369 (M + H)+. | 3 | 3 | 4 |
| 70 | 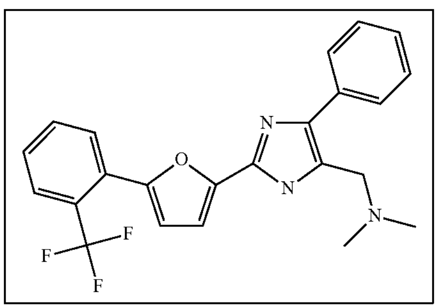 [SMILES: CN(C)Cc1[nH]c(-c2ccc(-c3ccccc3C(F)(F)F)o2)nc1-c1ccccc1] | Method A followed by introduction of the CH$_2$N(CH$_3$)$_2$ group as described in Examples section (70%) | $^1$H NMR (400 MHz, DMSO-d$_6$): δ 2.27 (6H, s, 2 × CH$_3$), 3.60 (2H, s, CH$_2$), 6.92 (1H, d, J = 3.6 Hz, furan), 7.06 (1H, d, J = 3.6 Hz, furan), 7.28 (1H, m, phenyl), 7.41 (2H, m, phenyl), 7.60 (1H, m, CF$_3$-phenyl), 7.77 (1H, m, CF$_3$-phenyl), 7.87 (2H, m, phenyl), 7.91 (1H, d, J = 8.0 Hz, CF$_3$-phenyl), 7.99 (1H, d, J = 8.0 Hz, CF$_3$-phenyl) | Procedure 1, RT = 2.80 min. Purity 97%. Electrospray positive ion mode: m/z 412 (M + H)+. | 3 | 1 | 1 |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | Streptococcus pneumoniae | Staphylococcus aureus (MSSA) | Staphylococcus aureus (MRSA) |
| 76 | 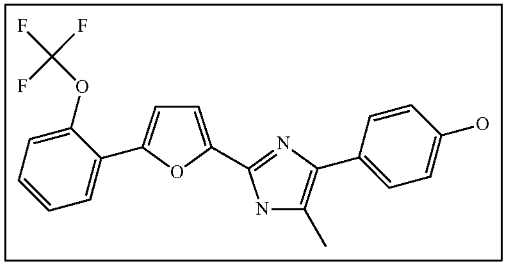 [SMILES: Cc1[nH]c(-c2ccc(-c3ccccc3OC(F)(F)F)o2)nc1-c1ccc(O)cc1] | A (69%) | | Procedure 1, RT = 2.15 min. Purity 100%. Electrospray positive ion mode: m/z 401 (M + H)+. | 3 | 3 | 4 |
| 77 | 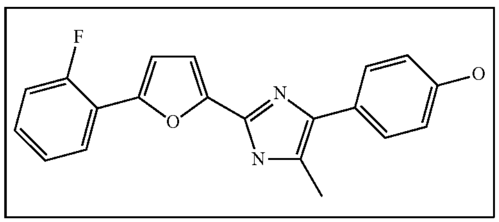 [SMILES: Cc1[nH]c(-c2ccc(-c3ccccc3F)o2)nc1-c1ccc(O)cc1] | A (63%) | | Procedure 1, RT = 2.08 min. Purity 96%. Electrospray positive ion mode: m/z 335 (M + H)+. | 3 | 3 | 3 |
| 78 | 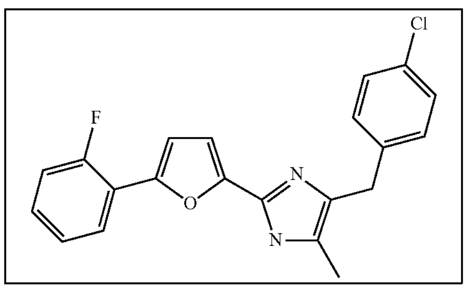 [SMILES: Cc1[nH]c(-c2ccc(-c3ccccc3F)o2)nc1Cc1ccc(Cl)cc1] | B (68%) | | Procedure 1, RT = 2.12 min. Purity 92%. Electrospray positive ion mode: m/z 349 (M + H)+. | 1 | | |

TABLE AA-continued

Compounds of the invention, synthesis, characterization, and antibacterial properties

| Compound Number | Structure | Synthetic route (yield) | Analytics | | Antibacterial activity | | |
|---|---|---|---|---|---|---|---|
| | | | NMR | LC/MS | Streptococcus pneumoniae | Staphylococcus aureus (MSSA) | Staphylococcus aureus (MRSA) |
| 23 | [structure: 4-fluorophenyl-methylimidazole-furan-2-(trifluoromethoxy)phenyl] | A (70%) | $^1$H NMR (400 MHz, DMSO-d$_6$): δ 2.49 (3H, s, CH$_3$), 6.98 (1H, d, J = 3.2 Hz, furan), 7.02 (1H, d, J = 3.2 Hz, furan), 7.27 (2H, m, OCF$_3$-phenyl), 7.50 (2H, m, OCF$_3$-phenyl), 7.58 (1H, m, OCF$_3$-phenyl), 7.73 (2H, m, F-phenyl), 8.21 (1H, d, J = 8.0 Hz, OCF$_3$-phenyl) | Procedure 1, RT = 3.04 min. Purity 98%. Electrospray positive ion mode: m/z 403 (M + H)+. | 4 | 3 | 4 |
| 38 | [structure: 4-fluorophenyl-methylimidazole-furan-3-(trifluoromethyl)phenyl] | A (59%) | $^1$H NMR (400 MHz, DMSO-d$_6$): δ 2.51 (3H, s, CH$_3$), 6.99 (1H, d, J = 3.6 Hz, furan), 7.25 (2H, m, F-phenyl), 7.28 (1H, d, J = 3.6 Hz, furan), 7.67 (2H, m, CF$_3$-phenyl), 7.71 (2H, m, F-phenyl), 8.17 (2H, m, CF$_3$-phenyl) | Procedure 1, RT = 3.02 min. Purity 98%. Electrospray positive ion mode: m/z 387 (M + H)+. | 3 | 4 | 4 |
| 24 | [structure: 4-chlorophenyl-methylimidazole-furan-2-(trifluoromethoxy)phenyl] | A (71%) | $^1$H NMR (400 MHz, DMSO-d$_6$): δ 2.51 (3H, s, CH$_3$), 6.98 (1H, d, J = 3.6 Hz, furan), 7.03 (1H, d, J = 3.6 Hz, furan), 7.49 (2H, m, OCF$_3$-phenyl), 7.50 (2H, d, J = 8.4 Hz, Cl-phenyl), 7.57 (1H, m, OCF$_3$-phenyl), 7.74 (2H, d, J = 8.4 Hz, Cl-phenyl), 8.20 (1H, d, J = 7.6 Hz, OCF$_3$-phenyl) | Procedure 1, RT = 3.11 min. Purity 96%. Electrospray positive ion mode: m/z 419 (M + H)+. | 4 | 3 | 3 |

TABLE AA-continued

Compounds of the invention, synthesis, characterization, and antibacterial properties

| Compound Number | Structure | Synthetic route (yield) | Analytics NMR | LC/MS | Antibacterial activity Streptococcus pneumoniae | Staphylococcus aureus (MSSA) | Staphylococcus aureus (MRSA) |
|---|---|---|---|---|---|---|---|
| 29 | 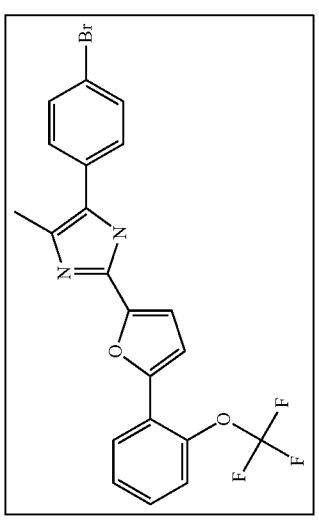 | A (67%) | | Procedure 1, RT = 3.20 min. Purity 95%. Electrospray positive ion mode: m/z 463, 465 (M + H)+. | 3 | 3 | 2 |
| 25 | 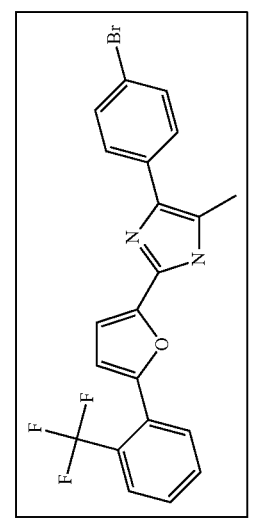 | A (59%) | $^1$H NMR (400 MHz, DMSO-d$_6$): δ 2.48 (3H, s, CH$_3$), 6.92 (1H, d, J = 3.6 Hz, furan), 7.00 (1H, d, J = 3.6 Hz, furan), 7.59 (2H, d, J = 8.4 Hz, Br-phenyl), 7.65 (1H, m, CF$_3$-phenyl), 7.68 (2H, d, J = 8.4 Hz, Br-phenyl), 7.82 (1H, m, CF$_3$-phenyl), 7.89 (1H, d, J = 7.6 Hz, CF$_3$-phenyl), 8.01 (1H, d, J = 8.0 Hz, CF$_3$-phenyl) | Procedure 1, RT = 3.06 min. Purity 98%. Electrospray positive ion mode: m/z 447, 449 (M + H)+. | 3 | | |
| 28 | 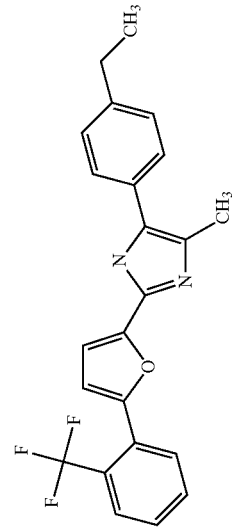 | A (70%) | | Procedure 1, RT = 3.33 min. Purity 92%. Electrospray positive ion mode: m/z 397 (M + H)+. | 3 | 1 | 1 |

TABLE AA-continued

Compounds of the invention, synthesis, characterization, and antibacterial properties

| Compound Number | Structure | Synthetic route (yield) | Analytics | | Antibacterial activity | | |
|---|---|---|---|---|---|---|---|
| | | | NMR | LC/MS | Streptococcus pneumoniae | Staphylococcus aureus (MSSA) | Staphylococcus aureus (MRSA) |
| 26 | [structure: 4-methyl-5-(4-trifluoromethylphenyl)-2-[5-(2-trifluoromethoxyphenyl)furan-2-yl]imidazole] | A (49%) | ¹H NMR (400 MHz, DMSO-d₆): δ 2.55 (3H, s, CH₃), 7.04 (1H, d, J = 3.6 Hz, furan), 7.24 (1H, d, J = 3.6 Hz, furan), 7.51 (2H, m, OCF₃-phenyl), 7.58 (1H, d, J = 7.2 Hz, OCF₃-phenyl), 7.84 (2H, d, J = 8.0 Hz, CF₃-phenyl), 7.94 (2H, d, J = 8.0 Hz, CF₃-phenyl), 8.21 (1H, d, J = 7.2 Hz, OCF₃-phenyl) | Procedure 1, RT = 3.14 min. Purity 95%. Electrospray positive ion mode: m/z 453 (M + H)+. | 3 | | |
| 30 | [structure: 4-(4-bromobenzyl)-5-methyl-2-[5-(2-trifluoromethoxyphenyl)furan-2-yl]imidazole] | B (53%) | ¹H NMR (400 MHz, DMSO-d₆): δ 2.45 (3H, s, CH₃), 3.95 (2H, s, CH₂), 6.99 (1H, d, J = 3.6 Hz, furan), 7.17 (1H, d, J = 3.6 Hz, furan), 7.23 (2H, d, J = 8.4 Hz, Br-phenyl), 7.40 (2H, m, OCF₃-phenyl), 7.46 (2H, d, J = 8.4 Hz, Br-phenyl), 7.53 (1H, m, OCF₃-phenyl), 8.22 (1H, d, J = 8.0 Hz, OCF₃-phenyl) | Procedure 1, RT = 3.14 min. Purity 100%. Electrospray positive ion mode: m/z 477, 479 (M + H)+. | 4 | 3 | 3 |
| 4 | [structure: 4-methyl-5-phenyl-2-[5-(3-chlorophenyl)furan-2-yl]imidazole] | A (85%) | | Procedure 1, RT = 2.98 min. Purity 100%. Electrospray positive ion mode: m/z 335 (M + H)+. | 4 | 4 | 2 |

TABLE AA-continued

Compounds of the invention, synthesis, characterization, and antibacterial properties

| Compound Number | Structure | Synthetic route (yield) | Analytics | | Antibacterial activity | | |
|---|---|---|---|---|---|---|---|
| | | | NMR | LC/MS | Streptococcus pneumoniae | Staphylococcus aureus (MSSA) | Staphylococcus aureus (MRSA) |
| 5 | [structure: 4-methyl-5-phenyl-2-(5-(4-chlorophenyl)furan-2-yl)imidazole] | A (73) | | Procedure 1, RT = 2.96 min. Purity 100%. Electrospray positive ion mode: m/z 335 (M + H)+. | 4 | 4 | 3 |
| 79 | [structure: 4-methyl-5-(4-methoxyphenyl)-2-(5-(4-hydroxyphenyl)furan-2-yl)imidazole] | A (62%) | | Procedure 1, RT = 1.92 min. Purity 95%. Electrospray positive ion mode: m/z 347 (M + H)+. | 3 | | |
| 80 | [structure: 4-methyl-5-(4-hydroxyphenyl)-2-(5-(2,4-difluorophenyl)furan-2-yl)imidazole] | A (69%) | | Procedure 1, RT = 2.01 min. Purity 95%. Electrospray positive ion mode: m/z 353 (M + H)+. | 3 | 3 | 2 |
| 81 | [structure: 4-phenyl-2-(5-(2-chlorophenyl)thiophen-2-yl)imidazole] | A (23%) | | Procedure 1, RT = 2.01 min. Purity 98%. Electrospray positive ion mode: m/z 337 (M + H)+. | 1 | | |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | Streptococcus pneumoniae | Staphylococcus aureus (MSSA) | Staphylococcus aureus (MRSA) |
| 82 | 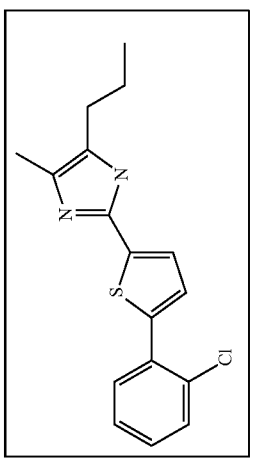 | A (82%) | | Procedure 1, RT = 2.86 min. Purity 100%. Electrospray positive ion mode: m/z 317 (M + H)+. | 4 | | 3 |
| 83 | 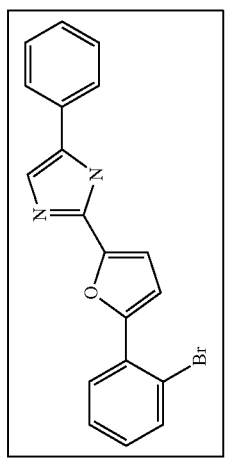 | A (24%) | | Procedure 1, RT = 2.88 min. Purity 97%. Electrospray positive ion mode: m/z 365, 367 (M + H)+. | 3 | | |
| 84 | 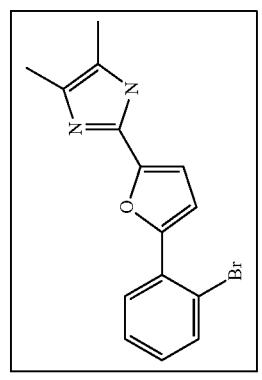 | A (77%) | | Procedure 1, RT = 2.78 min. Purity 100%. Electrospray positive ion mode: m/z 317, 319 (M + H)+. | 2 | | 2 |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | *Streptococcus pneumoniae* | *Staphylococcus aureus* (MSSA) | *Staphylococcus aureus* (MRSA) |
| 85 | 4,5-dimethyl-2-[5-(2-trifluoromethoxyphenyl)furan-2-yl]imidazole | A (78%) | | Procedure 1, RT = 2.75 min. Purity 100%. Electrospray positive ion mode: m/z 323 (M + H)+. | 4 | | 4 |
| 86 | 4,5-dimethyl-2-[5-(2-chlorophenyl)furan-2-yl]imidazole | A (46%) | | Procedure 1, RT = 2.67 min. Purity 100%. Electrospray positive ion mode: m/z 273 (M + H)+. | 3 | | |
| 87 | 2-[5-(2-trifluoromethylphenyl)furan-2-yl]-4,5,6,7-tetrahydrobenzimidazole | A (62%) | | Procedure 1, RT = 2.77 min. Purity 96%. Electrospray positive ion mode: m/z 333 (M + H)+. | 4 | | 4 |

TABLE AA-continued

Compounds of the invention, synthesis, characterization, and antibacterial properties

| Compound Number | Structure | Synthetic route (yield) | NMR | Analytics LC/MS | Antibacterial activity | | |
|---|---|---|---|---|---|---|---|
| | | | | | Streptococcus pneumoniae | Staphylococcus aureus (MSSA) | Staphylococcus aureus (MRSA) |
| 88 | [structure: tetrahydrobenzimidazole-furan-phenyl-OCF3] | A (79%) | | Procedure 1, RT = 2.87 min. Purity 98%. Electrospray positive ion mode: m/z 349 (M + H)+. | 4 | | 4 |
| 89 | [structure: methyl-propyl-imidazole-furan-phenyl-OCF3] | A (71%) | | Procedure 1, RT = 3.01 min. Purity 97%. Electrospray positive ion mode: m/z 351 (M + H)+. | 4 | | 4 |

TABLE AA-continued

Compounds of the invention, synthesis, characterization, and antibacterial properties

| Compound Number | Structure | Synthetic route (yield) | Analytics | | Antibacterial activity | | |
|---|---|---|---|---|---|---|---|
| | | | NMR | LC/MS | Streptococcus pneumoniae | Staphylococcus aureus (MSSA) | Staphylococcus aureus (MRSA) |
| 90 | | A (74%) | | Procedure 1, RT = 2.93 min. Purity 94%. Electrospray positive ion mode: m/z 349 (M + H)+. | 3 | | 4 |
| 91 | | A (70%) | | Procedure 1, RT = 3.07 min. Purity 96%. Electrospray positive ion mode: m/z 365 (M + H)+. | 4 | | 4 |
| 92 | | A (73%) | | Procedure 1, RT = 2.90 min. Purity 96%. Electrospray positive ion mode: m/z 349 (M + H)+. | 4 | | 4 |

TABLE AA-continued

Compounds of the invention, synthesis, characterization, and antibacterial properties

| Compound Number | Structure | Synthetic route (yield) | NMR | Analytics LC/MS | Antibacterial activity | | |
|---|---|---|---|---|---|---|---|
| | | | | | Streptococcus pneumoniae | Staphylococcus aureus (MSSA) | Staphylococcus aureus (MRSA) |
| 93 | (4-methyl-5-isobutyl-imidazol-2-yl linked to furan linked to 2-(trifluoromethoxy)phenyl) | A (70%) | | Procedure 1, RT = 3.01 min. Purity 95%. Electrospray positive ion mode: m/z 365 (M + H)+. | 4 | | |
| 94 | (4-methyl-5-propyl-imidazol-2-yl linked to furan linked to phenyl) | A (46%) | | Procedure 1, RT = 2.70 min. Purity 100%. Electrospray positive ion mode: m/z 267 (M + H)+. | 3 | | 3 |
| 95 | (4-methyl-5-propyl-imidazol-2-yl linked to furan linked to 2-chlorophenyl) | A (53%) | | Procedure 1, RT = 2.85 min. Purity 99%. Electrospray positive ion mode: m/z 301 (M + H)+. | 4 | | 4 |

TABLE AA-continued

Compounds of the invention, synthesis, characterization, and antibacterial properties

| Compound Number | Structure | Synthetic route (yield) | NMR | Analytics LC/MS | Antibacterial activity | | |
|---|---|---|---|---|---|---|---|
| | | | | | *Streptococcus pneumoniae* | *Staphylococcus aureus* (MSSA) | *Staphylococcus aureus* (MRSA) |
| 96 | (structure: 4-methyl-5-propyl-2-(5-(2-bromophenyl)furan-2-yl)-1H-imidazole) | A (54%) | | Procedure 1, RT = 2.91 min. Purity 99%. Electrospray positive ion mode: m/z 345, 347 (M + H)+. | 4 | | 4 |
| 97 | (structure: 4-methyl-5-propyl-2-(5-(2-nitrophenyl)furan-2-yl)-1H-imidazole) | A (52%) | | Procedure 1, RT = 2.62 min. Purity 92%. Electrospray positive ion mode: m/z 312 (M + H)+. | 2 | | 2 |

TABLE AA-continued

Compounds of the invention, synthesis, characterization, and antibacterial properties

| Compound Number | Structure | Synthetic route (yield) | Analytics | | Antibacterial activity | | |
|---|---|---|---|---|---|---|---|
| | | | NMR | LC/MS | Streptococcus pneumoniae | Staphylococcus aureus (MSSA) | Staphylococcus aureus (MRSA) |
| 40 | (4-methyl-5-phenyl-imidazol-2-yl)-furan-2-yl-(2-chloro-5-trifluoromethyl-phenyl) structure | A (88%) | | Procedure 1, RT = 3.30 min. Purity 94%. Electrospray positive ion mode: m/z 403 (M + H)+. | 2 | | |
| 98 | (4-propyl-5-methyl-imidazol-2-yl)-furan-2-yl-(2-dimethylamino-phenyl) structure | C (66%) | ¹H NMR (400 MHz, DMSO-d₆): δ: 0.9 (3H, m, CH3), 1.6 (1H, m CH2), 2.2 (d, 2H, CH2), 2.5-2.6, (1H, m, CH2), 2.7 (6H, s, N(CH3)2), 3.4 (3H, s, CH3), 6.8 (1H, m, Furan), 7.1-7.4 (3H, m, phenyl), 8.0 (1H, m, Furan), 12.3 (1H, 2s, NH). | Procedure 2. RT = 2.73 min. Purity 100%. Electrospray positive ion mode: m/z 310 (M + H)+ | 4 | | 3 |

TABLE AA-continued

Compounds of the invention, synthesis, characterization, and antibacterial properties

| Compound Number | Structure | Synthetic route (yield) | Analytics | | Antibacterial activity | | | |
|---|---|---|---|---|---|---|---|---|
| | | | NMR | LC/MS | *Streptococcus pneumoniae* | *Staphylococcus aureus* (MSSA) | *Staphylococcus aureus* (MRSA) |
| 99 | 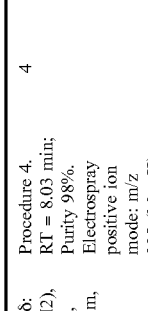 | C (57%) | ¹H NMR (400 MHz, DMSO-d₆): δ: 0.9 (3H, m, CH3), 1.6 (1H, m CH2) 2.2 (d, 2H, CH2), 2.5-2.6, (1H, m, CH2), 3.4 (3H, s, CH3) 6.8 (1H, m, Furan), 7.3 (1H, m, Furan), 7.7 (2H, m, Phenyl), 8.1 (1H, m, Phenyl), 12.2 (1H, 2s, NH), | Procedure 4. RT = 8.03 min; Purity 98%. Electrospray positive ion mode: m/z 335 (M + H)+ | 4 | | 4 |
| 100 | 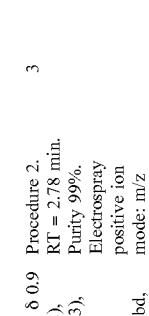 | C (65%) | 1H NMR (400 MHz, DMSO-d₆): δ 0.9 (3H, t, CH3), 1.7 (2H, quin, CH2), 2.2 (2H, d, CH2), 2.6 (3H, s, CH3), 3.4 (3H, s, CH3), 6.8 (2H, 2s, Furan), 7.3-7.4 (3H, m, aromate), 8.0 (1H, m, aromatic), 12.1 (1H, bd, NH) | Procedure 2. RT = 2.78 min. Purity 99%. Electrospray positive ion mode: m/z 281 (M + H)+ | 3 | | 2 |
| 138 | 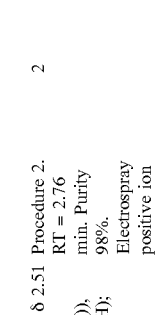 | C (22%) | ¹H NMR (400 MHz, DMSO-d₆): δ 2.51 (3H, s, CH₃), 7.00-7.80 (12H, m, aromatic H Indole, Furan, Phenyl)), 8.30 (1H, s, NH); 11.4 (1H, s, NH); 12.5 (1H, bs, NH) | Procedure 2. RT = 2.76 min. Purity 98%. Electrospray positive ion mode: m/z 340 (M + H)+ | 2 | | 2 |

TABLE AA-continued

Compounds of the invention, synthesis, characterization, and antibacterial properties

| Compound Number | Structure | Synthetic route (yield) | Analytics NMR | LC/MS | Antibacterial activity | | |
|---|---|---|---|---|---|---|---|
| | | | | | Streptococcus pneumoniae | Staphylococcus aureus (MSSA) | Staphylococcus aureus (MRSA) |
| 101 | | C (61%) | ¹H NMR (400 MHz, DMSO-d₆): δ: 0.8 (3H, m, CH3), 1.5 (2H, m CH2), 2.1 (s, 3H, CH3), 2.4 (2H, m, CH2), 6.7 (2H, s, Furan), 7.5-7.9 (4H, m, phenyl), 12.3 (1H, bs, NH). | | 3 | 5 | 4 |
| 102 | | C (15%) | ¹H NMR (400 MHz, DMSO-d₆): δ: 0.9 (3H, m, CH3), 1.6 (2H, m CH2), 2.2 (d, 2H, CH2), 2.6 (3H, m, CH3), 4.0 (3H, s, OCH3) 6.8 (2H, s, Furan), 7.0-7.4 (3H, m, phenyl), 8.1 (1H, m, aromate) 12.2 (1H, bs, NH). | Procedure 2. RT = 2.73 min. Purity 100%. Electrospray positive ion mode: m/z 297 (M + H)+ | 3 | | |

TABLE AA-continued

Compounds of the invention, synthesis, characterization, and antibacterial properties

| Compound Number | Structure | Synthetic route (yield) | Analytics NMR | Analytics LC/MS | Antibacterial activity Streptococcus pneumoniae | Staphylococcus aureus (MSSA) | Staphylococcus aureus (MRSA) |
|---|---|---|---|---|---|---|---|
| 103 | (structure) | C (41%) | 1H NMR (400 MHz, DMSO-d6): δ: 0.9 (3H, t, CH3), 1.6 (2H, m, CH2), 2.1-2.2 (2H, m, CH2), 2.3 (6H, s, 2 CH3), 2.5 (3H, s, CH3), 6.5 (1H, s, furan), 6.8 (1H, s, furan), 7.2-7.3 (3H, m, aromatic), 12.0 (1H, bd, NH); | Procedure 2. RT = 2.79 min. Purity 96%. Electrospray positive ion mode: m/z 295 (M + H)+ | 3 | | 3 |
| 104 | (structure) | C (57%) | ¹H NMR (400 MHz, DMSO-d₆): δ: 0.9 (3H, m, CH3), 1.6 (1H, m CH2), 2.2 (d, 2H, CH2), 2.5-2.6, (1H, m, CH2), 3.4 (3H, s, CH3), 6.9 (1H, m, Furan), 7.3 (1H, m, Furan), 7.9 (2H, d, Phenyl), 8.1 (2H, d, Phenyl), 12.3 (1H, 2s, NH). | Procedure 3. RT = 4.17 min. Purity 95%. Electrospray positive ion mode: m/z 335 (M + H)+; negative ion mode 333 (M − H)− | 3 | | 3 |
| 139 | (structure) | C (46%) | ¹H NMR (400 MHz, DMSO-d₆): δ 2.5 (3H, s, CH₃), 6.8 (1H, s, Furan), 7.0 (1H, s, Furan), 7.2-7.8 (7H, m, aromatic), 8.3 (1H, s, aromatic), 12.5 (1H, bs, NH); | Procedure 3. RT = 3.37 min. Purity 96%. Electrospray positive ion mode: m/z 385 (M + H)+ | 3 | 4 | 4 |

TABLE AA-continued

Compounds of the invention, synthesis, characterization, and antibacterial properties

| Compound Number | Structure | Synthetic route (yield) | Analytics NMR | Analytics LC/MS | Antibacterial activity Streptococcus pneumoniae | Antibacterial activity Staphylococcus aureus (MSSA) | Antibacterial activity Staphylococcus aureus (MRSA) |
|---|---|---|---|---|---|---|---|
| 31a | 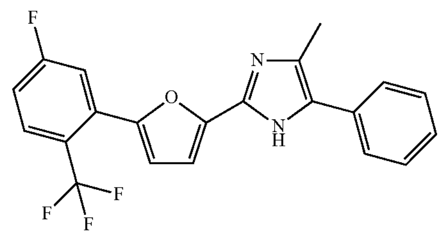 [SMILES: Cc1nc(-c2ccc(-c3cc(F)ccc3C(F)(F)F)o2)[nH]c1-c1ccccc1] | C (6%) | | Procedure 2. RT = 3.32 min. Purity 98%. Electrospray positive ion mode: m/z 387 (M + H)+ | 3 | 1 | |
| 106 | 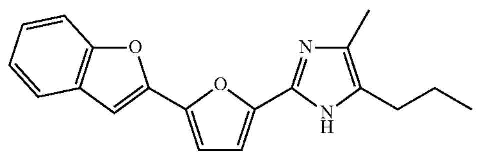 [SMILES: CCCc1[nH]c(-c2ccc(-c3cc4ccccc4o3)o2)nc1C] | C (64%) | | Procedure 4. RT = 7.93 min; Purity 98%. Electrospray positive ion mode: m/z 307 (M + H)+ | 4 | | 4 |
| 107 | 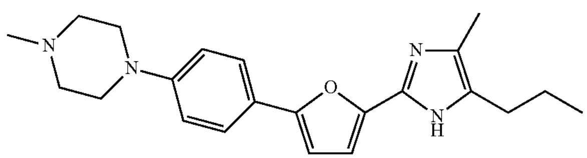 [SMILES: CCCc1[nH]c(-c2ccc(-c3ccc(N4CCN(C)CC4)cc3)o2)nc1C] | C (40%) | | Procedure 2. RT = 2.12 min. Purity 95%. Electrospray positive ion mode: m/z 365 (M + H)+ | 1 | | 1 |
| 108 | 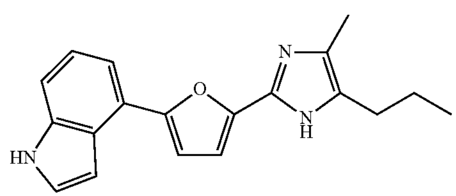 [SMILES: CCCc1[nH]c(-c2ccc(-c3cccc4[nH]ccc34)o2)nc1C] | C (28%) | $^1$H NMR (400 MHz, DMSO-d$_6$): δ 0.9 (3H, m, CH3), 1.6 (2H, m CH2), 2.2 (d, 2H, CH2), 2.5 (3H, s, CH3), 6.9-7.6 (7H, m, aromatic), 11.4 (1H, bs, NH), 12.1-12.5 (1H, bs, NH) | Procedure 2. RT = 2.69 min. Purity 99%. Electrospray positive ion mode: m/z 306 (M + H)+ | 2 | | 2 |

TABLE AA-continued

Compounds of the invention, synthesis, characterization, and antibacterial properties

| Compound Number | Structure | Synthetic route (yield) | Analytics NMR | LC/MS | Antibacterial activity | | |
|---|---|---|---|---|---|---|---|
| | | | | | Streptococcus pneumoniae | Staphylococcus aureus (MSSA) | Staphylococcus aureus (MRSA) |
| 109 | 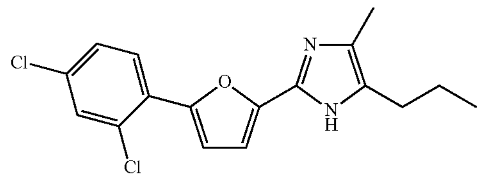 [SMILES: CCCc1[nH]c(-c2ccc(-c3ccc(Cl)cc3Cl)o2)nc1C] | C (33%) | | Procedure 6. RT = 11.74 min, Purity 93%. Electrospray positive ion mode: m/z 335 (M + H)+ | 4 | | 2 |
| 61 | 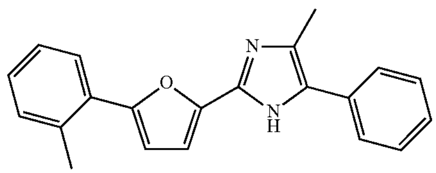 [SMILES: Cc1ccccc1-c1ccc(-c2nc(C)c(-c3ccccc3)[nH]2)o1] | C (59%) | 1H NMR (400 MHz, DMSO-d$_6$): δ 2.6 (3H, s, CH3), 3.4 (3H, s, CH3), 6.8-8.0 (11H, m, aromatics), 12.6 (1H, bs, NH); | Procedure 2. RT = 2.92 min. Purity 97%. Electrospray positive ion mode: m/z 315 (M + H)+ | 3 | | |
| 1 | 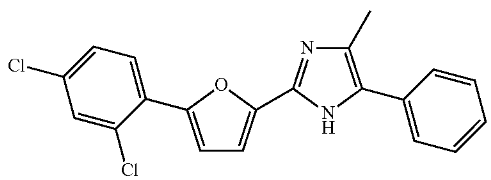 [SMILES: Cc1nc(-c2ccc(-c3ccc(Cl)cc3Cl)o2)[nH]c1-c1ccccc1] | C (37%) | $^1$H NMR (400 MHz, DMSO-d$_6$): δ 2.51 (3H, s, CH$_3$), 7.0-8.4 (10H, m; Phenyl), 12.8 (1H, bs, NH); | Procedure 3. RT = 4.11 min. Purity 95%. Electrospray positive ion mode: m/z 369 (M + H)+ | 4 | 4 | 4 |
| 62 | 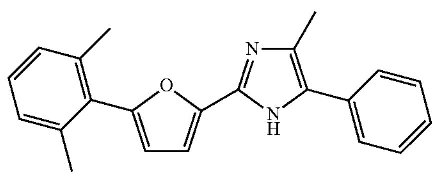 [SMILES: Cc1cccc(C)c1-c1ccc(-c2nc(C)c(-c3ccccc3)[nH]2)o1] | C (11%) | | Procedure 2. RT = 2.96 min. Purity 95%. Electrospray positive ion mode: m/z 329 (M + H)+ | 3 | | |

TABLE AA-continued

Compounds of the invention, synthesis, characterization, and antibacterial properties

| Compound Number | Structure | Synthetic route (yield) | Analytics NMR | LC/MS | Antibacterial activity Streptococcus pneumoniae | Staphylococcus aureus (MSSA) | Staphylococcus aureus (MRSA) |
|---|---|---|---|---|---|---|---|
| 110 | (structure) | C (58%) | 1H NMR (400 MHz, DMSO-d6): δ 0.6 (3H, m, CH3), 1.4 (2H, m, CH2), 1.9 (2H, m, CH2), 2.3 (3H, s, CH3), 6.4 (1H, m, furan), 6.6 (1H, m, furan), 7.0-7.5 (2H, m, phenyl), 8.0 (1H, s, phenyl), 11.5-12.0 (1H, vbs, NH); | Procedure 2. RT = 2.73 min. Purity 99%. Electrospray positive ion mode: m/z 351 (M + H)+ | 3 |  | 3 |
| 111 | (structure) | C (9%) |  | Procedure 4. RT = 7.98 min; Purity 92%. APCI positive ion mode: m/z 353 (M + H)+ | 3 |  |  |
| 71 | (structure) | C (40%) | 1H NMR (400 MHz, DMSO-d6): δ: 2.4 (3H, s, CH3), 2.7 (6H, s, N(CH3)2), 7.0-8.1 (11H, m, aromatic), 12.7 (1H, s, NH); | Procedure 3. RT = 4.22 min. Purity 95%. Electrospray positive ion mode: m/z 344 (M + H)+ | 3 |  |  |
| 140 | (structure) | C (53%) |  | Procedure 2. RT = 3.12 min. Purity 100%. Electrospray positive ion mode: m/z 341 (M + H)+ | 4 |  | 2 |

TABLE AA-continued

Compounds of the invention, synthesis, characterization, and antibacterial properties

| Compound Number | Structure | Synthetic route (yield) | Analytics NMR | Analytics LC/MS | Antibacterial activity Streptococcus pneumoniae | Staphylococcus aureus (MSSA) | Staphylococcus aureus (MRSA) |
|---|---|---|---|---|---|---|---|
| 141 | 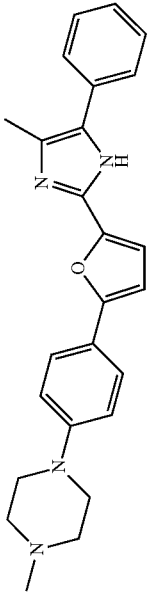 | C (32%) | | Procedure 2. RT = 2.21 min. Purity 93%. Electrospray positive ion mode: m/z 399 (M + H)+ | 1 | 1 | 1 |
| 142 | 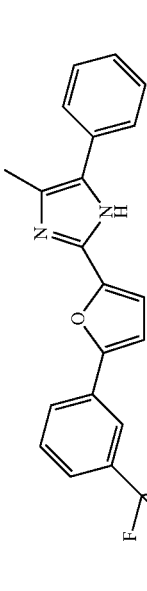 | C (59%) | 1H NMR (400 MHz, DMSO-d6): δ: 3.4 (3H, s, CH3), 7.0-8.3 (11H, m, Furan, Phenyl), 12.7 (1H, bs, NH); | Procedure 2. RT = 3.16 min. Purity 100%. Electrospray positive ion mode: m/z 369 (M + H)+ | 4 | 4 | 4 |
| 45 |  | C (60%) | ¹H NMR (400 MHz, DMSO-d₆): δ: 3.4 (3H, s, CH₃), 7.0-8.2 (11H, m, Furan, Phenyl), 12.7 (1H, s, NH); | Procedure 2. RT = 3.17 min. Purity 99%. Electrospray positive ion mode: m/z 369 (M + H)+ | 4 | 3 | 3 |
| 143 | 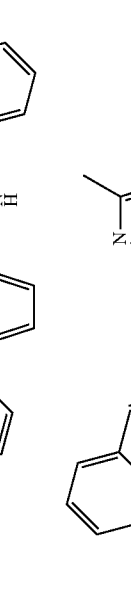 | C (72%) | 1H NMR (400 MHz, DMSO-d6): δ 2.6 (3H, s, CH3), 6.8 (1H, m, furan), 7.0 (1H, m, furan), 7.2-7.8 (12H, m, alkene H, phenyl), 12.7 (1H, bs, NH); | Procedure 3. RT = 4.20 min. Purity 99%. Electrospray positive ion mode: m/z 327 (M + H)+ | 3 | 3 | |
| 144 | 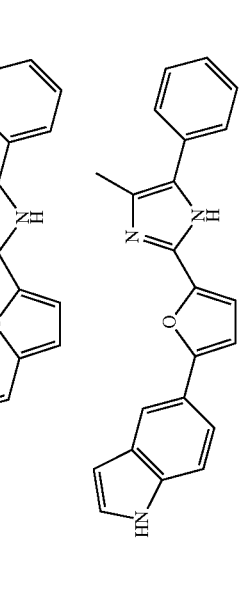 | C (9%) | ¹H NMR (400 MHz, DMSO-d₆): δ: 2.5 (3H, s, CH3), 6.5 (1H, s, Indole), 6.9 (2H, s, aromatic, Furan), 7.3 (1H, d, Furan), 7.4-7.8 (9H, m, aromatics), 11.2 (1H, s, NH), 12.7 (bs, 1H, NH). | Procedure 2. RT = 2.79 min. Purity 99%. Electrospray positive ion mode: m/z 340 (M + H)+ | 3 | 3 | 3 |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | Streptococcus pneumoniae | Staphylococcus aureus (MSSA) | Staphylococcus aureus (MRSA) |
| 34 | 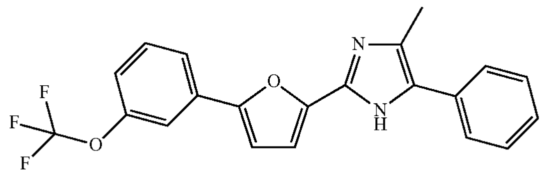 [SMILES: Cc1nc(-c2ccc(-c3cccc(OC(F)(F)F)c3)o2)[nH]c1-c1ccccc1] | C (41%) | ¹H NMR (400 MHz, DMSO-d₆): δ: 3.4 (3H, s, CH₃), 7.0-7.9 (11H, m, Furan, Phenyl), 12.7 (1H, s, NH); | Procedure 5. RT = 10.48 min; Purity 98%. Electrospray positive ion mode: m/z 385 (M + H)+ | 3 | 4 | 4 |
| 145 | 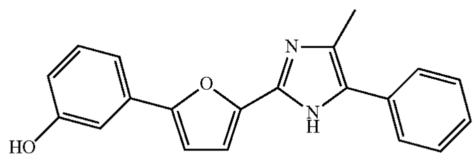 [SMILES: Cc1nc(-c2ccc(-c3cccc(O)c3)o2)[nH]c1-c1ccccc1] | C (52%) | ¹H NMR (400 MHz, DMSO-d₆): δ 2.4 (3H, s, CH₃), 6.8, 7.0 (2H, d, Furan), 7.1-7.8 (9H, m, aromatic), 8.2 (1H, s, aromatic), 12.6 (1H, bs, NH); | Procedure 2. RT = 2.64 min. Purity 92%. Electrospray positive ion mode: m/z 317 (M + H)+ | 2 | 2 | 1 |
| 146 | 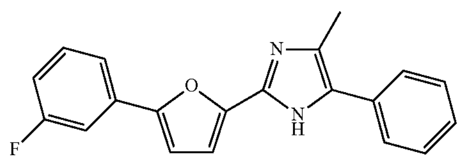 [SMILES: Cc1nc(-c2ccc(-c3cccc(F)c3)o2)[nH]c1-c1ccccc1] | C (54%) | ¹H NMR (400 MHz, DMSO-d₆): δ 2.5 (3H, s, CH₃), 7.0 (1H, s, Furan), 7.2-7.8 (8H, m, aromatic), 8.2 (1H, s, aromatic), 12.5 (1H, bs, NH); | Procedure 2. RT = 2.93 min. Purity 98%. Electrospray positive ion mode: m/z 319 (M + H)+ | 3 | 3 | 3 |
| 147 | 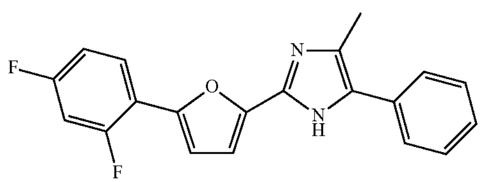 [SMILES: Cc1nc(-c2ccc(-c3ccc(F)cc3F)o2)[nH]c1-c1ccccc1] | C (44%) | ¹H NMR (400 MHz, DMSO-d₆): δ 3.3 (3H, s, CH₃), 7.0-7.8 (9H, s, aromatic), 8.1-8.3 (1H, m, aromatic), 12.7 (1H, s, NH); | Procedure 2. RT = 2.98 min. Purity 97%. Electrospray positive ion mode: m/z 337 (M + H)+ | 4 | 4 | 4 |
| 148 | 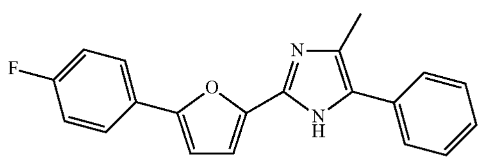 [SMILES: Cc1nc(-c2ccc(-c3ccc(F)cc3)o2)[nH]c1-c1ccccc1] | C (53%) | ¹H NMR (400 MHz, DMSO-d₆): δ: 2.4 (3H, s, CH3), 6.9, 7.1 (2H, d, Furan), 7.3-8.2 (9H, m, aromatics), 12.7 (bs, 1H, NH). | Procedure 2. RT = 2.88 min. Purity 98%. Electrospray positive ion mode: m/z 319 (M + H)+ | 3 | 3 | 3 |

TABLE AA-continued

Compounds of the invention, synthesis, characterization, and antibacterial properties

| Compound Number | Structure | Synthetic route (yield) | Analytics NMR | Analytics LC/MS | Antibacterial activity Streptococcus pneumoniae | Antibacterial activity Staphylococcus aureus (MSSA) | Antibacterial activity Staphylococcus aureus (MRSA) |
|---|---|---|---|---|---|---|---|
| 149 | (2-hydroxyphenyl-furan-imidazole-phenyl) | C (40%) | $^1$H NMR (400 MHz, DMSO-d$_6$): δ 2.5 (3H, s, CH$_3$), 6.9-7.8 (11H, m, aromatic), 8.2 (1H, s, aromatic), 10.2 (1H, bs, NH), 12.5 (1H, bs, NH); | Procedure 3. RT = 3.14 min. Purity 99%. APCI positive ion mode: m/z 317 (M + H)+ | 1 | 2 | 1 |
| 150 | (4-hydroxyphenyl-furan-imidazole-phenyl) | C (16%) | $^1$H NMR (400 MHz, DMSO-d$_6$): δ 2.5 (3H, s, CH$_3$), 6.9-7.8 (11H, m, aromatic), 12.5 (1H, s, NH); | Procedure 2. RT = 2.63 min. Purity 99%. Electrospray positive ion mode: m/z 317 (M + H)+ | 2 | 2 | 2 |
| 35 | (3,5-bis(trifluoromethyl)phenyl-furan-imidazole-phenyl) | C (44%) | $^1$H NMR (400 MHz, DMSO-d$_6$): δ 2.5 (3H, s, CH$_3$), 7.1-8.6 (10H, m, aromatic), 12.8 (1H, bs, NH); | Procedure 2. RT = 3.60 min. Purity 98%. Electrospray positive ion mode: m/z 437 (M + H)+ | 2 | 3 | 1 |
| 31 | (2-trifluoromethyl-4-methoxyphenyl-furan-imidazole-phenyl) | C (52%) | $^1$H NMR (400 MHz, DMSO-d$_6$): δ 3.4 (3H, s, CH$_3$), 4.0 (s, 3H, OCH3) 6.8-7.0 (2H, m, Furan,) 7.1-8.0 (8H, m; Phenyl), 12.6-12.7 (1H, m, NH); | Procedure 2. RT = 3.09 min. Purity 98%. Electrospray positive ion mode: m/z 399 (M + H)+ | 4 | 3 | 3 |

TABLE AA-continued

Compounds of the invention, synthesis, characterization, and antibacterial properties

| Compound Number | Structure | Synthetic route (yield) | Analytics NMR | LC/MS | Antibacterial activity | | |
|---|---|---|---|---|---|---|---|
| | | | | | Streptococcus pneumoniae | Staphylococcus aureus (MSSA) | Staphylococcus aureus (MRSA) |
| 151 | [structure] | C (39%) | | Procedure 2. RT = 2.54 min. Purity 96%. Electrospray positive ion mode: m/z 356 (M + H)+ | 1 | | |
| 152 | [structure] | C (58%) | ¹H NMR (400 Mhz, DMSO-d₆): δ 2.5 (3H, s, CH₃), 6.5 (1H, s, aromatic), 6.9-7.2 (2H, m, aromatic), 7.4-7.8 (7H, m, aromatic), 7.9 (1H, s, aromatic, )8.2 (1H, s, aromatic), 11.3 (1H, bs, NH), 12.5 (1H, bs, NH); | Procedure 2. RT = 2.86 min. Purity 94%. APCI positive ion mode: m/z 340 (M + H)+ | 3 | 3 | 3 |
| 153 | [structure] | C (77%) | ¹H NMR (400 MHz, DMSO-d₆): δ 2.5 (3H, s, CH₃), 7.0, 7.2 (2H, d, Furan), 7.3-8.0 (7H, m, aromatic), 8.2 (1H, s, aromatic), 12.5 (1H, bs, NH); | Procedure 3. RT = 3.67 min. Purity 98%. Electrospray positive ion mode: m/z 337 (M + H)+; negative ion mode m/z 335 (M − H)− | 3 | 3 | 3 |
| 154 | [structure] | C (74%) | | Procedure 3. RT = 2.69 min. Purity 90%. Electrospray positive ion mode: m/z 367 (M + H)+; negative ion mode 365 (M − H)− | 2 | 2 | 2 |

TABLE AA-continued

Compounds of the invention, synthesis, characterization, and antibacterial properties

| Compound Number | Structure | Synthetic route (yield) | Analytics NMR | Analytics LC/MS | Antibacterial activity Streptococcus pneumoniae | Staphylococcus aureus (MSSA) | Staphylococcus aureus (MRSA) |
|---|---|---|---|---|---|---|---|
| 155 | (structure) | C (8%) | ¹H NMR (400 MHz, DMSO-d₆): δ 2.5 (3H, s, CH₃), 6.6 (1H, s, aromatic), 7.0 (2H, m, aromatic) 7.3-7.8 (5H, m, aromatic), 8.2 (2H, d, aromatic), 11.3 (1H, s, OH), 12.5 (1H, bs, NH); | Procedure 3. RT = 3.35 min. Purity 96%. Electrospray positive ion mode: m/z 385 (M + H)+ | 3 | 3 | 2 |
| 156 | (structure) | C (26%) | ¹H NMR (400 MHz, DMSO-d₆): δ 2.5 (3H, s, CH₃), 7.0-8.2 (11H, m, aromatic), 12.7 (1H, bs, NH), 13.2 (1H, s, NH); | Procedure 3. RT = 3.00 min. Purity 95%. Electrospray positive ion mode: m/z 341 (M + H)+ | 1 | | |
| 157 | (structure) | C (48%) | ¹H NMR (400 MHz, DMSO-d₆): δ 2.5 (3H, s, CH₃), 6.9-7.9 (9H, m, aromatic), 8.2 (1H, s, aromatic), 12.5 (1H, bs, NH); | Procedure 5. RT = 9.58 min; Purity 90%. APCI positive ion mode: m/z 351 (M + H)+ | 3 | 3 | 2 |
| 32 | (structure) | C (46%) | ¹H NMR (400 MHz, DMSO-d₆): δ 3.5 (3H, s, CH₃), 7.0-8.2 (10H, m; Phenyl), 12.8 (1H, bs, NH); | Procedure 2. RT = 3.35 min. Purity 98%. Electrospray positive ion mode: m/z 403 (M + H)+ | 3 | 4 | 3 |

TABLE AA-continued

Compounds of the invention, synthesis, characterization, and antibacterial properties

| Compound Number | Structure | Synthetic route (yield) | Analytics | | Antibacterial activity | | |
|---|---|---|---|---|---|---|---|
| | | | NMR | LC/MS | Streptococcus pneumoniae | Staphylococcus aureus (MSSA) | Staphylococcus aureus (MRSA) |
| 158 | 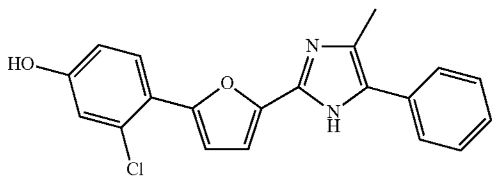 [SMILES: Cc1nc(-c2ccc(-c3ccc(O)cc3Cl)o2)[nH]c1-c1ccccc1] | C (8%) | $^1$H NMR (400 MHz, DMSO-$d_6$): δ 2.5 (3H, s, CH$_3$), 6.8-7.9 (9H, m, aromatic), 8.1 (1H, s, aromatic), 12.5 (1H, bs, NH); | Procedure 2. RT = 2.81 min. Purity 98%. Electrospray positive ion mode: m/z 351 (M + H)+; negative ion mode 349 (M − H)− | 3 | 4 | 4 |
| 159 | 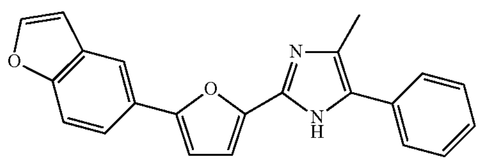 [SMILES: Cc1nc(-c2ccc(-c3ccc4occc4c3)o2)[nH]c1-c1ccccc1] | C (71%) | $^1$H NMR (400 MHz, DMSO-$d_6$): δ 2.5 (3H, s, CH$_3$), 6.9-8.2 (12H, m, aromatic), 12.6 (1H, bs, NH); | Procedure 2. RT = 2.92 min. Purity 93%. Electrospray positive ion mode: m/z 341 (M + H)+ | 3 | 3 | 1 |
| 160 | 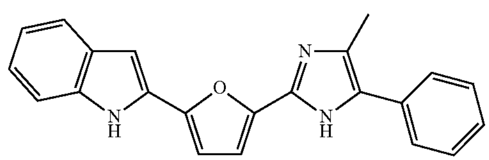 [SMILES: Cc1nc(-c2ccc(-c3cc4ccccc4[nH]3)o2)[nH]c1-c1ccccc1] | C (53%) | $^1$H NMR (400 MHz, DMSO-$d_6$): δ 2.6 (3H, s, CH$_3$), 6.9-8.3 (12H, m, aromatic), 11.7 (1H, s, NH), 12.6 (1H, bs, NH); | Procedure 2. RT = 2.98 min. Purity 98%. APCI positive ion mode: m/z 340 (M + H)+ | | 3 | 2 |
| 161 | 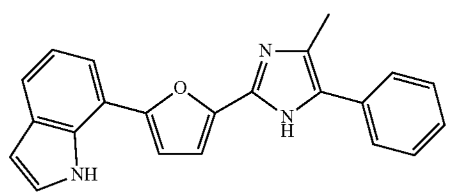 [SMILES: Cc1nc(-c2ccc(-c3cccc4cc[nH]c34)o2)[nH]c1-c1ccccc1] | C (65%) | $^1$H NMR (400 MHz, DMSO-$d_6$): δ 2.5 (3H, s, CH$_3$), 6.6, 7.1 (2H, d, Furan), 7.2-7.8 (10H, m, aromatic), 11.0 (1H, s, NH), 12.5 (1H, bs, NH); | Procedure 2. RT = 2.94 min. Purity 100%. Electrospray positive ion mode: m/z 340 (M + H)+ | 3 | 3 | 4 |

TABLE AA-continued

Compounds of the invention, synthesis, characterization, and antibacterial properties

| Compound Number | Structure | Synthetic route (yield) | Analytics NMR | LC/MS | Antibacterial activity Streptococcus pneumoniae | Staphylococcus aureus (MSSA) | Staphylococcus aureus (MRSA) |
|---|---|---|---|---|---|---|---|
| 112 | (2-trifluoromethylphenyl-furan-imidazole with propyl, methyl) | E (22%) | 1H NMR (300 MHz, DMSO) δ 11.83 (d, 1H, NH), 8.14 (s, 1H), 7.92-7.70 (m, 3H), 7.67-7.51 (m, 1H), 7.14 (s, 1H), 2.37 (br. s., 2H), 2.19-1.92 (m, 3H, methyl), 1.66-1.43 (m, J = 7.1 Hz, 2H), 0.87 (t, J = 7.1 Hz, 3H) | Procedure 8. RT = 8.98 min. Purity 99.8%. Electrospray positive ion mode: m/z 335 (M + H)+ | 4 | | 3 |
| 113 | (2-trifluoromethylphenyl-thiophene-imidazole with propyl, methyl) | D (29%) | 1H NMR (300 MHz, DMSO) δ 11.87 (d, 1H, NH), 7.92-7.79 (m, 2H), 7.78-7.69 (m, 1H), 7.69-7.54 (m, 2H), 7.51 (s, 1H), 2.37 (br. s., 2H), 2.20-1.97 (m, 3H, methyl), 1.64-1.40 (m, J = 7.3 Hz, 2H), 0.87 (t, J = 7.3 Hz, 3H) | Procedure 8. RT = 9.18 min. Purity 98.2%. Electrospray positive ion mode: m/z 351 (M + H)+ | 4 | | 3 |
| 72 | (2-trifluoromethylphenyl-furan-imidazole with phenyl, methyl) | E (13%) | 1H NMR (300 MHz, DMSO) δ 12.30 (s, 1H, NH), 8.36-8.16 (m, 1H), 7.87 (m, 2H), 7.82-7.74 (m, 1H), 7.71-7.61 (m, 2H), 7.61-7.51 (m, 1H), 7.50-7.43 (m, 1H), 7.38 (m, 2H), 73.2-7.13 (m, 1H), 2.45-2.32 (d, 3H, methyl) | Procedure 8. RT = 9.43 min. Purity 99.2%. Electrospray positive ion mode: m/z 369 (M + H)+ | 2 | | |

TABLE AA-continued

Compounds of the invention, synthesis, characterization, and antibacterial properties

| Compound Number | Structure | Synthetic route (yield) | Analytics | | Antibacterial activity | | |
|---|---|---|---|---|---|---|---|
| | | | NMR | LC/MS | Streptococcus pneumoniae | Staphylococcus aureus (MSSA) | Staphylococcus aureus (MRSA) |
| 114 | [structure: thieno-dioxine with trifluoromethylphenyl and methyl-propyl-imidazole] | D (36%) | 1H NMR (300 MHz, DMSO) δ 11.22 (d, 1H), 7.83 (d, 1H), 7.76-7.67 (m, 1H), 7.66-7.58 (m, 1H), 7.54 (d, 1H), 4.33 (d, J = 3.7 Hz, 2H), 4.22 (d, J = 3.7 Hz, 2H), 2.53-2.33 (m, J = 7.1 Hz, 2H), 2.15-2.02 (d, 3H, methyl), 1.62-1.37 (m, 2H), 0.85 (t, J = 7.1 Hz, 3H) | Procedure 9. RT = 4.88 min. Purity 95.1%. Electrospray positive ion mode: m/z 409 (M + H)+ | | | 3 |
| 115 | [structure: methylthiophene with trifluoromethylphenyl and methyl-propyl-imidazole] | D (24%) | 1H NMR (600 MHz, DMSO) δ 12.09-11.84 (m, 1H), 7.85 (d, 1H), 7.78-7.71 (m, 1H), 7.69-7.62 (m, 1H), 7.47 (d, 1H), 7.28-7.13 (m, 1H), 2.49-2.46 (m, 1H), 2.33 (t, J = 7.1 Hz, 1H), 2.14-2.02 (d, 3H, methyl), 1.92 (s, 3H, methyl), 1.61-1.43 (m, J = 7.4 Hz, J = 7.1 Hz, 2H), 0.92-0.72 (m, J = 7.4 Hz, 3H) | Procedure 8. RT = 9.16 min. Purity 99.8%. Electrospray positive ion mode: m/z 365 (M + H)+ | 4 | | |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | Streptococcus pneumoniae | Staphylococcus aureus (MSSA) | Staphylococcus aureus (MRSA) |
| 60 | 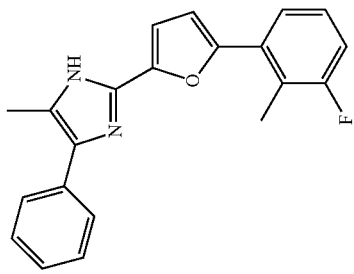 | F (7%) | 1H NMR (400 MHz, DMSO) δ 12.56 (s, 1H, NH), 7.88-7.66 (m, 2H), 7.66-7.21 (m, 4H), 7.21-7.05 (m, 2H), 7.02-6.95 (m, 1H, furan), 6.93 (d, J = 3.1 Hz, 1H, furan), 2.44 (s, 3H, methyl), 2.41 (s, 3H, C6H4—CH3). | Procedure 7. RT = 1.220 min, Purity 96.5%. Electrospray positive ion mode: m/z 333 (M + H)+ | 3 | 3 | 1 |
| 39 | 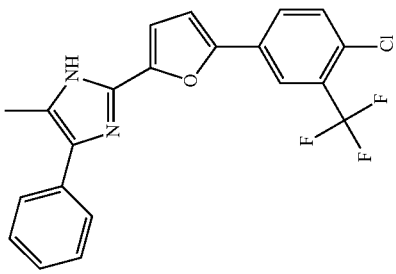 | F (56%) | 1H NMR (500 MHz, DMSO) δ 12.25 (br s, 1H, NH), 8.23 (s, 1H), 8.16 (d, J = 7.5 Hz, 1H), 7.77-7.58 (m, 3H), 7.49-7.36 (m, 2H), 7.34-7.26 (m, 1H), 7.26-7.11 (m, 2H), 2.48 (s, 3H, methyl). | Procedure 7. RT = 1.340 min, Purity 90.8%. Electrospray positive ion mode: m/z 403 (M + H)+ | 4 | 3 | 3 |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | Streptococcus pneumoniae | Staphylococcus aureus (MSSA) | Staphylococcus aureus (MRSA) |
| 3 | [structure: 4-methyl-5-phenyl-2-(5-(2-chlorophenyl)furan-2-yl)-1H-imidazole] | F (7%) | 1H NMR (500 MHz, DMSO) δ 12.60 (br s, 1H, NH), 8.22 (d, J = 7.9 Hz, 1H), 7.65 (d, J = 7.4 Hz, 2H), 7.53-7.32 (m, 4H), 7.32-7.14 (m, 3H), 6.99-6.96 (m, 1H, furan), 2.49 (s, 3H, methyl). | Procedure 7. RT = 1.218 min, Purity 100%. Electrospray positive ion mode: m/z 335 (M + H)+ | 4 | 3 | 2 |
| 162 | [structure: 4-methyl-5-phenyl-2-(5-(2-fluorophenyl)furan-2-yl)-1H-imidazole] | F (33%) | | Procedure 7. RT = 1.189 min, Purity 100%. Electrospray positive ion mode: m/z 319 (M + H)+ | 3 | 3 | 3 |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | Streptococcus pneumoniae | Staphylococcus aureus (MSSA) | Staphylococcus aureus (MRSA) |
| 52 | [structure: 4-methyl-2-(5-(p-tolyl)furan-2-yl)-5-phenyl-1H-imidazole] | F (43%) | | Procedure 7. RT = 1.094 min, Purity 100%. Electrospray positive ion mode: m/z 315 (M + H)+ | 4 | | 1 |
| 2 | [structure: 2-(5-(2,3-dichlorophenyl)furan-2-yl)-4-methyl-5-phenyl-1H-imidazole] | F (93%) | 1H NMR (500 MHz, DMSO) δ 12.67 (s, 1H, NH), 8.25-8.02 (m, 1H), 7.91-7.66 (m, 2H), 7.64 (d, J = 7.0 Hz, 1H), 7.52 (t, J = 8.0 Hz, 2H), 7.47-7.33 (m, 2H), 7.33-7.16 (m, 1H), 7.16-6.80 (m, 1H), 2.44 (s, 3H, methyl). | Procedure 7. RT = 1.251 min, Purity 95.6%. Electrospray positive ion mode: m/z 369 (M + H)+ | 3 | 1 | |

TABLE AA-continued

Compounds of the invention, synthesis, characterization, and antibacterial properties

| Compound Number | Structure | Synthetic route (yield) | NMR | Analytics LC/MS | Antibacterial activity Streptococcus pneumoniae | Staphylococcus aureus (MSSA) | Staphylococcus aureus (MRSA) |
|---|---|---|---|---|---|---|---|
| 163 | (structure) | F (52%) | | Procedure 7. RT = 1.120 min, Purity 95.8%. Electrospray positive ion mode: m/z 337 (M + H)+ | 3 | | |
| 53 | (structure) | F (81%) | | Procedure 7. RT = 1.221 min, Purity 96.2%. Electrospray positive ion mode: m/z 329 (M + H)+ | 3 | 3 | 1 |

TABLE AA-continued

Compounds of the invention, synthesis, characterization, and antibacterial properties

| Compound Number | Structure | Synthetic route (yield) | NMR | Analytics LC/MS | Antibacterial activity | | |
|---|---|---|---|---|---|---|---|
| | | | | | Streptococcus pneumoniae | Staphylococcus aureus (MSSA) | Staphylococcus aureus (MRSA) |
| 164 | [structure: methyl-phenyl-imidazole-furan-(2-methyl-4-fluorophenyl)] | F (66%) | | Procedure 7. RT = 1.105 min, Purity 96.2%. Electrospray positive ion mode: m/z 333 (M + H)+ | 3 | 3 | |
| 165 | [structure: methyl-phenyl-imidazole-furan-(4-tert-butylphenyl)] | F (92%) | | Procedure 7. RT = 1.365 min, Purity 96.2%. Electrospray positive ion mode: m/z 357 (M + H)+ | 2 | | |

TABLE AA-continued

Compounds of the invention, synthesis, characterization, and antibacterial properties

| Compound Number | Structure | Synthetic route (yield) | NMR | Analytics LC/MS | Antibacterial activity | | |
|---|---|---|---|---|---|---|---|
| | | | | | Streptococcus pneumoniae | Staphylococcus aureus (MSSA) | Staphylococcus aureus (MRSA) |
| 166 | [structure: 4-methyl-5-phenyl-2-(1-(4-fluorophenyl)-1H-pyrazol-4-yl)-1H-imidazole] | F (95%) | | Procedure 7. RT = 1.079 min, Purity 96.9%. Electrospray positive ion mode: m/z 319 (M + H)+ | 1 | 1 | 1 |
| 167 | [structure: 4-methyl-5-phenyl-2-(1-phenyl-1H-pyrazol-4-yl)-1H-imidazole] | F (96%) | | Procedure 7. RT = 1.054 min, Purity 95.3%. Electrospray positive ion mode: m/z 301 (M + H)+ | 1 | | 1 |

TABLE AA-continued

Compounds of the invention, synthesis, characterization, and antibacterial properties

| Compound Number | Structure | Synthetic route (yield) | NMR | Analytics LC/MS | Antibacterial activity Streptococcus pneumoniae | Staphylococcus aureus (MSSA) | Staphylococcus aureus (MRSA) |
|---|---|---|---|---|---|---|---|
| 74 | (structure) | F (62%) | | Procedure 7. RT = 1.127 min, Purity 97.1%. Electrospray positive ion mode: m/z 317 (M + H)+ | 3 | | |
| 13 | (structure) | F (29%) | | Procedure 7. RT = 1.286 min, Purity 100%. Electrospray positive ion mode: m/z 395 (M + H)+ | 2 | | |

TABLE AA-continued

Compounds of the invention, synthesis, characterization, and antibacterial properties

| Compound Number | Structure | Synthetic route (yield) | Analytics | | Antibacterial activity | | |
|---|---|---|---|---|---|---|---|
| | | | NMR | LC/MS | Streptococcus pneumoniae | Staphylococcus aureus (MSSA) | Staphylococcus aureus (MRSA) |
| 57 | | F (68%) | 1H NMR (500 MHz, DMSO) δ 12.50 (s, 1H, NH), 8.56 (s, 1H, oxazole), 7.96 (d, J = 8.0 Hz, 2H), 7.70 (d, J = 7.4 Hz, 2H), 7.43-7.35 (m, 4H), 7.22 (t, J = 7.1 Hz, 1H), 2.47 (s, 3H, methyl), 2.39 (s, 3H, methyl) | Procedure 7. RT = 1.161 min, Purity 94.3%. Electrospray positive ion mode: m/z 316 (M + H)+ | 3 | | |
| 8 | | F (14%) | 1H NMR (500 MHz, DMSO) δ 11.65 (s, 1H, NH), 7.68-7.60 (m, 2H), 7.61 (d, J = 8.5 Hz, 2H), 7.48-7.40 (m, 1H), 7.37 (d, J = 8.5 Hz, 2H), 7.20-7.15 (m, 2H), 6.40-6.30 (m, 1H), 2.46-2.26 (m, 6H, 2xCH3), 2.01 (s, 3H, methyl). | Procedure 7. RT = 1.086 min, Purity 96.3%. Electrospray positive ion mode: m/z 362 (M + H)+ | 3 | | 1 |

TABLE AA-continued

Compounds of the invention, synthesis, characterization, and antibacterial properties

| Compound Number | Structure | Synthetic route (yield) | Analytics | | Antibacterial activity | | |
|---|---|---|---|---|---|---|---|
| | | | NMR | LC/MS | Streptococcus pneumoniae | Staphylococcus aureus (MSSA) | Staphylococcus aureus (MRSA) |
| 11 | | F (96%) | 1H NMR (400 MHz, DMSO) δ 12.49 (s, 1H, NH), 8.35-8.05 (m, 2H), 8.01 (s, 1H, thiazole), 7.80-7.55 (m, 2H), 7.52-7.31 (m, 4H), 7.31-7.12 (m, 1H), 2.44 (s, 3H, methyl). | Procedure 7. RT = 1.151 min, Purity 92.5%. Electrospray positive ion mode: m/z 336 (M + H)+ | 3 | | |
| 73 | | F (31%) | | Procedure 7. RT = 1.104 min, Purity 90.3%. Electrospray positive ion mode: m/z 302 (M + H)+ | 2 | | |

TABLE AA-continued

Compounds of the invention, synthesis, characterization, and antibacterial properties

| Compound Number | Structure | Synthetic route (yield) | Analytics | | Antibacterial activity | | |
| | | | NMR | LC/MS | Streptococcus pneumoniae | Staphylococcus aureus (MSSA) | Staphylococcus aureus (MRSA) |
| --- | --- | --- | --- | --- | --- | --- | --- |
| 14 | [structure] | F (52%) | 1H NMR (500 MHz, DMSO) δ 12.49 (s, 1H, NH), 8.59-8.22 (m, 1H), 8.22-7.90 (m, 2H), 7.90-7.59 (m, 3H), 7.59-6.66 (m, 4H), 2.44 (s, 3H, methyl). | Procedure 7. RT = 1.246 min, Purity 98.7%. Electrospray positive ion mode: m/z 396 (M + H)+ | 3 | | |
| 116 | [structure] | F (25%) | | Procedure 7. RT = 1.071 min, Purity 97.5%. Electrospray positive ion mode: m/z 348 (M + H)+ | 3 | | |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | Streptococcus pneumoniae | Staphylococcus aureus (MSSA) | Staphylococcus aureus (MRSA) |
| 56 | 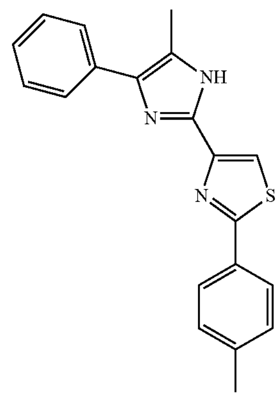 | F (24%) | 1H NMR (400 MHz, DMSO) δ 12.46 (s, 1H, NH), 8.10-7.91 (m, 3H), 7.71 (d, J = 6.2 Hz, 2H, p-phenyl), 7.52-7.29 (m, 4H), 7.28-7.10 (m, 1H), 2.44 (s, 3H, methyl2.38 (s, 3H, C6H4—CH3). | Procedure 7. RT = 1.169 min, Purity 100%, Electrospray positive ion mode: m/z 332 (M + H)+ | 3 | | |
| 58 | 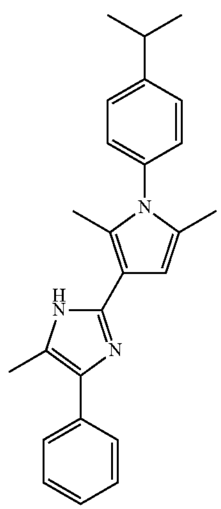 | F (54%) | | Procedure 7. RT = 1.318 min, Purity 95.2%, Electrospray positive ion mode: m/z 370 (M + H)+ | 4 | | |

TABLE AA-continued

Compounds of the invention, synthesis, characterization, and antibacterial properties

| | | Synthetic | | Analytics | Antibacterial activity | | |
|---|---|---|---|---|---|---|---|
| Compound Number | Structure | route (yield) | NMR | LC/MS | *Strepto-coccus pneumoniae* | *Staphylo-coccus aureus* (MSSA) | *Staphylo-coccus aureus* (MRSA) |
| 36 | 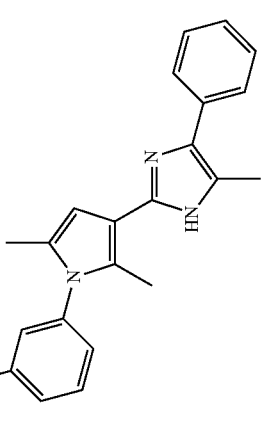 | F (32%) | | Procedure 7. RT = 1.248 min, Purity 100%. Electrospray positive ion mode: m/z 396 (M + H)+ | 3 | | 2 |
| 59 | 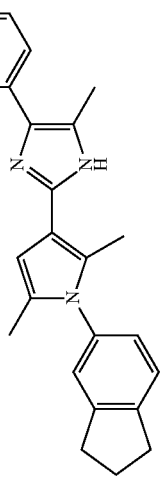 | F (16%) | | Procedure 7. RT = 1.321 min, Purity 92.4%. Electrospray positive ion mode: m/z 368 (M + H)+ | 3 | | |

TABLE AA-continued

Compounds of the invention, synthesis, characterization, and antibacterial properties

| Compound Number | Structure | Synthetic route (yield) | NMR | Analytics LC/MS | Antibacterial activity Streptococcus pneumoniae | Staphylococcus aureus (MSSA) | Staphylococcus aureus (MRSA) |
|---|---|---|---|---|---|---|---|
| 117 | (4-methyl-5-phenyl-1H-imidazol-2-yl)-thiophene-3-fluorophenyl | F (11%) | | Procedure 7. RT = 1.192 min, Purity 98.0%. Electrospray positive ion mode: m/z 335 (M + H)+ | 1 | 1 | |
| 118 | (4-methyl-5-phenyl-1H-imidazol-2-yl)-thiophene-4-bromophenyl | F (19%) | | Procedure 7. RT = 1.266 min, Purity 90.1%. Electrospray positive ion mode: m/z 395 (M + H)+ | 1 | | |

TABLE AA-continued

Compounds of the invention, synthesis, characterization, and antibacterial properties

| Compound Number | Structure | Synthetic route (yield) | Analytics NMR | LC/MS | Antibacterial activity Streptococcus pneumoniae | Staphylococcus aureus (MSSA) | Staphylococcus aureus (MRSA) |
|---|---|---|---|---|---|---|---|
| 54 | (4-methylphenyl-thiophene-imidazole-phenyl structure) | F (25%) | | Procedure 7. RT = 1.194 min, Purity 96.5%. Electrospray positive ion mode: m/z 331 (M + H)+ | 2 | | |
| 7 | (4-fluorophenyl-thiophene-imidazole-phenyl structure) | F (21%) | 1H NMR (500 MHz, DMSO) δ 12.20 (br s, 1H, NH), 7.77-7.58 (m, 4H), 7.58-7.49 (m, 1H), 7.38 (t, J = 7.0 Hz, 2H), 7.31 (d, J = 2.3 Hz, 1H), 7.22 (t, J = 7.1 Hz, 1H), 7.15 (t, J = 7.9 Hz, 2H), 2.48 (s, 3H, methyl). | Procedure 7. RT = 1.098 min, Purity 95.1%. Electrospray positive ion mode: m/z 335 (M + H)+ | 3 | | |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | Streptococcus pneumoniae | Staphylococcus aureus (MSSA) | Staphylococcus aureus (MRSA) |
| 15 | [structure: 4-methyl-5-phenyl-2-(5-(2-fluorophenyl)thiophen-2-yl)-1H-imidazole] | F (20%) | 1H NMR (500 MHz, DMSO) δ 12.57 (s, 1H, NH), 7.84 (t, J = 7.1 Hz, 1H), 7.69 (d, J = 7.4 Hz, 2H), 7.64-7.26 (m, 7H), 7.23 (t, J = 7.1 Hz, 1H), 2.33 (s, 3H, methyl). | Procedure 7. RT = 1.164 min, Purity 95.9%. Electrospray positive ion mode: m/z 335 (M + H)+ | 3 | | |
| 46 | [structure: 4-methyl-5-phenyl-2-(5-(4-(trifluoromethyl)phenyl)thiophen-2-yl)-1H-imidazole] | F (45%) | 1H NMR (500 MHz, DMSO) δ 12.89-12.21 (m, 1H, NH), 7.91 (d, J = 7.7 Hz), 7.77 (d, J = 8.0 Hz, 2H), 7.69 (d, J = 8.1 Hz, 2H), 7.59 (d, J = 7.7 Hz, 1H), 7.53 (d, J = 3.7 Hz, 1H, thiophene), 7.49 (t, J = 7.7 Hz, 1H), 7.40 (t, J = 7.6 Hz, 1H), 7.23 (t, J = 7.3 Hz, 1H), 2.48 (s, 3H, methyl). | Procedure 7. RT = 1.294 min, Purity 100%, Electrospray positive ion mode: m/z 385 (M + H)+ | 3 | 2 | |

TABLE AA-continued

Compounds of the invention, synthesis, characterization, and antibacterial properties

| Compound Number | Structure | Synthetic route (yield) | Analytics | | Antibacterial activity | | |
|---|---|---|---|---|---|---|---|
| | | | NMR | LC/MS | Streptococcus pneumoniae | Staphylococcus aureus (MSSA) | Staphylococcus aureus (MRSA) |
| 6 | (4-methyl-5-phenyl-imidazol-2-yl)-thiophene-(4-chlorophenyl) structure | F (47%) | 1H NMR (500 MHz, DMSO) δ 12.54 (s, 1H), 7.71 (d, J = 8.4 Hz, 2H), 7.69-7.58 (m, 2H), 7.55 (d, J = 3.7 Hz, 1H), 7.49-7.47 (m, 3H), 7.45-6.97 (m, 3H), 2.45 (s, 3H, methyl). | Procedure 7. RT = 1.270 min, Purity 100%. Electrospray positive ion mode: m/z 351 (M + H)+ | 3 | | |
| 9 | (4-methyl-5-phenyl-imidazol-2-yl)-(2,5-dimethyl-1-(2,4-difluorophenyl)pyrrol) structure | F (46%) | | Procedure 7. RT = 1.194 min, Purity 90.3%. Electrospray positive ion mode: m/z 364 (M + H)+ | 2 | | 1 |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | Streptococcus pneumoniae | Staphylococcus aureus (MSSA) | Staphylococcus aureus (MRSA) |
| 10 | 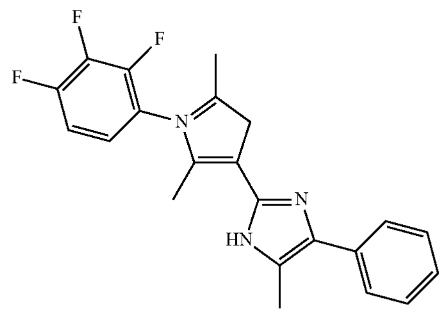 | F (11%) | | Procedure 7. RT = 1.070 min, Purity 95.0%. Electrospray positive ion mode: m/z 382 (M + H)+ | 2 | | |
| 55 | 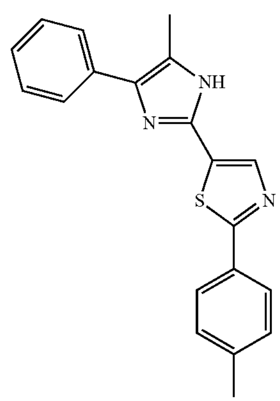 [SMILES: Cc1ccc(-c2ncc(-c3nc(-c4ccccc4)c(C)[nH]3)s2)cc1] | F (41%) | 1H NMR (500 MHz, DMSO) δ 13.04-12.32 (m, 1H, NH), 8.20 (s, 1H, thiazole), 7.87 (d, J = 7.8 Hz, 2H), 7.68 (d, J = 7.3 Hz, 1H), 7.59 (d, J = 7.4 Hz, 1H), 7.49 (t, J = 7.6 Hz, 1H), 7.40 (t, J = 7.6 Hz, 1H), 7.33 (d, J = 7.8 Hz, 2H), 7.24 (t, J = 7.3 Hz, 1H), 2.45 (s, 3H, methyl), 2.33 (s, 3H, methyl). | Procedure 7. RT = 1.222 min, Purity 100%. Electrospray positive ion mode: m/z 332 (M + H)+ | 3 | | |

TABLE AA-continued

Compounds of the invention, synthesis, characterization, and antibacterial properties

| Compound Number | Structure | Synthetic route (yield) | Analytics | | | Antibacterial activity | | |
|---|---|---|---|---|---|---|---|---|
| | | | NMR | LC/MS | | Streptococcus pneumoniae | Staphylococcus aureus (MSSA) | Staphylococcus aureus (MRSA) |
| 12 | | F (58%) | 1H NMR (400 MHz, DMO) δ 12.79-12.30 (m, 1H, NH), 7.85-7.52 (m, 5H), 7.53-7.26 (m, 5H), 7.26-7.07 (m, 1H, thiophene), 2.47 (s, 3H). | Procedure 7. RT = 1.255 min, Purity 96.3%. Electrospray positive ion mode: m/z 351 (M + H)+ | | 3 | | |
| 119 | | F (77%) | 1H NMR (500 MHz, DMSO) δ 11.68 (s, 1H, NH), 7.75-7.61 (m, 2H), 7.61-7.52 (m, 1H), 7.52-7.43 (m, 2H), 7.43-7.27 (m, 3H), 7.22-7.08 (m, 1H), 6.40 (s, 1H, pyrrole), 2.41 (s, 3H, methyl), 2.33 (s, 3H, methyl), 1.98 (s, 3H, methyl). | Procedure 7. RT = 1.142 min, Purity 96.9%. Electrospray positive ion mode: m/z 346 (M + H)+ | | 1 | | 1 |

TABLE AA-continued

Compounds of the invention, synthesis, characterization, and antibacterial properties

| Compound Number | Structure | Synthetic route (yield) | Analytics NMR | LC/MS | Antibacterial activity | | |
|---|---|---|---|---|---|---|---|
| | | | | | *Streptococcus pneumoniae* | *Staphylococcus aureus* (MSSA) | *Staphylococcus aureus* (MRSA) |
| 69 | [Structure: 4-(2-methylphenyl)-2-[5-(2-trifluoromethylphenyl)furan-2-yl]imidazole] | G | 1H NMR (500 MHz, CDCl3) δ 9.67 (br s, 1H, NH), 7.79 (d, J = 7.9 Hz, 1H), 7.74 (d, J = 7.6 Hz, 1H), 7.69-7.50 (m, 1H), 7.58 (t, J = 7.5 Hz, 1H), 7.45 (t, J = 7.6 Hz, 1H), 7.33-7.14 (m, 4H), 7.05 (d, J = 2.4 Hz, 1H, furan), 6.80 (d, J = 2.9 Hz, 1H, furan), 2.49 (s, 3H, methyl). | Procedure 7. RT = 1.309 min, Purity 100%. Electrospray positive ion mode: m/z 369 (M + H)+ | 4 | 3 | 2 |
| 66 | [Structure: 4-(2-methylphenyl)-2-[5-(2-trifluoromethoxyphenyl)furan-2-yl]imidazole] | G | 1H NMR (500 MHz, DMSO) δ 13.00 (s, 1H, NH), 8.21 (d, J = 7.1 Hz, 1H), 8.04-7.72 (m, 1H), 7.72-7.40 (m, 4H), 7.39-7.11 (m, 3H), 7.07 (d, J = 2.0 Hz, 1H, furan), 6.98 (d, J = 2.0 Hz, 1H, furan), 2.36 (s, 3H, methyl). | Procedure 7. RT = 1.288 min, Purity 100%. Electrospray positive ion mode: m/z 385 (M + H)+ | 4 | 3 | 2 |

TABLE AA-continued

Compounds of the invention, synthesis, characterization, and antibacterial properties

| Compound Number | Structure | Synthetic route (yield) | Analytics NMR | LC/MS | Antibacterial activity | | |
|---|---|---|---|---|---|---|---|
| | | | | | Streptococcus pneumoniae | Staphylococcus aureus (MSSA) | Staphylococcus aureus (MRSA) |
| 33 | (structure) | F | 1H NMR (500 MHz, DMSO) δ 11.97 (s, 1H, NH), 7.93 (d, J = 7.3 Hz, 1H), 7.82 (t, J = 6.9 Hz, 1H), 7.77-7.50 (m, 4H), 7.50-7.29 (m, 3H), 7.29-7.07 (m, 1H), 6.99 (s, 1H), 6.74 (s, 1H), 2.40 (s, 3H, methyl). | Procedure 7. RT = 1.060 min, Purity 100%. Electrospray positive ion mode: m/z 368 (M + H)+ | 2 | 3 | 1 |
| 168 | (structure) | F & H | 1H NMR (500 MHz, DMSO) δ 14.86 (s, 1H, OH), 10.51 (s, 1H, NH), 8.02 (t, J = 9.0 Hz, 1H), 7.83-7.09 (m, 7H), 7.13-6.15 (m, 2H), 2.43 (s, 3H, methyl). | Procedure 7. RT = 0.992 min, Purity 98.5%. Electrospray positive ion mode: m/z 335 (M + H)+ | 3 | 3 | 3 |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | Streptococcus pneumoniae | Staphylococcus aureus (MSSA) | Staphylococcus aureus (MRSA) |
| 120 | 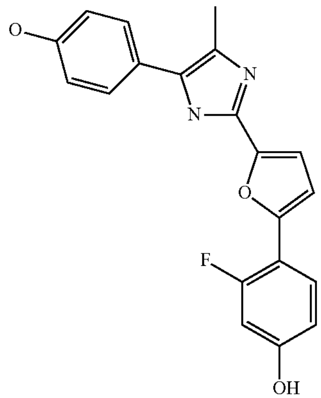 [SMILES: Cc1nc(-c2ccc(-c3ccc(O)cc3F)o2)[nH]c1-c1ccc(O)cc1] | F & H | 1H NMR (500 MHz, DMSO) δ 10.22 (s, 1H, OH), 9.45 (s, 1H, OH), 7.86 (t, J = 8.8 Hz, 1H), 7.45 (d, J = 8.2 Hz, 2H, p-pheynyl), 6.89 (d, J = 3.3 Hz, 1H), 6.82 (d, J = 8.4 Hz, 2H, p-pheynyl), 6.78-6.47 (m, 4H), 2.37 (s, 3H, methyl). | Procedure 7. RT = 0.965 min, Purity 93.8%. Electrospray positive ion mode: m/z 351 (M + H)+ | 3 | 2 | 2 |
| 19 | 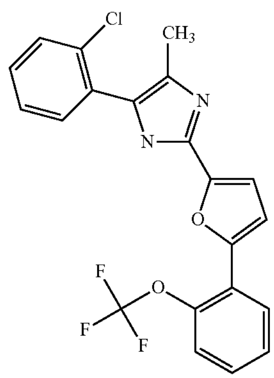 [SMILES: Cc1nc(-c2ccc(-c3ccccc3OC(F)(F)F)o2)[nH]c1-c1ccccc1Cl] | F & H (20%) | 1H NMR (500 MHz, DMSO) δ 8.32-8.29 (m, 1H), 8.18 (d, J = 7.6 Hz, 1H), 7.75-7.09 (m, 7H), 6.99 (d, J = 3.4 Hz, 1H, furan), 6.96 (d, J = 3.4 Hz, 1H, furan), 2.18 (s, 3H, methyl). | Procedure 7. RT = 1.226 min, Purity 98.0%. Electrospray positive ion mode: m/z 419 (M + H)+ | 4 | 1 | 1 |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | Streptococcus pneumoniae | Staphylococcus aureus (MSSA) | Staphylococcus aureus (MRSA) |
| 20 | 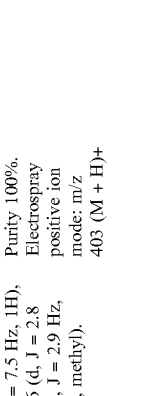 | F & H (16%) | 1H NMR (500 MHz, DMSO) δ 12.66 (s, 1H, NH), 8.00 (d, J = 7.7 Hz, 1H), 7.87 (d, J = 7.9 Hz, 1H), 7.79 (t, J = 7.5 Hz, 1H), 7.61 (t, J = 7.5 Hz, 1H), 7.58-7.12 (m, 4H), 6.96 (d, J = 2.8 Hz, 1H, furan), 6.90 (d, J = 2.9 Hz, 1H, furan), 2.17 (s, 3H, methyl). | Procedure 7. RT = 1.179 min, Purity 100%. Electrospray positive ion mode: m/z 403 (M + H)+ | 4 | 1 | |
| 21 | 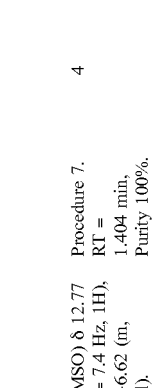 | F & H (23%) | 1H NMR (500 MHz, DMSO) δ 12.77 (s, 1H, NH), 8.17 (d, J = 7.4 Hz, 1H), 7.87-7.16 (m, 7H), 7.16-6.62 (m, 2H), 2.45 (s, 3H, methyl). | Procedure 7. RT = 1.404 min, Purity 100%. Electrospray positive ion mode: m/z 419 (M + H)+ | 4 | 3 | 3 |

TABLE AA-continued

Compounds of the invention, synthesis, characterization, and antibacterial properties

| Compound Number | Structure | Synthetic route (yield) | NMR | LC/MS | Antibacterial activity | | |
|---|---|---|---|---|---|---|---|
| | | | | | Streptococcus pneumoniae | Staphylococcus aureus (MSSA) | Staphylococcus aureus (MRSA) |
| 22 | 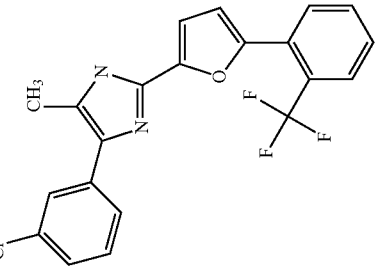 | F & H (21%) | | Procedure 7. RT = 1.352 min, Purity 100%. Electrospray positive ion mode: m/z 403 (M + H)+ | 3 | 2 | |
| 64 | 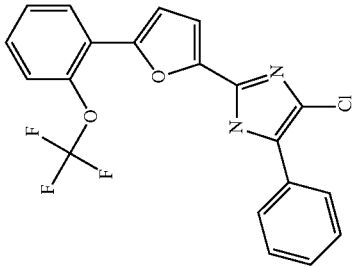 | I (15%) | 1H NMR (400 MHz, DMSO) δ 13.25 (s, 1H, NH), 8.22 (d, J = 7.6 Hz, 1H), 7.79 (d, J = 7.4 Hz, 2H), 7.68-7.44 (m, 5H), 7.40 (t, J = 7.0 Hz, 1H), 7.15 (d, J = 3.2 Hz, 1H, furan), 7.00 (d, J = 3.2 Hz, 1H, furan). | Procedure 7. RT = 1.562 min, Purity 100%. Electrospray positive ion mode: m/z 405 (M + H)+ | 4 | 2 | |

TABLE AA-continued

Compounds of the invention, synthesis, characterization, and antibacterial properties

| | | | Analytics | | Antibacterial activity | | |
|---|---|---|---|---|---|---|---|
| Compound Number | Structure | Synthetic route (yield) | NMR | LC/MS | Streptococcus pneumoniae | Staphylococcus aureus (MSSA) | Staphylococcus aureus (MRSA) |
| 65 | [structure: 2-(trifluoromethyl)phenyl-furan-imidazole-Cl, phenyl] | I (9%) | | Procedure 7. RT = 1.480 min, Purity 100%. Electrospray positive ion mode: m/z 389 (M + H)+ | 4 | 2 | |
| 27 | [structure: 2-(trifluoromethyl)phenyl-furan-methylimidazole-4-ethynylphenyl] | F (23%) | 1H NMR (500 MHz, DMSO) δ 9.24 (br s, 1H, NH), 7.79 (d, J = 8.1 Hz, 1H), 7.74 (d, J = 7.8 Hz, 1H), 7.85-7.49 (m, 5H), 7.46 (t, J = 7.2 Hz, 1H), 7.06 (d, J = 2.9 Hz, 1H, furan), 6.80 (d, J = 3.5 Hz, 1H, furan), 3.12 (s, 1H, acetylene), 2.51 (s, 3H, methyl). | Procedure 7. RT = 1.277 min, Purity 93.2%. Electrospray positive ion mode: m/z 393 (M + H)+ | 4 | | |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | Streptococcus pneumoniae | Staphylococcus aureus (MSSA) | Staphylococcus aureus (MRSA) |
| 41 | (structure) | F & H (40%) | 1H NMR (500 MHz, CDCl3) δ 7.85 (br s, 1H, NH), 7.72-7.27 (m, 8H), 6.98-6.92 (m, 1H, furan), 6.73-6.69 (m, 1H, furan), 2.47 (s, 3H, methyl). | Procedure 7. RT = 1.409 min, Purity 94.9%. Electrospray positive ion mode: m/z 419 (M + H)+ | 4 | 3 | 3 |
| 42 | (structure) | F (45%) | 1H NMR (400 MHz, CDCl3) δ 7.92 (s, 1H, NH), 7.67 (d, J = 8.3 Hz, 1H), 7.61-7.49 (m, 2H), 7.45 (d, J = 7.5 Hz, 1H), 7.24 (d, J = 2.3 Hz, 1H), 7.15-7.00 (m, 2H), 7.01-6.91 (m, 1H, furan), 6.82-6.71 (m, 1H, furan), 2.45 (s, 3H, methyl). | Procedure 7. RT = 1.265 min, Purity 100%. Electrospray positive ion mode: m/z 421 (M + H)+ | 4 | 4 | 4 |

TABLE AA-continued

Compounds of the invention, synthesis, characterization, and antibacterial properties

| | | | Analytics | | Antibacterial activity | | |
|---|---|---|---|---|---|---|---|
| Compound Number | Structure | Synthetic route (yield) | NMR | LC/MS | Streptococcus pneumoniae | Staphylococcus aureus (MSSA) | Staphylococcus aureus (MRSA) |
| 43 | [structure: 4-methyl-5-(4-fluorophenyl)imidazol-2-yl furan linked to 4-chloro-3-(trifluoromethoxy)phenyl] | F & H (35%) | 1H NMR (500 MHz, CDCl3) δ 8.78 (br s, 1H, NH), 7.87-7.30 (m, 5H), 7.21-7.01 (m, 2H), 7.01-6.85 (m, 1H, furan), 6.85-6.42 (m, 1H, furan), 2.45 (s, 3H, mehtyl). | Procedure 7. RT = 1.43 min, Purity 93.9%. Electrospray positive ion mode: m/z 437 (M + H)+ | 4 | 3 | 2 |
| 37 | [structure: 4-methyl-5-(4-fluorophenyl)imidazol-2-yl furan linked to 3-(trifluoromethoxy)phenyl] | F & H (37%) | 1H NMR (400 MHz, CDCl3) δ 7.67-7.33 (m, 3H), 7.29 (t, J = 7.7 Hz, 1H), 7.19-6.98 (m, 2H), 6.98-6.81 (m, 1H), 6.81-6.46 (m, 1H), 2.42 (s, 3H, methyl). | Procedure 7. RT = 1.310 min, Purity 98.5%. Electrospray positive ion mode: m/z 403 (M + H)+ | 4 | 3 | 3 |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | Streptococcus pneumoniae | Staphylococcus aureus (MSSA) | Staphylococcus aureus (MRSA) |
| 44 | [structure: 4-(4-chlorophenyl)-5-methyl-imidazole linked to furan linked to 4-chloro-3-(trifluoromethoxy)phenyl] | F & H (42%) | 1H NMR (500 MHz, DMSO) δ 8.13-7.77 (m, 2H), 7.77-7.47 (m, 3H), 7.60 (br s, 1H, NH), 7.39 (d, J = 8.1 Hz, 2H), 7.17 (d, J = 3.3 Hz, 1H, furan), 6.96-6.93 (m, 1H, furan), 2.47 (s, 3H, methyl). | Procedure 7. RT = 1.453 min, Purity 100%. Electrospray positive ion mode: m/z 453 (M + H)+ | 4 | 4 | 2 |
| 16 | [structure: 4-(4-fluorophenyl)-5-methyl-imidazole linked to furan linked to 2,4-dichlorophenyl] | F & H (27%) | 1H NMR (400 MHz, CDCl3) δ 10.46 (s, 1H, NH), 7.84-7.27 (m, 4H), 7.20-6.42 (m, 5H), 2.43 (s, 3H, methyl). | Procedure 7. RT = 1.249 min, Purity 96.9%. Electrospray positive ion mode: m/z 387 (M + H)+ | 3 | 4 | 4 |

TABLE AA-continued

Compounds of the invention, synthesis, characterization, and antibacterial properties

| Compound Number | Structure | Synthetic route (yield) | Analytics | | Antibacterial activity | | |
|---|---|---|---|---|---|---|---|
| | | | NMR | LC/MS | *Streptococcus pneumoniae* | *Staphylococcus aureus* (MSSA) | *Staphylococcus aureus* (MRSA) |
| 47 | [structure: 4-trifluoromethylphenyl-furan-imidazole-4-chlorophenyl with methyl] | F & H (16%) | 1H NMR (500 MHz, CDCl3) δ 9.96 (br s, 1H, NH), 7.95-7.20 (m, 8H), 7.16-6.91 (m, 1H, furan), 6.91-6.67 (m, 1H, furan), 2.49 (s, 3H, methyl). | Procedure 7. RT = 1.331 min, Purity 100%,. Electrospray positive ion mode: m/z 403 (M + H)+ | 4 | 4 | 3 |
| 48 | [structure: 4-trifluoromethoxyphenyl-furan-imidazole-4-chlorophenyl with methyl] | F & H (61%) | 1H NMR (400 MHz, DMSO) δ 12.67 (s, 1H, NH), 7.97 (d, J = 8.7 Hz, 2H), 7.70 (d, J = 8.2 Hz, 2H), 7.49-7.45 (m, 4H), 7.16 (d, J = 3.4 Hz, 1H, furan), 6.96 (d, J = 3.4 Hz, 1H, furan), 2.46 (s, 3H, methyl). | Procedure 7. RT = 1.322 min, Purity 100%. Electrospray positive ion mode: m/z 419 (M + H)+ | 4 | 3 | 3 |

TABLE AA-continued

Compounds of the invention, synthesis, characterization, and antibacterial properties

| Compound Number | Structure | Synthetic route (yield) | Analytics | | Antibacterial activity | | |
|---|---|---|---|---|---|---|---|
| | | | NMR | LC/MS | Streptococcus pneumoniae | Staphylococcus aureus (MSSA) | Staphylococcus aureus (MRSA) |
| 49 | [structure: 3-chloro-4-(trifluoromethyl)phenyl-furan-imidazole-4-methylphenyl] | F (15%) H | 1H NMR (400 MHz, DMSO) δ 12.71 (s, 1H, NH), 8.19 (s, 1H, CH—C6H3), 7.98 (d, J = 7.9 Hz, 1H, p-C6H4), 7.92 (d, J = 8.2 Hz, 1H, p-C6H4), 7.82-7.49 (m, 2H), 7.44 (d, J = 3.4 Hz, 1H), 7.37-7.06 (m, 2H), 7.07-6.91 (m, 1H, furan), 2.47 (s, 3H, methyl). | Procedure 7. RT = 1.379 min, Purity 100%. Electrospray positive ion mode: m/z 421 (M + H)+ | 3 | 3 | 2 |
| 50 | [structure: 3-chloro-4-(trifluoromethoxy)phenyl-furan-imidazole-4-chlorophenyl] | F (14%) H | 1H NMR (500 MHz, DMSO) δ 12.69 (s, 1H, NH), 8.17 (d, J = 1.6 Hz, 1H), 7.92 (d, J = 8.5 Hz, 1H), 7.72 (d, J = 8.4 Hz, 2H), 7.66 (d, J = 8.3 Hz, 1H), 7.58 (dd, J = 34.4, 8.3 Hz, 1H), 7.45 (d, J = 8.4 Hz, 2H), 7.29 (d, J = 3.4 Hz, 1H, furan), 6.96 (d, J = 3.4 Hz, 1H, furan), 2.49 (s, 3H, methyl). | Procedure 7. RT = 1.439 min, Purity 100%. Electrospray positive ion mode: m/z 453 (M + H)+ | 3 | 3 | 2 |

TABLE AA-continued

Compounds of the invention, synthesis, characterization, and antibacterial properties

| Compound Number | Structure | Synthetic route (yield) | Analytics | | Antibacterial activity | | |
| --- | --- | --- | --- | --- | --- | --- | --- |
| | | | NMR | LC/MS | Streptococcus pneumoniae | Staphylococcus aureus (MSSA) | Staphylococcus aureus (MRSA) |
| 67 | | G (4%) | 1H NMR (400 MHz, CDCl3) δ 8.04-7.85 (m, 1H), 7.85-7.71 (m, 1H), 7.66 (s, 1H, imidazole), 7.42 (d, J = 7.9 Hz, 1H), 7.38-7.21 (m, 5H), 7.19 (t, J = 7.2 Hz, 1H), 7.04 (d, J = 3.3 Hz, 1H, furan), 6.92 (d, J = 3.4 Hz, 1H, furan). | Procedure 7. RT = 1.628 min, Purity 100%. Electrospray positive ion mode: m/z 405 (M + H)+ | 3 | | |

TABLE AA-continued

Compounds of the invention, synthesis, characterization, and antibacterial properties

| | | | Analytics | | Antibacterial activity | | |
|---|---|---|---|---|---|---|---|
| Compound Number | Structure | Synthetic route (yield) | NMR | LC/MS | Streptococcus pneumoniae | Staphylococcus aureus (MSSA) | Staphylococcus aureus (MRSA) |
| 68 | [structure: 2-(trifluoromethoxy)phenyl-furan-imidazole-2,4-dichlorophenyl] | G (6%) | 1H NMR (400 MHz, DMSO) δ 13.15 (s, 1H, NH), 8.21 (d, J = 8.2 Hz, 2H), 7.96 (s, 1H, CH—C6H3), 7.64 (s, 1H, imidazole), 7.60-7.21 (m, 4H), 7.12 (d, J = 3.3 Hz, 1H, furan), 6.99 (d, J = 3.3 Hz, 1H, furan). | Procedure 7. RT = 1.628 min, Purity 100%. Electrospray positive ion mode: m/z 439 (M + H)+ | 2 | 2 | 2 |

TABLE AA-continued

Compounds of the invention, synthesis, characterization, and antibacterial properties

| Compound Number | Structure | Synthetic route (yield) | Analytics NMR | Analytics LC/MS | Antibacterial activity Streptococcus pneumoniae | Antibacterial activity Staphylococcus aureus (MSSA) | Antibacterial activity Staphylococcus aureus (MRSA) |
|---|---|---|---|---|---|---|---|
| 51 | 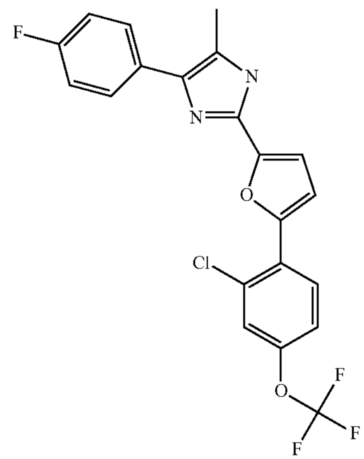 [SMILES: Cc1[nH]c(-c2ccc(-c3ccc(OC(F)(F)F)cc3Cl)o2)nc1-c1ccc(F)cc1] | F (12%); H | 1H NMR (400 MHz, DMSO) δ 12.68 (s, 1H, NH), 8.23 (d, J = 8.6 Hz, 1H), 7.81-7.59 (m, 2H), 7.56 (d, J = 8.4 Hz, 1H), 7.70-7.39 (m, 1H), 7.34 (d, J = 2.1 Hz, 1H, furan), 7.31-7.09 (m, 2H), 7.06-6.93 (m, 1H, furan), 2.46 (s, 3H, methyl). | Procedure 7. RT = 1.293 min, Purity 95%. Electrospray positive ion mode: m/z 437 (M + H)+ | 3 | 2 | 1 |
| 121 | 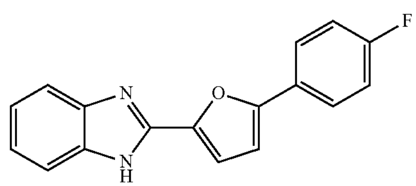 [SMILES: Fc1ccc(-c2ccc(-c3nc4ccccc4[nH]3)o2)cc1] | | | | inactive | | inactive |
| 122 | 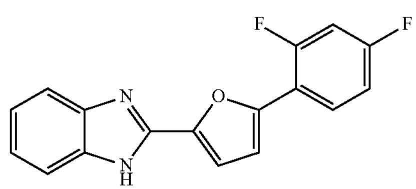 [SMILES: Fc1ccc(-c2ccc(-c3nc4ccccc4[nH]3)o2)c(F)c1] | | | | inactive | | inactive |

TABLE BB

Antibacterial and cytotoxic activities of compounds of the invention

| compound number | structure | Antibacterial activity | | | | | | | | | | | | cyto-toxicity cell line | | |
|---|---|---|---|---|---|---|---|---|---|---|---|---|---|---|---|
| | | Bacterial species | | | | | | | | EC | MRSA strains with additional resistance | | | | | |
| | | SP | ARSP | MSSA | MRSA | SE | BS | EFm | VREFm | EFs | VREFs | MS | A | D | V | L | M | T | P | H | K |
| 1 | ![structure 1] | 4 | 4 | 4 | 4 | 3 | 3 | | 1 | | | 2 | | 4 | 4 | 4 | 3 | 4 | 3 | 2 | 2 |
| 2 | ![structure 2] | 3 | 3 | 1 | | 1 | | | | | 1 | | | 3 | 1 | 1 | | | | 2 | 1 |

TABLE BB-continued

Antibacterial and cytotoxic activities of compounds of the invention

| compound number | structure | Antibacterial activity - Bacterial species | | | | | | | | | EC | MRSA strains with additional resistance | | | | | | cytotoxicity cell line | |
|---|---|---|---|---|---|---|---|---|---|---|---|---|---|---|---|---|---|---|---|
| | | SP | ARSP | MSSA | MRSA | SE | BS | EFm | VREFm | EFs | VREFs | MS | A | D | V | L | M | T | P | H | K |
| 3 | | 4 | 3 | 2 | 2 | | | | | | | | | | | | | | | 3 | 1 |
| 4 | | 4 | 4 | 2 | 3 | | | | | | | | | | | | | | | 2 | |
| 5 | | 4 | 4 | 3 | 3 | | | | | | | | | | | | | | | 2 | |

TABLE BB-continued

Antibacterial and cytotoxic activities of compounds of the invention

| compound number | structure | Antibacterial activity | | | | | | | | | | MRSA strains with additional resistance | | | | | | cytotoxicity cell line | |
|---|---|---|---|---|---|---|---|---|---|---|---|---|---|---|---|---|---|---|---|
| | | Bacterial species | | | | | | | | | EC | | | | | | | | |
| | | SP | ARSP | MSSA | MRSA | SE | BS | EFm | VREFm | EFs | VREFs | MS | A | D | V | L | M | T | P | H | K |
| 6 | [structure: 4-methyl-5-phenyl-2-(5-(4-chlorophenyl)thiophen-2-yl)-1H-imidazole] | 3 | 3 | | | | 2 | | | | | 2 | | | | | | | | 0 | 0 |
| 7 | [structure: 4-methyl-5-phenyl-2-(5-(4-fluorophenyl)thiophen-2-yl)-1H-imidazole] | | 3 | | | | | | | | | | | | | | | | | 1 | 2 |

TABLE BB-continued

Antibacterial and cytotoxic activities of compounds of the invention

| compound number | structure | Antibacterial activity — Bacterial species | | | | | | | | | | EC | MRSA strains with additional resistance | | | | | | cytotoxicity cell line | |
|---|---|---|---|---|---|---|---|---|---|---|---|---|---|---|---|---|---|---|---|---|
| | | SP | ARSP | MSSA | MRSA | SE | BS | EFm | VREFm | EFs | VREFs | MS | A | D | V | L | M | T | P | H | K |
| 8 | 4-Cl-phenyl-N-pyrrole-imidazole-phenyl | 3 | | | 1 | | | | | | | | | | | | | | | 2 | 1 |
| 9 | 2,4-diF-phenyl-N-pyrrole-imidazole-phenyl | 3 | | | 1 | | | | | | | | | | | | | | | 3 | 2 |
| 10 | 2,3,4-triF-phenyl-N-pyrrole-imidazole-phenyl | 3 | | | | | | | | | | | | | | | | | | 3 | 2 |

TABLE BB-continued

Antibacterial and cytotoxic activities of compounds of the invention

| compound number | structure | Antibacterial activity | | | | | | | | | | | | cyto-toxicity cell line | |
|---|---|---|---|---|---|---|---|---|---|---|---|---|---|---|
| | | Bacterial species | | | | | | | | EC | MRSA strains with additional resistance | | | | |
| | | SP | ARSP | MSSA | MRSA | SE | BS | EFm | VREFm | EFs | VREFs | MS | A | D V L M T P | H K |
| 11 | 4-methyl-2-(2-(4-fluorophenyl)thiazol-4-yl)-5-phenyl-1H-imidazole | 3 | | | | | | | | | | | | | 1 2 |
| 12 | 4-methyl-2-(5-(3-chlorophenyl)thiophen-2-yl)-5-phenyl-1H-imidazole | 3 | | | | | | | | | | | | | 1 2 |

TABLE BB-continued

Antibacterial and cytotoxic activities of compounds of the invention

| compound number | structure | Antibacterial activity ||||||||||| cyto- toxicity ||
| | | Bacterial species |||||||| EC | MRSA strains with additional resistance |||||| cell line ||
| | | SP | ARSP | MSSA | MRSA | SE | BS | EFm | VREFm | EFs | VREFs | MS | A | D | V | L | M | T | P | H | K |
| 13 | ![structure] | 3 | | | | | | | | | | | | | | | | | | 1 | 1 |
| 14 | ![structure] | 3 | | | | | | | | | | | | | | | | | | 1 | 1 |

TABLE BB-continued

Antibacterial and cytotoxic activities of compounds of the invention

| compound number | structure | Antibacterial activity - Bacterial species | | | | | | | | | | | EC | MRSA strains with additional resistance | | | | | | cytotoxicity cell line | |
|---|---|---|---|---|---|---|---|---|---|---|---|---|---|---|---|---|---|---|---|---|---|
| | | SP | ARSP | MSSA | MRSA | SE | BS | EFm | VREFm | EFs | VREFs | MS | A | D | V | L | M | T | P | H | K |
| 15 | 4-methyl-2-[5-(2-fluorophenyl)thiophen-2-yl]-5-phenyl-1H-imidazole | 3 | 3 | | | | | | | | | 2 | 1 | | | | | | | 1 | 1 |
| 16 | 2-[5-(2,4-dichlorophenyl)furan-2-yl]-4-methyl-5-(4-fluorophenyl)imidazole | 3 | 4 | 4 | 4 | 3 | 3 | | 1 | 1 | 1 | | | | | | | | | 3 | 1 |

TABLE BB-continued

Antibacterial and cytotoxic activities of compounds of the invention

| compound number | structure | Antibacterial activity | | | | | | | | | | | | | | | cyto-toxicity |
|---|---|---|---|---|---|---|---|---|---|---|---|---|---|---|---|---|
| | | Bacterial species | | | | | | | | | EC | MRSA strains with additional resistance | | | | | cell line |
| | | SP | ARSP | MSSA | MRSA | SE | BS | EFm | VREFm | EFs | VREFs | MS | A | D | V | L | M | T | P | H | K |
| 17 | *(structure)* | 3 | 3 | | 4 | 1 | 4 | 1 | | | | | 1 | | | | | | | 3 | 3 |
| 18 | *(structure)* | 3 | 4 | 4 | 3 | 3 | 4 | 1 | 1 | 1 | 1 | | 1 | 4 | 4 | 4 | 4 | 4 | 2 | 2 | 2 |
| 19 | *(structure)* | 4 | 3 | 1 | 1 | | | | | | | 2 | | 3 | 1 | 3 | | | 3 | 3 | 0 |

TABLE BB-continued

Antibacterial and cytotoxic activities of compounds of the invention

| compound number | structure | Antibacterial activity — Bacterial species | | | | | | | | | | | | MRSA strains with additional resistance | | | | | | cytotoxicity cell line | |
|---|---|---|---|---|---|---|---|---|---|---|---|---|---|---|---|---|---|---|---|---|
| | | SP | ARSP | MSSA | MRSA | SE | BS | EFm | VREFm | EFs | VREFs | MS | EC | D | V | L | M | T | P | H | K |
| 20 | [structure: 4-methyl-5-(2-chlorophenyl)-2-(5-(2-(trifluoromethyl)phenyl)furan-2-yl)imidazole] | 4 | 3 | 1 | | | 1 | | | | | | | | | | | | | 3 | 0 |
| 21 | [structure: 4-methyl-5-(3-chlorophenyl)-2-(5-(2-(trifluoromethoxy)phenyl)furan-2-yl)imidazole] | 4 | 4 | 4 | 3 | 1 | 3 | | 1 | 1 | 1 | | | 4 | | | 3 | 3 | 3 | 3 | 2 |

TABLE BB-continued
Antibacterial and cytotoxic activities of compounds of the invention
| compound number | structure | Antibacterial activity ||||||||||| cytotoxicity |
|---|---|---|---|---|---|---|---|---|---|---|---|---|
| | | Bacterial species ||||||||| MRSA strains with additional resistance |||| cell line |
| | | SP | ARSP | MSSA | MRSA | SE | BS | EFm | VREFm | EFs | VREFs | MS | EC | D V L M T P | H K |
| 22 | 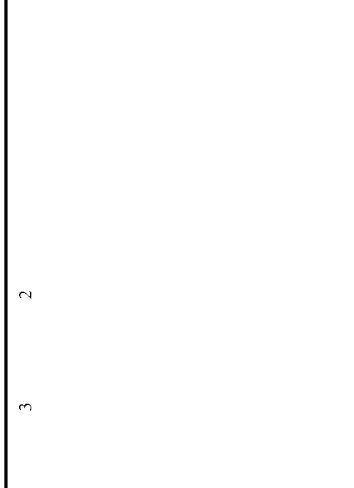 | 3 | | 2 | | | | | | | | | | | 2 |
| 23 | 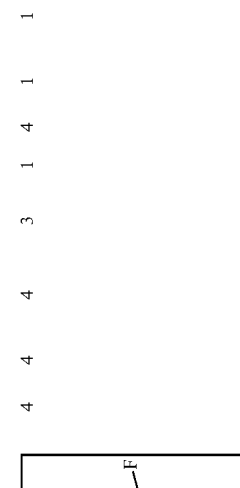 | 4 | 4 | 4 | 3 | 3 | 1 | 4 | 1 | 1 | 1 | | | | 3 2 |
| 24 |  | 4 | 4 | 3 | 3 | 1 | 3 | | | 1 | 1 | | | 4 4 3 3 4 2 | 2 2 |

TABLE BB-continued
Antibacterial and cytotoxic activities of compounds of the invention
| compound number | structure | Antibacterial activity | | | | | | | | | | | | cytotoxicity cell line | |
|---|---|---|---|---|---|---|---|---|---|---|---|---|---|---|---|
| | | Bacterial species | | | | | | | | EC | MRSA strains with additional resistance | | | | |
| | | SP | ARSP | MSSA | MRSA | SE | BS | EFm | VREFm | EFs | VREFs | MS | A | D V L M T P H | K |
| 25 | 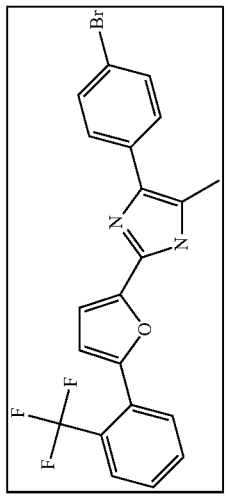 | 3 | | | 1 | | | | | | | | | 0 | 0 |
| 26 | 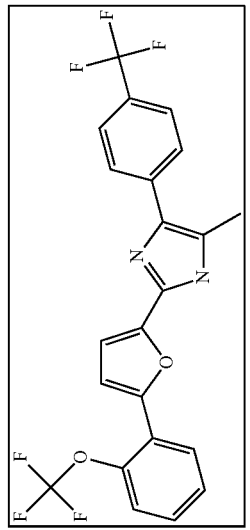 | 3 | 2 | | | | | | | | | | | 1 | 0 |
| 27 | 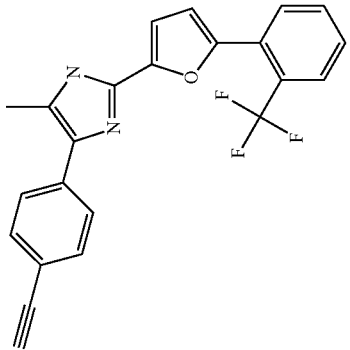 | 4 | | | | | | | | | | | | 1 | 2 |

TABLE BB-continued

Antibacterial and cytotoxic activities of compounds of the invention

| compound number | structure | Antibacterial activity | | | | | | | | | | | | | cyto-toxicity cell line |
|---|---|---|---|---|---|---|---|---|---|---|---|---|---|---|---|
| | | Bacterial species | | | | | | | | EC | MRSA strains with additional resistance | | | | |
| | | SP | ARSP | MSSA | MRSA | SE | BS | EFm | VREFm | EFs | VREFs | MS | A | D V L M T P | H K |
| 28 | (structure) | 3 | 1 | 1 | 1 | 4 | | | | | | | | | 1 0 |
| 29 | (structure) | 3 | 3 | 3 | 2 | | 2 | | 1 | | | | | | |
| 30 | (structure) | 4 | 4 | 3 | 3 | 2 | 3 | | 1 | | | | | 4 2 1 3 | 3 3 |

TABLE BB-continued

Antibacterial and cytotoxic activities of compounds of the invention

| compound number | structure | Antibacterial activity | | | | | | | | | | | cyto-toxicity cell line |
|---|---|---|---|---|---|---|---|---|---|---|---|---|---|
| | | Bacterial species | | | | | | | | | EC | MRSA strains with additional resistance | |
| | | SP | ARSP | MSSA | MRSA | SE | BS | EFm | VREFm | EFs | VREFs | MS | A | D V L M T P | H K |
| 31 | *structure with methoxy-trifluoromethylphenyl-furan-imidazole-phenyl* | 4 | 3 | 3 | 3 | | | | | | | | | | 3 0 |
| 31a | *structure with fluoro-trifluoromethylphenyl-furan-imidazole-phenyl* | 3 | 3 | 1 | | | 1 | | | | | | | | 2 1 |
| 32 | *structure with chloro-trifluoromethylphenyl-furan-imidazole-phenyl* | 3 | 4 | 3 | 3 | | 1 | | | | | | | | 2 |

TABLE BB-continued

Antibacterial and cytotoxic activities of compounds of the invention

| compound number | structure | Antibacterial activity — Bacterial species | | | | | | | | | | | EC | MRSA strains with additional resistance | | | | | | cytotoxicity cell line | |
| --- | --- | --- | --- | --- | --- | --- | --- | --- | --- | --- | --- | --- | --- | --- | --- | --- | --- | --- | --- | --- |
| | | SP | ARSP | MSSA | MRSA | SE | BS | EFm | VREFm | EFs | VREFs | MS | D | V | L | M | T | P | H | K |
| 33 | | 2 | 3 | 1 | 2 | | | | | | | | | | | | | | | 3 |
| 34 | | 3 | 4 | 4 | 1 | 3 | | | 1 | 1 | | 2 | 4 | 4 | 4 | 3 | 3 | 2 | 2 | 2 |
| 35 | | 2 | 2 | 3 | 1 | 1 | 3 | | | | | | | | | | | | 1 | 1 |

TABLE BB-continued

Antibacterial and cytotoxic activities of compounds of the invention

| compound number | structure | Antibacterial activity ||||||||||| cytotoxicity cell line ||
|---|---|---|---|---|---|---|---|---|---|---|---|---|---|---|---|---|
| | | Bacterial species |||||||||| EC | MRSA strains with additional resistance ||||| |||
| | | SP | ARSP | MSSA | MRSA | SE | BS | EFm | VREFm | EFs | VREFs | MS | A | D | V | L | M | T | P | H | K |
| 36 | | 3 | | | 2 | | | | | | | | | | | | | | | 3 | 2 |
| 37 | | 4 | 3 | 3 | 3 | 1 | 3 | | 1 | 1 | 1 | 2 | | | | | | | | 3 | 2 |

TABLE BB-continued

Antibacterial and cytotoxic activities of compounds of the invention

| compound number | structure | Antibacterial activity | | | | | | | | | | | cyto- toxicity cell line | |
|---|---|---|---|---|---|---|---|---|---|---|---|---|---|
| | | Bacterial species | | | | | | | | EC | MRSA strains with additional resistance | | | |
| | | SP | ARSP | MSSA | MRSA | SE | BS | EFm | VREFm | EFs | VREFs | MS | D V L M T P | H K |
| 38 | (structure shown) | 3 | 4 | 4 | 4 | 3 | | | 1 | | 1 | | 4 4 4 3 | 1 2 |
| 39 | (structure shown) | 4 | 3 | 4 | 3 | 4 | 3 | | 1 | 1 | | 1 | 4 4 4 4 3 | 1 2 |

TABLE BB-continued

Antibacterial and cytotoxic activities of compounds of the invention

| compound number | structure | Antibacterial activity | | | | | | | | | | | | | | cyto-toxicity cell line | |
|---|---|---|---|---|---|---|---|---|---|---|---|---|---|---|---|---|
| | | Bacterial species | | | | | | | | | EC | MRSA strains with additional resistance | | | | | |
| | | SP | ARSP | MSSA | MRSA | SE | BS | EFm | VREFm | EFs | VREFs | MS | D | V L M T P | H | K |
| 40 | | 2 | | | | | | | | | | | | | 2 | 1 |
| 41 | | 4 | 4 | 3 | 3 | 2 | 3 | 1 | 1 | 1 | 1 | 1 | | | 2 | 2 |

TABLE BB-continued

Antibacterial and cytotoxic activities of compounds of the invention

| compound number | structure | Antibacterial activity ||||||||||| | | MRSA strains with additional resistance ||||||| | cytotoxicity cell line |
|---|---|---|---|---|---|---|---|---|---|---|---|---|---|---|---|---|---|---|---|---|---|
| | | Bacterial species ||||||||||| EC | | | | | | | | |
| | | SP | ARSP | MSSA | MRSA | SE | BS | EFm | VREFm | EFs | VREFs | MS | A | D | V | L | M | T | P | H | K |
| 42 | 4-methyl-5-(4-fluorophenyl)-2-[5-(4-chloro-3-trifluoromethylphenyl)furan-2-yl]imidazole | 4 | 4 | 4 | 4 | 3 | 4 | 1 | 1 | 2 | 2 | 1 | | 4 | 4 | 4 | 4 | 4 | 4 | 1 | 3 |
| 43 | 4-methyl-5-(4-fluorophenyl)-2-[5-(4-chloro-3-trifluoromethoxyphenyl)furan-2-yl]imidazole | 4 | 4 | 3 | 2 | 1 | 3 | | | 1 | | | | | | | | | | | 3 |

TABLE BB-continued

Antibacterial and cytotoxic activities of compounds of the invention

| compound number | structure | Antibacterial activity | | | | | | | | | | | | cyto- toxicity cell line | | | | | | |
|---|---|---|---|---|---|---|---|---|---|---|---|---|---|---|---|---|---|---|---|
| | | Bacterial species | | | | | | | | | EC | MRSA strains with additional resistance | | | | | | | | |
| | | SP | ARSP | MSSA | MRSA | SE | BS | EFm | VREFm | EFs | VREFs | MS | A | D | V | L | M | T | P | H | K |
| 44 | ![structure] | 4 | 4 | 4 | 2 | 2 | 4 | 1 | 1 | 2 | 2 | 1 | | | | | | | | 2 |
| 45 | ![structure] | 4 | 3 | 3 | 2 | 3 | 3 | | | | 1 | | | 4 | 4 | 4 | 3 | 3 | 3 | 1 | 1 |

TABLE BB-continued

Antibacterial and cytotoxic activities of compounds of the invention

| compound number | structure | Antibacterial activity | | | | | | | | | | | | | | | | cytotoxicity cell line |
|---|---|---|---|---|---|---|---|---|---|---|---|---|---|---|---|---|---|
| | | Bacterial species | | | | | | | | | EC | MRSA strains with additional resistance | | | | | | |
| | | SP | ARSP | MSSA | MRSA | SE | BS | EFm | VREFm | EFs | VREFs | MS | A | D | V | L | M | T | P | H | K |
| 46 | structure with methyl-imidazole-thiophene-phenyl-CF3 | 3 | 3 | 2 | | | | | | | 1 | | | | | | | | | 1 | 1 |
| 47 | structure with chlorophenyl-methyl-imidazole-furan-phenyl-CF3 | 4 | 4 | 4 | 3 | 3 | 3 | 1 | 1 | 1 | 3 | | | | | | | | | 1 | 2 |

TABLE BB-continued

Antibacterial and cytotoxic activities of compounds of the invention

| compound number | structure | Antibacterial activity | | | | | | | | | | | cyto-toxicity cell line | |
|---|---|---|---|---|---|---|---|---|---|---|---|---|---|
| | | Bacterial species | | | | | | | | EC | MRSA strains with additional resistance | | | |
| | | SP | ARSP | MSSA | MRSA | SE | BS | EFm | VREFm | EFs | VREFs | MS | D V L M T P | H K |
| 48 | (structure with 4-trifluoromethoxyphenyl-furan-imidazole-methyl-4-chlorophenyl) | 4 | 4 | 3 | 3 | 2 | 3 | | 1 | | 1 | | | 2 1 |
| 49 | (structure with 3-chloro-4-trifluoromethylphenyl-furan-imidazole-methyl-4-fluorophenyl) | 3 | 4 | 3 | 3 | 2 | | 1 | 1 | 2 | 1 | | 4 3 2 3 4 3 | 3 2 |

TABLE BB-continued

Antibacterial and cytotoxic activities of compounds of the invention

| compound number | structure | Antibacterial activity | | | | | | | | | | cytotoxicity | |
|---|---|---|---|---|---|---|---|---|---|---|---|---|---|
| | | Bacterial species | | | | | | | | EC | MRSA strains with additional resistance | | cell line |
| | | SP | ARSP | MSSA | MRSA | SE | BS | EFm | VREFm | EFs | VREFs | MS | A | D | V | L | M | T | P | H | K |
| 50 | *structure with chlorophenyl-imidazole-furan-chloro-trifluoromethoxyphenyl* | 3 | 3 | 3 | 2 | 1 | | | | | | | | | | | | | | 1 | 1 |
| 51 | *structure with fluorophenyl-methylimidazole-furan-chloro-trifluoromethoxyphenyl* | 3 | 3 | 2 | 1 | 1 | 3 | | | | | | | 4 | | | 3 | 2 | 3 | 3 |

TABLE BB-continued

Antibacterial and cytotoxic activities of compounds of the invention

| compound number | structure | Antibacterial activity | | | | | | | | | | | | | | | cyto-toxicity | |
|---|---|---|---|---|---|---|---|---|---|---|---|---|---|---|---|---|---|
| | | Bacterial species | | | | | | | | | EC | MRSA strains with additional resistance | | | | | cell line | |
| | | SP | ARSP | MSSA | MRSA | SE | BS | EFm | VREFm | EFs | VREFs | MS | A | D | V | L | M | T | P | H | K |
| 52 | (structure) | | | 2 | | | | | | | | | | | | | | | | 3 | 2 |
| 53 | (structure) | | | 3 | 3 | 1 | | | | | | | | | | | | | | 3 | 1 |

TABLE BB-continued

Antibacterial and cytotoxic activities of compounds of the invention

| compound number | structure | Antibacterial activity | | | | | | | | | | | | cyto-toxicity | |
|---|---|---|---|---|---|---|---|---|---|---|---|---|---|---|---|
| | | Bacterial species | | | | | | | | EC | MRSA strains with additional resistance | | | | cell line | |
| | | SP | ARSP | MSSA | MRSA | SE | BS | EFm | VREFm | EFs | VREFs | MS | A | D V L M T P | H | K |
| 54 | | 2 | | | | | | | | | | | | | 1 | 1 |
| 55 | | 3 | | | | | | | | | | | | | 1 | |

TABLE BB-continued

Antibacterial and cytotoxic activities of compounds of the invention

| compound number | structure | Antibacterial activity | | | | | | | | | | | | | cyto-toxicity cell line | |
|---|---|---|---|---|---|---|---|---|---|---|---|---|---|---|---|---|
| | | Bacterial species | | | | | | | | EC | MRSA strains with additional resistance | | | | | |
| | | SP | ARSP | MSSA | MRSA | SE | BS | EFm | VREFm | EFs | VREFs | MS | A | D | V | L | M | T | P | H | K |
| 56 | (5-methyl-4-phenyl-1H-imidazol-2-yl)-thiazole-2-(4-methylphenyl) | 3 | | | | | | | | | | | | | | | | | | 1 | 3 |
| 57 | (5-methyl-4-phenyl-1H-imidazol-2-yl)-oxazole-2-(4-methylphenyl) | 3 | | | | | | | | | | | | | | | | | | 1 | 3 |

TABLE BB-continued

Antibacterial and cytotoxic activities of compounds of the invention

| compound number | structure | Antibacterial activity ||||||||||| cytotoxicity ||
| | | Bacterial species |||||||| EC | MRSA strains with additional resistance |||||| cell line ||
| | | SP | ARSP | MSSA | MRSA | SE | BS | EFm | VREFm | EFs | VREFs | MS | A | D | V | L | M | T | P | H | K |
|---|---|---|---|---|---|---|---|---|---|---|---|---|---|---|---|---|---|---|---|---|---|
| 58 | | 4 | | | 1 | | | | | | | | | | | | | | | 3 | 2 |
| 59 | | 3 | | | | | | | | | | | | | | | | | | 2 | 2 |

TABLE BB-continued

Antibacterial and cytotoxic activities of compounds of the invention

| compound number | structure | Antibacterial activity | | | | | | | | | | | | | | | cyto-toxicity cell line |
|---|---|---|---|---|---|---|---|---|---|---|---|---|---|---|---|---|
| | | Bacterial species | | | | | | | | | EC | MRSA strains with additional resistance | | | | | |
| | | SP | ARSP | MSSA | MRSA | SE | BS | EFm | VREFm | EFs | VREFs | MS | A | D | V | L | M | T | P | H | K |
| 60 | | 3 | 3 | 3 | 1 | 1 | 3 | | | 1 | | 2 | 1 | 4 | 3 | 4 | 3 | 3 | 3 | 3 | 2 |
| 61 | | 3 | | | | | | | | | | | | | | | | | | 3 | 2 |
| 62 | | 3 | | | | | | | | | | | | | | | | | | 3 | 2 |

TABLE BB-continued

Antibacterial and cytotoxic activities of compounds of the invention

| compound number | structure | Antibacterial activity ||||||||||| cyto-toxicity cell line |
|---|---|---|---|---|---|---|---|---|---|---|---|---|---|---|---|
| | | Bacterial species |||||||| EC | MRSA strains with additional resistance ||||| |
| | | SP | ARSP | MSSA | MRSA | SE | BS | EFm | VREFm | EFs | VREFs | MS | D | V | L | M | T | P | H | K |
| 63 | | 3 | 3 | 3 | 3 | 3 | | | | | | | | | | | | | 2 | |
| 64 | | 4 | 3 | 3 | 1 | 1 | 1 | | | | | 1 | 4 | 4 | 4 | 4 | | | 3 | 3 |

TABLE BB-continued

Antibacterial and cytotoxic activities of compounds of the invention

| compound number | structure | Antibacterial activity | | | | | | | | | | | | cyto- toxicity cell line | |
|---|---|---|---|---|---|---|---|---|---|---|---|---|---|---|
| | | Bacterial species | | | | | | | | | EC | MRSA strains with additional resistance | | | |
| | | SP | ARSP | MSSA | MRSA | SE | BS | EFm | VREFm | EFs | VREFs | MS | D V L M T P | H K |
| 65 | | 4 | | 2 | | | | | | | | | | 2 |
| 66 | | 4 | 3 | 3 | 2 | 1 | 3 | 1 | | 1 | | 2 | 4 3 4 3 3 2 | 3 1 |

TABLE BB-continued

Antibacterial and cytotoxic activities of compounds of the invention

| compound number | structure | Antibacterial activity ||||||||||| | cyto-toxicity |||||||||
| --- | --- | --- | --- | --- | --- | --- | --- | --- | --- | --- | --- | --- | --- | --- | --- | --- | --- | --- | --- | --- |
| | | Bacterial species ||||||||||| EC | MRSA strains with additional resistance |||||| cell line ||
| | | SP | ARSP | MSSA | MRSA | SE | BS | EFm | VREFm | EFs | VREFs | MS | | D | V | L | M | T | P | H | K |
| 67 | ![structure: 2-(trifluoromethoxy)phenyl-furan-imidazole-(2-chlorophenyl)] | 3 | 2 | | | 2 | | | | | | | | | | | | | | 2 | 2 |

TABLE BB-continued

Antibacterial and cytotoxic activities of compounds of the invention

| compound number | structure | Antibacterial activity ||||||||||| MRSA strains with additional resistance |||||| cytotoxicity cell line ||
|---|---|---|---|---|---|---|---|---|---|---|---|---|---|---|---|---|---|---|---|
| | | Bacterial species |||||||||| EC | | | | | | | | |
| | | SP | ARSP | MSSA | MRSA | SE | BS | EFm | VREFm | EFs | VREFs | MS | D | V | L | M | T | P | H | K |
| 68 | | 2 | 3 | 2 | 2 | 3 | 3 | | | | | | 4 | | | | | 1 | 2 | 2 |
| 69 | | 4 | 3 | 2 | | | 1 | 1 | | | 2 | 1 | | | | | | | 2 | 1 |

TABLE BB-continued
Antibacterial and cytotoxic activities of compounds of the invention
| compound number | structure | Antibacterial activity | | | | | | | | | | | cyto-toxicity cell line | |
|---|---|---|---|---|---|---|---|---|---|---|---|---|---|
| | | Bacterial species | | | | | | | | EC | MRSA strains with additional resistance | | | |
| | | SP | ARSP | MSSA | MRSA | SE | BS | EFm | VREFm | EFs | VREFs | MS | A | D V L M T P | H K |
| 70 | 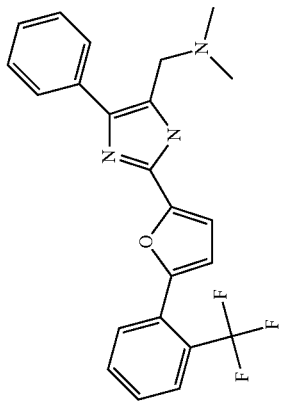 | 3 | 1 | 1 | 1 | 2 | 1 | 2 | 2 | 2 | 2 | 2 | 3 | 3 1 1 1 1 1 | 3 2 |
| 71 | 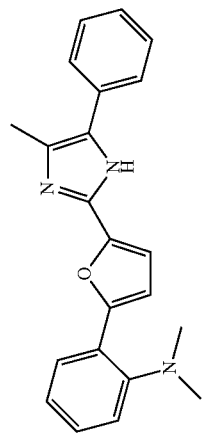 | 3 | | | | | | | | | | | | | 3 1 |

TABLE BB-continued
Antibacterial and cytotoxic activities of compounds of the invention
| | | Antibacterial activity | | | | | | | | | | | | | | cyto- | |
| | | Bacterial species | | | | | | | | | EC | MRSA strains with additional resistance | | | | | toxicity cell line | |
| compound number | structure | SP | ARSP | MSSA | MRSA | SE | BS | EFm | VREFm | EFs | VREFs | MS | A | D | V | L | M | T | P | H | K |
|---|---|---|---|---|---|---|---|---|---|---|---|---|---|---|---|---|---|---|---|---|---|
| 72 | 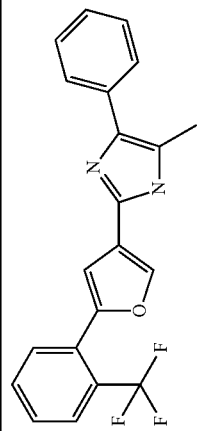 | 2 | | | | | | | | | | | | | | | | | 3 | 2 |
| 73 | 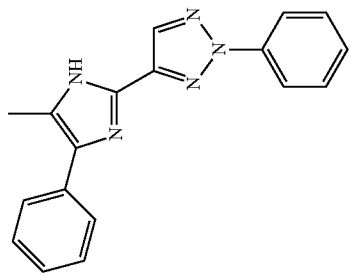 | 2 | | | | | | | | | | | | | | | | | 1 | |

TABLE BB-continued

Antibacterial and cytotoxic activities of compounds of the invention

| compound number | structure | Antibacterial activity | | | | | | | | | | | | | | | | | cytotoxicity cell line | |
|---|---|---|---|---|---|---|---|---|---|---|---|---|---|---|---|---|---|---|---|
| | | Bacterial species | | | | | | | | | | MRSA strains with additional resistance | | | | | | | | |
| | | SP | ARSP | MSSA | MRSA | SE | BS | EFm | VREFm | EFs | VREFs | MS | EC Δ | D | V | L | M | T | P | H | K |
| 74 | (structure of 5-methyl-4-phenyl-2-(5-phenylthiophen-2-yl)-1H-imidazole) | 3 | | | | | | | | | | | | | | | | | | 1 | 3 |

*Streptococcus pneumoniae* = SP
multi-drug resistant-SP = ARSP
*Staphylococcus aureus* MSSA = MSSA
*Staphylococcus aureus* MRSA = MRSA
*Staphylococcus epidermidis* = SE
*Bacillus subtilis* = BS
*Enterococcus faecium* = EFm
vancomycin-resistant EFm = VREFm
*Enterococcus faecalis* = EFs
vancomycin-resistant EFs = VREFs
*Mycobacterium smegmatis* = MS
*Escherichia coli* ΔtolC = EC Δ
daptomycin = D
vancomycin = V
linezolid = L
moenomycin = M
triclosan = T
platensimycin = P
hepatocytes = H
keratinocytes = K

The invention claimed is:
1. An antimicrobial composition comprising a compound, said compound consisting of the structural moiety of formula (I) or a pharmaceutically-acceptable salt of said compound, for use as a medicament

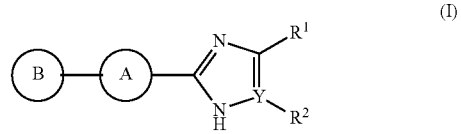
(I)

wherein
(i) Y is C;
(ii) R¹ is selected from the group consisting of:
—CH₃, C$_{2to6}$alkyl, an optionally substituted aryl ring, and an optionally substituted benzyl ring, and
(iii) R² is selected from the group consisting of:
H, an alkyl group, a halogen, and —(CH₂)$_n$N(CH₃)₂ where n is an integer from 1 to 3, with the proviso that at least one of R¹ or R² possesses 3 or more carbon atoms;
or
R¹ and R² are connected to form a four-, five- or six-membered non-aromatic carbocyclic ring thus providing a fused bicyclic moiety in which one or more of the carbon atoms of the ring comprising groups R¹ and R² is optionally replaced by a heteroatom selected from O, N, or S, and where one or more of the atoms of the ring comprising groups R¹ and R² is optionally substituted with one or more substituents independently selected from the group consisting of —CH₃, C$_{2to4}$alkyl, halogen, hydroxyl, —OCH₃, —OC$_{2to4}$alkyl, ethynyl, —OCF₃, and —CF₃; and
(iv) A is selected from the group consisting of

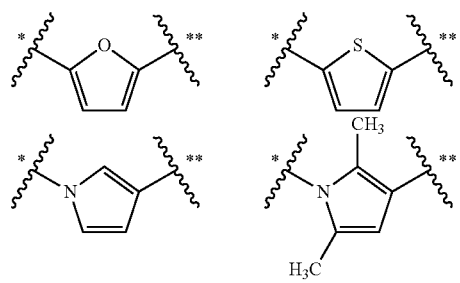

where * is the point of connection to the correspondingly-labeled atom of B and ** is the point of connection to the correspondingly-labeled atom of

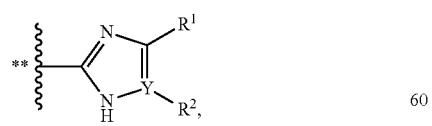

and wherein the aromatic ring of A is optionally substituted by one or more substituents independently selected from —CH₃, C$_{2to4}$alkyl, halogen, OCH₃, and —OC$_{2to4}$ alkyl; and
(v) B is aryl.

2. The antimicrobial composition of claim 1, wherein B is an unsubstituted phenyl ring or a substituted phenyl ring.

3. The antimicrobial composition of claim 1, wherein B is a phenyl ring optionally substituted with one or more substituents independently selected from the group consisting of —CH₃, C$_{2to4}$alkyl, halogen, hydroxyl, —OCH₃, —OC$_{2to4}$alkyl, —CF₃, —OCF₃, —NH₂, —CH₂NH₂, —N(CH₃)₂, —NO₂, —CH₂OH, —CO₂CH₃, —CO₂C$_{2to4}$alkyl, —CO₂H, —N(alkyl)₂ where the two alkyl groups are independently selected from —CH₃ or C$_{2to4}$alkyl, —NH(alkyl) where the alkyl group is selected from —CH₃ or C$_{2to4}$alkyl, 4-morpholinyl, 1-piperidinyl, 4H-piperazinyl, 4-C$_{1to4}$alkyl-piperazinyl, and 4-C$_{3to6}$cycloalkyl-piperazinyl.

4. The antimicrobial composition of claim 1, wherein R¹ is substituted or unsubstituted phenyl.

5. The antimicrobial composition of claim 1, wherein R¹ is phenyl substituted with one or more substituents independently selected from the group consisting of —CH₃, C$_{2to4}$alkyl, halogen, hydroxyl, —OCH₃, —OC$_{2to4}$alkyl, ethynyl, —OCF₃, and —CF₃.

6. The antimicrobial composition of claim 1, wherein the antimicrobial composition further comprises a pharmaceutically acceptable carrier.

7. A combination of the antimicrobial composition of claim 1 and at least one inhibitor of bacterial lipid biosynthesis, wherein the combination treats a microbial infection and/or a disorder, affliction or illness caused by or at least in part by the microbial infection, where said microbial infection is a bacterial infection.

8. A combination as defined in claim 7, wherein the combination is provided by combining the antimicrobial composition of claim 1 and the at least one inhibitor in a single formulation before dosing or by dosing the antimicrobial composition of claim 1 and the at least one inhibitor separately.

9. The antimicrobial composition of claim 1, wherein the compound is selected from

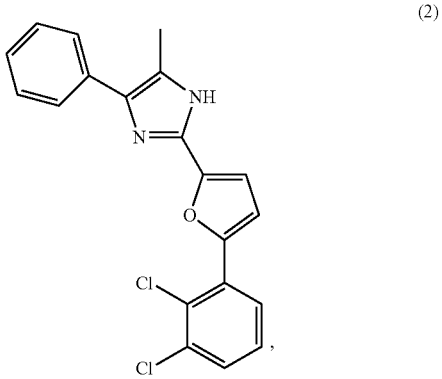
(2)

-continued
(6)
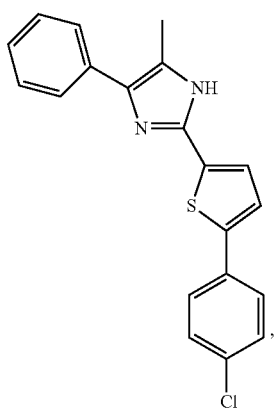
(19)
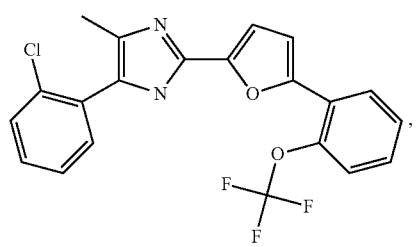
(25)
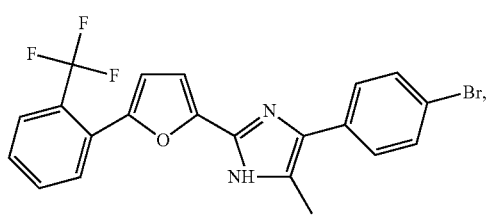
(26)
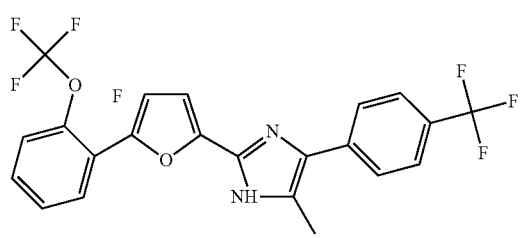
(48)
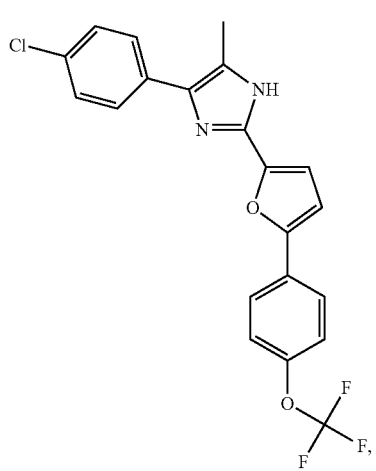
-continued
(43)
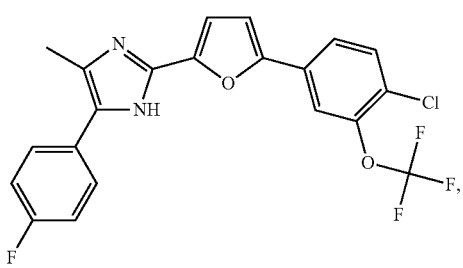
(44)
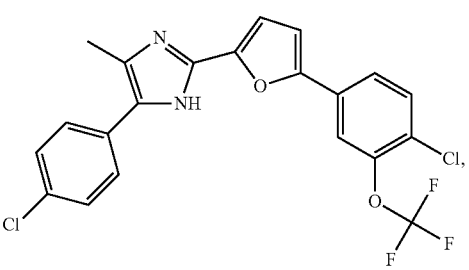
(50)
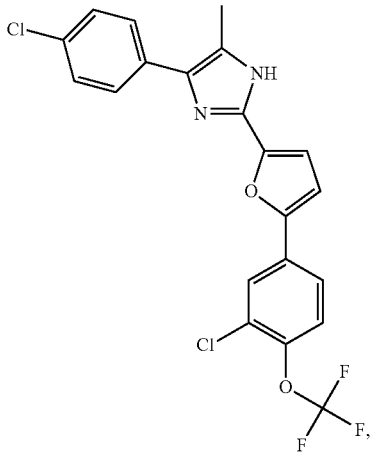
(49)
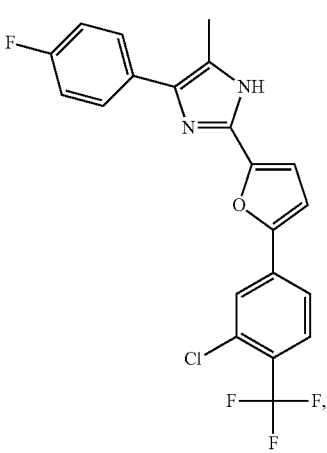

(65)
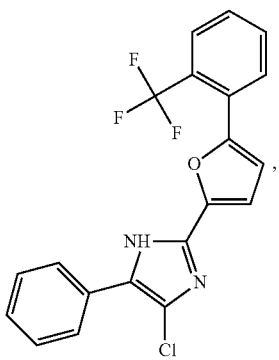
(64)
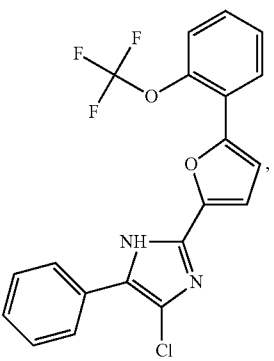
(68)
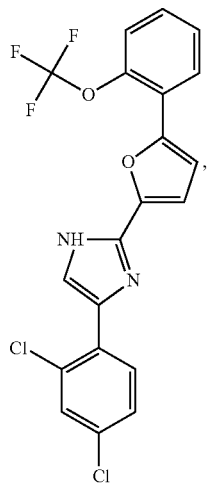
(70)
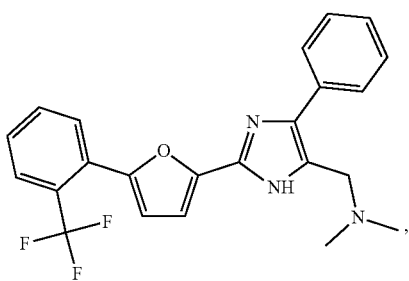
or a combination thereof.
10. The antimicrobial composition of claim 9, wherein the compound is selected from compounds 2, 6, 19, 25, 26, 48, and 50.
11. The antimicrobial composition of claim 10, further comprising at least one inhibitor of bacterial lipid biosynthesis.
* * * * *